United States Patent
Pfau et al.

(10) Patent No.: US 7,476,663 B2
(45) Date of Patent: Jan. 13, 2009

(54) SUBSTITUTED THIOPHENE CARBOXAMIDES

(75) Inventors: Roland Pfau, Biberach (DE); Henning Priepke, Warthausen (DE); Kai Gerlach, Biberach (DE); Wolfgang Wienen, Biberach (DE); Annette Schuler-Metz, Ulm (DE); Herbert Nar, Ochsenhausen (DE); Sandra Handschuh, Warthausen (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 151 days.

(21) Appl. No.: 11/125,731

(22) Filed: May 10, 2005

(65) Prior Publication Data

US 2005/0277628 A1    Dec. 15, 2005

(30) Foreign Application Priority Data

May 13, 2004   (EP)   ................................. 04011384
Aug. 7, 2004   (EP)   ................................. 04018807

(51) Int. Cl.
    *A61K 31/55*   (2006.01)
    *A61K 31/453*  (2006.01)
    *C07D 409/02*  (2006.01)
    *C07D 401/00*  (2006.01)

(52) U.S. Cl. .................. 514/217.03; 514/218; 514/326; 514/422; 540/597; 546/207; 548/527

(58) Field of Classification Search ............ 514/217.03; 540/597
See application file for complete search history.

(56) References Cited

U.S. PATENT DOCUMENTS

| 2003/0153610 A1 | 8/2003 | Straub et al. |
| 2004/0038858 A1 | 2/2004 | Dorsch et al. |
| 2004/0176363 A1 | 9/2004 | Liebeschuetz et al. |

FOREIGN PATENT DOCUMENTS

| WO | WO 01/47919 A1 | 7/2001 |
| WO | WO 01/96303 A1 | 12/2001 |
| WO | WO 02/48099 A1 | 6/2002 |
| WO | WO 2004/031145 A2 | 4/2004 |
| WO | WO 2004/046138 A1 | 6/2004 |

OTHER PUBLICATIONS

Werner W. K. R. Mederski, et al; Chlorothiophenecarboxamides as P1 surrogates of inhibitors of blood coagulation factor Xa; Bioorganic & Medicinal Chemistry Letters 14; vol. 14; pp. 5817-5822; Sep. 17, 2004; Elsevier "Publisher".
Carlos Cativiela, et al; Stereoselective Synthesis of Quaternary α-Amino Acids. Part 1: Acyclic Compounds; Tetrahedron: Asymmetry (1998) vol. 9 pp. 3517-3599.
Carlos Cativiela, et al; Stereoselective Synthesis of Quaternary α-Amino Acids. Part 2: Acyclic Compounds; Tetrahedron: Asymmetry (2000) vol. 11 pp. 645-732.
Patrick D. Bailey, et al; Comprehensive Functional Group Interconversions; vol. 5 pp. 257-307; Pergamon 1995.
Molina Mhatre, et al; Thrombin, A Mediator of Neurotoxicity and Memory Impairment; Neurobiology of Aging (2004) vol. 25 pp. 783-793.
Haruhiko Akiyama, et al; Thrombin Accumulation in Brains of Patients with Alzheimer's Disease; Neuroscience Letters (1992) vol. 146 pp. 152-154.
Sang-H. Choi, et al; Thrombin-Induced Microglial Activation Produces Degeneration of Nigral Dopaminergic Neurons In Vivo; The Journal of Neuroscience (2003) vol. 23 pp. 5877-5886.
Isamu Shiina, et al; An Effective Method for Formylation of Weakly Nucleophilic Anilines and Indole; Heterocycles (1995) vol. 19 No. 1 pp. 141-148.
International Search Report for PCT/EP2005/004975 mailed Sep. 16, 2005.
European Search Report for EP04011384 mailed Nov. 24, 2004.

*Primary Examiner*—Kamal A Saeed
(74) *Attorney, Agent, or Firm*—Michael P. Morris; Mary-Ellen M. Devlin; Edouard G. Lebel

(57) ABSTRACT

The present invention relates to new substituted thiophene-2-carboxylic acid amides of general formula

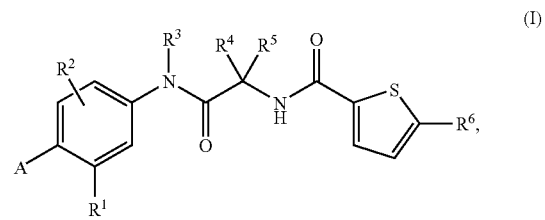

(I)

wherein A, and $R^1$ to $R^{8c}$ are defined as in claim 1, the tautomers, the enantiomers, the diastereomers, the mixtures thereof and the salts thereof, particularly the physiologically acceptable salts thereof with inorganic or organic acids or bases, which have valuable properties.

14 Claims, No Drawings

SUBSTITUTED THIOPHENE CARBOXAMIDES

This application claims benefit of European application EP 04 011 384, filed May 13, 2004 and of European application EP 04 018 807, filed Aug. 7, 2004, the contents of which are incorporated herein.

The present invention relates to new substituted thiophene-2-carboxylic acid amides of general formula

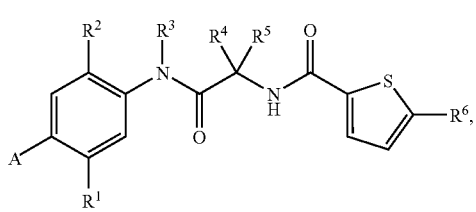

the tautomers, the enantiomers, the diastereomers, the mixtures thereof and the salts thereof, particularly the physiologically acceptable salts thereof with inorganic or organic acids or bases, which have valuable properties.

The compounds of the above general formula I as well as the tautomers, the enantiomers, the diastereomers, the mixtures thereof and the salts thereof, particularly the physiologically acceptable salts thereof with inorganic or organic acids or bases, and the stereoisomers thereof have valuable pharmacological properties, particularly an antithrombotic activity and a factor Xa-inhibiting activity.

The present application relates to new compounds of the above general formula I, the preparation thereof, the pharmaceutical compositions containing the pharmacologically effective compounds, the preparation thereof and their use.

A 1st embodiment of the present invention comprises those compounds of general formula 1, wherein A denotes a group of general formula

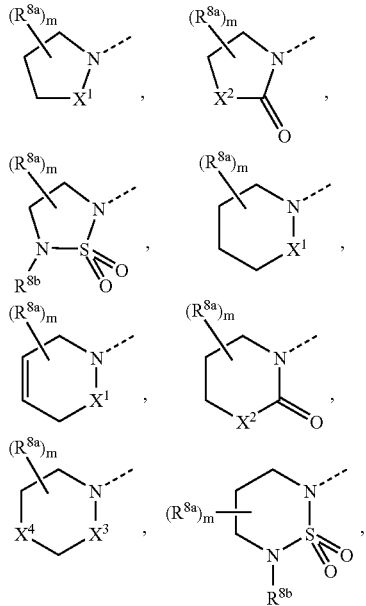

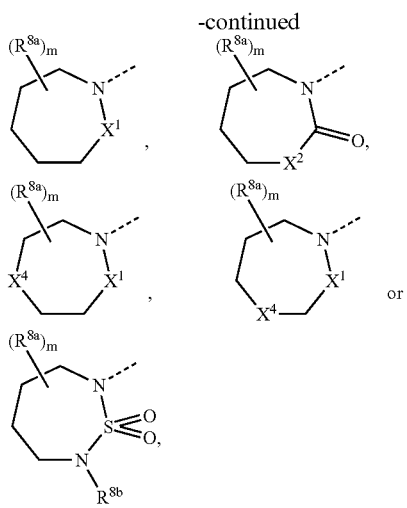

wherein m is the number 1 or 2, $R^{8a}$ in each case independently of one another denotes a hydrogen or halogen atom or a $C_{1-5}$-alkyl, hydroxy, hydroxy-$C_{1-5}$-alkyl, $C_{1-5}$-alkoxy, $C_{1-5}$-alkoxy-$C_{1-5}$-alkyl, amino, $C_{1-5}$-alkylamino, di-($C_{1-5}$-alkyl)-amino, amino-$C_{1-5}$-alkyl, $C_{1-5}$-alkylamino-$C_{1-5}$-alkyl, di-($C_{1-5}$-alkyl)-amino-$C_{1-5}$-alkyl, aminocarbonyl, $C_{1-5}$-alkylaminocarbonyl, di-($C_{1-5}$-alkyl)-aminocarbonyl or $C_{1-5}$-alkylcarbonylamino group, while in the previously mentioned substituted 5- to 7-membered groups A the heteroatoms F, Cl, Br, I, O or N optionally introduced with $R^{8a}$ as substituent are not separated by precisely one carbon atom from a heteroatom selected from among N, O, S.

$R^{8b}$ each independently of one another denote a hydrogen atom or a $C_{1-5}$-alkyl group, $X^1$ denotes a carbonyl, thiocarbonyl, C=$NR^{8c}$, C=N—$OR^{8c}$, C=N—$NO_2$, C=N—CN or sulphonyl group, $R^{8c}$ each independently of one another denote a hydrogen atom, a $C_{1-5}$-alkyl, $C_{1-5}$-alkylcarbonyl, $C_{1-5}$-alkyloxycarbonyl or $C_{1-5}$-alkylsulphonyl group, $X^2$ denotes an oxygen atom or a —$NR^{8b}$ group, $X^3$ denotes a carbonyl, thiocarbonyl, C=$NR^{8c}$, C=N—$OR^{8c}$, C=N—$NO_2$, C=N—CN or sulphonyl group, $X^4$ denotes an oxygen or sulphur atom or a —$NR^{8c}$ group, $R^1$ denotes a halogen atom, a $C_{1-3}$-alkyl or $C_{1-3}$-alkoxy group, while the hydrogen atoms of the $C_{1-3}$-alkyl or $C_{1-3}$-alkoxy group may optionally be wholly or partly replaced by fluorine atoms, a $C_{2-3}$-alkenyl, $C_{2-3}$-alkynyl, nitrile, nitro or amino group, $R^2$ denotes a hydrogen or halogen atom or a $C_{1-3}$-alkyl group, $R^3$ denotes a hydrogen atom or a $C_{1-3}$-alkyl group, $R^4$ and $R^5$ in each case independently of one another denote a hydrogen atom, a $C_{2-6}$-alkenyl or $C_{2-6}$-alkynyl group, a straight-chain or branched $C_{1-6}$-alkyl group,
while the hydrogen atoms of the straight-chain or branched $C_{1-6}$-alkyl group may optionally be wholly or partly replaced by fluorine atoms, and may optionally be substituted by a $C_{3-5}$-cycloalkyl group, a nitrile, hydroxy, a $C_{1-5}$-alkyloxy group, while the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-5}$-alkyloxy, $C_{1-5}$-alkyloxycarbonyl-$C_{1-5}$-alkyloxy, mercapto, $C_{1-5}$-alkylsulphanyl, $C_{1-5}$-alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, aminosulphonyl, $C_{1-5}$-alkylaminosulphonyl, di-($C_{1-5}$-alkyl)-aminosulphonyl, $C_{3-6}$-cycloalkyleneiminosulphonyl, amino, $C_{1-5}$-alkylamino, di-($C_{1-5}$-alkyl)-amino, $C_{1-5}$-alkylcarbonylamino, $C_{1-5}$-alkylsulphonylamino, N—($C_{1-5}$-alkylsulphonyl)-$C_{1-5}$-alkylamino or $C_{3-6}$-cycloalkylcarbonylamino group, a carboxy, aminocarbonyl, $C_{1-5}$-alkylaminocarbonyl, $C_{3-6}$-cycloalkylaminocarbonyl, di-($C_{1-5}$-alkyl)-aminocarbonyl, $C_{1-5}$-alkoxycarbonyl, $C_{4-6}$-cycloalkyleneiminocarbonyl group, a phenyl, heteroaryl, phenyl-$C_{1-5}$-alkyl or heteroaryl-$C_{1-5}$-alkyl group,
which may optionally be mono- to trisubstituted in the phenyl or heteroaryl moiety by identical or different substituents selected from the group consisting of halogen atoms, $C_{1-5}$-alkyl, di-($C_{1-5}$-alkyl)-amino, hydroxy, $C_{1-5}$-alkyloxy, mono-, di- or trifluoromethoxy, carboxy and $C_{1-5}$-alkyloxycarbonyl groups, a 3- to 7-membered cycloalkyl, cycloalkyleneimino, cycloalkyl-$C_{1-5}$-alkyl or cycloalkyleneimino-$C_{1-3}$-alkyl group,
wherein in 4- to 7-membered cyclic groups in the cyclic moiety a methylene group may optionally be replaced by an —N($R^{8c}$) group, an oxygen or sulphur atom or a —S(O) or —S(O)$_2$ group, or
wherein in 4- to 7-membered cyclic groups in the cyclic moiety two adjacent methylene groups may together optionally be replaced by a —C(O)N($R^{8b}$) or —S(O)$_2$N($R^{8b}$) group, or
wherein in 6- to 7-membered cyclic groups in the cyclic moiety three adjacent methylene groups may optionally be replaced together by a substituted 'OC(O)N($R^{8b}$) or —N($R^{8b}$)C(O)N($R^{8b}$) or —N($R^{8b}$)S(O)$_2$N($R^{8b}$) group,
with the proviso that a 3- to 7-membered cycloalkyl, cycloalkyleneimino, cycloalkyl-$C_{1-5}$-alkyl or cycloalkyleneimino-$C_{1-3}$-alkyl group as hereinbefore defined wherein two heteroatoms selected from among oxygen and nitrogen are separated from one another by precisely one optionally substituted —CH$_2$ group, is excluded,
while a 3- to 7-membered cycloalkyl, cycloalkyleneimino, cycloalkyl-$C_{1-5}$-alkyl or cycloalkyleneimino-$C_{1-3}$-alkyl group as hereinbefore defined may be substituted at one or two —CH$_2$ groups by one or two $C_{1-3}$-alkyl groups in each case, or $R^4$ and $R^5$ together with the carbon atom to which they are bound form a $C_{3-8}$-cycloalkyl or $C_{3-8}$-cycloalkenyl group,
while one of the methylene groups of a $C_{4-8}$-cycloalkyl group may be replaced by an oxygen or sulphur atom or an —N($R^{8c}$), or a carbonyl, sulphinyl or sulphonyl group, and/or
two directly adjacent methylene groups of a $C_{4-8}$-cycloalkyl group may be replaced together by a —C(O)N($R^{8b}$) or —S(O)$_2$N($R^{8b}$) group, and/or
three directly adjacent methylene groups of a $C_{6-8}$-cycloalkyl group may be replaced together by a —OC(O)N($R^{8b}$), —N($R^{8b}$)C(O)N($R^{8b}$) or —N($R^{8b}$)S(O)$_2$N($R^{8b}$) group,
while 1 to 3 carbon atoms of a $C_{3-8}$-cycloalkyl group may optionally be substituted independently of one another by in each case one or two identical or different halogen atoms or $C_{1-5}$-alkyl, nitrile, hydroxy, $C_{1-5}$-alkyloxy, $C_{1-5}$-alkylcarbonyloxy, carboxy-$C_{1-5}$-alkyl, $C_{1-5}$-alkyloxycarbonyl-$C_{1-5}$-alkyl, $C_{1-5}$-alkylsulphanyl, $C_{1-5}$-alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, aminosulphonyl, $C_{1-5}$-alkylaminosulphonyl, di-($C_{1-5}$-alkyl)-aminosulphonyl, $C_{3-6}$-cycloalkyleneiminosulphonyl, amino, $C_{1-5}$-alkylamino, di-($C_{1-5}$-alkyl)-amino, $C_{1-5}$-alkylcarbonylamino, $C_{1-5}$-alkyl-sulphonylamino, N-($C_{1-5}$-alkylsulphonyl)-$C_{1-5}$-alkylamino or $C_{3-6}$-cycloalkylcarbonylamino groups,
while 1 to 2 carbon atoms of a $C_{3-8}$-cycloalkenyl group may optionally be substituted independently of one another by in each case a $C_{1-5}$-alkyl, nitrile, carboxy-$C_{1-5}$-alkyl, $C_{1-5}$-alkyloxycarbonyl-$C_{1-5}$-alkyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, aminosulphonyl, $C_{1-5}$-alkylaminosulphonyl, di-($C_{1-5}$-alkyl)-aminosulphonyl, $C_{3-6}$-cycloalkyleneiminosulphonyl group,
and 1 to 2 carbon atoms of a $C_{4-8}$-cycloalkenyl group which are not bound to another carbon atom by a double bond may optionally be substituted independently of one another by a fluorine atom or a hydroxy, $C_{1-5}$-alkyloxy, $C_{1-5}$-alkylcarbonyloxy, $C_{1-5}$-alkylsulphanyl, $C_{1-5}$-alkylsulphonyl, amino, $C_{1-5}$-alkylamino, di-($C_{1-5}$-alkyl)-amino, $C_{1-5}$-alkylcarbonylamino, $C_{1-5}$-alkylsulphonylamino, N—($C_{1-5}$-alkylsulphonyl)-$C_{1-5}$-alkylamino or $C_{3-6}$-cycloalkylcarbonyl-amino group,
with the proviso that a $C_{3-8}$-cycloalkyl or $C_{3-8}$-cycloalkenyl group of this kind, formed from $R^4$ and $R^5$ together,
wherein two heteroatoms in the cyclic group selected from among oxygen and nitrogen are separated from one another by precisely one optionally substituted —CH$_2$ group, and/or
wherein one or both methylene groups of the cyclic group which are directly connected to the carbon atom to which the groups $R^4$ and $R^5$ are bound, are replaced by a heteroatom selected from among oxygen, nitrogen and sulphur, and/or
wherein a substituent bound to the cyclic group, which is characterised in that a heteroatom selected from among an oxygen, nitrogen, sulphur and halogen atom is bound directly to the cyclic group, is separated from another heteroatom selected from among oxygen, nitrogen and sulphur, with the exception of the sulphone group, by precisely one, optionally substituted, methylene group, and/or
wherein two oxygen atoms are joined together directly,
is excluded, $R^6$ denotes a hydrogen, fluorine, chlorine, bromine or iodine atom, a nitrile group, a $C_{1-3}$-alkyl group, or a $C_{1-3}$-alkoxy group, while the hydrogen atoms of the $C_{1-3}$-alkyl or $C_{1-3}$-alkoxy group may optionally be wholly or partly replaced by fluorine atoms, while, unless otherwise stated, by the term "heteroaryl group" mentioned hereinbefore in the definitions is meant a monocyclic 5- or 6-membered heteroaryl group, while the 6-membered heteroaryl group contains one, two or three nitrogen atoms and the 5-membered heteroaryl group contains an imino group optionally substituted by a $C_{1-3}$-alkyl, phenyl or phenyl-$C_{1-3}$-alkyl group, an oxygen or sulphur atom or an imino group optionally substituted by a $C_{1-3}$-alkyl, phenyl, amino-$C_{2-3}$-alkyl, $C_{1-3}$-alkylamino-$C_{2-3}$-alkyl, di-($C_{1-3}$-alkyl)-amino-$C_{2-3}$-alkyl, a $C_{3-6}$-cycloalkyleneimino-$C_{1-3}$-alkyl or phenyl-$C_{1-3}$-alkyl group or an oxygen or sulphur atom and additionally a nitrogen atom or an imino group optionally substituted by a $C_{1-3}$-alkyl or phenyl-$C_{1-3}$-alkyl group and two or three nitrogen atoms, and moreover a phenyl ring optionally substituted by a fluorine, chlorine or bromine atom, a $C_{1-3}$-alkyl, hydroxy, $C_{1-3}$-alkyloxy group, amino, $C_{1-3}$-alkylamino, di-($C_{1-3}$-alkyl)-amino or $C_{3-6}$-cycloalkyleneimino group may be fused to the above-mentioned monocyclic heteroaryl groups via two adjacent carbon atoms and the bond is effected via a nitrogen atom or a carbon atom of the heterocyclic moiety or a fused-on phenyl ring, while, unless otherwise stated, by the term "halogen atom" mentioned hereinbefore in the definitions is meant an atom selected from among fluorine, chlorine, bromine and iodine, while the alkyl, alkenyl, alkynyl and alkoxy groups contained in the foregoing definitions which have more than two carbon atoms, unless otherwise stated, may be straight-chain or branched and the alkyl groups in the previously mentioned dialkylated groups, for example the dialkylamino groups, may be identical or different, and the hydrogen atoms of the methyl or ethyl groups contained in the foregoing definitions, unless otherwise stated, may be wholly or partly replaced by fluorine atoms, the tautomers, the enantiomers, the diastereomers, the mixtures thereof and the salts thereof.

Examples of monocyclic heteroaryl groups are the pyridyl, N-oxy-pyridyl, pyrazolyl, pyridazinyl, pyrimidinyl, pyrazinyl, [1,2,3]triazinyl, [1,3,5]triazinyl, [1,2,4]triazinyl, pyrrolyl, imidazolyl, [1,2,4]triazolyl, [1,2,3]triazolyl, tetrazolyl, furanyl, isoxazolyl, oxazolyl, [1,2,3]oxadiazolyl, [1,2,4]oxadiazolyl, furazanyl, thiophenyl, thiazolyl, isothiazolyl, [1,2,3]thiadiazolyl, [1,2,4]thiadiazolyl or [1,2,5]thiadiazolyl group.

Examples of bicyclic heteroaryl groups are the benzimidazolyl, benzofuranyl, benzo[c]furanyl, benzothiophenyl, benzo[c]thiophenyl, benzothiazolyl, benzo[c]-isothiazolyl, benzo[d]isothiazolyl, benzoxazolyl, benzo[c]isoxazolyl, benzo[d]-isoxazolyl, benzo[1,2,5]oxadiazolyl, benzo[1,2,5]thiadiazolyl, benzo[1,2,3]thia-diazolyl, benzo[d][1,2,3]triazinyl, benzo[1,2,4]triazinyl, benzotriazolyl, cinnolinyl, quinolinyl, N-oxy-quinolinyl, isoquinolinyl, quinazolinyl, N-oxy-quinazolinyl, quinoxalinyl, phthalazinyl, indolyl, isoindolyl or 1-oxa-2,3-diaza-indenyl group.

Examples of the $C_{1-6}$-alkyl groups mentioned hereinbefore in the definitions are the methyl, ethyl, 1-propyl, 2-propyl, n-butyl, sec-butyl, tert-butyl, 1-pentyl, 2-pentyl, 3-pentyl, neo-pentyl, 3-methyl-2-butyl, 1-hexyl, 2-hexyl, 3-hexyl, 3-methyl-2-pentyl, 4-methyl-2-pentyl, 3-methyl-3-pentyl, 2-methyl-3-pentyl, 2,2-dimethyl-3-butyl or 2,3-dimethyl-2-butyl group.

Examples of the $C_{1-5}$-alkyloxy groups mentioned hereinbefore in the definitions are the methyloxy, ethyloxy, 1-propyloxy, 2-propyloxy, n-butyloxy, sec-butyloxy, tert-butyloxy, 1-pentyloxy, 2-pentyloxy, 3-pentyloxy or neo-pentyloxy group.

Examples of the $C_{2-6}$-alkenyl groups mentioned hereinbefore in the definitions are the ethenyl, 1-propen-1-yl, 2-propen-1-yl, 1-buten-1-yl, 2-buten-1-yl, 3-buten-1-yl, 1-penten-1-yl, 2-penten-1-yl, 3-penten-1-yl, 4-penten-1-yl, 1-hexen-1-yl, 2-hexen-1-yl, 3-hexen-1-yl, 4-hexen-1-yl, 5-hexen-1-yl, but-1-en-2-yl, but-2-en-2-yl, but-1-en-3-yl, 2-methyl-prop-2-en-1-yl, pent-1-en-2-yl, pent-2-en-2-yl, pent-3-en-2-yl, pent-4-en-2-yl, pent-1-en-3-yl, pent-2-en-3-yl, 2-methyl-but-1-en-1-yl, 2-methyl-but-2-en-1-yl, 2-methyl-but-3-en-1-yl, 2-ethyl-prop-2-en-1-yl, hex-1-en-2-yl, hex-2-en-2-yl, hex-3-en-2-yl, hex-4-en-2-yl, hex-5-en-2-yl, hex-1-en-3-yl, hex-2-en-3-yl, hex-3-en-3-yl, hex-4-en-3-yl, hex-5-en-3-yl, hex-1-en-4-hex-2-en-4-yl, hex-3-en-4-yl, hex-4-en-4-yl, hex-5-en-4-yl, 4-methyl-pent-1-en-3-yl, 3-methyl-pent-1-en-3-yl, 2-methyl-pent-1-en-3-yl, 2,3-dimethyl-but-1-en-3-yl, 3,3-dimethyl-but-1-en-2-yl or 2-ethyl-but-1-en-3-yl group, Examples of the $C_{2-6}$-alkynyl groups mentioned hereinbefore in the definitions are the ethynyl, 1-propynyl, 2-propynyl, 1-butyn-1-yl, 1-butyn-3-yl, 2-butyn-1-yl, 3-butyn-1-yl, 1-pentyn-1-yl, 1-pentyn-3-yl, 1-pentyn-4-yl, 2-pentyn-1-yl, 2-pentyn-3-yl, 3-pentyn-1-yl, 4-pentyn-1-yl, 2-methyl-1-butyn-4-yl, 3-methyl-1-butyn-1-yl, 3-methyl-1-butyn-3-yl, 1-hexyn-1-yl, 2-hexyn-1-yl, 3-hexyn-1-yl, 4-hexyn-1-yl, 5-hexyn-1-yl, 1-hexyn-3-yl, 1-hexyn-4-yl, 1-hexyn-5-yl, 2-hexyn-4-yl, 2-hexyn-5-yl, 3-hexyn-5-yl, 3-methyl-1-pentyn-3-yl, 4-methyl-1-pentyn-3-yl, 3-methyl-1-pentyn-4-yl, 4-methyl-1-pentyn-4-yl, 4-methyl-2-pentyn-4-yl, 4-methyl-2-pentyn-1-yl, 2,2-dimethyl-3-butyn-1-yl or 2-ethyl-3-butyn-1-yl group.

By a group which may be converted in vivo into a carboxy group is meant for example a carboxy group esterified with an alcohol wherein the alcoholic moiety preferably denotes a $C_{1-6}$-alkanol, a phenyl-$C_{1-3}$-alkanol, a $C_{3-9}$-cycloalkanol, a $C_{5-7}$-cycloalkenol, a $C_{3-5}$-alkenol, a phenyl-$C_{3-5}$-alkenol, a $C_{3-5}$-alkynol or phenyl-$C_{3-5}$-alkynol, with the proviso that no bond to the oxygen atom starts from a carbon atom which carries a double or triple bond, a $C_{3-8}$-cycloalkyl-$C_{1-3}$-alkanol or an alcohol of formula

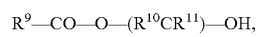

wherein $R^9$ denotes a $C_{1-8}$-alkyl, $C_{5-7}$-cycloalkyl, phenyl or phenyl-$C_{1-3}$-alkyl group, $R^{10}$ denotes a hydrogen atom, a $C_{1-3}$-alkyl, $C_{5-7}$-cycloalkyl or phenyl group and $R^{11}$ denotes a hydrogen atom or a $C_{1-3}$-alkyl group.

Preferred groups which may be cleaved from a carboxy group in vivo include a $C_{1-6}$-alkoxy group such as the methoxy, ethoxy, n-propyloxy, isopropyloxy, n-butyloxy, n-pentyloxy, n-hexyloxy or cyclohexyloxy group or a phenyl-$C_{1-3}$-alkoxy group such as the benzyloxy group.

By a group which may be converted in vivo into a hydroxyl group is meant for example a hydroxyl group esterified with a carboxylic acid wherein the carboxylic acid moiety is preferably a $C_{1-7}$-alkanoic acid, a phenyl-$C_{1-3}$-alkanoic acid, a $C_{3-9}$-cycloalkylcarboxylic acid, a $C_{5-7}$-cycloalkenecarboxylic acid, a $C_{3-7}$-alkenoic acid, a phenyl-$C_{3-5}$-alkenoic acid, a $C_{3-7}$-alkynoic acid or phenyl-$C_{3-5}$-alkynoic acid, while individual methylene groups of the carboxylic acid group may be replaced by oxygen atoms, with the proviso that no bond to the oxygen atom starts from a carbon atom which carries a double or triple bond.

Examples of preferred groups which may be cleaved in vivo from a hydroxyl group include a $C_{1-7}$-acyl group such as the formyl, acetyl, n-propionyl, isopropionyl, n-propanoyl, n-butanoyl, n-pentanoyl, n-hexanoyl or cyclohexylcarbonyl group or a benzoyl group as well as also a methoxyacetyl, 1-methoxypropionyl, 2-methoxypropionyl or 2-methoxyethoxyacetyl group.

The compounds of general formula I, wherein A, $R^4$ and/or $R^5$ contains a group which may be converted in vivo into a carboxy or hydroxyl group are prodrugs for those compounds of general formula I wherein A, $R^4$ and/or $R^5$ contains a carboxy or hydroxyl group.

A 2nd embodiment of the present invention comprises those compounds of general formula I wherein A denotes a group of general formula

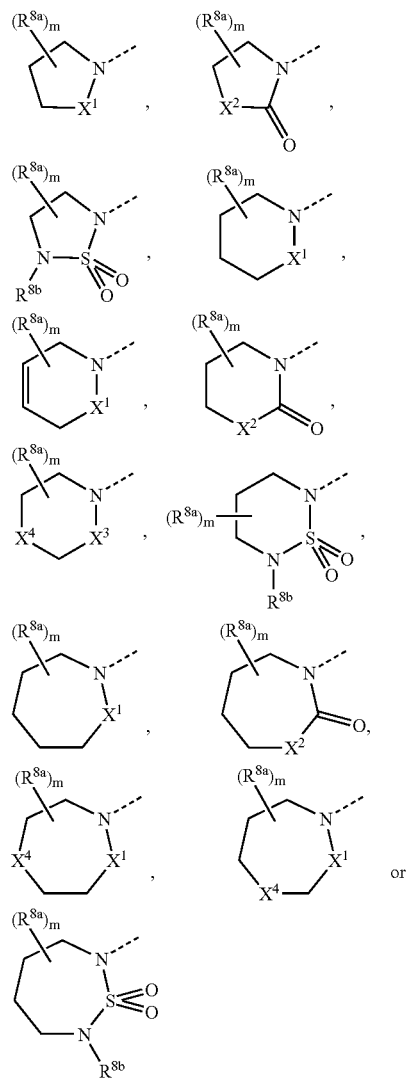

wherein
m is the number 1 or 2,
$R^{8a}$ each independently of one another denote a hydrogen or halogen atom or a $C_{1-5}$-alkyl, hydroxy, hydroxy-$C_{1-5}$-alkyl, $C_{1-5}$-alkoxy, $C_{1-5}$-alkoxy-$C_{1-5}$-alkyl, amino, $C_{1-5}$-alkylamino, di-($C_{1-5}$-alkyl)-amino, amino-$C_{1-5}$-alkyl, $C_{1-5}$-alkylamino-$C_{1-5}$-alkyl, di-($C_{1-5}$-alkyl)-amino-$C_{1-5}$-alkyl, aminocarbonyl, $C_{1-5}$-alkylaminocarbonyl, di-($C_{1-5}$-alkyl)-aminocarbonyl or $C_{1-5}$-alkylcarbonylamino group, while in the previously mentioned substituted 5- to 7-membered groups A the heteroatoms F, Cl, Br, I, O or N optionally introduced with $R^{8a}$ as substituent are not separated by precisely one carbon atom from a heteroatom selected from among N, O, S,
$R^{8b}$ each independently of one another denote a hydrogen atom or a $C_{1-5}$-alkyl group,
$X^1$ denotes a carbonyl, thiocarbonyl, C=$NR^{8c}$, C=N—$OR^{8c}$, C=N—$NO_2$, C=N—CN or sulphonyl group,
$R^{8c}$ each independently of one another denote a hydrogen atom, a $C_{1-5}$-alkyl, $C_{1-5}$-alkylcarbonyl, $C_{1-5}$-alkyloxycarbonyl or $C_{1-5}$-alkylsulphonyl group,
$X^2$ denotes an oxygen atom or a —$NR^{8b}$ group,
$X^3$ denotes a carbonyl, thiocarbonyl, C=$NR^{8c}$, C=N—$OR^{8c}$, C=N—$NO_2$, C=N—CN or sulphonyl group,
$X^4$ denotes an oxygen or sulphur atom or a —$NR^{8c}$ group,
$R^1$ denotes a halogen atom, a $C_{1-3}$-alkyl or $C_{1-3}$-alkoxy group, while the hydrogen atoms of the $C_{1-3}$-alkyl or $C_{1-3}$-alkoxy group may optionally be wholly or partly replaced by fluorine atoms, a $C_{2-3}$-alkenyl, $C_{2-3}$-alkynyl, nitrile, nitro or amino group,
$R^2$ denotes a hydrogen or halogen atom or a $C_{1-3}$-alkyl group,
$R^3$ denotes a hydrogen atom or a $C_{1-3}$-alkyl group,
$R^4$ and $R^5$ in each case independently of one another denote a hydrogen atom, a $C_{2-6}$-alkenyl or $C_{2-6}$-alkynyl group, a straight-chain or branched $C_{1-6}$-alkyl group,
while the hydrogen atoms of the straight-chain or branched $C_{1-6}$-alkyl group may optionally be wholly or partly replaced by fluorine atoms, and may optionally be substituted by a $C_{3-5}$-cycloalkyl group, a nitrile, hydroxy, a $C_{1-5}$-alkyloxy group, while the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-5}$-alkyloxy, $C_{1-5}$-alkyloxycarbonyl-$C_{1-5}$-alkyloxy, mercapto, $C_{1-5}$-alkylsulphanyl, $C_{1-5}$-alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, aminosulphonyl, $C_{1-5}$-alkylaminosulphonyl, di-($C_{1-5}$-alkyl)-aminosulphonyl, $C_{3-6}$-cycloalkyleneiminosulphonyl, amino, $C_{1-5}$-alkylamino, di-($C_{1-5}$-alkyl)-amino, $C_{1-5}$-alkylcarbonylamino, $C_{1-5}$-alkylsulphonylamino, N-($C_{1-5}$-alkylsulphonyl)-$C_{1-5}$-alkylamino or $C_{3-6}$-cycloalkylcarbonylamino group,
a carboxy, aminocarbonyl, $C_{1-5}$-alkylaminocarbonyl, $C_{3-6}$-cycloalkylaminocarbonyl, di-($C_{1-5}$-alkyl)-aminocarbonyl, $C_{1-5}$-alkoxycarbonyl, $C_{4-6}$-cycloalkyleneiminocarbonyl group,
a phenyl, heteroaryl, phenyl-$C_{1-5}$-alkyl or heteroaryl-$C_{1-5}$-alkyl group,
which may optionally be mono- to trisubstituted in the phenyl or heteroaryl moiety by identical or different substituents selected from among halogen atoms, $C_{1-5}$-alkyl, di-($C_{1-5}$-alkyl)-amino, hydroxy, $C_{1-5}$-alkyloxy, mono-, di- or trifluoromethoxy, carboxy- and $C_{1-5}$-alkyloxycarbonyl groups, a 3- to 7-membered cycloalkyl, cycloalkyleneimino, cycloalkyl-$C_{1-5}$-alkyl or cycloalkyleneimino-$C_{1-3}$-alkyl group, while in 4- to 7-membered cyclic groups in the cyclic moiety a methylene group may optionally be replaced by an —N($R^{8c}$) group, an oxygen or sulphur atom or a —S(O) or —S(O)$_2$ group, or wherein in 4- to 7-membered cyclic groups in the cyclic moiety two adjacent methylene groups together may optionally be replaced by a —C(O)N($R^{8b}$) or —S(O)$_2$N($R^{8b}$) group, or wherein in 6- to 7-membered cyclic groups in the cyclic moiety three adjacent methylene groups together may optionally be replaced by a substituted —OC(O)N($R^{8b}$) or —N($R^{8b}$)C(O)N($R^{8b}$) or —N($R^{8b}$)S(O)$_2$N($R^{8b}$) group, with the proviso that a 3- to 7-membered cycloalkyl, cycloalkyleneimino, cycloalkyl-$C_{1-5}$-alkyl or cycloalkyleneimino-$C_{1-3}$-alkyl group as hereinbefore defined wherein two heteroatoms selected from among oxygen and nitrogen are separated from one another by precisely one optionally substituted —CH$_2$ group is excluded, while a 3- to 7-membered cycloalkyl, cycloalkyleneimino, cycloalkyl-$C_{1-5}$-alkyl or cycloalkyleneimino-$C_{1-3}$-alkyl group as hereinbefore defined may be substituted at one or two —CH$_2$ groups by one or two $C_{1-3}$-alkyl groups in each case, or $R^4$ and $R^5$ together with the carbon atom to which they are bound form a $C_{3-8}$-cycloalkyl or $C_{3-8}$-cycloalkenyl group, while one of the methylene groups of a $C_{4-8}$-cycloalkyl group may be replaced by an oxygen or sulphur atom or an —N($R^{8c}$), or a carbonyl, sulphynyl or sulphonyl group, and/or two directly adjacent methylene groups of a $C_{4-8}$-cycloalkyl group may together be replaced by a —C(O)N($R^{8b}$) or —S(O)$_2$N($R^{8b}$) group, and/or three directly adjacent methylene groups of a $C_{6-8}$-cycloalkyl group may together be replaced by a —OC(O)N($R^{8b}$), —N($R^{8b}$)C(O)N($R^{8b}$) or —N($R^{8b}$)S(O)$_2$N($R^{8b}$) group, while 1 to 3 carbon atoms of a $C_{3-8}$-cycloalkyl group may optionally be substituted independently of one another in each case by one or two identical or different halogen atoms or $C_{1-5}$-alkyl, nitrile, hydroxy, $C_{1-5}$-alkyloxy, $C_{1-5}$-alkylcarbonyloxy, carboxy-$C_{1-5}$-alkyl, $C_{1-5}$-alkyloxycarbonyl-$C_{1-5}$-alkyl, $C_{1-5}$-alkylsulphanyl, $C_{1-5}$-alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, aminosulphonyl, $C_{1-5}$-alkylaminosulphonyl, di-($C_{1-5}$-alkyl)-aminosulphonyl, $C_{3-6}$-cycloalkyleneiminosulphonyl, amino, $C_{1-5}$-alkylamino, di-($C_{1-5}$-alkyl)-amino, $C_{1-5}$-alkylcarbonylamino, $C_{1-5}$-alkyl-sulphonylamino, N-($C_{1-5}$-alkylsulphonyl)-$C_{1-5}$-alkylamino or $C_{3-6}$-cycloalkylcarbonylamino groups, while 1 to 2 carbon atoms of a $C_{3-8}$-cycloalkenyl group may optionally be substituted independently of one another by a $C_{1-5}$-alkyl, nitrile, carboxy-$C_{1-5}$-alkyl, $C_{1-5}$-alkyloxycarbonyl-$C_{1-5}$-alkyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, aminosulphonyl, $C_{1-5}$-alkylaminosulphonyl, di-($C_{1-5}$-alkyl)-aminosulphonyl, $C_{3-6}$-cycloalkyleneiminosulphonyl group, and 1 to 2 carbon atoms of a $C_{4-8}$-cycloalkenyl group which are not bound to another carbon atom by a double bond may optionally be substituted independently of one another by a fluorine atom or a hydroxy, $C_{1-5}$-alkyloxy, $C_{1-5}$-alkylcarbonyloxy, $C_{1-5}$-alkylsulphanyl, $C_{1-5}$-alkylsulphonyl, amino, $C_{1-5}$-alkylamino, di-($C_{1-5}$-alkyl)-amino, $C_{1-5}$-alkylcarbonylamino, $C_{1-5}$-alkylsulphonylamino, N-($C_{1-5}$-alkylsulphonyl)-$C_{1-5}$-alkylamino or $C_{3-6}$-cycloalkylcarbonyl-amino group, with the proviso that a $C_{3-8}$-cycloalkyl or $C_{3-8}$-cycloalkenyl group of this kind, formed together from $R^4$ and $R^5$, wherein two heteroatoms in the cyclic group selected from among oxygen and nitrogen are separated from one another by precisely one optionally substituted —CH$_2$ group, and/or wherein one or both methylene groups of the cyclic group which are directly connected to the carbon atom to which the groups $R^4$ and $R^5$ are bound are replaced by a heteroatom selected from among oxygen, nitrogen and sulphur, and/or wherein a substituent bound to the cyclic group, which is characterised in that a heteroatom selected from among oxygen, nitrogen, sulphur and halogen atom is bound directly to the cyclic group is separated from another heteroatom selected from among oxygen, nitrogen and sulphur, with the exception of the sulphone group, by precisely one, optionally substituted, methylene group, and/or wherein two oxygen atoms are joined together directly, is excluded, $R^6$ denotes a fluorine, chlorine, bromine or iodine atom, a nitrile group, a $C_{1-3}$-alkyl group, or a $C_{1-3}$-alkoxy group, while the hydrogen atoms of the $C_{1-3}$-alkyl or $C_{1-3}$-alkoxy group may be wholly or partly replaced by fluorine atoms, while, unless otherwise stated, by the term "heteroaryl group" mentioned hereinbefore in the definitions is meant a monocyclic 5- or 6-membered heteroaryl group, while the 6-membered heteroaryl group contains one, two or three nitrogen atoms and the 5-membered heteroaryl group contains an imino group optionally substituted by a $C_{1-3}$-alkyl, phenyl or phenyl-$C_{1-3}$-alkyl group, an oxygen or sulphur atom or an imino group optionally substituted by a $C_{1-3}$-alkyl, phenyl, amino-$C_{2-3}$-alkyl, $C_{1-3}$-alkylamino-$C_{2-3}$-alkyl, di-($C_{1-3}$-alkyl)-amino-$C_{2-3}$-alkyl, a $C_{3-6}$-cycloalkyleneimino-$C_{1-3}$-alkyl or phenyl-$C_{1-3}$-alkyl group or an oxygen or sulphur atom and additionally a nitrogen atom or an imino group optionally substituted by a $C_{1-3}$-alkyl or phenyl-$C_{1-3}$-alkyl group and two or three nitrogen atoms, and moreover a phenyl ring optionally substituted by a fluorine, chlorine or bromine atom, a $C_{1-3}$-alkyl, hydroxy, $C_{1-3}$-alkyloxy group, amino, $C_{1-3}$-alkylamino, di-($C_{1-3}$-alkyl)-amino or $C_{3-6}$-cycloalkyleneimino group may be fused to the above-mentioned monocyclic heteroaryl groups via two adjacent carbon atoms and the bond is effected via a nitrogen atom or a carbon atom of the heterocyclic moiety or a fused-on phenyl ring, while, unless otherwise stated, by the term "halogen atom" mentioned hereinbefore in the definitions is meant an atom selected from among fluorine, chlorine, bromine and iodine, while unless otherwise stated the alkyl, alkenyl, alkynyl and alkoxy groups contained in the foregoing definitions which have more than two carbon atoms may be straight-chain or branched and the alkyl groups in the previously mentioned dialkylated groups, for example the dialkylamino groups, may be identical or different, and the hydrogen atoms of the methyl or ethyl groups contained in the foregoing definitions, unless otherwise stated, may be wholly or partly replaced by fluorine atoms, the tautomers, the enantiomers, the diastereomers, the mixtures thereof and the salts thereof.

A 3rd embodiment of the present invention comprises those compounds of general formula I, wherein A denotes a group of general formula wherein m is the number 1 or 2, $R^{8a}$ each independently of one another denote a hydrogen or halogen atom or a $C_{1-5}$-alkyl, hydroxy, hydroxy-$C_{1-5}$-alkyl, $C_{1-5}$-alkoxy, $C_{1-5}$-alkoxy-$C_{1-5}$-alkyl, amino, $C_{1-5}$-alkylamino, di-($C_{1-5}$-alkyl)-amino, amino-$C_{1-5}$-alkyl, $C_{1-5}$-alkylamino-$C_{1-5}$-alkyl, di-($C_{1-5}$-alkyl)-amino-$C_{1-5}$-alkyl, aminocarbonyl, $C_{1-5}$-alkylaminocarbonyl, di-($C_{1-5}$-alkyl)-aminocarbonyl or $C_{1-5}$-alkylcarbonylamino group, while in the previously mentioned substituted 5- to 7-membered groups A the heteroatoms F, Cl, Br, I, O or N optionally introduced with $R^{8a}$ as substituent are not separated by precisely one carbon atom from a heteroatom selected from among N, O, S, $R^{8b}$ each independently of one another denote a hydrogen atom or a $C_{1-5}$-alkyl group, $X^1$ denotes a carbonyl, thiocarbonyl, C=$NR^{8c}$, C=N—$OR^{8c}$, C=N—$NO_2$, C=N—CN or sulphonyl group, $R^{8c}$ each independently of one another denote a hydrogen atom, a $C_{1-5}$-alkyl, $C_{1-5}$-alkylcarbonyl, $C_{1-5}$-alkyloxycarbonyl or $C_{1-5}$-alkylsulphonyl group, $X^2$ denotes an oxygen atom or a —$NR^{8b}$ group, $X^3$ denotes a carbonyl, thiocarbonyl, C=$NR^{8c}$, C=N—$OR^{8c}$, C=N—$NO_2$, C=N—CN or sulphonyl group, $X^4$ denotes an oxygen atom or a —$NR^{8c}$ group, $R^1$ denotes a fluorine, chlorine, bromine or iodine atom, a $C_{1-3}$-alkyl or $C_{1-3}$-alkoxy group, while the hydrogen atoms of the $C_{1-3}$-alkyl or $C_{1-3}$-alkoxy group may optionally be wholly or partly replaced by fluorine atoms, or a nitrile group, $R^2$ denotes a hydrogen or halogen atom or a methyl group, $R^3$ denotes a hydrogen atom or a methyl group, $R^4$ denotes a $C_{2-6}$-alkenyl or $C_{2-6}$-alkynyl group, a straight-chain or branched $C_{1-6}$-alkyl group, while the hydrogen atoms of the straight-chain or branched $C_{1-6}$-alkyl group may optionally be wholly or partly replaced by fluorine atoms, and may optionally be substituted by a $C_{3-5}$-cycloalkyl group, a nitrile, hydroxy, a $C_{1-5}$-alkyloxy group, while the hydrogen atoms of the $C_{1-5}$-alkyloxy group may optionally be wholly or partly replaced by fluorine atoms, a benzyloxy, $C_{1-5}$-alkylcarbonyloxy, $C_{1-5}$-alkyloxycarbonyloxy, carboxy-$C_{1-5}$-alkyloxy, $C_{1-5}$-alkyloxycarbonyl-$C_{1-5}$-alkyloxy, $C_{1-5}$-alkylsulphanyl, $C_{1-5}$-alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, aminosulphonyl, $C_{1-5}$-alkylaminosulphonyl, di-($C_{1-5}$-alkyl)-aminosulphonyl, $C_{3-6}$-cycloalkyleneiminosulphonyl, amino, $C_{1-5}$-alkylamino, di-($C_{1-5}$-alkyl)-amino, $C_{1-5}$-alkylcarbonylamino, $C_{1-5}$-alkylsulphonylamino, or an N—($C_{1-5}$-alkylsulphonyl)-$C_{1-5}$-alkylamino group, a carboxy, aminocarbonyl, $C_{1-5}$-alkylaminocarbonyl, $C_{3-6}$-cycloalkylamino-carbonyl, di-($C_{1-5}$-alkyl)-aminocarbonyl, $C_{1-5}$-alkoxycarbonyl, $C_{4-6}$-cycloalkyleneiminocarbonyl group, a phenyl, heteroaryl, phenyl-$C_{1-5}$-alkyl or heteroaryl-$C_{1-5}$-alkyl group, which may optionally be mono- to trisubstituted in the phenyl or heteroaryl moiety by identical or different substituents selected from among halogen atoms, $C_{1-5}$-alkyl, di-($C_{1-5}$-alkyl)-amino, hydroxy, $C_{1-5}$-alkyloxy, mono-, di- or trifluoromethoxy, carboxy- and $C_{1-5}$-alkyloxycarbonyl groups, a 3- to 7-membered cycloalkyl, cycloalkyleneimino, cycloalkyl-$C_{1-5}$-alkyl or cycloalkyleneimino-$C_{1-3}$-alkyl group, while in 4- to 7-membered cyclic groups in the cyclic moiety a methylene group may optionally be replaced by an —N($R^{8c}$) group, an oxygen or sulphur atom or a —S(O) or —S(O)$_2$ group, or while in 4- to 7-membered cyclic groups in the cyclic moiety two adjacent methylene groups together may optionally be replaced by a —C(O)N($R^{8b}$) or —S(O)$_2$N($R^{8b}$) group, or wherein in 6- to 7-membered cyclic groups in the cyclic moiety three adjacent methylene groups together may optionally be replaced by a substituted —OC(O)N($R^{8b}$) or —N($R^{8b}$)C(O)N($R^{8b}$) or —N($R^{8b}$)S(O)$_2$N($R^{8b}$) group, with the proviso that a 3- to 7-membered cycloalkyl, cycloalkyleneimino, cycloalkyl-$C_{1-5}$-alkyl or cycloalkyleneimino-$C_{1-3}$-alkyl group as hereinbefore defined wherein two heteroatoms from the group oxygen and nitrogen are separated from one another by precisely one optionally substituted —CH$_2$ group is excluded, while a 3- to 7-membered cycloalkyl, cycloalkyleneimino, cycloalkyl-$C_{1-5}$-alkyl or cycloalkyleneimino-$C_{1-3}$-alkyl group as hereinbefore defined may be substituted at one or two —CH$_2$ groups by one or two $C_{1-3}$-alkyl groups in each case, $R^5$ denotes a hydrogen atom, a $C_{2-6}$-alkenyl or $C_{2-6}$-alkynyl group, a straight-chain or branched $C_{1-6}$-alkyl group, while the hydrogen atoms of the straight-chain or branched $C_{1-6}$-alkyl group may optionally be wholly or partly replaced by fluorine atoms, and may optionally be substituted by a $C_{1-5}$-alkyloxy group, while the hydrogen atoms of the $C_{1-5}$-alkyloxy group may optionally be wholly or partly replaced by fluorine atoms, or $R^4$ and $R^5$ together with the carbon atom to which they are bound, form a $C_{3-8}$-cycloalkyl or $C_{3-8}$-cycloalkenyl group, while one of the methylene groups of a $C_{4-8}$-cycloalkyl group may be replaced by an oxygen or sulphur atom or an —N($R^{8c}$), or a carbonyl, or sulphonyl group, and/or two directly adjacent methylene groups of a $C_{4-8}$-cycloalkyl group may together be replaced by a —C(O)N($R^{8b}$) or —S(O)$_2$N($R^{8b}$) group, and/or three directly adjacent methylene groups of a $C_{6-8}$-cycloalkyl group may together be replaced by a —OC(O)N($R^{8b}$), —N($R^{8b}$)C(O)N($R^{8b}$) or —N($R^{8b}$)S(O)$_2$N($R^{8b}$) group, while 1 to 3 carbon atoms of a $C_{3-8}$-cycloalkyl group may optionally be substituted independently of one another in each case by one or two identical or different halogen atoms or $C_{1-5}$-alkyl, nitrile, hydroxy, $C_{1-5}$-alkyloxy, $C_{1-5}$-alkylcarbonyloxy, carboxy-$C_{1-5}$-alkyl, $C_{1-5}$-alkyloxycarbonyl-$C_{1-5}$-alkyl, $C_{1-5}$-alkylsulphanyl, $C_{1-5}$-alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, aminosulphonyl, $C_{1-5}$-alkylaminosulphonyl, di-($C_{1-5}$-alkyl)-aminosulphonyl, $C_{3-6}$-cycloalkyleneiminosulphonyl, amino, $C_{1-5}$-alkylamino, di-($C_{1-5}$-alkyl)-amino, $C_{1-5}$-alkyl-carbonylamino, $C_{1-5}$-alkyl-sulphonylamino, or N-($C_{1-5}$-alkylsulphonyl)-$C_{1-5}$-alkylamino groups, while 1 to 2 carbon atoms of a $C_{3-8}$-cycloalkenyl group may optionally be substituted independently of one another by a $C_{1-5}$-alkyl, nitrile, carboxy-$C_{1-5}$-alkyl, $C_{1-5}$-alkyloxycarbonyl-$C_{1-5}$-alkyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, aminosulphonyl, $C_{1-5}$-alkylaminosulphonyl, di-($C_{1-5}$-alkyl)-aminosulphonyl, $C_{3-6}$-cycloalkyleneiminosulphonyl groups, and 1 to 2 carbon atoms of a $C_{4-8}$-cycloalkenyl group which are not bound to another carbon atom by a double bond may optionally be substituted independently of one another by a fluorine atom or a hydroxy, $C_{1-5}$-alkyloxy, $C_{1-5}$-alkylcarbonyloxy, $C_{1-5}$-alkylsulphanyl, $C_{1-5}$-alkylsulphonyl, amino, $C_{1-5}$-alkylamino, di-($C_{1-5}$-alkyl)-amino, $C_{1-5}$-alkylcarbonylamino, $C_{1-5}$-alkylsulphonylamino, N—($C_{1-5}$-alkylsulphonyl)-$C_{1-5}$-alkylamino or $C_{3-6}$-cycloalkylcarbonyl-amino groups, with the proviso that a $C_{3-8}$-cycloalkyl or $C_{3-8}$-cycloalkenyl group of this kind, formed from $R^4$ and $R^5$ together, wherein two heteroatoms in the cyclic group selected from among oxygen and nitrogen are separated from one another by precisely one optionally substituted —CH$_2$ group, and/or wherein one or both methylene groups of the cyclic group which are directly connected to the carbon atom to which the groups $R^4$ and $R^5$ are bound, are replaced by a heteroatom selected from among oxygen, nitrogen and sulphur, and/or wherein a substituent bound to the cyclic group, which is characterised in that a heteroatom selected from among oxygen, nitrogen, sulphur and halogen atom is bound directly to the cyclic group, is separated from another heteroatom selected from among oxygen, nitrogen and sulphur, with the exception of the sulphone group, by precisely one, optionally substituted, methylene group, and/or wherein two oxygen atoms are joined together directly, is excluded, $R^6$ denotes a fluorine, chlorine, bromine or iodine atom, a nitrile group, a $C_{1-3}$-alkyl group, or a $C_{1-3}$-alkoxy group, while the hydrogen atoms of the $C_{1-3}$-alkyl or $C_{1-3}$-alkoxy group may optionally be wholly or partly replaced by fluorine atoms, while, unless otherwise stated, by the term "heteroaryl group" mentioned hereinbefore in the definitions is meant a monocyclic 5- or 6-membered heteroaryl group, while the 6-membered heteroaryl group contains one, two or three nitrogen atoms and the 5-membered heteroaryl group contains an imino group optionally substituted by a $C_{1-3}$-alkyl, phenyl or phenyl-$C_{1-3}$-alkyl group, an oxygen or sulphur atom or an imino group optionally substituted by a $C_{1-3}$-alkyl, phenyl, amino-$C_{2-3}$-alkyl, $C_{1-3}$-alkylamino-$C_{2-3}$-alkyl, di-($C_{1-3}$-alkyl)-amino-$C_{2-3}$-alkyl, a $C_{3-6}$-cycloalkyleneimino-$C_{1-3}$-alkyl or phenyl-$C_{1-3}$-alkyl group or an oxygen or sulphur atom and additionally a nitrogen atom or an imino group optionally substituted by a $C_{1-3}$-alkyl or phenyl-$C_{1-3}$-alkyl group and two or three nitrogen atoms, and moreover a phenyl ring optionally substituted by a fluorine, chlorine or bromine atom, a $C_{1-3}$-alkyl, hydroxy, $C_{1-3}$-alkyloxy group, amino, $C_{1-3}$-alkylamino, di-($C_{1-3}$-alkyl)-amino or $C_{3-6}$-cycloalkyleneimino group may be fused to the above-mentioned monocyclic heteroaryl groups via two adjacent carbon atoms and the bond is effected via a nitrogen atom or a carbon atom of the heterocyclic moiety or a fused-on phenyl ring, while, unless otherwise stated, by the term "halogen atom" mentioned hereinbefore in the definitions is meant an atom selected from among fluorine, chlorine, bromine and iodine, while, unless otherwise stated, the alkyl, alkenyl, alkynyl and alkoxy groups contained in the foregoing definitions which have more than two carbon atoms may be straight-chain or branched and the alkyl groups in the previously mentioned dialkylated groups, for example the dialkylamino groups, may be identical or different, and the hydrogen atoms of the methyl or ethyl groups contained in the foregoing definitions, unless otherwise stated, may be wholly or partly replaced by fluorine atoms, the tautomers, the enantiomers, the diastereomers, the mixtures thereof and the salts thereof.

A 4th embodiment of the present invention comprises those compounds of general formula I wherein A denotes a group of general formula

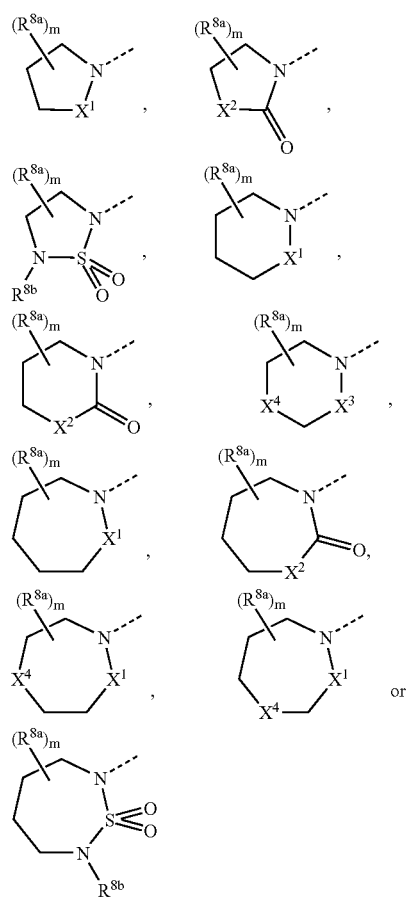

wherein m is the number 1 or 2, $R^{8a}$ each independently of one another denote a hydrogen or halogen atom or a $C_{1-3}$-alkyl, hydroxy, hydroxy-$C_{1-3}$-alkyl, $C_{1-3}$-alkoxy, $C_{1-3}$-alkoxy-$C_{1-3}$-alkyl, amino, $C_{1-3}$-alkylamino, di-($C_{1-3}$-alkyl)-amino, amino-$C_{1-3}$-alkyl, $C_{1-3}$-alkylamino-$C_{1-3}$-alkyl, di-($C_{1-3}$-alkyl)-amino-$C_{1-3}$-alkyl, aminocarbonyl, $C_{1-3}$-alkylaminocarbonyl, di-($C_{1-3}$-alkyl)-aminocarbonyl or $C_{1-3}$-alkylcarbonylamino group, while in the previously mentioned substituted 5- to 7-membered groups A the heteroatoms F, Cl, Br, I, O or N optionally introduced with $R^{8a}$ as substituent are not separated by precisely one carbon atom from a heteroatom selected from among N, O, S, $R^{8b}$ each independently of one another denote a hydrogen atom or a $C_{1-3}$-alkyl group, $X^1$ denotes a carbonyl, thiocarbonyl, C=$NR^{8c}$, C=N—$OR^{8c}$, C=N—$NO_2$, C=N—CN or sulphonyl group, $R^{8c}$ each independently of one another denote a hydrogen atom, a $C_{1-3}$-alkyl, $C_{1-3}$-alkylcarbonyl, $C_{1-4}$-alkyloxycarbonyl or $C_{1-3}$-alkylsulphonyl group, $X^2$ denotes an oxygen atom or a —$NR^{8b}$ group, $X^3$ denotes a carbonyl, thiocarbonyl, C=$NR^{8c}$, C=N—$OR^{8c}$, C=N—$NO_2$, C=N—CN or sulphonyl group, $X^4$ denotes an oxygen atom or a —$NR^{8c}$ group, $R^1$ denotes a fluorine, chlorine, bromine or iodine atom, a $C_{1-3}$-alkyl or a $C_{1-3}$-alkoxy group, while the hydrogen atoms of the $C_{1-3}$-alkyl or $C_{1-3}$-alkoxy group may optionally be wholly or partly replaced by fluorine atoms, $R^2$ denotes a hydrogen or halogen atom or a methyl group, $R^3$ denotes a hydrogen atom, $R^4$ denotes a $C_{2-4}$-alkenyl or $C_{2-4}$-alkynyl group, a straight-chain or branched $C_{1-4}$-alkyl group, while the hydrogen atoms of the straight-chain or branched $C_{1-4}$-alkyl group may optionally be wholly or partly replaced by fluorine atoms, and may optionally be substituted by a $C_{3-5}$-cycloalkyl group, a nitrile, hydroxy, a $C_{1-3}$-alkyloxy group, while the hydrogen atoms of the $C_{1-3}$-alkyloxy group may optionally be wholly or partly replaced by fluorine atoms, a benzyloxy, $C_{1-3}$-alkylcarbonyloxy, $C_{1-3}$-alkyloxycarbonyl-$C_{1-3}$-alkyloxy, $C_{1-3}$-alkyloxycarbonyl, aminocarbonyl, $C_{1-3}$-alkylaminocarbonyl, di-($C_{1-3}$-alkyl)-aminocarbonyl, $C_{3-6}$-cycloalkyleneiminocarbonyl, aminosulphonyl, $C_{1-3}$-alkylaminosulphonyl, di-($C_{1-3}$-alkyl)-aminosulphonyl, $C_{3-6}$-cycloalkyleneiminosulphonyl, amino, $C_{1-3}$-alkylamino, di-($C_{1-3}$-alkyl)-amino, $C_{1-3}$-alkylcarbonylamino, $C_{1-3}$-alkyl-sulphonylamino, or an N—($C_{1-3}$-alkylsulphonyl)-$C_{1-3}$-alkylamino group, a phenyl, heteroaryl, phenyl-$C_{1-3}$-alkyl or heteroaryl-$C_{1-3}$-alkyl group, which may optionally be mono- to trisubstituted in the phenyl or heteroaryl moiety by identical or different substituents selected from among halogen atoms, $C_{1-3}$-alkyl, di-($C_{1-3}$-alkyl)-amino, hydroxy, $C_{1-3}$-alkyloxy, mono-, di- or trifluoromethoxy, carboxy- and $C_{1-3}$-alkyloxycarbonyl groups, $R^5$ denotes a hydrogen atom, a $C_{2-4}$-alkenyl or $C_{2-4}$-alkynyl group, a straight-chain or branched $C_{1-4}$-alkyl group, while the hydrogen atoms of the straight-chain or branched $C_{1-4}$-alkyl group may optionally be wholly or partly replaced by fluorine atoms, and may optionally be substituted by a $C_{1-3}$-alkyloxy group, while the hydrogen atoms of the $C_{1-3}$-alkyloxy group may optionally be wholly or partly replaced by fluorine atoms, or $R^4$ and $R^5$ together with the carbon atom to which they are bound form a $C_{3-8}$-cycloalkyl or $C_{3-8}$-cycloalkenyl group, while one of the methylene groups of a $C_{4-8}$-cycloalkyl group may be replaced by an oxygen or sulphur atom or a sulphonyl or —N($R^{8c}$) group, and/or two directly adjacent methylene groups of a $C_{4-8}$-cycloalkyl group may together be replaced by a —C(O)N($R^{8b}$) or —S(O)$_2$N($R^{8b}$) group, and/or three directly adjacent methylene groups of a $C_{6-8}$-cycloalkyl group may together be replaced by a —OC(O)N($R^{8b}$), —N($R^{8b}$)C(O)N($R^{8b}$) or —N($R^{8b}$)S(O)$_2$N($R^{8b}$) group, while 1 to 3 carbon atoms of a $C_{3-8}$-cycloalkyl group may optionally be substituted independently of one another by a $C_{1-3}$-alkyl, hydroxy, $C_{1-3}$-alkyloxy, $C_{1-3}$-alkylcarbonyloxy, $C_{1-3}$-alkyloxycarbonyl, amino, $C_{1-3}$-alkylamino, di-($C_{1-3}$-alkyl)-amino, $C_{1-3}$-alkylcarbonylamino, $C_{1-3}$-alkylsulphonylamino groups, while 1 to 2 carbon atoms of a $C_{3-8}$-cycloalkenyl group may optionally be substituted independently of one another by a $C_{1-3}$-alkyl group, and 1 to 2 carbon atoms of a $C_{4-8}$-cycloalkenyl group which are not bound to another carbon atom by a double bond may optionally be substituted independently of one another by a hydroxy, $C_{1-3}$-alkyloxy, di-($C_{1-3}$-alkyl)-amino group, with the proviso that a $C_{3-8}$-cycloalkyl or $C_{3-8}$-cycloalkenyl group of this kind, formed from $R^4$ and $R^5$ together, wherein two heteroatoms in the cyclic group selected from among oxygen and nitrogen are separated from one another by precisely one optionally substituted —CH$_2$ group, and/or wherein one or both methylene groups of the cyclic group which are directly connected to the carbon atom to which the groups $R^4$ and $R^5$ are bound, are replaced by a heteroatom selected from among oxygen, nitrogen and sulphur, and/or wherein a substituent bound to the cyclic group, which is characterised in that a heteroatom selected from among oxygen, nitrogen, sulphur and halogen atom is bound directly to the cyclic group, is separated from another heteroatom selected from among oxygen, nitrogen and sulphur, with the exception of the sulphone group, by precisely one, optionally substituted, methylene group, and/or wherein two oxygen atoms are joined together directly, is excluded, $R^6$ denotes a fluorine, chlorine, bromine or iodine atom, a methyl group, or a methoxy group, while the hydrogen atoms of the methyl or methoxy group may optionally be wholly or partly replaced by fluorine atoms, while, unless otherwise stated, by the term "heteroaryl group" mentioned hereinbefore in the definitions is meant a monocyclic 5- or 6-membered heteroaryl group, while the 6-membered heteroaryl group contains one, two or three nitrogen atoms and the 5-membered heteroaryl group contains an imino group optionally substituted by a $C_{1-3}$-alkyl, phenyl or phenyl-$C_{1-3}$-alkyl group, an oxygen or sulphur atom or an imino group optionally substituted by a $C_{1-3}$-alkyl, phenyl, amino-$C_{2-3}$-alkyl, $C_{1-3}$-alkylamino-$C_{2-3}$-alkyl, di-($C_{1-3}$-alkyl)-amino-$C_{2-3}$-alkyl, a $C_{3-6}$-cycloalkyleneimino-$C_{1-3}$-alkyl or phenyl-$C_{1-3}$-alkyl group or an oxygen or sulphur atom and additionally a nitrogen atom or an imino group optionally substituted by a $C_{1-3}$-alkyl or phenyl-$C_{1-3}$-alkyl group and two or three nitrogen atoms, and moreover a phenyl ring optionally substituted by a fluorine, chlorine or bromine atom, a $C_{1-3}$-alkyl, hydroxy, $C_{1-3}$-alkyloxy group, amino, $C_{1-3}$-alkylamino, di-($C_{1-3}$-alkyl)-amino or $C_{3-6}$-cycloalkyleneimino group may be fused to the above-mentioned monocyclic heteroaryl groups via two adjacent carbon atoms and the bond is effected via a nitrogen atom or a carbon atom of the heterocyclic moiety or a fused-on phenyl ring, while, unless otherwise stated, by the term "halogen atom" mentioned hereinbefore in the definitions is meant an atom selected from among fluorine, chlorine, bromine and iodine, while, unless otherwise stated, the alkyl, alkenyl, alkynyl and alkoxy groups contained in the foregoing definitions which have more than two carbon atoms may be straight-chain or branched and the alkyl groups in the previously mentioned dialkylated groups, for example the dialkylamino groups, may be identical or different, and the hydrogen atoms of the methyl or ethyl groups contained in the foregoing definitions, unless otherwise stated, may be wholly or partly replaced by fluorine atoms, the tautomers, the enantiomers, the diastereomers, the mixtures thereof and the salts thereof.

A 5th embodiment of the present invention comprises those compounds of general formula I wherein A denotes a group of general formula -continued

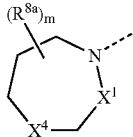

wherein
m is the number 1 or 2,
R$^{8a}$ each independently of one another denote a hydrogen or fluorine atom or a C$_{1-3}$-alkyl, hydroxy, hydroxy-C$_{1-3}$-alkyl, C$_{1-3}$-alkoxy, C$_{1-3}$-alkoxy-C$_{1-3}$-alkyl, amino, C$_{1-3}$-alkylamino, di-(C$_{1-3}$-alkyl)-amino, amino-C$_{1-3}$-alkyl, C$_{1-3}$-alkylamino-C$_{1-3}$-alkyl, or di-(C$_{1-3}$-alkyl)-amino-C$_{1-3}$-alkyl group, while in the previously mentioned substituted 5- to 7-membered groups A the heteroatoms F, O or N optionally introduced with R$^{8a}$ as substituent are not separated by precisely one carbon atom from a heteroatom selected from among N, O, S,
X$^1$ denotes a carbonyl, thiocarbonyl, C=NR$^{8c}$, C=N—OR$^{8c}$, C=N—NO$_2$, C=N—CN or sulphonyl group,
R$^{8c}$ each independently of one another denote a hydrogen atom, a C$_{1-3}$-alkyl, C$_{1-3}$-alkylcarbonyl, or a C$_{1-4}$-alkyloxycarbonyl group,
X$^2$ denotes an oxygen atom or a —NR$^{8b}$ group,
R$^{8b}$ each independently of one another denote a hydrogen atom or a C$_{1-3}$-alkyl group,
X$^3$ denotes a carbonyl, thiocarbonyl, C=NR$^{6c}$, C=N—OR$^{8c}$, C=N—NO$_2$, C=N—CN or sulphonyl group,
X$^4$ denotes an oxygen atom or a —NR$^{8c}$ group,
R$^1$ denotes a fluorine, chlorine, bromine or iodine atom, a methyl or a methoxy group, while the hydrogen atoms of the methyl or methoxy group may optionally be wholly or partly replaced by fluorine atoms,
R$^2$ denotes a hydrogen or fluorine atom or a methyl group,
R$^3$ denotes a hydrogen atom,
R$^4$ denotes a C$_{2-4}$-alkenyl or C$_{2-4}$-alkynyl group,
a straight-chain or branched C$_{1-4}$-alkyl group, while the hydrogen atoms of the straight-chain or branched C$_{1-4}$-alkyl group may optionally be wholly or partly replaced by fluorine atoms, and may optionally be substituted by a nitrile, hydroxy, a C$_{1-3}$-alkyloxy group, while the hydrogen atoms of the C$_{1-3}$-alkyloxy group may optionally be wholly or partly replaced by fluorine atoms, a benzyloxy, C$_{1-3}$-alkylcarbonyloxy, C$_{1-3}$-alkyloxycarbonyl, aminocarbonyl, C$_{1-3}$-alkylaminocarbonyl, di-(C$_{1-3}$-alkyl)-aminocarbonyl, C$_{3-6}$-cycloalkyleneiminocarbonyl, aminosulphonyl, C$_{1-3}$-alkylaminosulphonyl, di-(C$_{1-3}$-alkyl)-aminosulphonyl, C$_{3-6}$-cycloalkyleneiminosulphonyl, amino, C$_{1-3}$-alkylamino, di-(C$_{1-3}$-alkyl)-amino, C$_{1-3}$-alkylcarbonylamino, or C$_{1-3}$-alkylsulphonylamino group,
a phenyl, heteroaryl, phenyl-C$_{1-3}$-alkyl or heteroaryl-C$_{1-3}$-alkyl group, which may optionally be mono- to trisubstituted in the phenyl or heteroaryl moiety by identical or different substituents selected from among halogen atoms, C$_{1-3}$-alkyl, di-(C$_{1-3}$-alkyl)-amino, hydroxy, C$_{1-3}$-alkyloxy, Mono, di- and trifluoromethoxy groups,
R$^5$ denotes a hydrogen atom,
a straight-chain or branched C$_{1-4}$-alkyl group,
while the hydrogen atoms of the straight-chain or branched C$_{1-4}$-alkyl group may optionally be wholly or partly replaced by fluorine atoms, and may optionally be substituted by a C$_{1-3}$-alkyloxy group, while the hydrogen atoms of the C$_{1-3}$-alkyloxy group may optionally be wholly or partly replaced by fluorine atoms, or
R$^4$ and R$^5$ together with the carbon atom to which they are bound form a C$_{3-8}$-cycloalkyl group,
while one of the methylene groups of a C$_{4-8}$-cycloalkyl group may be replaced by an oxygen or sulphur atom or a sulphonyl or —N(R$^{8c}$) group, and/or
two directly adjacent methylene groups of a C$_{4-8}$-cycloalkyl group may together be replaced by a —C(O)N(R$^{8b}$) or —S(O)$_2$N(R$^{8b}$) group, and/or
three directly adjacent methylene groups of a C$_{6-8}$-cycloalkyl group may together be replaced by a —OC(O)N(R$^{8b}$), —N(R$^{8b}$)C(O)N(R$^{8b}$) or —N(R$^{8b}$)S(O)$_2$N(R$^{8b}$) group,
while 1 to 2 carbon atoms of a C$_{3-8}$-cycloalkyl group may optionally be substituted independently of one another by a C$_{1-3}$-alkyl, hydroxy, C$_{1-3}$-alkyloxy, C$_{1-3}$-alkylcarbonyloxy, C$_{1-3}$-alkyloxycarbonyl, C$_{1-3}$-alkylamino, di-(C$_{1-3}$-alkyl)-amino, C$_{1-3}$-alkylcarbonylamino, C$_{1-3}$-alkylsulphonylamino groups,
with the proviso that a C$_{3-8}$-cycloalkyl group of this kind, formed from R$^4$ and R$^5$ together,
wherein two heteroatoms in the cyclic group selected from among oxygen and nitrogen are separated from one another by precisely one optionally substituted —CH$_2$ group, and/or
wherein one or both methylene groups of the cyclic group which are directly connected to the carbon atom to which the groups R$^4$ and R$^5$ are bound are replaced by a heteroatom selected from among oxygen, nitrogen and sulphur, and/or
wherein a substituent bound to the cyclic group, which is characterised in that a heteroatom selected from among oxygen, nitrogen, sulphur and halogen atom is bound directly to the cyclic group is separated from another heteroatom selected from among oxygen, nitrogen and sulphur, with the exception of the sulphone group, by precisely one, optionally substituted, methylene group, and/or
wherein two oxygen atoms are joined together directly,
is excluded,
R$^6$ denotes a fluorine, chlorine, bromine or iodine atom, a methyl group, or a methoxy group, while the hydrogen atoms of the methyl or methoxy group may optionally be wholly or partly replaced by fluorine atoms, while, unless otherwise stated, by the term "heteroaryl group" mentioned hereinbefore in the definitions is meant a monocyclic 5- or 6-membered heteroaryl group, while
the 6-membered heteroaryl group contains one, two or three nitrogen atoms and
the 5-membered heteroaryl group contains an imino group optionally substituted by a C$_{1-3}$-alkyl, phenyl or phenyl-C$_{1-3}$-alkyl group, an oxygen or sulphur atom or
an imino group optionally substituted by a C$_{1-3}$-alkyl, phenyl, amino-C$_{2-3}$-alkyl, C$_{1-3}$-alkylamino-C$_{2-3}$-alkyl, di-(C$_{1-3}$-alkyl)-amino-C$_{2-3}$-alkyl, a C$_{3-6}$-cycloalkyleneimino-C$_{1-3}$-alkyl or phenyl-C$_{1-3}$-alkyl group or an oxygen or sulphur atom and additionally a nitrogen atom or
an imino group optionally substituted by a C$_{1-3}$-alkyl or phenyl-C$_{1-3}$-alkyl group and two or three nitrogen atoms, and moreover a phenyl ring optionally substituted by a fluorine, chlorine or bromine atom, a $C_{1-3}$-alkyl, hydroxy, $C_{1-3}$-alkyloxy group, amino, $C_{1-3}$-alkylamino, di-($C_{1-3}$-alkyl)-amino or $C_{3-6}$-cycloalkyleneimino group may be fused to the above-mentioned monocyclic heteroaryl groups via two adjacent carbon atoms and the bond is effected via a nitrogen atom or a carbon atom of the heterocyclic moiety or a fused-on phenyl ring, while, unless otherwise stated, by the term "halogen atom" mentioned hereinbefore in the definitions is meant an atom selected from among fluorine, chlorine, bromine and iodine, while, unless otherwise stated, the alkyl, alkynyl and alkoxy groups contained in the foregoing definitions which have more than two carbon atoms may be straight-chain or branched and the alkyl groups in the previously mentioned dialkylated groups, for example the dialkylamino groups, may be identical or different, and the hydrogen atoms of the methyl or ethyl groups contained in the foregoing definitions, unless otherwise stated, may be wholly or partly replaced by fluorine atoms, the tautomers, the enantiomers, the diastereomers, the mixtures thereof and the salts thereof.

A 6th embodiment of the present invention comprises those compounds of general formula 1, wherein A denotes a group of general formula

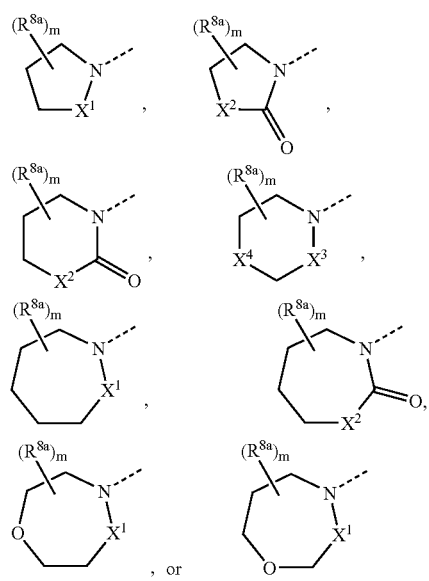

wherein m is the number 1 or 2, $R^{8a}$ each independently of one another denote a hydrogen or fluorine atom or a $C_{1-3}$-alkyl, hydroxy, hydroxy-$C_{1-3}$-alkyl, $C_{1-3}$-alkoxy, $C_{1-3}$-alkoxy-$C_{1-3}$-alkyl, amino, $C_{1-3}$-alkylamino, di-($C_{1-3}$-alkyl)-amino, amino-$C_{1-3}$-alkyl, $C_{1-3}$-alkylamino-$C_{1-3}$-alkyl, di-($C_{1-3}$-alkyl)-amino-$C_{1-3}$-alkyl group, while in the previously mentioned substituted 5- to 7-membered groups A the heteroatoms F, O or N optionally introduced with $R^{8a}$ as substituent are not separated by precisely one carbon atom from a heteroatom selected from among N, O, S, $X^1$ denotes a carbonyl, thiocarbonyl, $C=NR^{8c}$, $C=N-OR^{8c}$, $C=N-NO_2$, $C=N-CN$ or sulphonyl group, $R^{8c}$ each independently of one another denote a hydrogen atom, a $C_{1-3}$-alkyl, $C_{1-3}$-alkylcarbonyl, or a $C_{1-4}$-alkyloxycarbonyl group, $X^2$ denotes an oxygen atom or a $—NR^{8b}$ b group, $R^{8b}$ denotes a hydrogen atom or a $C_{1-3}$-alkyl group, $X^3$ denotes a carbonyl, thiocarbonyl, $C=NR^{8c}$, $C=N-OR^{8c}$, $C=N-NO_2$, $C=N-CN$ or sulphonyl group, $X^4$ denotes an oxygen atom or a $—NR^{8c}$ group, $R^1$ denotes a fluorine, chlorine, bromine or iodine atom, a methyl or a methoxy group, while the hydrogen atoms of the methyl or methoxy group may optionally be wholly or partly replaced by fluorine atoms, $R^2$ denotes a hydrogen or fluorine atom, $R^3$ denotes a hydrogen atom, $R^4$ denotes a straight-chain or branched $C_{1-4}$-alkyl group, while the hydrogen atoms may optionally be wholly or partly replaced by fluorine atoms, and may optionally be substituted by a hydroxy, a $C_{1-3}$-alkyloxy group, while the hydrogen atoms of the $C_{1-3}$-alkyloxy group may be wholly or partly replaced by fluorine atoms, a benzyloxy, $C_{1-3}$-alkylcarbonyloxy, $C_{1-3}$-alkyloxycarbonyl, aminocarbonyl, $C_{1-3}$-alkylaminocarbonyl, di-($C_{1-3}$-alkyl)-aminocarbonyl, $C_{3-6}$-cycloalkyleneiminocarbonyl, aminosulphonyl, $C_{1-3}$-alkylaminosulphonyl, di-($C_{1-3}$-alkyl)-aminosulphonyl, $C_{3-6}$-cycloalkyleneiminosulphonyl, amino, $C_{1-3}$-alkylamino, di-($C_{1-3}$-alkyl)-amino, $C_{1-3}$-alkylcarbonylamino, or $C_{1-3}$-alkylsulphonylamino group, a heteroaryl-$C_{1-2}$-alkyl or C-linked heteroaryl group while the heteroaryl group is selected from among pyrrolyl, oxazolyl, imidazolyl, furanyl, thiophenyl, thiazolyl, 1,2,3-triazolyl, 1,2,4-triazolyl, tetrazolyl, pyridynyl, pyrimidynyl and pyrazynyl, and may optionally be mono- to disubstituted in the heteroaryl moiety by identical or different substituents selected from among halogen atoms, $C_{1-3}$-alkyl, hydroxy, $C_{1-3}$-alkyloxy, mono-, di- and trifluoromethoxy groups, $R^5$ denotes a hydrogen atom, a straight-chain or branched $C_{1-4}$-alkyl group, while the hydrogen atoms may optionally be wholly or partly replaced by fluorine atoms, and may optionally be substituted by a $C_{1-3}$-alkyloxy group, while the hydrogen atoms of the $C_{1-3}$-alkyloxy group may optionally be wholly or partly replaced by fluorine atoms, or $R^4$ and $R^5$ together with the carbon atom to which they are bound form a $C_{3-7}$-cycloalkyl group, while one of the methylene groups of a $C_{4-6}$-cycloalkyl group may be replaced by an oxygen or sulphur atom or a sulphonyl or $—N(R^{8c})$ group, while 1 to 2 carbon atoms of a $C_{3-7}$-cycloalkyl group may optionally be substituted independently of one another by a $C_{1-3}$-alkyl, hydroxy, $C_{1-3}$-alkyloxy, di-($C_{1-3}$-alkyl)-amino group, with the proviso that a $C_{3-7}$-cycloalkyl group of this kind, formed together from $R^4$ and $R^5$, wherein two heteroatoms in the cyclic group selected from among oxygen and nitrogen are separated from one another by precisely one optionally substituted $—CH_2$ group, and/or wherein one or both methylene groups of the cyclic group which are directly connected to the carbon atom to which the groups $R^4$ and $R^5$ are bound, are replaced by a heteroatom selected from among oxygen, nitrogen and sulphur, and/or wherein a substituent bound to the cyclic group, which is characterised in that a heteroatom selected from among oxygen, nitrogen, sulphur and halogen atom is bound directly to the cyclic group, is separated from another heteroatom selected from among oxygen, nitrogen and sulphur, with the exception of the sulphone group, by precisely one, optionally substituted, methylene group, and/or wherein two oxygen atoms are joined together directly, is excluded, $R^6$ denotes a chlorine or bromine atom, while, unless otherwise stated, by the term "halogen atom" mentioned hereinbefore in the definitions is meant an atom selected from among fluorine, chlorine, bromine and iodine, while unless otherwise stated the alkyl and alkoxy groups contained in the foregoing definitions which have more than two carbon atoms may be straight-chain or branched and the alkyl groups in the previously mentioned dialkylated groups, for example the dialkylamino groups, may be identical or different, and the hydrogen atoms of the methyl or ethyl groups contained in the foregoing definitions, unless otherwise stated, may be wholly or partly replaced by fluorine atoms, the tautomers, the enantiomers, the diastereomers, the mixtures thereof and the salts thereof.

A 7th embodiment of the present invention comprises those compounds of general formula I wherein A denotes a group of general formula

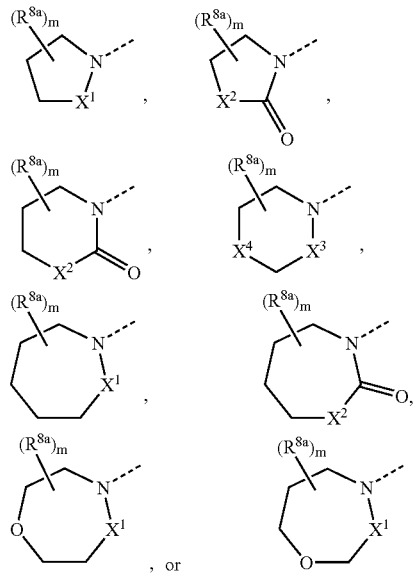

wherein m is the number 1 or 2, $R^{8a}$ each independently of one another denote a hydrogen or fluorine atom or a $C_{1-3}$-alkyl, hydroxy, hydroxy-$C_{1-3}$-alkyl, $C_{1-3}$-alkoxy, $C_{1-3}$-alkoxy-$C_{1-3}$-alkyl, amino, $C_{1-3}$-alkylamino, di-($C_{1-3}$-alkyl)-amino, amino-$C_{1-3}$-alkyl, $C_{1-3}$-alkylamino-$C_{1-3}$-alkyl, di-($C_{1-3}$-alkyl)-amino-$C_{1-3}$-alkyl group, while in the previously mentioned substituted 5- to 7-membered groups A the heteroatoms F, O or N optionally introduced with $R^{8a}$ as substituent are not separated by precisely one carbon atom from a heteroatom selected from among N, O, S, $X^1$ denotes a carbonyl, thiocarbonyl, C=$NR^{8c}$, C=N—$OR^{8c}$, C=N—CN or sulphonyl group, $R^{8c}$ denotes a hydrogen atom, a $C_{1-3}$-alkyl, $C_{1-3}$-alkylcarbonyl, or a $C_{1-4}$-alkyloxycarbonyl group, $X^2$ denotes an oxygen atom or a —$NR^{8b}$ group, $R^{8b}$ denotes a hydrogen atom or a $C_{1-3}$-alkyl group, $X^3$ denotes a carbonyl, thiocarbonyl, C=$NR^{8c}$, C=N—$OR^{8c}$, C=N—CN or sulphonyl group, $X^4$ denotes an oxygen atom or a —$NR^{8c}$ group, $R^1$ denotes a chlorine or bromine atom, a methyl, trifluoromethyl or a methoxy group, $R^2$ denotes a hydrogen or fluorine atom, $R^3$ denotes a hydrogen atom, $R^4$ denotes a methyl group which may optionally be substituted by a hydroxy, methoxy, benzyloxy, methoxycarbonyl or pyridyn-4-yl group, or a 1-methyl-pyrazyn-3-yl, phenyl, pyridyn-3-yl or pyrazin-2-yl group, $R^5$ denotes a hydrogen atom or a methyl group, or $R^4$ and $R^5$ together with the carbon atom to which they are bound form a $C_{3-6}$-cycloalkyl group, while one of the methylene groups of a $C_{4-6}$-cycloalkyl group may be replaced by an oxygen atom or an —N($R^{8c}$) group, with the proviso that a $C_{3-6}$-cycloalkyl group of this kind, formed together from $R^4$ and $R^5$, wherein one or both methylene groups of the cyclic group which are directly connected to the carbon atom to which the groups $R^4$ and $R^5$ are bound, are replaced by a heteroatom selected from among oxygen, nitrogen and sulphur, is excluded, $R^6$ denotes a chlorine or bromine atom while, unless otherwise stated, by the term "halogen atom" mentioned hereinbefore in the definitions is meant an atom selected from among fluorine, chlorine, bromine and iodine, while, unless otherwise stated, the alkyl and alkoxy groups contained in the foregoing definitions which have more than two carbon atoms may be straight-chain or branched and the alkyl groups in the previously mentioned dialkylated groups, for example the dialkylamino groups, may be identical or different, and the hydrogen atoms of the methyl or ethyl groups contained in the foregoing definitions, unless otherwise stated, may be wholly or partly replaced by fluorine atoms, the tautomers, the enantiomers, the diastereomers, the mixtures thereof and the salts thereof.

An 8th embodiment of the present invention comprises those compounds of general formula I corresponding to the embodiments 1, 2, 3, 4, 5, 6 and 7, wherein the group A denotes the group

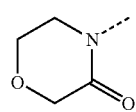

A 9th embodiment of the present invention comprises those compounds of general formula I, wherein A denotes a group of general formula

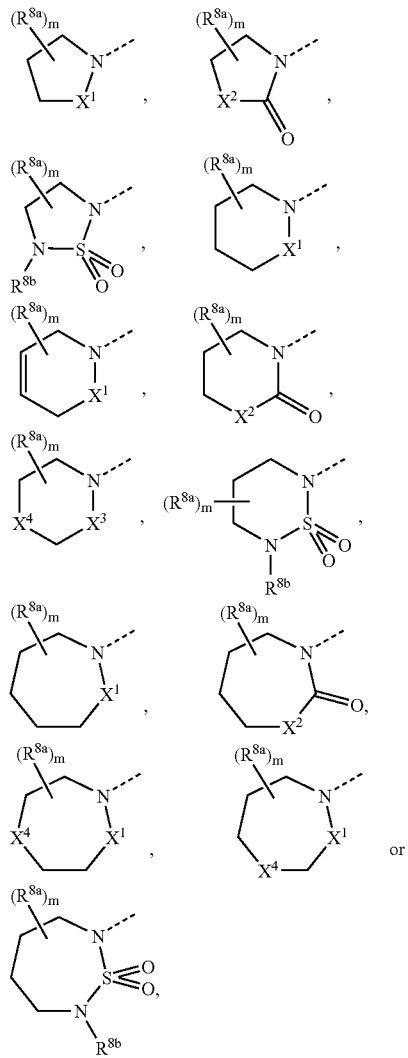

wherein
m is the number 1 or 2,
$R^{8a}$ each independently of one another denote a hydrogen or halogen atom or a $C_{1-5}$-alkyl, hydroxy, hydroxy-$C_{1-5}$-alkyl, $C_{1-5}$-alkoxy, $C_{1-5}$-alkoxy-$C_{1-5}$-alkyl, amino, $C_{1-5}$-alkylamino, di-($C_{1-5}$-alkyl)-amino, amino-$C_{1-5}$-alkyl, $C_{1-5}$-alkylamino-$C_{1-5}$-alkyl, di-($C_{1-5}$-alkyl)-amino-$C_{1-5}$-alkyl, aminocarbonyl, $C_{1-5}$-alkylaminocarbonyl, di-($C_{1-5}$-alkyl)-aminocarbonyl or $C_{1-5}$-alkylcarbonylamino group, while in the previously mentioned substituted 5- to 7-membered groups A the heteroatoms F, Cl, Br, I, O or N optionally introduced with $R^{8a}$ as substituent are not separated by precisely one carbon atom from a heteroatom selected from among N, O, S,
$R^{8b}$ each independently of one another denote a hydrogen atom or a $C_{1-5}$-alkyl group,
$X^1$ denotes a carbonyl, thiocarbonyl, C=$NR^{8c}$, C=N—$OR^{8c}$, C=N—$NO_2$, C=N—CN or sulphonyl group,
$R^{8c}$ each independently of one another denote a hydrogen atom, a $C_{1-5}$-alkyl, $C_{1-5}$-alkylcarbonyl, $C_{1-5}$-alkyloxycarbonyl or $C_{1-5}$-alkylsulphonyl group,
$X^2$ denotes an oxygen atom or a —$NR^{8b}$ group,
$X^3$ denotes a carbonyl, thiocarbonyl, C=$NR^{8c}$, C=N—$OR^{8c}$, C=N—$NO_2$, C=N—CN or sulphonyl group,
$X^4$ denotes an oxygen or sulphur atom or a —$NR^{8c}$ group,
$R^1$ denotes a fluorine, chlorine, bromine or iodine atom, a $C_{1-3}$-alkyl or $C_{1-3}$-alkoxy group, while the hydrogen atoms of the $C_{1-3}$-alkyl or $C_{1-3}$-alkoxy group may optionally be wholly or partly replaced by fluorine atoms, a $C_{2-3}$-alkenyl, $C_{2-3}$-alkynyl, nitrile, nitro or amino group,
$R^2$ denotes a hydrogen or halogen atom or a $C_{1-3}$-alkyl group,
$R^3$ denotes a hydrogen atom or a $C_{1-3}$-alkyl group,
$R^4$ and $R^5$ in each case independently of one another denote a hydrogen atom, a $C_{2-6}$-alkenyl or $C_{2-6}$-alkynyl group, a straight-chain or branched $C_{1-6}$-alkyl group,
while the hydrogen atoms of the straight-chain or branched $C_{1-6}$-alkyl group may optionally be wholly or partly replaced by fluorine atoms, and may optionally be substituted by a $C_{3-5}$-cycloalkyl group, a nitrile, hydroxy, a $C_{1-5}$-alkyloxy group, while the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-5}$-alkyloxy, $C_{1-5}$-alkyloxycarbonyl-$C_{1-5}$-alkyloxy, mercapto, $C_{1-5}$-alkylsulphanyl, $C_{1-5}$-alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, aminosulphonyl, $C_{1-5}$-alkylaminosulphonyl, di-($C_{1-5}$-alkyl)-aminosulphonyl, $C_{3-6}$-cycloalkyleneiminosulphonyl, amino, $C_{1-5}$-alkylamino, di-($C_{1-5}$-alkyl)-amino, $C_{1-5}$-alkylcarbonylamino, $C_{1-5}$-alkylsulphonylamino, N-($C_{1-5}$-alkylsulphonyl)-$C_{1-5}$-alkylamino or $C_{3-6}$-cycloalkylcarbonylamino group,
a carboxy, aminocarbonyl, $C_{1-5}$-alkylaminocarbonyl, $C_{3-6}$-cycloalkylaminocarbonyl, di-($C_{1-5}$-alkyl)-aminocarbonyl, $C_{1-5}$-alkoxycarbonyl, $C_{4-6}$-cycloalkyleneiminocarbonyl group,
a phenyl, heteroaryl, phenyl-$C_{1-5}$-alkyl or heteroaryl-$C_{1-5}$-alkyl group,
which may optionally be mono- to trisubstituted in the phenyl or heteroaryl moiety by identical or different substituents selected from among halogen atoms, $C_{1-5}$-alkyl, di-($C_{1-5}$-alkyl)-amino, hydroxy, $C_{1-5}$-alkyloxy, mono-, di- or trifluoromethoxy, carboxy and $C_{1-5}$-alkyloxycarbonyl groups,
a 3- to 7-membered cycloalkyl, cycloalkyleneimino, cycloalkyl-$C_{1-5}$-alkyl or cycloalkyleneimino-$C_{1-3}$-alkyl group,
while in 4- to 7-membered cyclic groups in the cyclic moiety a methylene group may optionally be replaced by an —N($R^{8c}$) group, an oxygen or sulphur atom or a —S(O) or —S(O)$_2$ group, or in 4- to 7-membered cyclic groups in the cyclic moiety two adjacent methylene groups together may optionally be replaced by a —C(O)N($R^{8b}$) or —S(O)$_2$N($R^{8b}$) group, or
wherein in 6- to 7-membered cyclic groups in the cyclic moiety three adjacent methylene groups together may optionally be replaced by a substituted —OC(O)N($R^{8b}$) or —N($R^{8b}$)C(O)N($R^{8b}$) or —N($R^{8b}$)S(O)$_2$N($R^{8b}$) group, with the proviso that a 3- to 7-membered cycloalkyl, cycloalkyleneimino, cycloalkyl-$C_{1-5}$-alkyl or cycloalkyleneimino-$C_{1-3}$-alkyl group as hereinbefore defined wherein two heteroatoms from the group oxygen and nitrogen are separated from one another by precisely one optionally substituted —CH$_2$ group, is excluded, while a 3- to 7-membered cycloalkyl, cycloalkyleneimino, cycloalkyl-$C_{1-5}$-alkyl or cycloalkyleneimino-$C_{1-3}$-alkyl group as hereinbefore defined may be substituted at one or two —CH$_2$ groups by one or two $C_{1-3}$-alkyl groups in each case, or $R^4$ and $R^5$ together with the carbon atom to which they are bound form a $C_{3-8}$-cycloalkyl or $C_{3-8}$-cycloalkenyl group, while a $C_{3-8}$-cycloalkyl or $C_{4-8}$-cycloalkenyl group may be substituted at an individual carbon atom by a $C_{2-5}$-alkylene group or simultaneously at two different carbon atoms by a $C_{1-4}$-alkylene group forming a corresponding spirocyclic group or a bridged bicyclic group, while one of the methylene groups of a $C_{4-8}$-cycloalkyl or $C_{5-8}$-cycloalkenyl group or a corresponding spirocyclic group as described above or a corresponding bridged bicyclic group may be replaced by an oxygen or sulphur atom or an —N($R^{8c}$), or a carbonyl, sulphinyl or sulphonyl group, and/or two directly adjacent methylene groups of a $C_{4-8}$-cycloalkyl group may together be replaced by a —C(O)N($R^{8b}$), —C(O)O or —S(O)$_2$N($R^{8b}$) group, and/or three directly adjacent methylene groups of a $C_{6-8}$-cycloalkyl group may together be replaced by a —OC(O)N($R^{8b}$), —N($R^{8b}$)C(O)N($R^{8b}$) or —N($R^{8b}$)S(O)$_2$N($R^8$b) group, while 1 to 3 carbon atoms of a $C_{3-8}$-cycloalkyl group or a corresponding spirocyclic group as described above or a corresponding bridged bicyclic group may optionally be substituted independently of one another by in each case one or two fluorine atoms or one or two identical or different $C_{1-5}$-alkyl, nitrile, hydroxy, $C_{1-5}$-alkyloxy, $C_{1-5}$-alkylcarbonyloxy, carboxy-$C_{1-5}$-alkyl, $C_{1-5}$-alkyloxycarbonyl-$C_{1-5}$-alkyl, $C_{1-5}$-alkylsulphanyl, $C_{1-5}$-alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, aminosulphonyl, $C_{1-5}$-alkylaminosulphonyl, di-($C_{1-5}$-alkyl)-aminosulphonyl, $C_{3-6}$-cycloalkyleneiminosulphonyl, amino, $C_{1-5}$-alkylamino, di-($C_{1-5}$-alkyl)-amino, $C_{1-5}$-alkylcarbonylamino, $C_{1-5}$-alkyl-sulphonylamino, N-($C_{1-5}$-alkylsulphonyl)-$C_{1-5}$-alkylamino or $C_{3-4}$-cycloalkylcarbonylamino groups, while 1 to 2 carbon atoms of a $C_{3-8}$-cycloalkenyl group may optionally be substituted independently of one another by in each case a $C_{1-5}$-alkyl, nitrile, carboxy-$C_{1-5}$-alkyl, $C_{1-5}$-alkyloxycarbonyl-$C_{1-5}$-alkyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, aminosulphonyl, $C_{1-5}$-alkylaminosulphonyl, di-($C_{1-5}$-alkyl)-aminosulphonyl, $C_{3-6}$-cycloalkyleneiminosulphonyl groups, and 1 to 2 carbon atoms of a $C_{4-8}$-cycloalkenyl group which are not bound to another carbon atom by a double bond may optionally be substituted independently of one another by one or two fluorine atoms or a hydroxy, $C_{1-5}$-alkyloxy, $C_{1-5}$-alkylcarbonyloxy, $C_{1-5}$-alkylsulphanyl, $C_{1-5}$-alkylsulphonyl, amino, $C_{1-5}$-alkylamino, di-($C_{1-5}$-alkyl)-amino, $C_{1-5}$-alkylcarbonylamino, $C_{1-5}$-alkyl-sulphonylamino, N-($C_{1-5}$-alkylsulphonyl)-$C_{1-5}$-alkylamino or $C_{3-6}$-cycloalkylcarbonylamino groups, with the proviso that a $C_{3-8}$-cycloalkyl or $C_{3-8}$-cycloalkenyl group of this kind formed together from $R^4$ and $R^5$ or a corresponding spirocyclic group as described above or a corresponding bridged bicyclic group, wherein two heteroatoms in the cyclic group selected from among oxygen and nitrogen are separated from one another by precisely one optionally substituted —CH$_2$ group, and/or wherein one or both methylene groups of the cyclic group which are directly connected to the carbon atom to which the groups $R^4$ and $R^5$ are bound, are replaced by a heteroatom selected from among oxygen, nitrogen and sulphur, and/or wherein a substituent bound to the cyclic group, which is characterised in that a heteroatom selected from among oxygen, nitrogen, sulphur and halogen atom is bound directly to the cyclic group, is separated from another heteroatom selected from among oxygen, nitrogen and sulphur, with the exception of the sulphone group, by precisely one, optionally substituted, methylene group, and/or wherein two oxygen atoms are joined together directly, and/or wherein a heteroatom selected from among oxygen, nitrogen and sulphur is linked directly to a carbon atom, which is linked to another carbon atom by a double bond, and/or which contains a cyclic group with three ring members, of which one or more corresponds to an oxygen or sulphur atom or —N($R^{8c}$) group, is excluded, $R^6$ denotes a hydrogen, fluorine, chlorine, bromine or iodine atom, a nitrile group, a $C_{1-3}$-alkyl group, or a $C_{1-3}$-alkoxy group, while the hydrogen atoms of the $C_{1-3}$-alkyl or $C_{1-3}$-alkoxy group may optionally be wholly or partly replaced by fluorine atoms, $R^7$ independently of one another denote a $C_{1-3}$-alkyl, while the hydrogen atoms may optionally be wholly or partly replaced by fluorine atoms, hydroxy, $C_{1-3}$-alkyloxy, while the hydrogen atoms may optionally be wholly or partly replaced by fluorine atoms, amino, $C_{1-3}$-alkylamino, di-($C_{1-3}$-alkyl)-amino, $C_{3-6}$-cycloalkyleneimino, carboxy, nitrile, $C_{1-3}$-alkoxycarbonyl, aminocarbonyl, $C_{1-3}$-alkylaminocarbonyl or a di-($C_{1-3}$-alkyl)-aminocarbonyl group, while, unless otherwise stated, by the term "heteroaryl group" mentioned hereinbefore in the definitions is meant a monocyclic 5- or 6-membered heteroaryl group, while the 6-membered heteroaryl group contains one, two or three nitrogen atoms and the 5-membered heteroaryl group contains an imino group optionally substituted by a $C_{1-3}$-alkyl, phenyl or phenyl-$C_{1-3}$-alkyl group, or an oxygen or sulphur atom or an imino group optionally substituted by a $C_{1-3}$-alkyl, phenyl, amino-$C_{2-3}$-alkyl, $C_{1-3}$-alkylamino-$C_{2-3}$-alkyl, di-($C_{1-3}$-alkyl)-amino-$C_{2-3}$-alkyl, a $C_{3-6}$-cycloalkyleneimino-$C_{1-3}$-alkyl or phenyl-$C_{1-3}$-alkyl group or an oxygen or sulphur atom and additionally a nitrogen atom or an imino group optionally substituted by a $C_{1-3}$-alkyl or phenyl-$C_{1-3}$-alkyl group and two or three nitrogen atoms, and the above-mentioned monocyclic heteroaryl groups in the carbon skeleton may be substituted by one or two groups $R^7$, and moreover a phenyl ring optionally substituted by a fluorine, chlorine or bromine atom or a group $R^7$ may be fused to the above-mentioned monocyclic heteroaryl groups via two adjacent carbon atoms and the bond is effected via a nitrogen atom or a carbon atom of the heterocyclic moiety or a fused-on phenyl ring, while, unless otherwise stated, by the term "halogen atom" mentioned hereinbefore in the definitions is meant an atom selected from among fluorine, chlorine, bromine and iodine, while, unless otherwise stated, the alkyl, alkenyl, alkynyl and alkoxy groups contained in the foregoing definitions which have more than two carbon atoms may be straight-chain or branched and the alkyl groups in the previously mentioned dialkylated groups, for example the dialkylamino groups, may be identical or different, and the hydrogen atoms of the methyl or ethyl groups contained in the foregoing definitions, unless otherwise stated, may be wholly or partly replaced by fluorine atoms, the tautomers, the enantiomers, the diastereomers, the mixtures thereof and the salts thereof.

Examples of monocyclic heteroaryl groups are the pyridyl, N-oxy-pyridyl, pyrazolyl, pyridazynyl, pyrimidynyl, pyrazynyl, [1,2,3]triazynyl, [1,3,5]triazynyl, [1,2,4]triazynyl, pyrrolyl, imidazolyl, [1,2,4]triazolyl, [1,2,3]triazolyl, tetrazolyl, furanyl, isoxazolyl, oxazolyl, [1,2,3]oxadiazolyl, [1,2,4]oxadiazolyl, furazanyl, thiophenyl, thiazolyl, isothiazolyl, [1,2,3]thiadiazolyl, [1,2,4]thiadiazolyl or [1,2,5]thiadiazolyl group.

Examples of bicyclic heteroaryl groups are the benzimidazolyl, benzofuranyl, benzo[c]furanyl, benzothiophenyl, benzo[c]thiophenyl, benzothiazolyl, benzo[c]-isothiazolyl, benzo[d]isothiazolyl, benzoxazolyl, benzo[c]isoxazolyl, benzo[d]-isoxazolyl, benzo[1,2,5]oxadiazolyl, benzo[1,2,5]thiadiazolyl, benzo[1,2,3]thia-diazolyl, benzo[d][1,2,3]triazynyl, benzo[1,2,4]triazynyl, benzotriazolyl, cinnolynyl, quinolynyl, N-oxy-quinolynyl, isoquinolynyl, quinazolynyl, N-oxy-quinazolynyl, quinoxalynyl, phthalazynyl, indolyl, isoindolyl or 1-oxa-2,3-diaza-indenyl group.

Examples of the $C_{1-6}$-alkyl groups mentioned hereinbefore in the definitions are the methyl, ethyl, 1-propyl, 2-propyl, n-butyl, sec-butyl, tert-butyl, 1-pentyl, 2-pentyl, 3-pentyl, neo-pentyl, 3-methyl-2-butyl, 1-hexyl, 2-hexyl, 3-hexyl, 3-methyl-2-pentyl, 4-methyl-2-pentyl, 3-methyl-3-pentyl, 2-methyl-3-pentyl, 2,2-dimethyl-3-butyl or 2,3-dimethyl-2-butyl group.

Examples of the $C_{1-5}$-alkyloxy groups mentioned hereinbefore in the definitions are the methyloxy, ethyloxy, 1-propyloxy, 2-propyloxy, n-butyloxy, sec-butyloxy, tert-butyloxy, 1-pentyloxy, 2-pentyloxy, 3-pentyloxy or neo-pentyloxy group. Examples of the $C_{2-6}$-alkenyl groups mentioned hereinbefore in the definitions are the ethenyl, 1-propen-1-yl, 2-propen-1-yl, 1-buten-1-yl, 2-buten-1-yl, 3-buten-1-yl, 1-penten-1-yl, 2- penten-1-yl, 3-penten-1-yl, 4-penten-1-yl, 1-hexen-1-yl, 2-hexen-1-yl, 3-hexen-1-yl, 4-hexen-1-yl, 5-hexen-1-yl, but-1-en-2-yl, but-2-en-2-yl, but-1-en-3-yl, 2-methyl-prop-2-en-1-yl, pent-1-en-2-yl, pent-2-en-2-yl, pent-3-en-2-yl, pent-4-en-2-yl, pent-1-en-3-yl, pent-2-en-3-yl, 2-methyl-but-1-en-1-yl, 2-methyl-but-2-en-1-yl, 2-methyl-but-3-en-1-yl, 2-ethyl-prop-2-en-1-yl, hex-1-en-2-yl, hex-2-en-2-yl, hex-3-en-2-yl, hex-4-en-2-yl, hex-5-en-2-yl, hex-1-en-3-yl, hex-2-en-3-yl, hex-3-en-3-yl, hex-4-en-3-yl, hex-5-en-3-yl, hex-1-en-4-hex-2-en-4-yl, hex-3-en-4-yl, hex-4-en4-yl, hex-5-en-4-yl, 4-methyl-pent-1-en-3-yl, 3-methyl-pent-1-en-3-yl, 2-methyl-pent-1-en-3-yl, 2,3-dimethyl-but-1-en-3-yl, 3,3-dimethyl-but-1-en-2-yl or 2-ethyl-but-1-en-3-yl group, Examples of the $C_{2-6}$-alkynyl groups mentioned hereinbefore in the definitions are the ethynyl, 1-propynyl, 2-propynyl, 1-butyn-1-yl, 1-butyn-3-yl, 2-butyn-1-yl, 3-butyn-1-yl, 1-pentyn-1-yl, 1-pentyn-3-yl, 1-pentyn-4-yl, 2-pentyn-1-yl, 2-pentyn-3-yl, 3-pentyn-1-yl, 4-pentyn-1-yl, 2-methyl-1-butyn-4-yl, 3-methyl-1-butyn-1-yl, 3-methyl-1-butyn-3-yl, 1-hexyn-1-yl, 2-hexyn-1-yl, 3-hexyn-1-yl, 4-hexyn-1-yl, 5-hexyn-1-yl, 1-hexyn-3-yl, 1-hexyn-4-yl, 1-hexyn-5-yl, 2-hexyn-4-yl, 2-hexyn-5-yl, 3-hexyn-5-yl, 3-methyl-1-pentyn-3-yl, 4-methyl-1-pentyn-3-yl, 3-methyl-1-pentyn-4-yl, 4-methyl-1-pentyn-4-yl, 4-methyl-2-pentyn-4-yl, 4-methyl-2-pentyn-1-yl, 2,2-dimethyl-3-butyn-1-yl or 2-ethyl-3-butyn-1-yl group.

By a group which may be converted in vivo into a carboxy group is meant for example a carboxy group esterified with an alcohol wherein the alcoholic moiety preferably denotes a $C_{1-6}$-alkanol, a phenyl-$C_{1-3}$-alkanol, a $C_{3-9}$-cycloalkanol, a $C_{5-7}$-cycloalkenol, a $C_{3-5}$-alkenol, a phenyl-$C_{3-5}$-alkenol, a $C_{3-5}$-alkynol or phenyl-$C_{3-5}$-alkynol, with the proviso that no bond to the oxygen atom starts from a carbon atom which carries a double or triple bond, a $C_{3-8}$-cycloalkyl-$C_{1-3}$-alkanol or an alcohol of formula

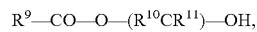

wherein
$R^9$ denotes a $C_{1-8}$-alkyl, $C_{5-7}$-cycloalkyl, phenyl or phenyl-$C_{1-3}$-alkyl group,
$R^{10}$ denotes a hydrogen atom, a $C_{1-3}$-alkyl, $C_{5-7}$-cycloalkyl or phenyl group and
$R^{11}$ denotes a hydrogen atom or a $C_{1-3}$-alkyl group.

Preferred groups which may be cleaved from a carboxy group in vivo include a $C_{1-6}$-alkoxy group such as the methoxy, ethoxy, n-propyloxy, isopropyloxy, n-butyloxy, n-pentyloxy, n-hexyloxy or cyclohexyloxy group or a phenyl-$C_{1-3}$-alkoxy group such as the benzyloxy group.

By a group which may be converted in vivo into a hydroxyl group is meant for example a hydroxyl group esterified with a carboxylic acid wherein the carboxylic acid moiety is preferably a $C_{1-7}$-alkanoic acid, a phenyl-$C_{1-3}$-alkanoic acid, a $C_{3-9}$-cycloalkylcarboxylic acid, a $C_{5-7}$-cycloalkenecarboxylic acid, a $C_{3-7}$-alkenoic acid, a phenyl-$C_{3-5}$-alkenoic acid, a $C_{3-7}$-alkynoic acid or phenyl-$C_{3-5}$-alkynoic acid, while individual methylene groups of the carboxylic acid group may be replaced by oxygen atoms, with the proviso that no bond to the oxygen atom starts from a carbon atom which carries a double or triple bond.

Examples of preferred groups which may be cleaved in vivo from a hydroxyl group include a $C_{1-7}$-acyl group such as the formyl, acetyl, n-propionyl, isopropionyl, n-propanoyl, n-butanoyl, n-pentanoyl, n-hexanoyl or cyclohexylcarbonyl group or a benzoyl group as well as also a methoxyacetyl, 1-methoxypropionyl, 2-methoxypropionyl or 2-methoxyethoxyacetyl group.

The compounds of general formula I, wherein A, $R^4$ and/or $R^5$ contains a group which may be converted in vivo into a carboxy or hydroxyl group are prodrugs for those compounds of general formula I wherein A, $R^4$ and/or $R^5$ contains a carboxy or hydroxyl group.

A 10th embodiment of the present invention comprises those compounds of general formula 1, wherein A denotes a group of general formula

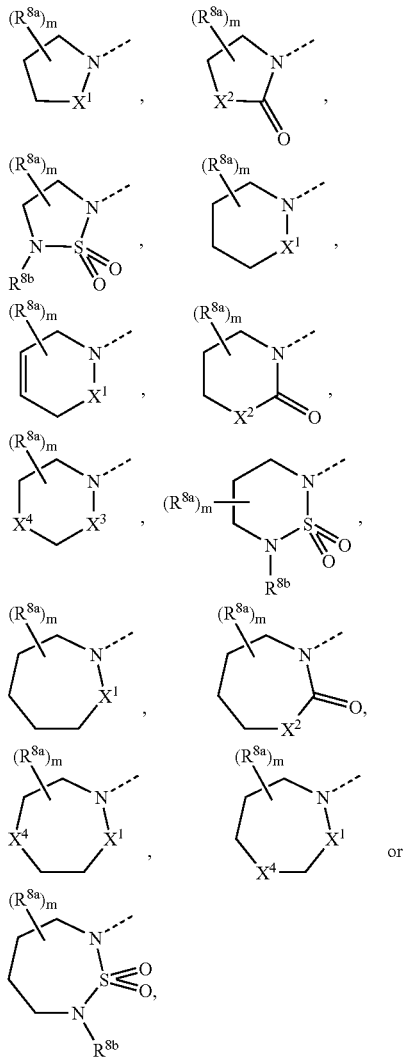

wherein
m is the number 1 or 2,
$R^{8a}$ each independently of one another denote a hydrogen or fluorine atom or a $C_{1-5}$-alkyl, hydroxy, hydroxy-$C_{1-5}$-alkyl, $C_{1-5}$-alkoxy, $C_{1-5}$-alkoxy-$C_{1-5}$-alkyl, amino, $C_{1-5}$-alkylamino, di-($C_{1-5}$-alkyl)-amino, amino-$C_{1-5}$-alkyl, $C_{1-5}$-alkylamino-$C_{1-5}$-alkyl, di-($C_{1-5}$-alkyl)-amino-$C_{1-5}$-alkyl, aminocarbonyl, $C_{1-5}$-alkylaminocarbonyl, di-($C_{1-5}$-alkyl)-aminocarbonyl or $C_{1-5}$-alkylcarbonylamino group, while in the previously mentioned substituted 5- to 7-membered groups A the heteroatoms F, O or N optionally introduced with $R^{8a}$ as substituent are not separated by precisely one carbon atom from a heteroatom selected from among N, O, S,
$R^{8b}$ each independently of one another denote a hydrogen atom or a $C_{1-5}$-alkyl group,
$X^1$ denotes a carbonyl, thiocarbonyl, C=$NR^{8c}$, C=N—$OR^{8c}$, C=N—$NO_2$, C=N—CN or sulphonyl group,
$R^{8c}$ each independently of one another denote a hydrogen atom, a $C_{1-5}$-alkyl, $C_{1-5}$-alkylcarbonyl, $C_{1-5}$-alkyloxycarbonyl or $C_{1-5}$-alkylsulphonyl group,
$X^2$ denotes an oxygen atom or a —$NR^{8b}$ group,
$X^3$ denotes a carbonyl, thiocarbonyl, C=$NR^{8c}$C, C=N—$OR^{8c}$, C=N—$NO_2$, C=N—CN or sulphonyl group,
$X^4$ denotes an oxygen or sulphur atom or a —$NR^{8c}$ group,
$R^1$ denotes a fluorine, chlorine, bromine or iodine atom, a $C_{1-3}$-alkyl or $C_{1-3}$-alkoxy group, while the hydrogen atoms of the $C_{1-3}$-alkyl or $C_{1-3}$-alkoxy group may optionally be wholly or partly replaced by fluorine atoms, a $C_{2-3}$-alkenyl, $C_{2-3}$-alkynyl, nitrile, nitro or amino group,
$R^2$ denotes a hydrogen or halogen atom or a $C_{1-3}$-alkyl group,
$R^3$ denotes a hydrogen atom or a $C_{1-3}$-alkyl group,
$R^4$ and $R^5$ in each case independently of one another denote a hydrogen atom, a $C_{2-6}$-alkenyl or $C_{2-6}$-alkynyl group, a straight-chain or branched $C_{1-6}$-alkyl group,
while the hydrogen atoms of the straight-chain or branched $C_{1-6}$-alkyl group may optionally be wholly or partly replaced by fluorine atoms, and may optionally be substituted by a $C_{3-5}$-cycloalkyl group, a nitrile, hydroxy, a $C_{1-5}$-alkyloxy group, while the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-5}$-alkyloxy, $C_{1-5}$-alkyloxycarbonyl-$C_{1-5}$-alkyloxy, mercapto, $C_{1-5}$-alkylsulphanyl, $C_{1-5}$-alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, aminosulphonyl, $C_{1-5}$-alkylaminosulphonyl, di-($C_{1-5}$-alkyl)-aminosulphonyl, $C_{3-6}$-cycloalkyleneiminosulphonyl, amino, $C_{1-5}$-alkylamino, di-($C_{1-5}$-alkyl)-amino, $C_{1-5}$-alkylcarbonylamino, $C_{1-5}$-alkylsulphonylamino, N-($C_{1-5}$-alkylsulphonyl)-$C_{1-5}$-alkylamino or $C_{3-6}$-cycloalkylcarbonylamino group,
a carboxy, aminocarbonyl, $C_{1-5}$-alkylaminocarbonyl, $C_{3-6}$-cycloalkylaminocarbonyl, di-($C_{1-5}$-alkyl)-aminocarbonyl, $C_{1-5}$-alkoxycarbonyl, $C_{4-6}$-cycloalkyleneiminocarbonyl group,
a phenyl, heteroaryl, phenyl-$C_{1-5}$-alkyl or heteroaryl-$C_{1-5}$-alkyl group,
which may optionally be mono- to trisubstituted in the phenyl or heteroaryl moiety by identical or different substituents selected from among halogen atoms, $C_{1-5}$-alkyl, di-($C_{1-5}$-alkyl)-amino, hydroxy, $C_{1-5}$-alkyloxy, mono-, di- or trifluoromethoxy, carboxy- and $C_{1-5}$-alkyloxycarbonyl groups,
a 3- to 7-membered cycloalkyl, cycloalkyleneimino, cycloalkyl-$C_{1-5}$-alkyl or cycloalkyleneimino-$C_{1-3}$-alkyl group,
while in 4- to 7-membered cyclic groups in the cyclic moiety a methylene group may optionally be replaced by an —N($R^{8c}$) group, an oxygen or sulphur atom or a —S(O) or —S(O)$_2$ group, or
in 4- to 7-membered cyclic groups in the cyclic moiety two adjacent methylene groups together may optionally be replaced by a —C(O)N($R^{8b}$) or —S(O)$_2$N($R^{8b}$) group, or
wherein in 6- to 7-membered cyclic groups in the cyclic moiety three adjacent methylene groups together may optionally be replaced by a substituted —OC(O)N($R^{8b}$) or —N($R^{8b}$)C(O)N($R^{8b}$) or —N($R^{8b}$)S(O)$_2$N($R^{8b}$) group, with the proviso that a 3- to 7-membered cycloalkyl, cycloalkyleneimino, cycloalkyl-$C_{1-5}$-alkyl or cycloalkyleneimino-$C_{1-3}$-alkyl group as hereinbefore defined wherein two heteroatoms from the group oxygen and nitrogen are separated from one another by precisely one optionally substituted —CH$_2$ group, is excluded, while a 3- to 7-membered cycloalkyl, cycloalkyleneimino, cycloalkyl-$C_{1-5}$-alkyl or cycloalkyleneimino-$C_{1-3}$-alkyl group as hereinbefore defined may be substituted at one or two —CH$_2$ groups by one or two $C_{1-3}$-alkyl groups in each case, or $R^4$ and $R^5$ together with the carbon atom to which they are bound form a $C_{3-8}$-cycloalkyl or $C_{3-8}$-cycloalkenyl group, while a $C_{3-8}$-cycloalkyl or $C_{4-8}$-cycloalkenyl group may be substituted at an individual carbon atom by a $C_{2-5}$-alkylene group or simultaneously at two different carbon atoms by a $C_{1-4}$-alkylene group forming a corresponding spirocyclic group or a bridged bicyclic group, while one of the methylene groups of a $C_{4-8}$-cycloalkyl or $C_{5-8}$-cycloalkenyl group or a corresponding spirocyclic group as described above or a corresponding bridged bicyclic group may be replaced by an oxygen or sulphur atom or an —N($R^{8c}$), or a carbonyl, sulphynyl or sulphonyl group, and/or two directly adjacent methylene groups of a $C_{4-8}$-cycloalkyl group may together be replaced by a —C(O)N($R^{8b}$), —C(O)O— or —S(O)$_2$N($R^{8b}$) group, and/or three directly adjacent methylene groups of a $C_{6-8}$-cycloalkyl group may together be replaced by a —OC(O)N($R^{8b}$), —N($R^{8b}$)C(O)N($R^{8b}$) or —N($R^8$b)S(O)$_2$N($R^{8b}$) group, while 1 to 3 carbon atoms of a $C_{3-8}$-cycloalkyl group or a corresponding spirocyclic group as described above or a corresponding bridged bicyclic group may optionally be substituted independently of one another by in each case one or two fluorine atoms or one or two identical or different $C_{1-5}$-alkyl, nitrile, hydroxy, $C_{1-5}$-alkyloxy, $C_{1-5}$-alkylcarbonyloxy, carboxy-$C_{1-5}$-alkyl, $C_{1-5}$-alkyloxycarbonyl-$C_{1-5}$-alkyl, $C_{1-5}$-alkylsulphanyl, $C_{1-5}$-alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, aminosulphonyl, $C_{1-5}$-alkylaminosulphonyl, di-($C_{1-5}$-alkyl)-aminosulphonyl, $C_{3-6}$-cycloalkyleneiminosulphonyl, amino, $C_{1-5}$-alkylamino, di-($C_{1-5}$-alkyl)-amino, $C_{1-5}$-alkylcarbonylamino, $C_{1-5}$-alkyl-sulphonylamino, N-($C_{1-5}$-alkylsulphonyl)-$C_{1-5}$-alkylamino or $C_{3-6}$-cycloalkylcarbonylamino groups, while 1 to 2 carbon atoms of a $C_{3-8}$-cycloalkenyl group may optionally be substituted independently of one another by a $C_{1-5}$-alkyl, nitrile, carboxy-$C_{1-5}$-alkyl, $C_{1-5}$-alkyloxycarbonyl-$C_{1-5}$-alkyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, aminosulphonyl, $C_{1-5}$-alkylaminosulphonyl, di-($C_{1\ \ \ \ 5}$-alkyl)-aminosulphonyl, $C_{3-6}$-cycloalkyleneiminosulphonyl groups, and 1 to 2 carbon atoms of a $C_{4-8}$-cycloalkenyl group which are not bound to another carbon atom by a double bond may optionally be substituted independently of one another by one or two fluorine atoms or a hydroxy, $C_{1-5}$-alkyloxy, $C_{1-5}$-alkylcarbonyloxy, $C_{1-5}$-alkylsulphanyl, $C_{1-5}$-alkylsulphonyl, amino, $C_{1-5}$-alkylamino, di-($C_{1-5}$-alkyl)-amino, $C_{1-5}$-alkylcarbonylamino, $C_{1-5}$-alkyl-sulphonylamino, N—($C_{1-5}$-alkylsulphonyl)-$C_{1-5}$-alkylamino or $C_{3-4}$-cycloalkylcarbonylamino groups, with the proviso that a $C_{3-8}$-cycloalkyl or $C_{3-8}$-cycloalkenyl group of this kind formed from $R^4$ and $R^5$ together or a corresponding spirocyclic group as described above or a corresponding bridged bicyclic group, wherein two heteroatoms in the cyclic group selected from among oxygen and nitrogen are separated from one another by precisely one optionally substituted —CH$_2$ group, and/or wherein one or both methylene groups of the cyclic group which are directly connected to the carbon atom to which the groups $R^4$ and $R^5$ are bound, are replaced by a heteroatom selected from among oxygen, nitrogen and sulphur, and/or wherein a substituent bound to the cyclic group, which is characterised in that a heteroatom selected from among oxygen, nitrogen, sulphur and halogen atom is bound directly to the cyclic group, is separated from another heteroatom selected from among oxygen, nitrogen and sulphur, with the exception of the sulphone group, by precisely one, optionally substituted, methylene group, and/or wherein two oxygen atoms are joined together directly, and/or wherein a heteroatom selected from among oxygen, nitrogen and sulphur is linked directly to a carbon atom, which is linked to another carbon atom by a double bond, and/or which contains a cyclic group with three ring members, of which one or more corresponds to an oxygen or sulphur atom or —N($R^{8c}$) group, is excluded, $R^6$ denotes a fluorine, chlorine, bromine or iodine atom, a nitrile group, a $C_{1-3}$-alkyl group, or a $C_{1-3}$-alkoxy group, while the hydrogen atoms of the $C_{1-3}$-alkyl or $C_{1-3}$-alkoxy group may be wholly or partly replaced by fluorine atoms, $R^7$ independently of one another denote a $C_{1-3}$-alkyl, while the hydrogen atoms may optionally be wholly or partly replaced by fluorine atoms, hydroxy, $C_{1-3}$-alkyloxy, while the hydrogen atoms may optionally be wholly or partly replaced by fluorine atoms, amino, $C_{1-3}$-alkylamino, di-($C_{1-3}$-alkyl)-amino, $C_{3-6}$-cycloalkyleneimino, carboxy, nitrile, $C_{1-3}$-alkoxycarbonyl, aminocarbonyl, $C_{1-3}$-alkylaminocarbonyl or a di-($C_{1-3}$-alkyl)-aminocarbonyl group, while, unless otherwise stated, by the term "heteroaryl group" mentioned hereinbefore in the definitions is meant a monocyclic 5- or 6-membered heteroaryl group, while the 6-membered heteroaryl group contains one, two or three nitrogen atoms and the 5-membered heteroaryl group contains an imino group optionally substituted by a $C_{1-3}$-alkyl, phenyl or phenyl-$C_{1-3}$-alkyl group, an oxygen or sulphur atom or an imino group optionally substituted by a $C_{1-3}$-alkyl, phenyl, amino-$C_{2-3}$-alkyl, $C_{1-3}$-alkylamino-$C_{2-3}$-alkyl, di-($C_{1-3}$-alkyl)-amino-$C_{2-3}$-alkyl, a $C_{3-6}$-cycloalkyleneimino-$C_{1-3}$-alkyl or phenyl-$C_{1-3}$-alkyl group or an oxygen or sulphur atom and additionally a nitrogen atom or an imino group optionally substituted by a $C_{1-3}$-alkyl or phenyl-$C_{1-3}$-alkyl group and two or three nitrogen atoms, and the above-mentioned monocyclic heteroaryl groups in the carbon skeleton may be substituted by one or two groups $R^7$, and moreover a phenyl ring optionally substituted by a fluorine, chlorine or bromine atom or a group $R^7$ may be fused to the above-mentioned monocyclic heteroaryl groups via two adjacent carbon atoms and the bond is effected via a nitrogen atom or a carbon atom of the heterocyclic moiety or a fused-on phenyl ring, while, unless otherwise stated, by the term "halogen atom" mentioned hereinbefore in the definitions is meant an atom selected from among fluorine, chlorine, bromine and iodine, while, unless otherwise stated, the alkyl, alkenyl, alkynyl and alkoxy groups contained in the foregoing definitions which have more than two carbon atoms may be straight-chain or branched and the alkyl groups in the previously mentioned dialkylated groups, for example the dialkylamino groups, may be identical or different, and the hydrogen atoms of the methyl or ethyl groups contained in the foregoing definitions, unless otherwise stated, may be wholly or partly replaced by fluorine atoms, the tautomers, the enantiomers, the diastereomers, the mixtures thereof and the salts thereof.

An 11th embodiment of the present invention comprises those compounds of general formula I, wherein A denotes a group of general formula

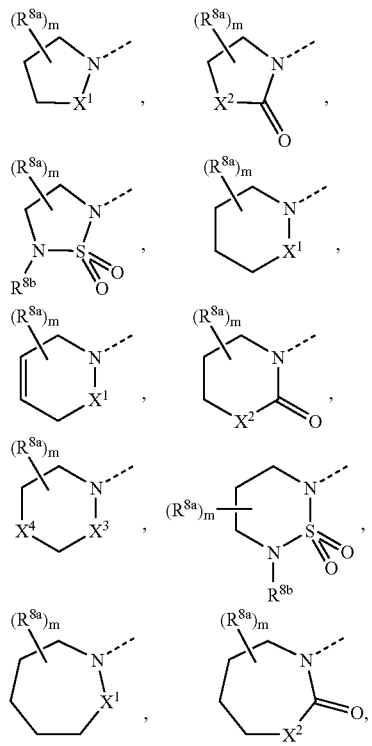

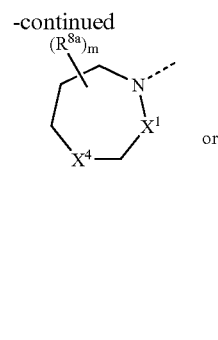

wherein m is the number 1 or 2, $R^{8a}$ each independently of one another denote a hydrogen or fluorine atom or a $C_{1-5}$-alkyl, hydroxy, hydroxy-$C_{1-5}$-alkyl, $C_{1-5}$-alkoxy, $C_{1-5}$-alkoxy-$C_{1-5}$-alkyl, amino, $C_{1-5}$-alkylamino, di-($C_{1-5}$-alkyl)-amino, amino-$C_{1-5}$-alkyl, $C_{1-5}$-alkylamino-$C_{1-5}$-alkyl, di-($C_{1-5}$-alkyl)-amino-$C_{1-5}$-alkyl, aminocarbonyl, $C_{1-5}$-alkylaminocarbonyl, di-($C_{1-5}$-alkyl)-aminocarbonyl or $C_{1-5}$-alkylcarbonylamino group, while in the previously mentioned substituted 5- to 7-membered groups A the heteroatoms F, O or N optionally introduced with $R^{8a}$ as substituent are not separated by precisely one carbon atom from a heteroatom selected from among N, O, S, $R^{8b}$ each independently of one another denote a hydrogen atom or a $C_{1-5}$-alkyl group, $X^1$ denotes a carbonyl, thiocarbonyl, C=$NR^{8c}$, C=N—$OR^{8c}$, C=N——$NO_2$, C=N—CN or sulphonyl group, $R^{8c}$ each independently of one another denote a hydrogen atom, a $C_{1-5}$-alkyl, $C_{1-5}$-alkylcarbonyl, $C_{1-5}$-alkyloxycarbonyl or $C_{1-5}$-alkylsulphonyl group, $X^2$ denotes an oxygen atom or a —$NR^{8b}$ group, $X^3$ denotes a carbonyl, thiocarbonyl, C=$NR^{8c}$, C=N—$OR^{8c}$, C=N—$NO_2$, C=N—CN or sulphonyl group, $X^4$ denotes an oxygen atom or a —$NR^{8c}$ group, $R^1$ denotes a fluorine, chlorine, bromine or iodine atom, a $C_{1-3}$-alkyl or $C_{1-3}$-alkoxy group, while the hydrogen atoms of the $C_{1-3}$-alkyl or $C_{1-3}$-alkoxy group may optionally be wholly or partly replaced by fluorine atoms, or a nitrile group, $R^2$ denotes a hydrogen or halogen atom or a methyl group, $R^3$ denotes a hydrogen atom or a methyl group, $R^4$ denotes a $C_{2-6}$-alkenyl or $C_{2-6}$-alkynyl group, a straight-chain or branched $C_{1-6}$-alkyl group, while the hydrogen atoms of the straight-chain or branched $C_{1-6}$-alkyl group may optionally be wholly or partly replaced by fluorine atoms, and may optionally be substituted by a $C_{3-5}$-cycloalkyl group, a nitrile, hydroxy, a $C_{1-5}$-alkyloxy group, while the hydrogen atoms of the $C_{1-5}$-alkyloxy group may optionally be wholly or partly replaced by fluorine atoms, a benzyloxy, $C_{1-5}$-alkylcarbonyloxy, $C_{1-5}$-alkyloxycarbonyloxy, carboxy-$C_{1-5}$-alkyloxy, $C_{1-5}$-alkyloxycarbonyl-$C_{1-5}$-alkyloxy, $C_{1-5}$-alkylsulphanyl, $C_{1-5}$-alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, aminosulphonyl, $C_{1-5}$-alkylaminosulphonyl, di-($C_{1-5}$-alkyl)-aminosulphonyl, $C_{3-6}$-cycloalkyleneiminosulphonyl, amino, $C_{1-5}$-alkylamino, di-($C_{1-5}$- alkyl)-amino, $C_{1-5}$-alkylcarbonylamino, $C_{1-5}$-alkylsulphonylamino, or an N-($C_{1-5}$-alkylsulphonyl)-$C_{1-5}$-alkylamino group, a carboxy, aminocarbonyl, $C_{1-5}$-alkylaminocarbonyl, $C_{3-6}$-cycloalkylamino-carbonyl, di-($C_{1-5}$-alkyl)-aminocarbonyl, $C_{1-5}$-alkoxycarbonyl, $C_{4-6}$-cycloalkyleneiminocarbonyl group, a phenyl, heteroaryl, phenyl-$C_{1-5}$-alkyl or heteroaryl-$C_{1-5}$-alkyl group,
  which may optionally be mono- to trisubstituted in the phenyl or heteroaryl moiety by identical or different substituents selected from among halogen atoms, $C_{1-5}$-alkyl, di-($C_{1-5}$-alkyl)-amino, hydroxy, $C_{1-5}$-alkyloxy, mono-, di- or trifluoromethoxy, carboxy and $C_{1-5}$-alkyloxycarbonyl groups, a 3- to 7-membered cycloalkyl, cycloalkyleneimino, cycloalkyl-$C_{1-5}$-alkyl or cycloalkyleneimino-$C_{1-3}$-alkyl group,
  while in 4- to 7-membered cyclic groups in the cyclic moiety a methylene group may optionally be replaced by an —N($R^{8c}$) group, an oxygen or sulphur atom or a —S(O) or —S(O)$_2$ group, or
  in 4- to 7-membered cyclic groups in the cyclic moiety two adjacent methylene groups may together optionally be replaced by a —C(O)N($R^{8b}$) or —S(O)$_2$N($R^{8b}$) group, or
  wherein in 6- to 7-membered cyclic groups in the cyclic moiety three adjacent methylene groups may together optionally be replaced by a substituted —OC(O)N($R^{8b}$) or —N($R^{8b}$)C(O)N($R^{8b}$) or —N($R^{8b}$)S(O)$_2$N($R^{8b}$) group,
  with the proviso that a 3- to 7-membered cycloalkyl, cycloalkyleneimino, cycloalkyl-$C_{1-5}$-alkyl or cycloalkyleneimino-$C_{1-3}$-alkyl group as hereinbefore defined wherein two heteroatoms from the group oxygen and nitrogen are separated from one another by precisely one optionally substituted —CH$_2$ group, is excluded,
  while a 3- to 7-membered cycloalkyl, cycloalkyleneimino, cycloalkyl-$C_{1-5}$-alkyl or cycloalkyleneimino-$C_{1-3}$-alkyl group as hereinbefore defined may be substituted at one or two —CH$_2$ groups by one or two $C_{1-3}$-alkyl groups in each case, $R^5$ denotes a hydrogen atom, a $C_{2-6}$-alkenyl or $C_{2-6}$-alkynyl group, a straight-chain or branched $C_{1-6}$-alkyl group,
  while the hydrogen atoms of the straight-chain or branched $C_{1-6}$-alkyl group may optionally be wholly or partly replaced by fluorine atoms, and may optionally be substituted by a $C_{1-5}$-alkyloxy group, while the hydrogen atoms of the $C_{1-5}$-alkyloxy group may optionally be wholly or partly replaced by fluorine atoms, or $R^4$ and $R^5$ together with the carbon atom to which they are bound form a $C_{3-8}$-cycloalkyl or $C_{3-8}$-cycloalkenyl group,
  while a $C_{3-8}$-cycloalkyl or $C_{4-8}$-cycloalkenyl group may be substituted at an individual carbon atom by a $C_{2-5}$-alkylene group or simultaneously at two different carbon atoms by a $C_{1-4}$-alkylene group forming a corresponding spirocyclic group or a bridged bicyclic group,
  while one of the methylene groups of a $C_{4-8}$-cycloalkyl or $C_{5-8}$-cycloalkenyl group or a corresponding spirocyclic group as described above or a corresponding bridged bicyclic group may be replaced by an oxygen or sulphur atom or an -N(R8c), or a carbonyl, or sulphonyl group, and/or two directly adjacent methylene groups of a $C_{4-8}$-cycloalkyl group may together be replaced by a —C(O)N($R^{8b}$), —C(O)O— or —S(O)$_2$N($R^{8b}$) group, and/or three directly adjacent methylene groups of a $C_{6-8}$-cycloalkyl group may together be replaced by a —OC(O)N($R^{8b}$), —N($R^{8b}$)C(O)N($R^{8b}$) or —N($R^{8b}$)S(O)$_2$N($R^{8b}$) group, while 1 to 3 carbon atoms of a $C_{3-8}$-cycloalkyl group or a corresponding spirocyclic group as described above or a corresponding bridged bicyclic group may optionally be substituted independently of one another by in each case one or two fluorine atoms or one or two identical or different $C_{1-5}$-alkyl, nitrile, hydroxy, $C_{1-5}$-alkyloxy, $C_{1-5}$-alkylcarbonyloxy, carboxy-$C_{1-5}$-alkyl, $C_{1-5}$-alkyloxycarbonyl-$C_{1-5}$-alkyl, $C_{1-5}$-alkylsulphanyl, $C_{1-5}$-alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, aminosulphonyl, $C_{1-5}$-alkylaminosulphonyl, di-($C_{1-5}$-alkyl)-aminosulphonyl, $C_{3-6}$-cycloalkyleneiminosulphonyl, amino, $C_{1-5}$-alkylamino, di-($C_{1-5}$-alkyl)-amino, $C_{1-5}$-alkylcarbonylamino, $C_{1-5}$-alkyl-sulphonylamino, or N-($C_{1-5}$-alkylsulphonyl)-$C_{1-5}$-alkylamino groups, while 1 to 2 carbon atoms of a $C_{3-8}$-cycloalkenyl group may optionally be substituted independently of one another by a $C_{1-5}$-alkyl, nitrile, carboxy-$C_{1-5}$-alkyl, $C_{1-5}$-alkyloxycarbonyl-$C_{1-5}$-alkyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, aminosulphonyl, $C_{1-5}$-alkylaminosulphonyl, di-($C_{1-5}$-alkyl)-aminosulphonyl, $C_{3-6}$-cycloalkyleneiminosulphonyl group, and 1 to 2 carbon atoms of a $C_{4-8}$-cycloalkenyl group which are not bound to another carbon atom by a double bond may optionally be substituted independently of one another by one or two fluorine atoms or a hydroxy, $C_{1-5}$-alkyloxy, $C_{1-5}$-alkylcarbonyloxy, $C_{1-5}$-alkylsulphanyl, $C_{1-5}$-alkylsulphonyl, amino, $C_{1-5}$-alkylamino, di-($C_{1-5}$-alkyl)-amino, $C_{1-5}$-alkylcarbonylamino, $C_{1-5}$-alkyl-sulphonylamino, N-($C_{1-5}$-alkylsulphonyl)-$C_{1-5}$-alkylamino or $C_{3-4}$-cycloalkylcarbonylamino groups, with the proviso that a $C_{3-8}$-cycloalkyl or $C_{3-8}$-cycloalkenyl group of this kind, formed together from $R^4$ and $R^5$ or a corresponding spirocyclic group as described above or a corresponding bridged bicyclic group,
  wherein two heteroatoms in the cyclic group selected from among oxygen and nitrogen are separated from one another by precisely one optionally substituted —CH$_2$ group, and/or
  wherein one or both methylene groups of the cyclic group which are directly connected to the carbon atom to which the groups $R^4$ and $R^5$ are bound, are replaced by a heteroatom selected from among oxygen, nitrogen and sulphur, and/or
  wherein a substituent bound to the cyclic group, which is characterised in that a heteroatom selected from among oxygen, nitrogen, sulphur and halogen atom is bound directly to the cyclic group, is separated from another heteroatom selected from among oxygen, nitrogen and sulphur, with the exception of the sulphone group, by precisely one, optionally substituted, methylene group, and/or
  wherein two oxygen atoms are joined together directly, and/or wherein a heteroatom selected from among oxygen, nitrogen and sulphur is linked directly to a carbon atom, which is linked to another carbon atom by a double bond, and/or
which contains a cyclic group with three ring members, of which one or more corresponds to an oxygen or sulphur atom or an —N($R^{8c}$) group,
is excluded, $R^6$ denotes a fluorine, chlorine, bromine or iodine atom, a nitrile group, a $C_{1-3}$-alkyl group, or a $C_{1-3}$-alkoxy group, while the hydrogen atoms of the $C_{1-3}$-alkyl or $C_{1-3}$-alkoxy group may optionally be wholly or partly replaced by fluorine atoms, $R^7$ independently of one another denote a $C_{1-3}$-alkyl, while the hydrogen atoms may optionally be wholly or partly replaced by fluorine atoms, hydroxy, $C_{1-3}$-alkyloxy, while the hydrogen atoms may optionally be wholly or partly replaced by fluorine atoms, amino, $C_{1-3}$-alkylamino, di-($C_{1-3}$-alkyl)-amino, $C_{3-6}$-cycloalkyleneimino, carboxy, nitrile, $C_{1-3}$-alkoxycarbonyl, aminocarbonyl, $C_{1-3}$-alkylaminocarbonyl or a di-($C_{1-3}$-alkyl)-aminocarbonyl group, while, unless otherwise stated, by the term "heteroaryl group" mentioned hereinbefore in the definitions is meant a monocyclic 5- or 6-membered heteroaryl group, while
the 6-membered heteroaryl group contains one, two or three nitrogen atoms and
the 5-membered heteroaryl group contains an imino group optionally substituted by a $C_{1-3}$-alkyl, phenyl or phenyl-$C_{1-3}$-alkyl group, an oxygen or sulphur atom or
an imino group optionally substituted by a $C_{1-3}$-alkyl, phenyl, amino-$C_{2-3}$-alkyl, $C_{1-3}$-alkylamino-$C_{2-3}$-alkyl, di-($C_{1-3}$-alkyl)-amino-$C_{2-3}$-alkyl, a $C_{3-6}$-cycloalkyleneimino-$C_{1-3}$-alkyl or phenyl-$C_{1-3}$-alkyl group or an oxygen or sulphur atom and additionally a nitrogen atom or an imino group optionally substituted by a $C_{1-3}$-alkyl or phenyl-$C_{1-3}$-alkyl group and two or three nitrogen atoms,
and moreover a phenyl ring optionally substituted by a fluorine, chlorine or bromine atom, a $C_{1-3}$-alkyl, hydroxy, $C_{1-3}$-alkyloxy group, amino, $C_{1-3}$-alkylamino, di-($C_{1-3}$-alkyl)-amino or $C_{3-6}$-cycloalkyleneimino group may be fused to the above-mentioned monocyclic heteroaryl groups via two adjacent carbon atoms
and the bond is effected via a nitrogen atom or a carbon atom of the heterocyclic moiety or a fused-on phenyl ring, while, unless otherwise stated, by the term "halogen atom" mentioned hereinbefore in the definitions is meant an atom selected from among fluorine, is chlorine, bromine and iodine, while, unless otherwise stated, the alkyl, alkenyl, alkynyl and alkoxy groups contained in the foregoing definitions which have more than two carbon atoms may be straight-chain or branched and the alkyl groups in the previously mentioned dialkylated groups, for example the dialkylamino groups, may be identical or different, and the hydrogen atoms of the methyl or ethyl groups contained in the foregoing definitions, unless otherwise stated, may be wholly or partly replaced by fluorine atoms, the tautomers, the enantiomers, the diastereomers, the mixtures thereof and the salts thereof.

A 12th embodiment of the present invention comprises those compounds of general formula I, wherein A denotes a group of general formula

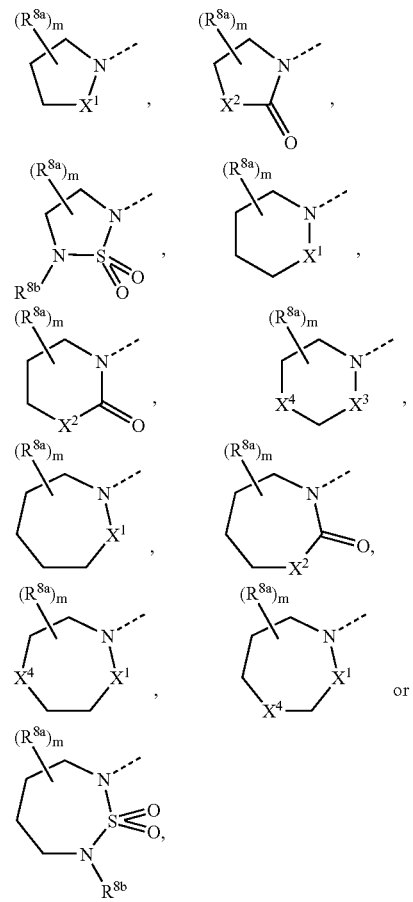

wherein
m is the number 1 or 2,
$R^{8a}$ each independently of one another denote a hydrogen or fluorine atom or a $C_{1-3}$-alkyl, hydroxy, hydroxy-$C_{1-3}$-alkyl, $C_{1-3}$-alkoxy, $C_{1-3}$-alkoxy-$C_{1-3}$-alkyl, amino, $C_{1-3}$-alkylamino, di-($C_{1-3}$-alkyl)-amino, amino-$C_{1-3}$-alkyl, $C_{1-3}$-alkylamino-$C_{1-3}$-alkyl, di-($C_{1-3}$-alkyl)-amino-$C_{1-3}$-alkyl, aminocarbonyl, $C_{1-3}$-alkylaminocarbonyl, di-($C_{1-3}$-alkyl)-aminocarbonyl or $C_{1-3}$-alkylcarbonylamino group, while in the previously mentioned substituted 5- to 7-membered groups A the heteroatoms F, Cl, Br, I, O or N optionally introduced with $R^{8a}$ as substituent are not separated by precisely one carbon atom from a heteroatom selected from among N, O, S, $R^{8b}$ each independently of one another denote a hydrogen atom or a $C_{1-3}$-alkyl group, $X^1$ denotes a carbonyl, thiocarbonyl, C=$NR^{8c}$, C=N—$OR^{8c}$, C=N—$NO_2$, C=N—CN or sulphonyl group, $R^{8c}$ each independently of one another denote a hydrogen atom, a $C_{1-3}$-alkyl, $C_{1-3}$-alkylcarbonyl, $C_{1-4}$-alkyloxycarbonyl or $C_{1-3}$-alkylsulphonyl group, $X^2$ denotes an oxygen atom or a —$NR^{8b}$ group, $X^3$ denotes a carbonyl, thiocarbonyl, C=$NR^{8c}$, C=N—$OR^{8c}$, C=N—$NO_2$, C=N—CN or sulphonyl group, $X^4$ denotes an oxygen atom or a —$NR^{8c}$ group, $R^1$ denotes a fluorine, chlorine, bromine or iodine atom, a $C_{1-3}$-alkyl or a $C_{1-3}$-alkoxy group, while the hydrogen atoms of the $C_{1-3}$-alkyl or $C_{1-3}$-alkoxy group may optionally be wholly or partly replaced by fluorine atoms, $R^2$ denotes a hydrogen or halogen atom or a methyl group, $R^3$ denotes a hydrogen atom, $R^4$ denotes a $C_{2-4}$-alkenyl or $C_{2-4}$-alkynyl group, a straight-chain or branched $C_{1-4}$-alkyl group, while the hydrogen atoms of the straight-chain or branched $C_{1-4}$-alkyl group may optionally be wholly or partly replaced by fluorine atoms, and may optionally be substituted by a $C_{3-5}$-cycloalkyl group, a nitrile, hydroxy, a $C_{1-3}$-alkyloxy group, while the hydrogen atoms of the $C_{1-3}$-alkyloxy group may optionally be wholly or partly replaced by fluorine atoms, a benzyloxy, $C_{1-3}$-alkylcarbonyloxy, $C_{1-3}$-alkyloxycarbonyl-$C_{1-3}$-alkyloxy, $C_{1-3}$-alkyloxycarbonyl, aminocarbonyl, $C_{1-3}$-alkylaminocarbonyl, di-($C_{1-3}$-alkyl)-aminocarbonyl, $C_{3-6}$-cycloalkyleneiminocarbonyl, aminosulphonyl, $C_{1-3}$-alkylaminosulphonyl, di-($C_{1-3}$-alkyl)-aminosulphonyl, $C_{3-6}$-cycloalkyleneiminosulphonyl, amino, $C_{1-3}$-alkylamino, di-($C_{1-3}$-alkyl)-amino, $C_{1-3}$-alkylcarbonylamino, $C_{1-3}$-alkyl-sulphonylamino, or an N-($C_{1-3}$-alkylsulphonyl)-$C_{1-3}$-alkylamino group, a phenyl, heteroaryl, phenyl-$C_{1-3}$-alkyl or heteroaryl-$C_{1-3}$-alkyl group, which may optionally be mono- to trisubstituted in the phenyl or heteroaryl moiety by identical or different substituents selected from among halogen atoms, $C_{1-3}$-alkyl, di-($C_{1-3}$-alkyl)-amino, hydroxy, $C_{1-3}$-alkyloxy, mono-, di- or trifluoromethoxy, carboxy- and $C_{1-3}$-alkyloxycarbonyl groups, $R^5$ denotes a hydrogen atom, a $C_{2-4}$-alkenyl or $C_{2-4}$-alkynyl group, a straight-chain or branched $C_{1-4}$-alkyl group, while the hydrogen atoms of the straight-chain or branched $C_{1-4}$-alkyl group may optionally be wholly or partly replaced by fluorine atoms, and may optionally be substituted by a $C_{1-3}$-alkyloxy group, while the hydrogen atoms of the $C_{1-3}$-alkyloxy group may optionally be wholly or partly replaced by fluorine atoms, or $R^4$ and $R^5$ together with the carbon atom to which they are bound form a $C_{3-8}$-cycloalkyl or $C_{3-8}$-cycloalkenyl group, while a $C_{3-8}$-cycloalkyl or $C_{4-8}$-cycloalkenyl group may be substituted at an individual carbon atom by a $C_{2-5}$-alkylene group or simultaneously at two different carbon atoms by a $C_{1-4}$-alkylene group forming a corresponding spirocyclic group or a bridged bicyclic group, while one of the methylene groups of a $C_{4-8}$-cycloalkyl or $C_{5-8}$-cycloalkenyl group or a corresponding spirocyclic group as described above or a corresponding bridged bicyclic group may be replaced by an oxygen or sulphur atom or a sulphonyl or —N($R^{8c}$) group, and/or two directly adjacent methylene groups of a $C_{4-8}$-cycloalkyl group may together be replaced by a —C(O)N($R^{8b}$), —C(O)O— or —S(O)$_2$N($R^{8b}$) group, and/or three directly adjacent methylene groups of a $C_{6-8}$-cycloalkyl group may together be replaced by a —OC(O)N($R^{8b}$), —N($R^{8b}$)C(O)N($R^{8b}$) or —N($R^{8b}$)S(O)$_2$N($R^{8b}$) group, while 1 to 3 carbon atoms of a $C_{3-8}$-cycloalkyl group or a corresponding spirocyclic group as described above or a corresponding bridged bicyclic group may optionally be substituted independently of one another by a $C_{1-3}$-alkyl, hydroxy, $C_{1-3}$-alkyloxy, $C_{1-3}$-alkylcarbonyloxy, $C_{1-3}$-alkyloxycarbonyl, amino, $C_{1-3}$-alkylamino, di-($C_{1-3}$-alkyl)-amino, $C_{1-3}$-alkylcarbonylamino, $C_{1-3}$-alkylsulphonylamino groups, while 1 to 2 carbon atoms of a $C_{3-8}$-cycloalkenyl group may optionally be substituted independently of one another by a $C_{1-3}$-alkyl group, and 1 to 2 carbon atoms of a $C_{4-8}$-cycloalkenyl group which are not bound to another carbon atom by a double bond may optionally be substituted independently of one another by a hydroxy, $C_{1-3}$-alkyloxy, di-($C_{1-3}$-alkyl)-amino group, with the proviso that a $C_{3-8}$-cycloalkyl or $C_{3-8}$-cycloalkenyl group of this kind formed together from $R^4$ and $R^5$ or a corresponding spirocyclic group as described above or a corresponding bridged bicyclic group, wherein two heteroatoms in the cyclic group selected from among oxygen and nitrogen are separated from one another by precisely one optionally substituted —CH$_2$ group, and/or wherein one or both methylene groups of the cyclic group which are directly connected to the carbon atom to which the groups $R^4$ and $R^5$ are bound are replaced by a heteroatom selected from among oxygen, nitrogen and sulphur, and/or wherein a substituent bound to the cyclic group, which is characterised in that a heteroatom selected from among oxygen, nitrogen, sulphur and halogen atom is bound directly to the cyclic group, is separated from another heteroatom selected from among oxygen, nitrogen and sulphur, with the exception of the sulphone group, by precisely one, optionally substituted, methylene group, and/or wherein two oxygen atoms are joined together directly, and/or wherein a heteroatom selected from among oxygen, nitrogen and sulphur is linked directly to a carbon atom, which is linked to another carbon atom by a double bond, and/or which contains a cyclic group with three ring members, of which one or more corresponds to an oxygen or sulphur atom or an —N($R^{8c}$) group, is excluded, $R^6$ denotes a fluorine, chlorine, bromine or iodine atom, a methyl group, or a methoxy group, while the hydrogen atoms of the methyl or methoxy group may optionally be wholly or partly replaced by fluorine atoms, $R^7$ independently of one another denote a $C_{1-3}$-alkyl, while the hydrogen atoms may optionally be wholly or partly replaced by fluorine atoms, hydroxy, $C_{1-3}$-alkyloxy, while the hydrogen atoms may optionally be wholly or partly replaced by fluorine atoms, amino, $C_{1-3}$-alkylamino, di-($C_{1-3}$-alkyl)-amino, $C_{3-6}$-cycloalkyleneimino, carboxy, nitrile, $C_{1-3}$-alkoxycarbonyl, aminocarbonyl, $C_{1-3}$-alkylaminocarbonyl or a di-($C_{1-3}$-alkyl)-aminocarbonyl group, while, unless otherwise stated, by the term "heteroaryl group" mentioned hereinbefore in the definitions is meant a monocyclic 5- or 6-membered heteroaryl group, while the 6-membered heteroaryl group contains one, two or three nitrogen atoms and the 5-membered heteroaryl group contains an imino group optionally substituted by a $C_{1-3}$-alkyl, phenyl or phenyl-$C_{1-3}$-alkyl group, an oxygen or sulphur atom or an imino group optionally substituted by a $C_{1-3}$-alkyl, phenyl, amino-$C_{2-3}$-alkyl, $C_{1-3}$-alkylamino-$C_{2-3}$-alkyl, di-($C_{1-3}$-alkyl)-amino-$C_{2-3}$-alkyl, a $C_{3-6}$-cycloalkyleneimino-$C_{1-3}$-alkyl or phenyl-$C_{1-3}$-alkyl group or an oxygen or sulphur atom and additionally a nitrogen atom or an imino group optionally substituted by a $C_{1-3}$-alkyl or phenyl-$C_{1-3}$-alkyl group and two or three nitrogen atoms, and moreover a phenyl ring optionally substituted by a fluorine, chlorine or bromine atom, a $C_{1-3}$-alkyl, hydroxy, $C_{1-3}$-alkyloxy group, amino, $C_{1-3}$-alkylamino, di-($C_{1-3}$-alkyl)-amino or $C_{3-6}$-cycloalkyleneimino group may be fused to the above-mentioned monocyclic heteroaryl groups via two adjacent carbon atoms and the bond is effected via a nitrogen atom or a carbon atom of the heterocyclic moiety or a fused-on phenyl ring, while, unless otherwise stated, by the term "halogen atom" mentioned hereinbefore in the definitions is meant an atom selected from among fluorine, chlorine, bromine and iodine, while, unless otherwise stated, the alkyl, alkenyl, alkynyl and alkoxy groups contained in the foregoing definitions which have more than two carbon atoms may be straight-chain or branched and the alkyl groups in the previously mentioned dialkylated groups, for example the dialkylamino groups, may be identical or different, and the hydrogen atoms of the methyl or ethyl groups contained in the foregoing definitions, unless otherwise stated, may be wholly or partly replaced by fluorine atoms, the tautomers, the enantiomers, the diastereomers, the mixtures thereof and the salts thereof.

A 13th embodiment of the present invention comprises those compounds of general formula I, wherein A denotes a group of general formula

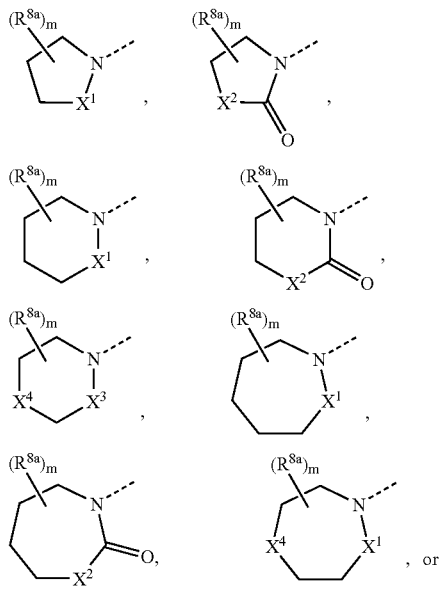

-continued

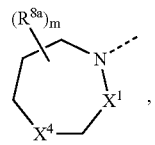

wherein m is the number 1 or 2, $R^{8a}$ each independently of one another denote a hydrogen or fluorine atom or a $C_{1-3}$-alkyl, hydroxy, hydroxy-$C_{1-3}$-alkyl, $C_{1-3}$-alkoxy, $C_{1-3}$-alkoxy-$C_{1-3}$-alkyl, amino, $C_{1-3}$-alkylamino, di-($C_{1-3}$-alkyl)-amino, amino-$C_{1-3}$-alkyl, $C_{1-3}$-alkylamino-$C_{1-3}$-alkyl, or di-($C_{1-3}$-alkyl)-amino-$C_{1-3}$-alkyl group, while in the previously mentioned substituted 5- to 7-membered groups A the heteroatoms F, O or N optionally introduced with $R^{8a}$ as substituent are not separated by precisely one carbon atom from a heteroatom selected from among N, O, S, $R^{8b}$ each independently of one another denote a hydrogen atom or a $C_{1-3}$-alkyl group, $X^1$ denotes a carbonyl, thiocarbonyl, C=$NR^{8c}$, C=N—$OR^{8c}$, C=N—$NO_2$, C=N—CN or sulphonyl group, $R^{8c}$ each independently of one another denote a hydrogen atom, a $C_{1-3}$-alkyl, $C_{1-3}$-alkylcarbonyl, or a $C_{1-4}$-alkyloxycarbonyl group, $X^2$ denotes an oxygen atom or a —$NR^{8b}$ group, $X^3$ denotes a carbonyl, thiocarbonyl, C=$NR^{8c}$, C=N—$OR^{8c}$, C=N—$NO_2$, C=N—CN or sulphonyl group, $X^4$ denotes an oxygen atom or a —$NR^{8c}$ group, $R^1$ denotes a fluorine, chlorine, bromine or iodine atom, a methyl or a methoxy group, while the hydrogen atoms of the methyl or methoxy group may optionally be wholly or partly replaced by fluorine atoms, $R^2$ denotes a hydrogen or fluorine atom or a methyl group, $R^3$ denotes a hydrogen atom, $R^4$ denotes a $C_{2-4}$-alkenyl or $C_{2-4}$-alkynyl group, a straight-chain or branched $C_{1-4}$-alkyl group, while the hydrogen atoms of the straight-chain or branched $C_{1-4}$-alkyl group may optionally be wholly or partly replaced by fluorine atoms, and may optionally be substituted by a nitrile, hydroxy, a $C_{1-3}$-alkyloxy group, while the hydrogen atoms of the $C_{1-3}$-alkyloxy group may optionally be wholly or partly replaced by fluorine atoms, a benzyloxy, $C_{1-3}$-alkylcarbonyloxy, $C_{1-3}$-alkyloxycarbonyl, aminocarbonyl, $C_{1-3}$-alkylaminocarbonyl, di-($C_{1-3}$-alkyl)-aminocarbonyl, $C_{3-6}$-cycloalkyleneiminocarbonyl, aminosulphonyl, $C_{1-3}$-alkylaminosulphonyl, di-($C_{1-3}$-alkyl)-aminosulphonyl, $C_{3-6}$-cycloalkyleneiminosulphonyl, amino, $C_{1-3}$-alkylamino, di-($C_{1-3}$-alkyl)-amino, $C_{1-3}$-alkylcarbonylamino, or $C_{1-3}$-alkylsulphonylamino group, a phenyl, heteroaryl, phenyl-$C_{1-3}$-alkyl or heteroaryl-$C_{1-3}$-alkyl group, which may optionally be mono- to trisubstituted in the phenyl or heteroaryl moiety by identical or different substituents selected from among halogen atoms, $C_{1-3}$-alkyl, di-($C_{1-3}$-alkyl)-amino, hydroxy, $C_{1-3}$-alkyloxy, mono-, di- and trifluoromethoxy groups, $R^5$ denotes a hydrogen atom, a straight-chain or branched $C_{1-4}$-alkyl group, while the hydrogen atoms of the straight-chain or branched $C_{1-4}$-alkyl group may optionally be wholly or partly replaced by fluorine atoms, and may optionally be substituted by a $C_{1-3}$-alkyloxy group, while the hydrogen atoms of the $C_{1-3}$-alkyloxy group may optionally be wholly or partly replaced by fluorine atoms, or $R^4$ and $R^5$ together with the carbon atom to which they are bound form a $C_{3-8}$-cycloalkyl or $C_{4-8}$-cycloalkenyl group, while a $C_{3-8}$-cycloalkyl or $C_{4-8}$-cycloalkenyl group may be substituted at an individual carbon atom by a $C_{2-5}$-alkylene group or may be substituted simultaneously at two different carbon atoms by a $C_{1-4}$-alkylene group forming a corresponding spirocyclic group or a bridged bicyclic group, while one of the methylene groups of a $C_{4-8}$-cycloalkyl or $C_{5-8}$-cycloalkenyl group or a corresponding spirocyclic group as described above or a corresponding bridged bicyclic group may be replaced by an oxygen or sulphur atom or a sulphonyl or —N($R^{8c}$) group, and/or two directly adjacent methylene groups of a $C_{4-8}$-cycloalkyl group may together be replaced by a —C(O)N($R^{8b}$), —C(O)O— or —S(O)$_2$N($R^{8b}$) group, and/or three directly adjacent methylene groups of a $C_{6-8}$-cycloalkyl group may together be replaced by a —C(O)N($R^{8b}$), —N($R^{8b}$)C(O)N($R^{8b}$) or —N($R^{8b}$)S(O)$_2$N($R^{8b}$) group, while 1 to 2 carbon atoms of a $C_{3-8}$-cycloalkyl group or a corresponding spirocyclic group as described above or a corresponding bridged bicyclic group may optionally be substituted independently of one another by a $C_{1-3}$-alkyl, hydroxy, $C_{1-3}$-alkyloxy, $C_{1-3}$-alkylcarbonyloxy, $C_{1-3}$-alkyloxycarbonyl, $C_{1-3}$-alkylamino, di-($C_{1-3}$-alkyl)-amino, $C_{1-3}$-alkylcarbonylamino, $C_{1-3}$-alkylsulphonylamino groups, with the proviso that a $C_{3-8}$-cycloalkyl or $C_{4-8}$-cycloalkenyl group of this kind formed from $R^4$ and $R^5$ together or a corresponding spirocyclic group as described above or a corresponding bridged bicyclic group, wherein two heteroatoms in the cyclic group selected from among oxygen and nitrogen are separated from one another by precisely one optionally substituted —CH$_2$ group, and/or wherein one or both methylene groups of the cyclic group which are directly connected to the carbon atom to which the groups $R^4$ and $R^5$ are bound, are replaced by a heteroatom selected from among oxygen, nitrogen and sulphur, and/or wherein a substituent bound to the cyclic group, which is characterised in that a heteroatom selected from among oxygen, nitrogen, sulphur and halogen atom is bound directly to the cyclic group, is separated from another heteroatom selected from among oxygen, nitrogen and sulphur, with the exception of the sulphone group, by precisely one, optionally substituted, methylene group, and/or wherein two oxygen atoms are joined together directly, and/or wherein a heteroatom selected from among oxygen, nitrogen and sulphur is linked directly to a carbon atom, which is linked to another carbon atom by a double bond, and/or which contains a cyclic group with three ring members, of which one or more corresponds to an oxygen or sulphur atom or an —N($R^{8c}$) group, is excluded, $R^6$ denotes a fluorine, chlorine, bromine or iodine atom, a methyl group, or a methoxy group, while the hydrogen atoms of the methyl or methoxy group may optionally be wholly or partly replaced by fluorine atoms, $R^7$ independently of one another denotes a $C_{1-3}$-alkyl, while the hydrogen atoms may optionally be wholly or partly replaced by fluorine atoms, hydroxy, $C_{1-3}$-alkyloxy, while the hydrogen atoms may optionally be wholly or partly replaced by fluorine atoms, amino, $C_{1-3}$-alkylamino, di-($C_{1-3}$-alkyl)-amino, $C_{3-6}$-cycloalkyleneimino, carboxy, nitrile, $C_{1-3}$-alkoxycarbonyl, aminocarbonyl, $C_{1-3}$-alkylaminocarbonyl or a di-($C_{1-3}$-alkyl)-aminocarbonyl group, while, unless otherwise stated, by the term "heteroaryl group" mentioned hereinbefore in the definitions is meant a monocyclic 5- or 6-membered heteroaryl group, while the 6-membered heteroaryl group contains one, two or three nitrogen atoms and the 5-membered heteroaryl group contains an imino group optionally substituted by a $C_{1-3}$-alkyl, phenyl or phenyl-$C_{1-3}$-alkyl group or an oxygen or sulphur atom or an imino group optionally substituted by a $C_{1-3}$-alkyl, phenyl, amino-$C_{2-3}$-alkyl, $C_{1-3}$-alkylamino-$C_{2-3}$-alkyl, di-($C_{1-3}$-alkyl)-amino-$C_{2-3}$-alkyl, a $C_{3-6}$-cycloalkyleneimino-$C_{1-3}$-alkyl or phenyl-$C_{1-3}$-alkyl group or an oxygen or sulphur atom and additionally a nitrogen atom or an imino group optionally substituted by a $C_{1-3}$-alkyl or phenyl-$C_{1-3}$-alkyl group and two or three nitrogen atoms, and moreover a phenyl ring optionally substituted by a fluorine, chlorine or bromine atom, a $C_{1-3}$-alkyl, hydroxy, $C_{1-3}$-alkyloxy group, amino, $C_{1-3}$-alkylamino, di-($C_{1-3}$-alkyl)-amino or $C_{3-6}$-cycloalkyleneimino group may be fused to the above-mentioned monocyclic heteroaryl groups via two adjacent carbon atoms and the bond is effected via a nitrogen atom or a carbon atom of the heterocyclic moiety or a fused-on phenyl ring, while, unless otherwise stated, by the term "halogen atom" mentioned hereinbefore in the definitions is meant an atom selected from among fluorine, chlorine, bromine and iodine, while, unless otherwise stated, the alkyl, alkynyl and alkoxy groups contained in the foregoing definitions which have more than two carbon atoms may be straight-chain or branched and the alkyl groups in the previously mentioned dialkylated groups, for example the dialkylamino groups, may be identical or different, and, unless otherwise stated, the hydrogen atoms of the methyl or ethyl groups contained in the foregoing definitions may be wholly or partly replaced by fluorine atoms, the tautomers, the enantiomers, the diastereomers, the mixtures thereof and the salts thereof.

A 14th embodiment of the present invention comprises those compounds of general formula I, wherein A denotes a group of general formula

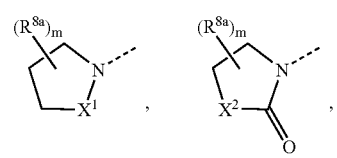

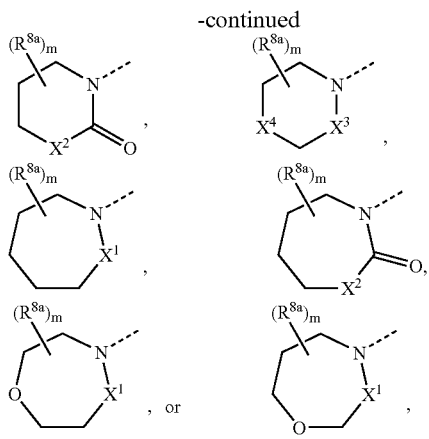

wherein m is the number 1 or 2, $R^{8a}$ each independently of one another denote a hydrogen or fluorine atom or a $C_{1-3}$-alkyl, hydroxy, hydroxy-$C_{1-3}$-alkyl, $C_{1-3}$-alkoxy, $C_{1-3}$-alkoxy-$C_{1-3}$-alkyl, amino, $C_{1-3}$-alkylamino, di-($C_{1-3}$-alkyl)-amino, amino-$C_{1-3}$-alkyl, $C_{1-3}$-alkylamino-$C_{1-3}$-alkyl or di-($C_{1-3}$-alkyl)-amino-$C_{1-3}$-alkyl group, while in the previously mentioned substituted 5- to 7-membered groups A the heteroatoms F, O or N optionally introduced with $R^{8a}$ as substituent are not separated by precisely one carbon atom from a heteroatom selected from among N, O, S, $R^{8b}$ denotes a hydrogen atom or a $C_{1-3}$-alkyl group, $X^1$ denotes a carbonyl, thiocarbonyl, C=$NR^{8c}$, C=N—$OR^{8c}$, C=N—$NO_2$, C=N—CN or sulphonyl group, $R^{8c}$ each independently of one another denote a hydrogen atom, a $C_{1-3}$-alkyl, $C_{1-3}$-alkylcarbonyl, or a $C_{1-4}$-alkyloxycarbonyl group, $X^2$ denotes an oxygen atom or a —$NR^{8b}$ group, $X^3$ denotes a carbonyl, thiocarbonyl, C=$NR^{8c}$, C=N—$OR^{8c}$, C=N—$NO_2$, C=N—CN or sulphonyl group, $X^4$ denotes an oxygen atom or a —$NR^{8c}$ group, $R^1$ denotes a fluorine, chlorine, bromine or iodine atom, a methyl or a methoxy group, while the hydrogen atoms of the methyl or methoxy group may optionally be wholly or partly replaced by fluorine atoms, $R^2$ denotes a hydrogen or fluorine atom, $R^3$ denotes a hydrogen atom, $R^4$ denotes a straight-chain or branched $C_{1-4}$-alkyl group, while the hydrogen atoms may optionally be wholly or partly replaced by fluorine atoms, and may optionally be substituted by a hydroxy, a $C_{1-3}$-alkyloxy group, while the hydrogen atoms of the $C_{1-3}$-alkyloxy group may be wholly or partly replaced by fluorine atoms, a benzyloxy, $C_{1-3}$-alkylcarbonyloxy, $C_{1-3}$-alkyloxycarbonyl, aminocarbonyl, $C_{1-3}$-alkylaminocarbonyl, di-($C_{1-3}$-alkyl)-aminocarbonyl, $C_{3-6}$-cycloalkyleneiminocarbonyl, aminosulphonyl, $C_{1-3}$-alkylaminosulphonyl, di-($C_{1-3}$-alkyl)-aminosulphonyl, $C_{3-6}$-cycloalkyleneiminosulphonyl, amino, $C_{1-3}$-alkylamino, di-($C_{1-3}$-alkyl)-amino, $C_{1-3}$-alkylcarbonylamino, or $C_{1-3}$-alkylsulphonylamino group, a phenyl, heteroaryl-$C_{1-2}$-alkyl or C-linked heteroaryl group while the heteroaryl group is selected from among pyrrolyl, oxazolyl, imidazolyl, furanyl, thiophenyl, thiazolyl, 1,2,3-triazolyl, 1,2,4-triazolyl, tetrazolyl, pyridynyl, pyrimidynyl and pyrazynyl, and may optionally be mono- to disubstituted in the phenyl or heteroaryl moiety by identical or different substituents selected from among halogen atoms, $C_{1-3}$-alkyl, hydroxy, $C_{1-3}$-alkyloxy, mono-, di- and trifluoromethoxy groups, $R^5$ denotes a hydrogen atom, a straight-chain or branched $C_{1-4}$-alkyl group,
while the hydrogen atoms may optionally be wholly or partly replaced by fluorine atoms, and may optionally be substituted by a $C_{1-3}$-alkyloxy group, while the hydrogen atoms of the $C_{1-3}$-alkyloxy group may optionally be wholly or partly replaced by fluorine atoms, or $R^4$ and $R^5$ together with the carbon atom to which they are bound form a $C_{3-7}$-cycloalkyl or $C_{4-7}$-cycloalkenyl group, while a $C_{3-7}$-cycloalkyl or $C_{4-7}$-cycloalkenyl group may be substituted at an individual carbon atom by a $C_{2-5}$-alkylene group or may be substituted simultaneously at two different carbon atoms by a $C_{1-4}$-alkylene group forming a corresponding spirocyclic group or a bridged bicyclic group, while one of the methylene groups of a $C_{4-7}$-cycloalkyl or $C_{4-7}$-cycloalkenyl group or a corresponding spirocyclic group as described above or a corresponding bridged bicyclic group may be replaced by an oxygen or sulphur atom or a sulphonyl or —N($R^{8c}$) group, and/or two directly adjacent methylene groups of a $C_{4-7}$-cycloalkyl group may together be replaced by a —C(O)N($R^{8b}$) or —C(O)O group, while 1 to 2 carbon atoms of a $C_{3-7}$-cycloalkyl group or a corresponding spirocyclic group as described above or a corresponding bridged bicyclic group may optionally be substituted independently of one another by a $C_{1-3}$-alkyl, hydroxy, $C_{1-3}$-alkyloxy, di-($C_{1-3}$-alkyl)-amino group, with the proviso that a $C_{3-7}$-cycloalkyl or $C_{4-7}$-cycloalkenyl group of this kind formed from $R^4$ and $R^5$ together or a corresponding spirocyclic group as described above or a corresponding bridged bicyclic group, wherein [a] methylene groups of the cyclic group which are directly connected to the carbon atom to which the groups $R^4$ and $R^5$ are bound, are replaced by a heteroatom selected from among oxygen, nitrogen and sulphur, and/or wherein a substituent bound to the cyclic group, which is characterised in that a heteroatom selected from among oxygen and nitrogen is bound directly to the cyclic group, is separated from another heteroatom selected from among oxygen, nitrogen and sulphur, with the exception of the sulphone group, by precisely one, optionally substituted, methylene group, and/or wherein a heteroatom selected from among oxygen, nitrogen and sulphur is linked directly to a carbon atom, which is linked to another carbon atom by a double bond, and/or which contains a cyclic group with three ring members, of which one or more corresponds to an oxygen or sulphur atom or an —N($R^{8c}$) group, is excluded, $R^6$ denotes a chlorine or bromine atom, while, unless otherwise stated, by the term "halogen atom" mentioned hereinbefore in the definitions is meant an atom selected from among fluorine, chlorine, bromine and iodine, while, unless otherwise stated, the alkyl and alkoxy groups contained in the foregoing definitions which have more than two carbon atoms may be straight-chain or branched and the alkyl groups in the previously mentioned dialkylated groups, for example the dialkylamino groups, may be identical or different, and the hydrogen atoms of the methyl or ethyl groups contained in the foregoing definitions, unless otherwise stated, may be wholly or partly replaced by fluorine atoms, the tautomers, the enantiomers, the diastereomers, the mixtures thereof and the salts thereof.

A 15th embodiment of the present invention comprises those compounds of general formula I, wherein A denotes a group of general formula wherein m is the number 1 or 2, $R^{8a}$ each independently of one another denote a hydrogen or fluorine atom or a $C_{1-3}$-alkyl, hydroxy, hydroxy-$C_{1-3}$-alkyl, $C_{1-3}$-alkoxy, $C_{1-3}$-alkoxy-$C_{1-3}$-alkyl, amino, $C_{1-3}$-alkylamino, di-($C_{1-3}$-alkyl)-amino, amino-$C_{1-3}$-alkyl, $C_{1-3}$-alkylamino-$C_{1-3}$-alkyl, di-($C_{1-3}$-alkyl)-amino-$C_{1-3}$-alkyl group, while in the previously mentioned substituted 5- to 7-membered groups A the heteroatoms F, O or N optionally introduced with $R^{8a}$ as substituent are not separated by precisely one carbon atom from a heteroatom selected from among N, O, S, $R^{8b}$ denotes a hydrogen atom or a $C_{1-3}$-alkyl group, $X^1$ denotes a carbonyl, thiocarbonyl, C=$NR^{8c}$, C=N—$OR^{8c}$, C=N—CN or sulphonyl group, $R^{8c}$ denotes a hydrogen atom, a $C_{1-3}$-alkyl, $C_{1-3}$-alkylcarbonyl, or a $C_{1-4}$-alkyloxycarbonyl group, $X^2$ denotes an oxygen atom or a —$NR^{8b}$ group, $X^3$ denotes a carbonyl, thiocarbonyl, C=$NR^{8c}$, C=N—$OR^{8c}$, C=N—CN or sulphonyl group, $X^4$ denotes an oxygen atom or a —$NR^{8c}$ group, $R^1$ denotes a chlorine or bromine atom, a methyl, trifluoromethyl or a methoxy group, $R^2$ denotes a hydrogen or fluorine atom, $R^3$ denotes a hydrogen atom, $R^4$ denotes a methyl group which may optionally be substituted by a hydroxy, methoxy, benzyloxy, methoxycarbonyl or pyridyn-4-yl group, or
  a 1-methyl-pyrazyn-3-yl, phenyl, pyridyn-3-yl or pyrazin-2-yl group, $R^5$ denotes a hydrogen atom or a methyl group, or $R^4$ and $R^5$ together with the carbon atom to which they are bound form a $C_{3-6}$-cycloalkyl or $C_{5-6}$-cycloalkenyl group,
  while a $C_{5-6}$-cycloalkyl or $C_{5-6}$-cycloalkenyl group may be substituted simultaneously at two different carbon atoms by a $C_{1-2}$-alkylene group forming a bridged bicyclic group,
  while one of the methylene groups of a $C_{4-6}$-cycloalkyl or $C_{5-6}$-cycloalkenyl group or of a corresponding bridged bicyclic group as described above, may be replaced by an oxygen atom or an —N($R^{8c}$) group,
  with the proviso that a $C_{3-6}$-cycloalkyl or $C_{5-6}$-cycloalkenyl group of this kind, formed from $R^4$ and $R^5$ together or a corresponding bridged bicyclic group as described above,
    wherein methylene groups of the cyclic group which are directly connected to the carbon atom to which the groups $R^4$ and $R^5$ are bound, are replaced by a heteroatom selected from among oxygen and nitrogen, and/or
    wherein a heteroatom selected from among oxygen and nitrogen is linked directly to a carbon atom, which is linked to another carbon atom by a double bond, and/or
    which contains a cyclic group with three ring members, of which one or more corresponds to an oxygen atom or —N($R^{8c}$) group,
  is excluded, $R^6$ denotes a chlorine or bromine atom while, unless otherwise stated, by the term "halogen atom" mentioned hereinbefore in the definitions is meant an atom selected from among fluorine, chlorine, bromine and iodine, while, unless otherwise stated, the alkyl and alkoxy groups contained in the foregoing definitions which have more than two carbon atoms may be straight-chain or branched and the alkyl groups in the previously mentioned dialkylated groups, for example the dialkylamino groups, may be identical or different, and the hydrogen atoms of the methyl or ethyl groups contained in the foregoing definitions, unless otherwise stated, may be wholly or partly replaced by fluorine atoms, the tautomers, the enantiomers, the diastereomers, the mixtures thereof and the salts thereof.

A 16th embodiment of the present invention comprises those compounds of general formula I corresponding to the embodiments 9, 10, 11, 12, 13, 14 and 15, wherein $R^4$ and $R^5$ do not represent hydrogen.

A 17th embodiment of the present invention comprises those compounds of general formula I corresponding to the embodiments 9, 10, 11, 12, 13, 14, 15 and 16, wherein $R^4$ and $R^5$ together with the carbon atom to which they are bound form a cyclic group which is defined in each case as in the 9th, 10th, 11th, 12th, 13th, 14th or 15th embodiment.

An 18th embodiment of the present invention comprises those compounds of general formula I corresponding to the embodiments 9, 10, 11, 12, 13, 14, 15, 16 and 17, wherein $R^4$ and $R^5$ together with the carbon atom to which they are bound form a cyclic group which is defined in each case as in the 9th, 10th, 11th, 12th, 13th, 14th or 15th embodiment, while in the cyclic group or the corresponding bridged bicyclic group or the spirocyclic group according to the method specified a methylene group is replaced by an oxygen atom or an $N(R^{8c})$ group.

A 19th embodiment of the present invention comprises those compounds of general formula I corresponding to the embodiments 9, 10, 11, 12, 13, 14, 15, 16, 17 and 18, wherein $R^4$ and $R^5$ together with the carbon atom to which they are bound form a cyclic group which does not denote a bridged bicyclic group or a spirocyclic group by corresponding substitution, as described in the 9th, 10th, 11th, 12th, 13th, 14th or 15th embodiment.

A 20th embodiment of the present invention comprises those compounds of general formula I corresponding to the embodiments 9, 10, 11, 12, 13, 14, 15, 16, 17 and 18, wherein $R^4$ and $R^5$ together with the carbon atom to which they are bound form a cyclic group which denotes a bridged bicyclic group or a spirocyclic group by corresponding substitution, as described in the 9th, 10th, 11th, 12th, 13th, 14th or 15th embodiment.

A 21st embodiment of the present invention comprises those compounds of general formula I corresponding to the embodiments 9, 10, 11, 12, 13, 14, 15, 16, 17, 18 and 19, wherein $R^4$ and $R^5$ together with the carbon atom to which they are bound denote a cyclic group

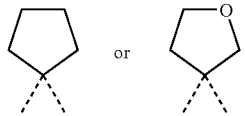

A 22nd embodiment of the present invention comprises those compounds of general formula I corresponding to the embodiments 9, 10, 11, 12, 13, 14, 15, 16, 17, 18 and 20, wherein $R^4$ and $R^5$ together with the carbon atom to which they are bound denote a bridged bicyclic group or

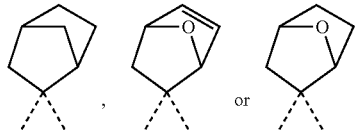

A 23rd embodiment of the present invention comprises those compounds of general formula I corresponding to the embodiments 9, 10, 11, 12, 13, 14, 15, 16, 17, 18, 19, 20, 21 and 22, wherein $X^1$ and $X^3$ independently of one another each denote a carbonyl or sulphonyl group.

A 24th embodiment of the present invention comprises those compounds of general formula I corresponding to the embodiments 9, 10, 11, 12, 13, 14, 15, 16, 17, 18, 19, 20, 21 and 22, wherein $X^1$ and $X^3$ independently of one another in each case denote a thiocarbonyl, $C=NR^{8c}$, $C=N—OR^{8c}$, $C=N—NO_2$ or $C=N—CN$ group.

A 25th embodiment of the present invention comprises those compounds of general formula I corresponding to the embodiments 9, 10, 11, 12, 13, 14, 15, 16, 17, 18, 19, 20, 21, 22 and 23, wherein the group A denotes the group

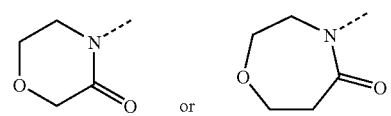

A 26th embodiment of the present invention comprises those compounds of general formula I corresponding to the embodiments 9, 10, 11, 12, 13, 14, 15, 16, 17, 18, 19, 20, 21, 22 and 24, wherein the group A denotes the group

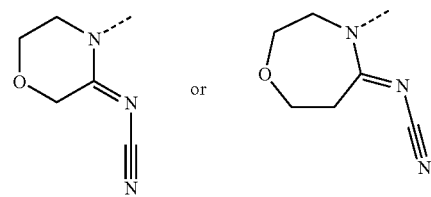

A 27th embodiment of the present invention comprises those compounds of general formula I corresponding to the embodiments 9, 10, 11, 12, 13, 14, 15, 16, 17, 18, 19, 20, 21, 22, 23, 24, 25 and 26, wherein $R^6$ denotes a bromine atom.

A 28th embodiment of the present invention comprises those compounds of general formula I corresponding to the embodiments 9, 10, 11, 12, 13, 14, 15, 16, 17, 18, 19, 20, 21, 22, 23, 24, 25 and 26, wherein $R^6$ denotes a chlorine atom.

The following preferred compounds of general formula I will now be mentioned by way of example:

(1) 5-chloro-thiophene-2-carboxylic acid-N-{1-[3-chloro-4-(3-oxo-morpholin-4-yl)-phenylcarbamoyl]-ethyl}-amide, (2) 5-bromo-thiophene-2-carboxylic acid-N-{(1R)-2-methoxy-1-[3-methyl-4-(3-oxo-morpholin-4-yl)-phenylcarbamoyl]-ethyl}-amide, (3) 5-chloro-thiophene-2-carboxylic acid-N-{(1R)-2-methoxy-1-[3-methyl-4-(3-oxo-morpholin-4-yl)-phenylcarbamoyl]-ethyl}-amide, (4) 5-bromo-thiophene-2-carboxylic acid-N-{(1S)-2-methoxy-1-[3-methyl-4-(3-oxo-morpholin-4-yl)-phenylcarbamoyl]-ethyl}-amide, (5) 5-chloro-thiophene-2-carboxylic acid-N-{(1S)-2-methoxy-1-[3-methyl-4-(3-oxo-morpholin-4-yl)-phenylcarbamoyl]-ethyl}-amide, (6) 5-chloro-thiophene-2-carboxylic acid-N-{1-[2-fluoro-5-methyl-4-(3-oxo-morpholin-4-yl)-phenylcarbamoyl]-ethyl}-amide, (7) 5-chloro-thiophene-2-carboxylic acid-N-{(1R)-1-[2-fluoro-5-methyl-4-(3-oxo-morpholin-4-yl)-phenylcarbamoyl]-2-methoxy-ethyl}-amide, (8) 5-bromo-thiophene-2-carboxylic acid-N-{(1R)-1-[2-fluoro-5-methyl-4-(3-oxo-morpholin-4-yl)-phenylcarbamoyl]-2-methoxy-ethyl}-amide, (9) 5-chloro-thiophene-2-carboxylic acid-N-{1-[3-methyl-4-(3-thioxo-morpholin-4-yl)-phenylcarbamoyl]-ethyl}-amide,

(10) 5-chloro-thiophene-2-carboxylic acid-N-{1-methyl-1-[3-methyl-4-(3-oxo-morpholin-4-yl)-phenylcarbamoyl]-ethyl}-amide,

(11) 5-bromo-thiophene-2-carboxylic acid-N-{1-methyl-1-[3-methyl-4-(3-oxo-morpholin-4-yl)-phenylcarbamoyl]-ethyl}-amide,

(12) 5-chloro-thiophene-2-carboxylic acid-N-{(1R)-2-benzyloxy-1-[3-methyl-4-(3-oxo-morpholin-4-yl)-phenylcarbamoyl]-ethyl}-amide,
(13) thiophene-2-carboxylic acid-N-{(1R)-2-benzyloxy-1-[3-methyl-4-(3-oxo-morpholin-4-yl)-phenylcarbamoyl]-ethyl}-amide,
(14) 5-chloro-thiophene-2-carboxylic acid-N-{1-[3-chloro-4-(4-methyl-oxazolidin-3-yl)-phenylcarbamoyl]-ethyl}-amide,
(15) 5-chloro-thiophene-2-carboxylic acid-N-{(1R)-2-hydroxy-1-[3-methyl-4-(3-oxo-morpholin-4-yl)-phenylcarbamoyl]-ethyl}-amide,
(16) 5-bromo-thiophene-2-carboxylic acid-N-((1R)-2-methoxy-1-[N'-methyl-N'-{3-methyl-4-(3-oxo-morpholin-4-yl)-phenyl}-carbamoyl]-ethyl)-amide,
(17) 5-chloro-thiophene-2-carboxylic acid-N-{1-[3-methyl-4-(3-oxo-morpholin-4-yl)-phenylcarbamoyl]-1-(pyridin-3-yl)-methyl}-amide,
(18) 5-chloro-thiophene-2-carboxylic acid-N-{1-phenyl-1-[3-methyl-4-(3-oxo-morpholin-4-yl)-phenylcarbamoyl]-methyl}-amide,
(19) 5-bromo-thiophene-2-carboxylic acid-N-{1-methyl-1-[3-cyano4-(3-oxo-morpholin-4-yl)-phenylcarbamoyl]-ethyl}-amide,
(20) 5-chloro-thiophene-2-carboxylic acid-N-{1-methyl-1-[3-methyl-4-(4-methyl-2-oxo-piperazin-1-yl)-phenylcarbamoyl]-ethyl}-amide,
(21) 5-bromo-thiophene-2-carboxylic acid-N-{1-methyl-1-[3-methyl-4-(4-methyl-2-oxo-piperazin-1-yl)-phenylcarbamoyl]-ethyl}-amide,
(22) 5-chloro-thiophene-2-carboxylic acid-N-{1-methyl-1-[3-chloro-4-(4-methyl-2-oxo-piperazin-1-yl)-phenylcarbamoyl]-ethyl}-amide,
(23) 5-chloro-thiophene-2-carboxylic acid-N-{1-methyl-1-[3-bromo-4-(4-methyl-2-oxo-piperazin-1-yl)-phenylcarbamoyl]-ethyl}-amide,
(24) 5-chloro-thiophene-2-carboxylic acid-N-(1-methyl-1-[N'-methyl-N'-{3-methyl-4-(3-oxo-morpholin-4-yl)-phenyl}-carbamoyl]-ethyl)-amide,
(25) 5-bromo-thiophene-2-carboxylic acid-N-(1-methyl-1-[N'-methyl-N'-{3-methyl-4-(3-oxo-morpholin-4-yl)-phenyl}-carbamoyl]-ethyl)-amide,
(26) 5-chloro-thiophene-2-carboxylic acid-N-{1-methyl-1-[3-chloro-4-(3-oxo-morpholin-4-yl)-phenylcarbamoyl]-ethyl}-amide,
(27) 5-bromo-thiophene-2-carboxylic acid-N-{1-methyl-1-[3-chloro-4-(3-oxo-morpholin-4-yl)-phenylcarbamoyl]-ethyl}-amide,
(28) 5-chloro-thiophene-2-carboxylic acid-N-{1-methyl-1-[3-bromo-4-(3-oxo-morpholin-4-yl)-phenylcarbamoyl]-ethyl}-amide,
(29) 5-bromo-thiophene-2-carboxylic acid-N-{1-methyl-1-[3-bromo-4-(3-oxo-morpholin-4-yl)-phenylcarbamoyl]-ethyl}-amide,
(30) 5-chloro-thiophene-2-carboxylic acid-N-{1-methyl-1-[3-trifluoromethyl-4-(3-oxo-morpholin-4-yl)-phenylcarbamoyl]-ethyl}-amide,
(31) 5-bromo-thiophene-2-carboxylic acid-N-{1-methyl-1-[3-trifluoromethyl-4-(3-oxo-morpholin-4-yl)-phenylcarbamoyl]-ethyl}-amide,
(32) 5-chloro-thiophene-2-carboxylic acid-N-{1-methyl-1-[3-methoxy-4-(3-oxo-morpholin-4-yl)-phenylcarbamoyl]-ethyl}-amide,
(33) 5-bromo-thiophene-2-carboxylic acid-N-{1-methyl-1-[3-methoxy-4-(3-oxo-morpholin-4-yl)-phenylcarbamoyl]-ethyl}-amide,
(34) 5-chloro-thiophene-2-carboxylic acid-N-{1-methyl-1-[2-fluoro-5-methyl-4-(3-oxo-morpholin-4-yl)-phenylcarbamoyl]-ethyl}-amide,
(35) 5-bromo-thiophene-2-carboxylic acid-N-{1-methyl-1-[2-fluoro-5-methyl-4-(3-oxo-morpholin-4-yl)-phenylcarbamoyl]-ethyl}-amide,
(36) 5-chloro-thiophene-2-carboxylic acid-N-(1-methyl-1-[N'-methyl-N'-{2-fluoro-5-methyl-4-(3-oxo-morpholin-4-yl)-phenyl}-carbamoyl]-ethyl)-amide,
(37) 5-bromo-thiophene-2-carboxylic acid-N-(1-methyl-1-[N'-methyl-N'-{2-fluoro-5-methyl-4-(3-oxo-morpholin-4-yl)-phenyl}-carbamoyl]-ethyl)-amide,
(38) 5-chloro-thiophene-2-carboxylic acid-N-{2-methoxy-1-[methoxymethyl]-1-[3-methyl-4-(3-oxo-morpholin-4-yl)-phenylcarbamoyl]-ethyl}-amide,
(39) 5-bromo-thiophene-2-carboxylic acid-N-{2-methoxy-1-[methoxymethyl]-1-[3-methyl-4-(3-oxo-morpholin-4-yl)-phenylcarbamoyl]-ethyl}-amide,
(40) 5-bromo-thiophene-2-carboxylic acid-N-{2-methoxy-1-[methoxymethyl]-1-[3-chloro-4-(3-oxo-morpholin-4-yl)-phenylcarbamoyl]-ethyl}-amide,
(41) 5-chloro-thiophene-2-carboxylic acid-N-{(1R)-2-methoxy-1-methyl-1-[3-methyl-4-(3-oxo-morpholin-4-yl)-phenylcarbamoyl]-ethyl}-amide,
(42) 5-bromo-thiophene-2-carboxylic acid-N-{(1R)-2-methoxy-1-methyl-1-[3-chloro-4-(3-oxo-morpholin-4-yl)-phenylcarbamoyl]-ethyl}-amide,
(43) 5-bromo-thiophene-2-carboxylic acid-N-{(1R)-2-methoxy-1-methyl-1-[3-methyl-4-(3-oxo-morpholin-4-yl)-phenylcarbamoyl]-ethyl}-amide,
(44) 5-chloro-thiophene-2-carboxylic acid-N-{(1S)-2-methoxy-1-methyl-1-[3-methyl-4-(3-oxo-morpholin-4-yl)-phenylcarbamoyl]-ethyl}-amide,
(45) 5-bromo-thiophene-2-carboxylic acid-N-{(1S)-2-methoxy-1-methyl-1-[3-chloro-4-(3-oxo-morpholin-4-yl)-phenylcarbamoyl]-ethyl}-amide,
(46) 5-chloro-thiophene-2-carboxylic acid-N-{1-[3-methyl-4-(3-oxo-morpholin-4-yl)-phenylcarbamoyl]-cyclopropyl}-amide,
(47) 5-bromo-thiophene-2-carboxylic acid-N-{1-[3-methyl-4-(3-oxo-morpholin-4-yl)-phenylcarbamoyl]-cyclopropyl}-amide,
(48) 5-chloro-thiophene-2-carboxylic acid-N-{1-[3-methyl-4-(3-oxo-morpholin-4-yl)-phenylcarbamoyl]-cyclobutyl}-amide,
(49) 5-bromo-thiophene-2-carboxylic acid-N-{1-[3-methyl-4-(3-oxo-morpholin-4-yl)-phenylcarbamoyl]-cyclobutyl}-amide,
(50) 5-chloro-thiophene-2-carboxylic acid-N-{1-[3-methyl-4-(3-oxo-morpholin-4-yl)-phenylcarbamoyl]-cyclopentyl}-amide,
(51) 5-bromo-thiophene-2-carboxylic acid-N-{1-[3-methyl-4-(3-oxo-morpholin-4-yl)-phenylcarbamoyl]-cyclopentyl}-amide,
(52) 5-chloro-thiophene-2-carboxylic acid-N-{1-[3-methyl-4-(3-oxo-morpholin-4-yl)-phenylcarbamoyl]-cyclohexyl}-amide,
(53) 5-bromo-thiophene-2-carboxylic acid-N-{1-[3-methyl-4-(3-oxo-morpholin-4-yl)-phenylcarbamoyl]-cyclohexyl}-amide,
(54) 5-chloro-thiophene-2-carboxylic acid-N-{3-[3-methyl-4-(3-oxo-morpholin-4-yl)-phenylcarbamoyl]-tetrahydrofuran-3-yl}-amide,
(55) 5-bromo-thiophene-2-carboxylic acid-N-{3-[3-methyl-4-(3-oxo-morpholin-4-yl)-phenylcarbamoyl]-tetrahydrofuran-3-yl}-amide,

(56) 5-bromo-thiophene-2-carboxylic acid-N-{3-[3-chloro-4-(3-oxo-morpholin-4-yl)-phenylcarbamoyl]-tetrahydro-furan-3-yl}-amide,
(57) 5-chloro-thiophene-2-carboxylic acid-N-{4-[3-methyl-4-(3-oxo-morpholin-4-yl)-phenylcarbamoyl]-tetrahydro-pyran-4-yl}-amide,
(58) 5-bromo-thiophene-2-carboxylic acid-N-{4-[3-methyl-4-(3-oxo-morpholin-4-yl)-phenylcarbamoyl]-tetrahydro-pyran-4-yl}-amide,
(59) 5-chloro-thiophene-2-carboxylic acid-N-{1-methyl-3-[3-methyl-4-(3-oxo-morpholin-4-yl)-phenylcarbamoyl]-pyrrolidin-3-yl}-amide,
(60) 5-bromo-thiophene-2-carboxylic acid-N-{1-methyl-3-[3-methyl-4-(3-oxo-morpholin-4-yl)-phenylcarbamoyl]-pyrrolidin-3-yl}-amide,
(61) 5-bromo-thiophene-2-carboxylic acid-N-{1-methyl-3-[3-chloro-4-(3-oxo-morpholin-4-yl)-phenylcarbamoyl]-pyrrolidin-3-yl}-amide,
(62) 5-chloro-thiophene-2-carboxylic acid-N-{1-acetyl-3-[3-methyl-4-(3-oxo-morpholin-4-yl)-phenylcarbamoyl]-pyrrolid in-3-yl}-amide,
(63) 5-chloro-thiophene-2-carboxylic acid-N-{1-methoxy-carbonyl-3-[3-methyl-4-(3-oxo-morpholin-4-yl)-phenyl-carbamoyl]-pyrrolidin-3-yl}-amide,
(64) 5-chloro-thiophene-2-carboxylic acid-N-{1-methyl-4-[3-methyl-4-(3-oxo-morpholin-4-yl)-phenylcarbamoyl]-piperidin-4-yl}-amide,
(65) 5-bromo-thiophene-2-carboxylic acid-N-{1-methyl-4-[3-methyl-4-(3-oxo-morpholin-4-yl)-phenylcarbamoyl]-piperidin-4-yl}-amide,
(66) 5-bromo-thiophene-2-carboxylic acid-N-{1-methyl-4-[3-chloro-4-(3-oxo-morpholin-4-yl)-phenylcarbamoyl]-piperidin-4-yl}-amide,
(67) 5-chloro-thiophene-2-carboxylic acid-N-{1-acetyl-4-[3-methyl-4-(3-oxo-morpholin-4-yl)-phenylcarbamoyl]-piperidin-4-yl}-amide,
(68) 5-bromo-thiophene-2-carboxylic acid-N-{1-acetyl-4-[3-methyl-4-(3-oxo-morpholin-4-yl)-phenylcarbamoyl]-piperidin-4-yl}-amide,
(69) 5-bromo-thiophene-2-carboxylic acid-N-{1-methyl-1-[3-methyl-4-(4,4-dimethyl-oxazolidin-2-on-3-yl)-phenyl-carbamoyl]-ethyl}-amide,
(70) 5-bromo-thiophene-2-carboxylic acid-N-{1-methyl-1-[3-methyl-4-(2-oxo-piperidin-1-yl)-phenylcarbamoyl]-ethyl}-amide,
(71) 5-bromo-thiophene-2-carboxylic acid-N-{1-methyl-1-[3-methyl-4-(2-oxo-[1,3]oxazinan-3-yl)-phenylcarbam-oyl]-ethyl}-amide,
(72) 5-bromo-thiophene-2-carboxylic acid-N-{1-methyl-1-[3-methyl-4-(4,4-dimethyl-2-oxo-imidazolidin-3-yl)-phenylcarbamoyl]-ethyl}-amide,
(73) 5-bromo-thiophene-2-carboxylic acid-N-{1-methyl-1-[3-methyl-4-(2-oxo-tetrahydropyrimidin-1-yl)-phenylcar-bamoyl]-ethyl}-amide,
(74) 5-bromo-thiophene-2-carboxylic acid-N-{1-methyl-1-[3-methyl-4-(2-oxo-3,6-dihydro-2H-pyridin-1-yl)-phe-nylcarbamoyl]-ethyl}-amide,
(75) 5-bromo-thiophene-2-carboxylic acid-N-{1-methyl-1-[3-methyl-4-(3-oxo-thiomorpholin-4-yl)-phenylcarbam-oyl]-ethyl}-amide,
(76) 5-bromo-thiophene-2-carboxylic acid-N-{1-methyl-1-[3-methyl-4-(2-oxo-[1,3]oxazepan-3-yl)-phenylcarbam-oyl]-ethyl}-amide,
(77) 5-bromo-thiophene-2-carboxylic acid-N-{1-methyl-1-[3-methyl-4-(3-oxo-[1,4]oxazepan-4-yl)-phenylcarbam-oyl]-ethyl}-amide,
(78) 5-bromo-thiophene-2-carboxylic acid-N-{1-methyl-1-[3-methyl-4-(5-oxo-[1,4]oxazepan-4-yl)-phenylcarbam-oyl]-ethyl}-amide,
(79) 5-bromo-thiophene-2-carboxylic acid-N-{1-methyl-1-[3-methyl-4-(2-oxo-[1,3]diazepan-1-yl)-phenylcarbam-oyl]-ethyl}-amide,
(80) 5-bromo-thiophene-2-carboxylic acid-N-{1-methyl-1-[3-methyl-4-(2-oxo-[1,4]diazepan-1-yl)-phenylcarbam-oyl]-ethyl}-amide,
(81) 5-bromo-thiophene-2-carboxylic acid-N-{1-methyl-1-[3-methyl-4-(7-oxo-[1,4]diazepan-1-yl)-phenylcarbam-oyl]-ethyl}-amide,
(82) 5-bromo-thiophene-2-carboxylic acid-N-{1-methyl-1-[3-methyl-4-(4-methyl-7-oxo-[1,4]diazepan-1-yl)-phe-nylcarbamoyl]-ethyl}-amide,
(83) 5-bromo-thiophene-2-carboxylic acid-N-{1-methyl-1-[3-methyl-4-(4-methyl-2-oxo-[1,4]diazepan-1-yl)-phe-nylcarbamoyl]-ethyl}-amide,
(84) 5-bromo-thiophene-2-carboxylic acid-N-{1-methyl-1-[3-methyl-4-(1,1-dioxo-isothiazolidin-2-yl)-phenylcar-bamoyl]-ethyl}-amide,
(85) 5-bromo-thiophene-2-carboxylic acid-N-{1-methyl-1-[3-methyl-4-(1,1-dioxo-[1,2,5]thiadiazolidin-2-yl)-phe-nylcarbamoyl]-ethyl}-amide,
(86) 5-bromo-thiophene-2-carboxylic acid-N-{1-methyl-1-[3-methyl-4-(1,1-dioxo-[1,2]thiazinan-2-yl)-phenylcar-bamoyl]-ethyl}-amide,
(87) 5-bromo-thiophene-2-carboxylic acid-N-{1-methyl-1-[3-methyl-4-(1,1-dioxo-[1,2,6]thiadiazinan-2-yl)-phenyl-carbamoyl]-ethyl}-amide,
(88) 5-bromo-thiophene-2-carboxylic acid-N-{1-methyl-1-[3-methyl-4-(1,1-dioxo-[1,2,5]thiadiazinan-2-yl)-phenyl-carbamoyl]-ethyl}-amide,
(89) 5-bromo-thiophene-2-carboxylic acid-N-{1-methyl-1-[3-methyl-4-(3,3-dioxo-[1,3,4]oxathiazinan-4-yl)-phe-nylcarbamoyl]-ethyl}-amide,
(90) 5-bromo-thiophene-2-carboxylic acid-N-{1-methyl-1-[3-methyl-4-(1,1-dioxo-[1,2]thiazepan-2-yl)-phenylcar-bamoyl]-ethyl}-amide,
(91) 5-bromo-thiophene-2-carboxylic acid-N-{1-methyl-1-[3-methyl-4-(2-thioxo-piperidin-1-yl)-phenylcarbamoyl]-ethyl}-amide,
(92) 5-bromo-thiophene-2-carboxylic acid-N-{1-methyl-1-[3-methyl-4-(3-thioxo-morpholin-4-yl)-phenylcarbam-oyl]-ethyl}-amide,
(93) 5-bromo-thiophene-2-carboxylic acid-N-{1-methyl-1-[3-methyl-4-(4-methyl-2-thioxo-piperazin-1-yl)-phenyl-carbamoyl]-ethyl}-amide,
(94) 5-bromo-thiophene-2-carboxylic acid-N-{1-methyl-1-[3-methyl-4-(2-thioxo-piperazin-1-yl)-phenylcarbam-oyl]-ethyl}-amide,
(95) 5-bromo-thiophene-2-carboxylic acid-N-{1-methyl-1-[3-methyl-4-(5-methyl-2-thioxo-pyrrolidin-1-yl)-phenyl-carbamoyl]-ethyl}-amide,
(96) 5-bromo-thiophene-2-carboxylic acid-N-{1-methyl-1-[3-methyl-4-(2-thioxo-azepan-1-yl)-phenylcarbamoyl]-ethyl}-amide,
(97) 5-bromo-thiophene-2-carboxylic acid-N-{1-methyl-1-[3-methyl-4-(2-thioxo-[1,4]oxazepan-4-yl)-phenylcar-bamoyl]-ethyl}-amide,
(98) 5-bromo-thiophene-2-carboxylic acid-N-{1-methyl-1-[3-methyl-4-(4-methyl-2-thioxo-[1,4]diazepan-1-yl)-phe-nylcarbamoyl]-ethyl}-amide,
(99) 5-bromo-thiophene-2-carboxylic acid-N-{5-dimethy-lamino-1-[3-methyl-4-(3-oxo-morpholin-4-yl)-phenyl-carbamoyl-pentyl}-amide, (100) 5-bromo-thiophene-2-carboxylic acid-N-{5-acetylamino-1-[3-methyl-4-(3-oxo-morpholin-4-yl)-phenylcarbamoyl]-pentyl}-amide,
(101) 5-bromo-thiophene-2-carboxylic acid-N-{5-methylsulphonylamino-1-[3-methyl-4-(3-oxo-morpholin-4-yl)-phenylcarbamoyl]-pentyl}-amide,
(102) 5-bromo-thiophene-2-carboxylic acid-N-{3-methylsulphanyl-1-[3-methyl-4-(3-oxo-morpholin-4-yl)-phenylcarbamoyl]-propyl}-amide,
(103) 5-bromo-thiophene-2-carboxylic acid-N-{3-methylsulphonyl-1-[3-methyl-4-(3-oxo-morpholin-4-yl)-phenylcarbamoyl]-propyl}-amide,
(104) 5-bromo-thiophene-2-carboxylic acid-N-{3-(tetrazol-5-yl)-1-[3-methyl-4-(3-oxo-morpholin-4-yl)-phenylcarbamoyl]-propyl}-amide,
(105) 5-bromo-thiophene-2-carboxylic acid-N-{3-methyl-1-[3-methyl-4-(3-oxo-morpholin-4-yl)-phenylcarbamoyl]-butyl}-amide,
(106) 5-bromo-thiophene-2-carboxylic acid-N-{4-methoxy-4-oxo-1-[3-methyl-4-(3-oxo-morpholin-4-yl)-phenylcarbamoyl]-butyl}-amide,
(107) 5-bromo-thiophene-2-carboxylic acid-N-{4-dimethylamino-4-oxo-1-[3-methyl-4-(3-oxo-morpholin-4-yl)-phenylcarbamoyl]-butyl}-amide,
(108) 5-bromo-thiophene-2-carboxylic acid-N-{2-methoxy-1-[3-methyl-4-(3-oxo-morpholin-4-yl)-phenylcarbamoyl]-propyl}-amide,
(109) 5-bromo-thiophene-2-carboxylic acid-N-{1-[3-fluoro-4-(3-oxo-morpholin-4-yl)-phenylcarbamoyl]-cyclobutyl}-amide,
(110) 5-bromo-thiophene-2-carboxylic acid-N-{1-[3-chloro-4-(3-oxo-morpholin-4-yl)-phenylcarbamoyl]-cyclobutyl}-amide,
(111) 5-bromo-thiophene-2-carboxylic acid-N-{1-[3-bromo-4-(3-oxo-morpholin-4-yl)-phenylcarbamoyl]-cyclobutyl}-amide,
(112) 5-bromo-thiophene-2-carboxylic acid-N-{1-[3-trifluoromethyl-4-(3-oxo-morpholin-4-yl)-phenylcarbamoyl]-cyclobutyl}-amide,
(113) 5-bromo-thiophene-2-carboxylic acid-N-{1-[3-methoxy-4-(3-oxo-morpholin-4-yl)-phenylcarbamoyl]-cyclobutyl}-amide,
(114) 5-bromo-thiophene-2-carboxylic acid-N-{1-[3-methyl-4-(3-thioxo-morpholin-4-yl)-phenylcarbamoyl]-cyclobutyl}-amide,
(115) 5-bromo-thiophene-2-carboxylic acid-N-{1-[3-methyl-4-(3-imino-morpholin-4-yl)-phenylcarbamoyl]-cyclobutyl}-amide,
(116) 5-bromo-thiophene-2-carboxylic acid-N-{1-[3-chloro-4-(3-imino-morpholin-4-yl)-phenylcarbamoyl]-cyclobutyl}-amide,
(117) 5-bromo-thiophene-2-carboxylic acid-N-{1-[3-methyl-4-(3-methylimino-morpholin-4-yl)-phenylcarbamoyl]-cyclobutyl}-amide,
(118) 5-bromo-thiophene-2-carboxylic acid-N-{1-[3-chloro-4-(3-hydroxylimino-morpholin-4-yl)-phenylcarbamoyl]-cyclobutyl}-amide,
(119) 5-bromo-thiophene-2-carboxylic acid-N-{1-[3-methyl-4-(3-methoxyimino-morpholin-4-yl)-phenylcarbamoyl]-cyclobutyl}-amide,
(120) 5-bromo-thiophene-2-carboxylic acid-N-{1-[3-methyl-4-(3-cyanimino-morpholin-4-yl)-phenylcarbamoyl]-cyclobutyl}-amide,
(121) 5-bromo-thiophene-2-carboxylic acid-N-{1-[3-chloro-4-(3-cyanimino-morpholin-4-yl)-phenylcarbamoyl]-cyclobutyl}-amide,
(122) 5-bromo-thiophene-2-carboxylic acid-N-{1-[3-methyl-4-(3-nitroimino-morpholin-4-yl)-phenylcarbamoyl]-cyclobutyl}-amide,
(123) 5-bromo-thiophene-2-carboxylic acid-N-{1-[3-methyl-4-(5-oxo-[1,4]-oxazepan-4-yl)-phenylcarbamoyl]-cyclobutyl}-amide,
(124) 5-bromo-thiophene-2-carboxylic acid-N-{1-[3-fluoro-4-(5-oxo-[1,4]-oxazepan-4-yl)-phenylcarbamoyl]-cyclobutyl}-amide,
(125) 5-bromo-thiophene-2-carboxylic acid-N-{1-[3-chloro-4-(5-oxo-[1,4]-oxazepan-4-yl)-phenylcarbamoyl]-cyclobutyl}-amide,
(126) 5-bromo-thiophene-2-carboxylic acid-N-{1-[3-bromo-4-(5-oxo-[1,4]-oxazepan-4-yl)-phenylcarbamoyl]-cyclobutyl}-amide,
(127) 5-bromo-thiophene-2-carboxylic acid-N-{1-[3-trifluoromethyl-4-(5-oxo-[1,4]-oxazepan-4-yl)-phenylcarbamoyl]-cyclobutyl}-amide,
(128) 5-bromo-thiophene-2-carboxylic acid-N-{1-[3-methoxy-4-(5-oxo-[1,4]-oxazepan-4-yl)-phenylcarbamoyl]-cyclobutyl}-amide,
(129) 5-bromo-thiophene-2-carboxylic acid-N-{1-[3-methyl-4-(5-thioxo-[1,4]-oxazepan-4-yl)-phenylcarbamoyl]-cyclobutyl}-amide,
(130) 5-bromo-thiophene-2-carboxylic acid-N-{1-[3-methyl-4-(5-imino-[1,4]-oxazepan-4-yl)-phenylcarbamoyl]-cyclobutyl}-amide,
(131) 5-bromo-thiophene-2-carboxylic acid-N-{1-[3-chloro-4-(5-methylimino-[1,4]-oxazepan-4-yl)-phenylcarbamoyl]-cyclobutyl}-amide,
(132) 5-bromo-thiophene-2-carboxylic acid-N-{1-[3-methyl-4-(5-hydroxylimino-[1,4]-oxazepan-4-yl)-phenylcarbamoyl]-cyclobutyl}-amide,
(133) 5-bromo-thiophene-2-carboxylic acid-N-{1-[3-methyl-4-(5-methoxyimino-[1,4]-oxazepan-4-yl)-phenylcarbamoyl]-cyclobutyl}-amide,
(134) 5-bromo-thiophene-2-carboxylic acid-N-{1-[3-chloro-4-(5-cyanimino-[1,4]-oxazepan-4-yl)-phenylcarbamoyl]-cyclobutyl}-amide,
(135) 5-bromo-thiophene-2-carboxylic acid-N-{1-[3-fluoro-4-(3-oxo-morpholin-4-yl)-phenylcarbamoyl]-cyclopentyl}-amide,
(136) 5-bromo-thiophene-2-carboxylic acid-N-{1-[3-chloro-4-(3-oxo-morpholin-4-yl)-phenylcarbamoyl]-cyclopentyl}-amide,
(137) 5-bromo-thiophene-2-carboxylic acid-N-{1-[3-bromo-4-(3-oxo-morpholin-4-yl)-phenylcarbamoyl]-cyclopentyl}-amide,
(138) 5-bromo-thiophene-2-carboxylic acid-N-{1-[3-trifluoromethyl-4-(3-oxo-morpholin-4-yl)-phenylcarbamoyl]-cyclopentyl}-amide,
(139) 5-bromo-thiophene-2-carboxylic acid-N-{1-[3-methoxy-4-(3-oxo-morpholin-4-yl)-phenylcarbamoyl]-cyclopentyl}-amide,
(140) 5-bromo-thiophene-2-carboxylic acid-N-{1-[3-nitro-4-(3-oxo-morpholin-4-yl)-phenylcarbamoyl]-cyclopentyl}-amide,
(141) 5-bromo-thiophene-2-carboxylic acid-N-{1-[3-methyl-4-(3-thioxo-morpholin-4-yl)-phenylcarbamoyl]-cyclopentyl}-amide,
(142) 5-bromo-thiophene-2-carboxylic acid-N-{1-[3-methyl-4-(2-imino-piperidin-1-yl)-phenylcarbamoyl]-cyclopentyl}-amide,
(143) 5-bromo-thiophene-2-carboxylic acid-N-{1-[3-chloro-4-(3-imino-morpholin-4-yl)-phenylcarbamoyl]-cyclopentyl}-amide, (144) 5-bromo-thiophene-2-carboxylic acid-N-{1-[3-methyl-4-(3-methylimino-morpholin-4-yl)-phenylcarbamoyl]-cyclopentyl}-amide,
(145) 5-bromo-thiophene-2-carboxylic acid-N-{1-[3-chloro-4-(3-hydroxylimino-morpholin-4-yl)-phenylcarbamoyl]-cyclopentyl}-amide,
(146) 5-bromo-thiophene-2-carboxylic acid-N-{1-[3-methyl-4-(3-methoxyimino-morpholin-4-yl)-phenylcarbamoyl]-cyclopentyl}-amide,
(147) 5-bromo-thiophene-2-carboxylic acid-N-{1-[3-methyl-4-(3-cyanimino-morpholin-4-yl)-phenylcarbamoyl]-cyclopentyl}-amide,
(148) 5-bromo-thiophene-2-carboxylic acid-N-{1-[3-chloro-4-(2-cyanimino-piperidin-1-yl)-phenylcarbamoyl]-cyclopentyl}-amide,
(149) 5-bromo-thiophene-2-carboxylic acid-N-{1-[3-methyl-4-(3-nitroimino-morpholin-4-yl)-phenylcarbamoyl]-cyclopentyl}-amide,
(150) 5-bromo-thiophene-2-carboxylic acid-N-{1-[3-methyl-4-(5-oxo-[1,4]-oxazepan-4-yl)-phenylcarbamoyl]-cyclopentyl}-amide,
(151) 5-bromo-thiophene-2-carboxylic acid-N-{1-[3-fluoro-4-(5-oxo-[1,4]-oxazepan-4-yl)-phenylcarbamoyl]-cyclopentyl}-amide,
(152) 5-bromo-thiophene-2-carboxylic acid-N-{1-[3-chloro-4-(5-oxo-[1,4]-oxazepan-4-yl)-phenylcarbamoyl]-cyclopentyl}-amide,
(153) 5-bromo-thiophene-2-carboxylic acid-N-{1-[3-bromo-4-(5-oxo-[1,4]-oxazepan-4-yl)-phenylcarbamoyl]-cyclopentyl}-amide,
(154) 5-bromo-thiophene-2-carboxylic acid-N-{1-[3-trifluoromethyl-4-(5-oxo-[1,4]-oxazepan-4-yl)-phenylcarbamoyl]-cyclopentyl}-amide,
(155) 5-bromo-thiophene-2-carboxylic acid-N-{1-[3-methoxy-4-(5-oxo-[1,4]-oxazepan-4-yl)-phenylcarbamoyl]-cyclopentyl}-amide,
(156) 5-bromo-thiophene-2-carboxylic acid-N-{1-[3-methyl-4-(5-thioxo-[1,4]-oxazepan-4-yl)-phenylcarbamoyl]-cyclopentyl}-amide,
(157) 5-bromo-thiophene-2-carboxylic acid-N-{1-[3-methyl-4-(5-imino-[1,4]-oxazepan-4-yl)-phenylcarbamoyl]-cyclopentyl}-amide,
(158) 5-bromo-thiophene-2-carboxylic acid-N-{1-[3-chloro-4-(5-methylimino-[1,4]-oxazepan-4-yl)-phenylcarbamoyl]-cyclopentyl}-amide,
(159) 5-bromo-thiophene-2-carboxylic acid-N-{1-[3-methyl-4-(5-hydroxylimino-[1,4]-oxazepan-4-yl)-phenylcarbamoyl]-cyclopentyl}-amide,
(160) 5-bromo-thiophene-2-carboxylic acid-N-{1-[3-methyl-4-(5-methoxyimino-[1,4]-oxazepan-4-yl)-phenylcarbamoyl]-cyclopentyl}-amide,
(161) 5-bromo-thiophene-2-carboxylic acid-N-{1-[3-chloro-4-(5-cyanimino-[1,4]-oxazepan-4-yl)-phenylcarbamoyl]-cyclopentyl}-amide,
(162) 5-bromo-thiophene-2-carboxylic acid-N-{3-[3-methyl-4-(3-oxo-morpholin-4-yl)-phenylcarbamoyl]-oxetan-3-yl}-amide,
(163) 5-bromo-thiophene-2-carboxylic acid-N-{3-[3-chloro-4-(3-oxo-morpholin-4-yl)-phenylcarbamoyl]-oxetan-3-yl}-amide,
(164) 5-bromo-thiophene-2-carboxylic acid-N-{3-[3-bromo-4-(3-oxo-morpholin-4-yl)-phenylcarbamoyl]-oxetan-3-yl}-amide,
(165) 5-bromo-thiophene-2-carboxylic acid-N-{3-[3-chloro-4-(3-hydroxylimino-morpholin-4-yl)-phenylcarbamoyl]-oxetan-3-yl}-amide,
(166) 5-bromo-thiophene-2-carboxylic acid-N-{3-[3-methyl-4-(3-methoxyimino-morpholin-4-yl)-phenylcarbamoyl]-oxetan-3-yl}-amide,
(167) 5-bromo-thiophene-2-carboxylic acid-N-{3-[3-methyl-4-(5-oxo-[1,4]-oxazepan-4-yl)-phenylcarbamoyl]-oxetan-3-yl}-amide,
(168) 5-bromo-thiophene-2-carboxylic acid-N-{3-[3-chloro-4-(5-oxo-[1,4]-oxazepan-4-yl)-phenylcarbamoyl]-oxetan-3-yl}-amide,
(169) 5-bromo-thiophene-2-carboxylic acid-N-{3-[3-methyl-4-(5-imino-[1,4]-oxazepan-4-yl)-phenylcarbamoyl]-oxetan-3-yl}-amide,
(170) 5-bromo-thiophene-2-carboxylic acid-N-{3-[3-chloro-4-(5-methylimino-[1,4]-oxazepan-4-yl)-phenylcarbamoyl]-oxetan-3-yl}-amide,
(171) 5-bromo-thiophene-2-carboxylic acid-N-{3-[3-methyl-4-(3-oxo-morpholin-4-yl)-phenylcarbamoyl]-thietan-3-yl}-amide,
(172) 5-bromo-thiophene-2-carboxylic acid-N-{3-[3-chloro-4-(3-oxo-morpholin-4-yl)-phenylcarbamoyl]-thietan-3-yl}-amide,
(173) 5-bromo-thiophene-2-carboxylic acid-N-{3-[3-methyl-4-(3-imino-morpholin-4-yl)-phenylcarbamoyl]-thietan-3-yl}-amide,
(174) 5-bromo-thiophene-2-carboxylic acid-N-{3-[3-chloro-4-(5-oxo-[1,4]-oxazepan-4-yl)-phenylcarbamoyl]-thietan-3-yl}-amide,
(175) 5-bromo-thiophene-2-carboxylic acid-N-{3-[3-methyl-4-(3-oxo-morpholin-4-yl)-phenylcarbamoyl]-1,1-dioxo-thietan-3-yl}-amide,
(176) 5-bromo-thiophene-2-carboxylic acid-N-{3-[3-chloro-4-(5-oxo-[1,4]-oxazepan-4-yl)-phenylcarbamoyl]-1,1-dioxo-thietan-3-yl}-amide,
(177) 5-bromo-thiophene-2-carboxylic acid-N-{3-[3-chloro-4-(5-methylimino-[1,4]-oxazepan-4-yl)-phenylcarbamoyl]-thietan-3-yl}-amide,
(178) 5-bromo-thiophene-2-carboxylic acid-N-{3-[3-methyl-4-(3-oxo-morpholin-4-yl)-phenylcarbamoyl]-1-methyl-azetidin-3-yl}-amide,
(179) 5-bromo-thiophene-2-carboxylic acid-N-{3-[3-chloro-4-(3-oxo-morpholin-4-yl)-phenylcarbamoyl]-1-methyl-azetidin-3-yl}-amide,
(180) 5-bromo-thiophene-2-carboxylic acid-N-{3-[3-chloro-4-(5-oxo-[1,4]-oxazepan-4-yl)-phenylcarbamoyl]-1-methyl-azetidin-3-yl}-amide,
(181) 5-bromo-thiophene-2-carboxylic acid-N-{3-[3-fluoro-4-(3-oxo-morpholin-4-yl)-phenylcarbamoyl]-tetrahydrofuran-3-yl}-amide,
(182) 5-bromo-thiophene-2-carboxylic acid-N-{3-[3-chloro-4-(3-oxo-morpholin-4-yl)-phenylcarbamoyl]-tetrahydrofuran-3-yl}-amide,
(183) 5-bromo-thiophene-2-carboxylic acid-N-{3-[3-bromo-4-(3-oxo-morpholin-4-yl)-phenylcarbamoyl]-tetrahydrofuran-3-yl}-amide,
(184) 5-bromo-thiophene-2-carboxylic acid-N-{3-[3-trifluoromethyl-4-(3-oxo-morpholin-4-yl)-phenylcarbamoyl]-tetrahydrofuran-3-yl}-amide,
(185) 5-bromo-thiophene-2-carboxylic acid-N-{3-[3-methoxy-4-(3-oxo-morpholin-4-yl)-phenylcarbamoyl]-tetrahydrofuran-3-yl}-amide,
(186) 5-bromo-thiophene-2-carboxylic acid-N-{3-[3-nitro-4-(3-oxo-morpholin-4-yl)-phenylcarbamoyl]-tetrahydrofuran-3-yl}-amide,
(187) 5-bromo-thiophene-2-carboxylic acid-N-{3-[3-methyl-4-(3-thioxo-morpholin-4-yl)-phenylcarbamoyl]-tetrahydrofuran-3-yl}-amide, (188) 5-bromo-thiophene-2-carboxylic acid-N-{3-[3-methyl-4-(3-imino-morpholin-4-yl)-phenylcarbamoyl]-tetrahydrofuran-3-yl}-amide,
(189) 5-bromo-thiophene-2-carboxylic acid-N-{3-[3-chloro-4-(2-imino-piperidin-1-yl)-phenylcarbamoyl]-tetrahydrofuran-3-yl}-amide,
(190) 5-bromo-thiophene-2-carboxylic acid-N-{3-[3-methyl-4-(3-methylimino-morpholin-4-yl)-phenylcarbamoyl]-tetrahydrofuran-3-yl}-amide,
(191) 5-bromo-thiophene-2-carboxylic acid-N-{3-[3-chloro-4-(3-hydroxyimino-morpholin-4-yl)-phenylcarbamoyl]-tetrahydrofuran-3-yl}-amide,
(192) 5-bromo-thiophene-2-carboxylic acid-N-{3-[3-methyl-4-(3-methoxyimino-morpholin-4-yl)-phenylcarbamoyl]-tetrahydrofuran-3-yl}-amide,
(193) 5-bromo-thiophene-2-carboxylic acid-N-{3-[3-methyl-4-(2-cyanimino-piperidin-1-yl)-phenylcarbamoyl]-tetrahydrofuran-3-yl}-amide,
(194) 5-bromo-thiophene-2-carboxylic acid-N-{3-[3-chloro-4-(3-cyanimino-morpholin-4-yl)-phenylcarbamoyl]-tetrahydrofuran-3-yl}-amide,
(195) 5-bromo-thiophene-2-carboxylic acid-N-{3-[3-methyl-4-(3-nitroimino-morpholin-4-yl)-phenylcarbamoyl]-tetrahydrofuran-3-yl}-amide,
(196) 5-bromo-thiophene-2-carboxylic acid-N-{3-[3-methyl-4-(5-oxo-[1,4]-oxazepan-4-yl)-phenylcarbamoyl]-tetrahydrofuran-3-yl}-amide,
(197) 5-bromo-thiophene-2-carboxylic acid-N-{3-[3-fluoro-4-(5-oxo-[1,4]-oxazepan-4-yl)-phenylcarbamoyl]-tetrahydrofuran-3-yl}-amide,
(198) 5-bromo-thiophene-2-carboxylic acid-N-{3-[3-chloro-4-(5-oxo-[1,4]-oxazepan-4-yl)-phenylcarbamoyl]-tetrahydrofuran-3-yl}-amide,
(199) 5-bromo-thiophene-2-carboxylic acid-N-{3-[3-bromo-4-(5-oxo-[1,4]-oxazepan-4-yl)-phenylcarbamoyl]-tetrahydrofuran-3-yl}-amide,
(200) 5-bromo-thiophene-2-carboxylic acid-N-{3-[3-methyl-4-(4-methyl-2-oxo-[1,4]-diazepan-1-yl)-phenylcarbamoyl]-tetrahydrofuran-3-yl}-amide,
(201) 5-bromo-thiophene-2-carboxylic acid-N-{3-[3-chloro-4-(1-methyl-5-oxo-[1,4]-diazepan-4-yl)-phenylcarbamoyl]-tetrahydrofuran-3-yl}-amide,
(202) 5-bromo-thiophene-2-carboxylic acid-N-{3-[3-trifluoromethyl-4-(5-oxo-[1,4]-oxazepan-4-yl)-phenylcarbamoyl]-tetrahydrofuran-3-yl}-amide,
(203) 5-bromo-thiophene-2-carboxylic acid-N-{3-[3-methyl-4-(5-thioxo-[1,4]-oxazepan-4-yl)-phenylcarbamoyl]-tetrahydrofuran-3-yl}-amide,
(204) 5-bromo-thiophene-2-carboxylic acid-N-{3-[3-methyl-4-(5-imino-[1,4]-oxazepan-4-yl)-phenylcarbamoyl]-tetrahydrofuran-3-yl}-amide,
(205) 5-bromo-thiophene-2-carboxylic acid-N-{3-[3-chloro-4-(5-methylimino-[1,4]-oxazepan-4-yl)-phenylcarbamoyl]-tetrahydrofuran-3-yl}-amide,
(206) 5-bromo-thiophene-2-carboxylic acid-N-{3-[3-methyl-4-(5-hydroxylimino-[1,4]-oxazepan-4-yl)-phenylcarbamoyl-tetrahydrofuran-3-yl}-amide,
(207) 5-bromo-thiophene-2-carboxylic acid-N-{3-[3-methyl-4-(5-methoxyimino-[1,4]-oxazepan-4-yl)-phenylcarbamoyl]-tetrahydrofuran-3-yl}-amide,
(208) 5-bromo-thiophene-2-carboxylic acid-N-{3-[3-chloro-4-(5-cyanimino-[1,4]-oxazepan-4-yl)-phenylcarbamoyl]-tetrahydrofuran-3-yl}-amide,
(209) 5-bromo-thiophene-2-carboxylic acid-N-{3-[3-methyl-4-(3-oxo-morpholin-4-yl)-phenylcarbamoyl]-tetrahydro-thiophen-3-yl}-amide,
(210) 5-bromo-thiophene-2-carboxylic acid-N-{3-[3-chloro-4-(5-oxo-[1,4]-oxazepan-4-yl)-phenylcarbamoyl]-tetrahydro-thiophen-3-yl}-amide,
(211) 5-bromo-thiophene-2-carboxylic acid-N-{3-[3-methyl-4-(3-oxo-morpholin-4-yl)-phenylcarbamoyl]-1,1-dioxo-tetrahydro-thiophen-3-yl}-amide,
(212) 5-bromo-thiophene-2-carboxylic acid-N-{3-[3-chloro-4-(5-oxo-[1,4]-oxazepan-4-yl)-phenylcarbamoyl]-1,1-dioxo-tetrahydro-thiophen-3-yl}-amide,
(213) 5-bromo-thiophene-2-carboxylic acid-N-{3-[3-fluoro-4-(3-oxo-morpholin-4-yl)-phenylcarbamoyl]-1-methyl-pyrrolidin-3-yl}-amide,
(214) 5-bromo-thiophene-2-carboxylic acid-N-{3-[3-bromo-4-(3-oxo-morpholin-4-yl)-phenylcarbamoyl]-1-methyl-pyrrolidin-3-yl}-amide,
(215) 5-bromo-thiophene-2-carboxylic acid-N-{3-[3-methyl-4-(3-imino-morpholin-4-yl)-phenylcarbamoyl]-1-methyl-pyrrolidin-3-yl}-amide,
(216) 5-bromo-thiophene-2-carboxylic acid-N-{3-[3-methyl-4-(3-methylimino-morpholin-4-yl)-phenylcarbamoyl]-1-methyl-pyrrolidin-3-yl}-amide,
(217) 5-bromo-thiophene-2-carboxylic acid-N-{3-[3-methyl-4-(3-cyanimino-morpholin-4-yl)-phenylcarbamoyl]-1-methyl-pyrrolidin-3-yl}-amide,
(218) 5-bromo-thiophene-2-carboxylic acid-N-{3-[3-methyl-4-(5-oxo-[1,4]-oxazepan-4-yl)-phenylcarbamoyl]-1-methyl-pyrrolidin-3-yl}-amide,
(219) 5-bromo-thiophene-2-carboxylic acid-N-{3-[3-chloro-4-(5-oxo-[1,4]-oxazepan-4-yl)-phenylcarbamoyl]-1-methyl-pyrrolidin-3-yl}-amide,
(220) 5-bromo-thiophene-2-carboxylic acid-N-{3-[3-chloro-4-(5-methylimino-[1,4]-oxazepan-4-yl)-phenylcarbamoyl]-1-methyl-pyrrolidin-3-yl}-amide,
(221) 5-bromo-thiophene-2-carboxylic acid-N-{3-[3-methyl-4-(5-methoxyimino-[1,4]-oxazepan-4-yl)-phenylcarbamoyl]-1-methyl-pyrrolidin-3-yl}-amide,
(222) 5-bromo-thiophene-2-carboxylic acid-N-{3-[3-chloro-4-(5-cyanimino-[1,4]-oxazepan-4-yl)-phenylcarbamoyl]-1-methyl-pyrrolidin-3-yl}-amide,
(223) 5-chloro-thiophene-2-carboxylic acid-N-{1-[3-methyl-4-(3-oxo-morpholin-4-yl)-phenylcarbamoyl]-1-(pyrazin-2-yl)-methyl}-amide,
(224) 5-chloro-thiophene-2-carboxylic acid-N-{(1R)-1-[3-methyl-4-(3-oxo-morpholin-4-yl)-phenylcarbamoyl]-1-phenyl-methyl}-amide,
(225) 5-chloro-thiophene-2-carboxylic acid-N-{(1S)-1-[3-methyl-4-(3-oxo-morpholin-4-yl)-phenylcarbamoyl]-1-phenyl-methyl}-amide,
(226) 5-bromo-thiophene-2-carboxylic acid-N-{1-methyl-1-[3-methyl-4-((4R)-4-methyl-2-oxo-oxazolidin-3-yl)-phenylcarbamoyl]-ethyl}-amide,
(227) 5-chloro-thiophene-2-carboxylic acid-N-{1-methyl-1-(3-methyl-4-[(4R)-4-methyl-2-oxo-oxazolidin-3-yl]-phenylcarbamoyl)-ethyl}-amide,
(228) 5-chloro-thiophene-2-carboxylic acid-N-{1-[3-methyl-4-(tetrahydro-pyrimidin-2-on-1-yl)-phenylcarbamoyl]-ethyl}-amide,
(229) 5-chloro-thiophene-2-carboxylic acid-N-{1-(1-methyl-pyrazol-3-yl)-1-[3-methyl-4-(3-oxo-morpholin-4-yl)-phenylcarbamoyl]-methyl}-amide,
(230) 5-chloro-thiophene-2-carboxylic acid-N-{(1R)-1-[3-methyl-4-(3-oxo-morpholin-4-yl)-phenylcarbamoyl]-2-[pyridin-4-yl]-ethyl}-amide,
(231) 5-bromo-thiophene-2-carboxylic acid-N-{2-(methoxy-carbonyl)-1-[3-methyl-4-(3-oxo-morpholin-4-yl)-phenylcarbamoyl]-ethyl}-amide, (232) 5-bromo-thiophene-2-carboxylic acid-N-{(1R)-1-[3-methyl-4-(3-oxo-morpholin-4-yl)-phenylcarbamoyl]-2-[pyridin-4-yl]-ethyl}-amide,
(233) 5-chloro-thiophene-2-carboxylic acid-N-{1-[3-methyl-4-(3-cyanimino-morpholin-4-yl)-phenylcarbamoyl]-cyclopentyl}-amide,
(234) 5-chloro-thiophene-2-carboxylic acid-N-{1-[3-methyl-4-(5-cyanimino-[1,4]-oxazepan-4-yl)-phenylcarbamoyl]-cyclopentyl}-amide,
(235) 5-bromo-thiophene-2-carboxylic acid-N-{3-[3-methyl-4-(3-cyanimino-morpholin-4-yl)-phenylcarbamoyl]-tetrahydrofuran-3-yl}-amide,
(236) 5-chloro-thiophene-2-carboxylic acid-N-{3-[3-methyl-4-(3-cyanimino-morpholin-4-yl)-phenylcarbamoyl]-tetrahydrofuran-3-yl}-amide,
(237) 5-chloro-thiophene-2-carboxylic acid-N-{3-[3-bromo-4-(3-cyanimino-morpholin-4-yl)-phenylcarbamoyl]-tetrahydrofuran-3-yl}-amide,
(238) 5-bromo-thiophene-2-carboxylic acid-N-{3-[3-methyl-4-(5-cyanimino-[1,4]-oxazepan-4-yl)-phenylcarbamoyl]-tetrahydrofuran-3-yl}-amide,
(239) 5-chloro-thiophene-2-carboxylic acid-N-{3-[3-methyl-4-(5-cyanimino-[1,4]-oxazepan-4-yl)-phenylcarbamoyl]-tetrahydrofuran-3-yl}-amide,
(240) 5-chloro-thiophene-2-carboxylic acid-N-{3-[3-bromo-4-(5-cyanimino-[1,4]-oxazepan-4-yl)-phenylcarbamoyl]-tetrahydrofuran-3-yl}-amide,
(241) 5-bromo-thiophene-2-carboxylic acid-N-{2-[3-methyl-4-(3-cyanimino-morpholin-4-yl)-phenylcarbamoyl]-bicyclo[2.2.1]hept-2-yl}-amide,
(242) 5-bromo-thiophene-2-carboxylic acid-N-{2-[3-methyl-4-(3-cyanimino-morpholin-4-yl)-phenylcarbamoyl]-7-oxa-bicyclo[2.2.1]hept-2-yl}-amide,
(243) 5-bromo-thiophene-2-carboxylic acid-N-{2-[3-methyl-4-(3-oxo-morpholin-4-yl)-phenylcarbamoyl]-7-oxa-bicyclo[2.2.1]hept-5-en-2-yl}-amide,
(244) 5-chloro-thiophene-2-carboxylic acid-N-{2-[3-methyl-4-(3-cyanimino-morpholin-4-yl)-phenylcarbamoyl]-7-oxa-bicyclo[2.2.1]hept-2-yl}-amide,
(245) 5-bromo-thiophene-2-carboxylic acid-N-{2-[3-methyl-4-(5-cyanimino-[1,4]oxazepan-4-yl)-phenylcarbamoyl]-7-oxa-bicyclo[2.2.1]hept-2-yl}-amide,
(246) 5-chloro-thiophene-2-carboxylic acid-N-{2-[3-methyl-4-(5 cyanimino-[1,4]oxazepan-4-yl)-phenylcarbamoyl]-7-oxa-bicyclo[2.2.1]hept-2-yl}-amide,
(247) 5-chloro-thiophene-2-carboxylic acid-N-{2-[3-chloro-4-(5-cyanimino-[1,4]oxazepan-4-yl)-phenylcarbamoyl]-7-oxa-bicyclo[2.2.1]hept-2-yl}-amide,
(248) 5-bromo-thiophene-2-carboxylic acid-N-{5-[3-methyl-4-(3-oxo-morpholin-4-yl)-phenylcarbamoyl]-spiro[2.4]hept-5-yl}-amide,
(249) 5-chloro-thiophene-2-carboxylic acid-N-{5-[3-chloro-4-(5-cyanimino-[1,4]oxazepan-4-yl)-phenylcarbamoyl]-spiro[2.4]hept-5-yl}-amide,
(250) 5-chloro-thiophene-2-carboxylic acid-N-{3-[3-methyl-4-(5-cyanimino-[1,4]oxazepan-4-yl)-phenylcarbamoyl]-bicyclo[3.1.0]hex-3-yl}-amide,
(251) 5-chloro-thiophene-2-carboxylic acid-N-{1-[3-methyl-4-(3-oxo-morpholin-4-yl)-phenylcarbamoyl]-cyclopent-3-en-1-yl}-amide,
(252) 5-bromo-thiophene-2-carboxylic acid-N-{1-[3-methyl-4-(2-oxo-tetrahydropyrimidin-1-yl)-phenylcarbamoyl]-cyclopentyl}-amide,
(253) 5-bromo-thiophene-2-carboxylic acid-N-{1-[3-methyl-4-(2-oxo-[1,3]oxazepan-3-yl)-phenylcarbamoyl]-cyclopentyl}-amide,
(254) 5-bromo-thiophene-2-carboxylic acid-N-{1-[3-methyl-4-(2-oxo-[1,3]oxazinan-3-yl)-phenylcarbamoyl]-cyclopentyl}-amide,
(255) 5-bromo-thiophene-2-carboxylic acid-N-{1-methyl-[3-methyl-4-(5-cyanimino-[1,4]oxazepan-4-yl)-phenylcarbamoyl]-ethyl}-amide,
(256) 5-bromo-thiophene-2-carboxylic acid-N-{1-methyl-[3-chloro-4-(5-cyanimino-[1,4]oxazepan-4-yl)-phenylcarbamoyl]-ethyl}-amide,
(257) 5-bromo-thiophene-2-carboxylic acid-N-{3-[3-methyl-4-(3-cyanimino-morpholin-4-yl)-phenylcarbamoyl]-tetrahydrofuran-3-yl}-amide,
(258) 5-chloro-thiophene-2-carboxylic acid-N-{3-[3-chloro-4-(3-cyanimino-morpholin-4-yl)-phenylcarbamoyl]-tetrahydrofuran-3-yl}-amide,
(259) 5-bromo-thiophene-2-carboxylic acid-N-{3-[3-methyl-4-(5-cyanimino-[1,4]-oxazepan-4-yl)-phenylcarbamoyl]-tetrahydrofuran-3-yl}-amide,
(260) 5-chloro-thiophene-2-carboxylic acid-N-{3-[3-chloro-4-(5-cyanimino-[1,4]-oxazepan-4-yl)-phenylcarbamoyl]-tetrahydrofuran-3-yl}-amide,
(261) 5-bromo-thiophene-2-carboxylic acid-N-{(1S)-2-methoxy-1-methyl-1-[3-methyl-4-(3-oxo-morpholin-4-yl)-phenylcarbamoyl]-ethyl}-amide,
(262) 5-bromo-thiophene-2-carboxylic acid-N-{1-[3-chloro-4-(3-oxo-morpholin-4-yl)-phenylcarbamoyl]-cyclohexyl}-amide,
(263) 5-chloro-thiophene-2-carboxylic acid-N-{2-[3-methyl-4-(3-oxo-morpholin-4-yl)-phenylcarbamoyl]-bicyclo[2.2.1]hept-2-yl}-amide, the tautomers, the enantiomers, the diastereomers, the mixtures thereof and the salts thereof, while the compounds (1) 5-chloro-thiophene-2-carboxylic acid-N-{1-[3-chloro-4-(3-oxo-morpholin-4-yl)-phenylcarbamoyl]-ethyl}-amide,
(2) 5-bromo-thiophene-2-carboxylic acid-N-{(1R)-2-methoxy-1-[3-methyl-4-(3-oxo-morpholin-4-yl)-phenylcarbamoyl]-ethyl}-amide,
(3) 5-chloro-thiophene-2-carboxylic acid-N-{(1R)-2-methoxy-1-[3-methyl-4-(3-oxo-morpholin-4-yl)-phenylcarbamoyl]-ethyl}-amide,
(4) 5-bromo-thiophene-2-carboxylic acid-N-{(1S)-2-methoxy-1-[3-methyl-4-(3-oxo-morpholin-4-yl)-phenylcarbamoyl]-ethyl}-amide,
(5) 5-chloro-thiophene-2-carboxylic acid-N-{(1S)-2-methoxy-1-[3-methyl-4-(3-oxo-morpholin-4-yl)-phenylcarbamoyl]-ethyl}-amide,
(6) 5-chloro-thiophene-2-carboxylic acid-N-{1-[2-fluoro-5-methyl-4-(3-oxo-morpholin-4-yl)-phenylcarbamoyl]-ethyl}-amide,
(7) 5-chloro-thiophene-2-carboxylic acid-N-{(1R)-1-[2-fluoro-5-methyl-4-(3-oxo-morpholin-4-yl)-phenylcarbamoyl]-2-methoxy-ethyl}-amide,
(8) 5-bromo-thiophene-2-carboxylic acid-N-{(1R)-1-[2-fluoro-5-methyl-4-(3-oxo-morpholin-4-yl)-phenylcarbamoyl]-2-methoxy-ethyl}-amide,
(9) 5-chloro-thiophene-2-carboxylic acid-N-{1-[3-methyl-4-(3-thioxo-morpholin-4-yl)-phenylcarbamoyl]-ethyl}-amide,
(10) 5-chloro-thiophene-2-carboxylic acid-N-{1-methyl-1-[3-methyl-4-(3-oxo-morpholin-4-yl)-phenylcarbamoyl]-ethyl}-amide,
(11) 5-bromo-thiophene-2-carboxylic acid-N-{1-methyl-1-[3-methyl-4-(3-oxo-morpholin-4-yl)-phenylcarbamoyl]-ethyl}-amide,

(12) 5-chloro-thiophene-2-carboxylic acid-N-{(1R)-2-benzyloxy-1-[3-methyl-4-(3-oxo-morpholin-4-yl)-phenylcarbamoyl]-ethyl}-amide,
(13) thiophene-2-carboxylic acid-N-{(1R)-2-benzyloxy-1-[3-methyl-4-(3-oxo-morpholin-4-yl)-phenylcarbamoyl]-ethyl}-amide,
(14) 5-chloro-thiophene-2-carboxylic acid-N-{1-[3-chloro-4-(4-methyl-oxazolidin-3-yl)-phenylcarbamoyl]-ethyl}-amide,
(15) 5-chloro-thiophene-2-carboxylic acid-N-{(1R)-2-hydroxy-1-[3-methyl-4-(3-oxo-morpholin-4-yl)-phenylcarbamoyl]-ethyl}-amide,
(16) 5-bromo-thiophene-2-carboxylic acid-N-((1R)-2-methoxy-1-[N'-methyl-N'-{3-methyl-4-(3-oxo-morpholin-4-yl)-phenyl}-carbamoyl]-ethyl)-amide,
(17) 5-chloro-thiophene-2-carboxylic acid-N-{1-[3-methyl-4-(3-oxo-morpholin-4-yl)-phenylcarbamoyl]-1-pyridin-3-yl-methyl}-amide,
(18) 5-chloro-thiophene-2-carboxylic acid-N-{1-phenyl-1-[3-methyl-4-(3-oxo-morpholin-4-yl)-phenylcarbamoyl]-ethyl}-amide,
(19) 5-bromo-thiophene-2-carboxylic acid-N-{1-methyl-1-[3-chloro-4-(4-methyl-2-oxo-piperazin-1-yl)-phenylcarbamoyl]-ethyl}-amide,
(20) 5-bromo-thiophene-2-carboxylic acid-N-{1-methyl-1-[3-bromo-4-(4-methyl-2-oxo-piperazin-1-yl)-phenylcarbamoyl]-ethyl}-amide,
(21) 5-chloro-thiophene-2-carboxylic acid-N-{1-methyl-1-[3-chloro-4-(3-oxo-morpholin-4-yl)-phenylcarbamoyl]-ethyl}-amide,
(22) 5-bromo-thiophene-2-carboxylic acid-N-{1-methyl-1-[3-chloro-4-(3-oxo-morpholin-4-yl)-phenylcarbamoyl]-ethyl}-amide,
(23) 5-chloro-thiophene-2-carboxylic acid-N-{1-methyl-1-[3-bromo-4-(3-oxo-morpholin-4-yl)-phenylcarbamoyl]-ethyl}-amide,
(24) 5-bromo-thiophene-2-carboxylic acid-N-{1-methyl-1-[3-bromo-4-(3-oxo-morpholin-4-yl)-phenylcarbamoyl]-ethyl}-amide,
(25) 5-chloro-thiophene-2-carboxylic acid-N-{1-methyl-1-[3-trifluoromethyl-4-(3-oxo-morpholin-4-yl)-phenylcarbamoyl]-ethyl}-amide,
(26) 5-bromo-thiophene-2-carboxylic acid-N-{1-methyl-1-[3-trifluoromethyl-4-(3-oxo-morpholin-4-yl)-phenylcarbamoyl]-ethyl}-amide,
(27) 5-chloro-thiophene-2-carboxylic acid-N-{1-methyl-1-[3-methoxy-4-(3-oxo-morpholin-4-yl)-phenylcarbamoyl]-ethyl}-amide,
(28) 5-bromo-thiophene-2-carboxylic acid-N-{1-methyl-i-[3-methoxy-4-(3-oxo-morpholin-4-yl)-phenylcarbamoyl]-ethyl}-amide,
(29) 5-chloro-thiophene-2-carboxylic acid-N-{2-methoxy-1-[methoxymethyl]-1-[3-methyl-4-(3-oxo-morpholin-4-yl)-phenylcarbamoyl]-ethyl}-amide,
(30) 5-bromo-thiophene-2-carboxylic acid-N-{2-methoxy-1-[methoxymethyl]-1-[3-methyl-4-(3-oxo-morpholin-4-yl)-phenylcarbamoyl]-ethyl}-amide,
(31) 5-bromo-thiophene-2-carboxylic acid-N-{2-methoxy-1-[methoxymethyl]-1-[3-chloro-4-(3-oxo-morpholin-4-yl)-phenylcarbamoyl]-ethyl}-amide,
(32) 5-chloro-thiophene-2-carboxylic acid-N-{(1R)-2-methoxy-1-methyl-1-[3-methyl-4-(3-oxo-morpholin-4-yl)-phenylcarbamoyl]-ethyl}-amide,
(33) 5-bromo-thiophene-2-carboxylic acid-N-{(1R)-2-methoxy-1-methyl-1-[3-chloro-4-(3-oxo-morpholin-4-yl)-phenylcarbamoyl]-ethyl}-amide,
(34) 5-bromo-thiophene-2-carboxylic acid-N-{(1R)-2-methoxy-1-methyl-1-[3-methyl-4-(3-oxo-morpholin-4-yl)-phenylcarbamoyl]-ethyl}-amide,
(35) 5-chloro-thiophene-2-carboxylic acid-N-{(1S)-2-methoxy-1-methyl-1-[3-methyl-4-(3-oxo-morpholin-4-yl)-phenylcarbamoyl]-ethyl}-amide,
(36) 5-bromo-thiophene-2-carboxylic acid-N-{(1S)-2-methoxy-1-methyl-1-[3-chloro-4-(3-oxo-morpholin-4-yl)-phenylcarbamoyl]-ethyl}-amide,
(37) 5-chloro-thiophene-2-carboxylic acid-N-{1-[3-methyl-4-(3-oxo-morpholin-4-yl)-phenylcarbamoyl]-cyclopropyl}-amide,
(38) 5-bromo-thiophene-2-carboxylic acid-N-{1-[3-methyl-4-(3-oxo-morpholin-4-yl)-phenylcarbamoyl]-cyclopropyl}-amide,
(39) 5-chloro-thiophene-2-carboxylic acid-N-{1-[3-methyl-4-(3-oxo-morpholin-4-yl)-phenylcarbamoyl]-cyclobutyl}-amide,
(40) 5-bromo-thiophene-2-carboxylic acid-N-{1-[3-methyl-4-(3-oxo-morpholin-4-yl)-phenylcarbamoyl]-cyclobutyl}-amide,
(41) 5-chloro-thiophene-2-carboxylic acid-N-{1-[3-methyl-4-(3-oxo-morpholin-4-yl)-phenylcarbamoyl]-cyclopentyl}-amide,
(42) 5-bromo-thiophene-2-carboxylic acid-N-{1-[3-methyl-4-(3-oxo-morpholin-4-yl)-phenylcarbamoyl]-cyclopentyl}-amide,
(43) 5-chloro-thiophene-2-carboxylic acid-N-{1-[3-methyl-4-(3-oxo-morpholin-4-yl)-phenylcarbamoyl]-cyclohexyl}-amide,
(44) 5-bromo-thiophene-2-carboxylic acid-N-{1-[3-methyl-4-(3-oxo-morpholin-4-yl)-phenylcarbamoyl]-cyclohexyl}-amide,
(45) 5-chloro-thiophene-2-carboxylic acid-N-{3-[3-methyl-4-(3-oxo-morpholin-4-yl)-phenylcarbamoyl]-tetrahydrofuran-3-yl}-amide,
(46) 5-bromo-thiophene-2-carboxylic acid-N-{3-[3-methyl-4-(3-oxo-morpholin-4-yl)-phenylcarbamoyl]-tetrahydrofuran-3-yl}-amide,
(47) 5-bromo-thiophene-2-carboxylic acid-N-{3-[3-chloro-4-(3-oxo-morpholin-4-yl)-phenylcarbamoyl]-tetrahydrofuran-3-yl}-amide,
(48) 5-chloro-thiophene-2-carboxylic acid-N-{4-[3-methyl-4-(3-oxo-morpholin-4-yl)-phenylcarbamoyl]-tetrahydropyran-4-yl}-amide,
(49) 5-bromo-thiophene-2-carboxylic acid-N-{4-[3-methyl-4-(3-oxo-morpholin-4-yl)-phenylcarbamoyl]-tetrahydropyran-4-yl}-amide,
(50) 5-chloro-thiophene-2-carboxylic acid-N-{1-methyl-3-[3-methyl-4-(3-oxo-morpholin-4-yl)-phenylcarbamoyl]-pyrrolidin-3-yl}-amide,
(51) 5-bromo-thiophene-2-carboxylic acid-N-{1-methyl-3-[3-methyl-4-(3-oxo-morpholin-4-yl)-phenylcarbamoyl]-pyrrolidin-3-yl}-amide,
(52) 5-bromo-thiophene-2-carboxylic acid-N-{1-methyl-3-[3-chloro-4-(3-oxo-morpholin-4-yl)-phenylcarbamoyl]-pyrrolidin-3-yl}-amide,
(53) 5-chloro-thiophene-2-carboxylic acid-N-{1-acetyl-3-[3-methyl-4-(3-oxo-morpholin-4-yl)-phenylcarbamoyl]-pyrrolidin-3-yl}-amide,
(54) 5-chloro-thiophene-2-carboxylic acid-N-{1-methoxycarbonyl-3-[3-methyl-4-(3-oxo-morpholin-4-yl)-phenylcarbamoyl]-pyrrolidin-3-yl}-amide,
(55) 5-chloro-thiophene-2-carboxylic acid-N-{1-methyl-4-[3-methyl-4-(3-oxo-morpholin-4-yl)-phenylcarbamoyl]-piperidin-4-yl}-amide,

(56) 5-bromo-thiophene-2-carboxylic acid-N-{1-methyl-4-[3-methyl-4-(3-oxo-morpholin-4-yl)-phenylcarbamoyl]-piperidin-4-yl}-amide,

(57) 5-bromo-thiophene-2-carboxylic acid-N-{1-methyl-4-[3-chloro-4-(3-oxo-morpholin-4-yl)-phenylcarbamoyl]-piperidin-4-yl}-amide,

(58) 5-chloro-thiophene-2-carboxylic acid-N-{1-acetyl-4-[3-methyl-4-(3-oxo-morpholin-4-yl)-phenylcarbamoyl]-piperidin-4-yl}-amide,

(59) 5-bromo-thiophene-2-carboxylic acid-N-{1-acetyl-4-[3-methyl-4-(3-oxo-morpholin-4-yl)-phenylcarbamoyl]-piperidin-4-yl}-amide,

(60) 5-bromo-thiophene-2-carboxylic acid-N-{1-methyl-1-[3-methyl-4-(4,4-dimethyl-oxazolidin-2-on-3-yl)-phenylcarbamoyl]-ethyl}-amide,

(61) 5-bromo-thiophene-2-carboxylic acid-N-{1-methyl-1-[3-methyl-4-(2-oxo-piperidin-1-yl)-phenylcarbamoyl]-ethyl}-amide,

(62) 5-bromo-thiophene-2-carboxylic acid-N-{1-methyl-1-[3-methyl-4-(2-oxo-[1,3]oxazinan-3-yl)-phenylcarbamoyl]-ethyl}-amide,

(63) 5-bromo-thiophene-2-carboxylic acid-N-{1-methyl-1-[3-methyl-4-(4,4-dimethyl-2-oxo-imidazolidin-3-yl)-phenylcarbamoyl]-ethyl}-amide,

(64) 5-bromo-thiophene-2-carboxylic acid-N-{1-methyl-1-[3-methyl-4-(2-oxo-tetrahydropyrimidin-1-yl)-phenylcarbamoyl]-ethyl}-amide,

(65) 5-bromo-thiophene-2-carboxylic acid-N-{1-methyl-1-[3-methyl-4-(2-oxo-[1,3]oxazepan-3-yl)-phenylcarbamoyl]-ethyl}-amide,

(66) 5-bromo-thiophene-2-carboxylic acid-N-{1-methyl-1-[3-methyl-4-(3-oxo-[1,4]oxazepan-4-yl)-phenylcarbamoyl]-ethyl}-amide,

(67) 5-bromo-thiophene-2-carboxylic acid-N-{1-methyl-1-[3-methyl-4-(5-oxo-[1,4]oxazepan-4-yl)-phenylcarbamoyl]-ethyl}-amide,

(68) 5-bromo-thiophene-2-carboxylic acid-N-{1-methyl-1-[3-methyl-4-(2-oxo-[1,3]diazepan-1-yl)-phenylcarbamoyl]-ethyl}-amide,

(69) 5-bromo-thiophene-2-carboxylic acid-N-{1-methyl-1-[3-methyl-4-(2-oxo-[1,4]diazepan-1-yl)-phenylcarbamoyl]-ethyl}-amide,

(70) 5-bromo-thiophene-2-carboxylic acid-N-{1-methyl-1-[3-methyl-4-(7-oxo-[1,4]diazepan-1-yl)-phenylcarbamoyl]-ethyl}-amide,

(71) 5-bromo-thiophene-2-carboxylic acid-N-{1-methyl-1-[3-methyl-4-(4-methyl-7-oxo-[1,4]diazepan-1-yl)-phenylcarbamoyl]-ethyl}-amide,

(72) 5-bromo-thiophene-2-carboxylic acid-N-{1-methyl-1-[3-methyl-4-(4-methyl-2-oxo-[1,4]diazepan-1-yl)-phenylcarbamoyl]-ethyl}-amide,

(73) 5-bromo-thiophene-2-carboxylic acid-N-{1-methyl-1-[3-methyl-4-(1,1-dioxo-isothiazolidin-2-yl)-phenylcarbamoyl]-ethyl}-amide,

(74) 5-bromo-thiophene-2-carboxylic acid-N-{5-dimethylamino-1-[3-methyl-4-(3-oxo-morpholin-4-yl)-phenylcarbamoyl]-pentyl}-amide,

(75) 5-bromo-thiophene-2-carboxylic acid-N-{5-acetylamino-1-[3-methyl-4-(3-oxo-morpholin-4-yl)-phenylcarbamoyl]-pentyl}-amide,

(76) 5-bromo-thiophene-2-carboxylic acid-N-{5-methylsulphonylamino-1-[3-methyl-4-(3-oxo-morpholin-4-yl)-phenylcarbamoyl]-pentyl}-amide,

(77) 5-bromo-thiophene-2-carboxylic acid-N-{3-methylsulphanyl-1-[3-methyl-4-(3-oxo-morpholin-4-yl)-phenylcarbamoyl]-propyl}-amide,

(78) 5-bromo-thiophene-2-carboxylic acid-N-{3-methylsulphonyl-1-[3-methyl-4-(3-oxo-morpholin-4-yl)-phenylcarbamoyl]-propyl}-amide,

(79) 5-bromo-thiophene-2-carboxylic acid-N-{3-(tetrazol-5-yl)-1-[3-methyl-4-(3-oxo-morpholin-4-yl)-phenylcarbamoyl]-propyl}-amide,

(80) 5-bromo-thiophene-2-carboxylic acid-N-{3-methyl-1-[3-methyl-4-(3-oxo-morpholin-4-yl)-phenylcarbamoyl]-butyl}-amide,

(81) 5-bromo-thiophene-2-carboxylic acid-N-{4-methoxy-4-oxo-1-[3-methyl-4-(3-oxo-morpholin-4-yl)-phenylcarbamoyl]-butyl}-amide,

(82) 5-bromo-thiophene-2-carboxylic acid-N-{4-dimethylamino-4-oxo-1-[3-methyl-4-(3-oxo-morpholin-4-yl)-phenylcarbamoyl]-butyl}-amide,

(83) 5-bromo-thiophene-2-carboxylic acid-N-{2-methoxy-1-[3-methyl-4-(3-oxo-morpholin-4-yl)-phenylcarbamoyl]-propyl}-amide,

(84) 5-bromo-thiophene-2-carboxylic acid-N-{1-[3-chloro-4-(3-oxo-morpholin-4-yl)-phenylcarbamoyl]-cyclobutyl}-amide,

(85) 5-bromo-thiophene-2-carboxylic acid-N-{1-[3-bromo-4-(3-oxo-morpholin-4-yl)-phenylcarbamoyl]-cyclobutyl}-amide,

(86) 5-bromo-thiophene-2-carboxylic acid-N-{1-[3-methyl-4-(3-imino-morpholin-4-yl)-phenylcarbamoyl]-cyclobutyl}-amide,

(87) 5-bromo-thiophene-2-carboxylic acid-N-{1-[3-chloro-4-(3-hydroxyimino-morpholin-4-yl)-phenylcarbamoyl]-cyclobutyl}-amide,

(88) 5-bromo-thiophene-2-carboxylic acid-N-{1-[3-chloro-4-(3-cyanimino-morpholin-4-yl)-phenylcarbamoyl]-cyclobutyl}-amide,

(89) 5-bromo-thiophene-2-carboxylic acid-N-{1-[3-methyl-4-(5-oxo-[1,4]-oxazepan-4-yl)-phenylcarbamoyl]-cyclobutyl}-amide,

(90) 5-bromo-thiophene-2-carboxylic acid-N-{1-[3-chloro-4-(5-oxo-[1,4]-oxazepan-4-yl)-phenylcarbamoyl]-cyclobutyl}-amide,

(91) 5-bromo-thiophene-2-carboxylic acid-N-{1-[3-methyl-4-(5-imino-[1,4]-oxazepan-4-yl)-phenylcarbamoyl]-cyclobutyl}-amide,

(92) 5-bromo-thiophene-2-carboxylic acid-N-{1-[3-chloro-4-(5-methylimino-[1,4]-oxazepan-4-yl)-phenylcarbamoyl]-cyclobutyl}-amide,

(93) 5-bromo-thiophene-2-carboxylic acid-N-{1-[3-methyl-4-(5-methoxyimino-[1,4]-oxazepan-4-yl)-phenylcarbamoyl]-cyclobutyl}-amide,

(94) 5-bromo-thiophene-2-carboxylic acid-N-{1-[3-chloro-4-(5-cyanimino-[1,4]-oxazepan-4-yl)-phenylcarbamoyl]-cyclobutyl}-amide,

(95) 5-bromo-thiophene-2-carboxylic acid-N-{1-[3-fluoro-4-(3-oxo-morpholin-4-yl)-phenylcarbamoyl]-cyclopentyl}-amide,

(96) 5-bromo-thiophene-2-carboxylic acid-N-{1-[3-chloro-4-(3-oxo-morpholin-4-yl)-phenylcarbamoyl]-cyclopentyl}-amide,

(97) 5-bromo-thiophene-2-carboxylic acid-N-{1-[3-bromo-4-(3-oxo-morpholin-4-yl)-phenylcarbamoyl]-cyclopentyl}-amide,

(98) 5-bromo-thiophene-2-carboxylic acid-N-{1-[3-trifluoromethyl-4-(3-oxo-morpholin-4-yl)-phenylcarbamoyl]-cyclopentyl}-amide,

(99) 5-bromo-thiophene-2-carboxylic acid-N-{1-[3-methyl-4-(3-thioxo-morpholin-4-yl)-phenylcarbamoyl]-cyclopentyl}-amide, (100) 5-bromo-thiophene-2-carboxylic acid-N-{1-[3-methyl-4-(2-imino-piperidin-1-yl)-phenylcarbamoyl]-cyclopentyl}-amide,
(101) 5-bromo-thiophene-2-carboxylic acid-N-{1-[3-chloro-4-(3-imino-morpholin-4-yl)-phenylcarbamoyl-cyclopentyl]}-amide,
(102) 5-bromo-thiophene-2-carboxylic acid-N-{1-[3-methyl-4-(3-methylimino-morpholin-4-yl)-phenylcarbamoyl]-cyclopentyl}-amide,
(103) 5-bromo-thiophene-2-carboxylic acid-N-{1-[3-chloro-4-(3-hydroxylimino-morpholin-4-yl)-phenylcarbamoyl]-cyclopentyl}-amide,
(104) 5-bromo-thiophene-2-carboxylic acid-N-{1-[3-methyl-4-(3-methoxyimino-morpholin-4-yl)-phenylcarbamoyl]-cyclopentyl}-amide,
(105) 5-bromo-thiophene-2-carboxylic acid-N-{1-[3-methyl-4-(3-cyanimino-morpholin-4-yl)-phenylcarbamoyl]-cyclopentyl}-amide,
(106) 5-bromo-thiophene-2-carboxylic acid-N-{1-[3-chloro-4-(2-cyanimino-piperidin-1-yl)-phenylcarbamoyl]-cyclopentyl}-amide,
(107) 5-bromo-thiophene-2-carboxylic acid-N-{1-[3-methyl-4-(5-oxo-[1,4]-oxazepan-4-yl)-phenylcarbamoyl]-cyclopentyl}-amide,
(108) 5-bromo-thiophene-2-carboxylic acid-N-{1-[3-chloro-4-(5-oxo-[1,4]-oxazepan-4-yl)-phenylcarbamoyl]-cyclopentyl}-amide,
(109) 5-bromo-thiophene-2-carboxylic acid-N-{1-[3-bromo-4-(5-oxo-[1,4]-oxazepan-4-yl)-phenylcarbamoyl]-cyclopentyl}-amide,
(110) 5-bromo-thiophene-2-carboxylic acid-N-{1-[3-methyl-4-(5-thioxo-[1,4]-oxazepan-4-yl)-phenylcarbamoyl]-cyclopentyl}-amide,
(111) 5-bromo-thiophene-2-carboxylic acid-N-{1-[3-methyl-4-(5-imino-[1,4]-oxazepan-4-yl)-phenylcarbamoyl]-cyclopentyl}-amide,
(112) 5-bromo-thiophene-2-carboxylic acid-N-{1-[3-methyl-4-(5-hydroxylimino-[1,4]-oxazepan-4-yl)-phenylcarbamoyl]-cyclopentyl}-amide,
(113) 5-bromo-thiophene-2-carboxylic acid-N-{1-[3-methyl-4-(5-methoxyimino-[1,4]-oxazepan-4-yl)-phenylcarbamoyl]-cyclopentyl}-amide,
(114) 5-bromo-thiophene-2-carboxylic acid-N-{1-[3-chloro-4-(5-cyanimino-[1,4]-oxazepan-4-yl)-phenylcarbamoyl]-cyclopentyl}-amide,
(115) 5-bromo-thiophene-2-carboxylic acid-N-{3-[3-methyl-4-(3-oxo-morpholin-4-yl)-phenylcarbamoyl]-oxetan-3-yl}-amide,
(116) 5-bromo-thiophene-2-carboxylic acid-N-{3-[3-chloro-4-(3-oxo-morpholin-4-yl)-phenylcarbamoyl]-oxetan-3-yl}-amide,
(117) 5-bromo-thiophene-2-carboxylic acid-N-{3-[3-chloro-4-(3-hydroxylimino-morpholin-4-yl)-phenylcarbamoyl]-oxetan-3-yl}-amide,
(118) 5-bromo-thiophene-2-carboxylic acid-N-{3-[3-methyl-4-(3-methoxyimino-morpholin-4-yl)-phenylcarbamoyl]-oxetan-3-yl}-amide,
(119) 5-bromo-thiophene-2-carboxylic acid-N-{3-[3-methyl-4-(5-oxo-[1,4]-oxazepan-4-yl)-phenylcarbamoyl]-oxetan-3-yl}-amide,
(120) 5-bromo-thiophene-2-carboxylic acid-N-{3-[3-chloro-4-(5-oxo-[1,4]-oxazepan-4-yl)-phenylcarbamoyl]-oxetan-3-yl}-amide,
(121) 5-bromo-thiophene-2-carboxylic acid-N-{3-[3-methyl-4-(5-imino-[1,4]-oxazepan-4-yl)-phenylcarbamoyl]-oxetan-3-yl}-amide,
(122) 5-bromo-thiophene-2-carboxylic acid-N-{3-[3-chloro-4-(5-methylimino-[1,4]-oxazepan-4-yl)-phenylcarbamoyl]-oxetan-3-yl}-amide,
(123) 5-bromo-thiophene-2-carboxylic acid-N-{3-[3-methyl-4-(3-oxo-morpholin-4-yl)-phenylcarbamoyl]-thietan-3-yl}-amide,
(124) 5-bromo-thiophene-2-carboxylic acid-N-{3-[3-chloro-4-(3-oxo-morpholin-4-yl)-phenylcarbamoyl]-thietan-3-yl}-amide,
(125) 5-bromo-thiophene-2-carboxylic acid-N-{3-[3-methyl-4-(3-imino-morpholin-4-yl)-phenylcarbamoyl]-thietan-3-yl}-amide,
(126) 5-bromo-thiophene-2-carboxylic acid-N-{3-[3-chloro-4-(5-oxo-[1,4]-oxazepan-4-yl)-phenylcarbamoyl]-thietan-3-yl}-amide,
(127) 5-bromo-thiophene-2-carboxylic acid-N-{3-[3-methyl-4-(3-oxo-morpholin-4-yl)-phenylcarbamoyl]-1,1-dioxo-thietan-3-yl}-amide,
(128) 5-bromo-thiophene-2-carboxylic acid-N-{3-[3-chloro-4-(5-oxo-[1,4]-oxazepan-4-yl)-phenylcarbamoyl]-1,1-dioxo-thietan-3-yl}-amide,
(129) 5-bromo-thiophene-2-carboxylic acid-N-{3-[3-chloro-4-(5-methylimino-[1,4]-oxazepan-4-yl)-phenylcarbamoyl]-thietan-3-yl}-amide,
(130) 5-bromo-thiophene-2-carboxylic acid-N-{3-[3-methyl-4-(3-oxo-morpholin-4-yl)-phenylcarbamoyl]-1-methyl-azetidin-3-yl}-amide,
(131) 5-bromo-thiophene-2-carboxylic acid-N-{3-[3-chloro-4-(3-oxo-morpholin-4-yl)-phenylcarbamoyl]-1-methyl-azetidin-3-yl}-amide,
(132) 5-bromo-thiophene-2-carboxylic acid-N-{3-[3-chloro-4-(5-oxo-[1,4]-oxazepan-4-yl)-phenylcarbamoyl]-1-methyl-azetidin-3-yl}-amide,
(133) 5-bromo-thiophene-2-carboxylic acid-N-{3-[3-fluoro-4-(3-oxo-morpholin-4-yl)-phenylcarbamoyl]-tetrahydrofuran-3-yl}-amide,
(134) 5-bromo-thiophene-2-carboxylic acid-N-{3-[3-chloro-4-(3-oxo-morpholin-4-yl)-phenylcarbamoyl]-tetrahydrofuran-3-yl}-amide,
(135) 5-bromo-thiophene-2-carboxylic acid-N-{3-[3-bromo-4-(3-oxo-morpholin-4-yl)-phenylcarbamoyl]-tetrahydrofuran-3-yl}-amide,
(136) 5-bromo-thiophene-2-carboxylic acid-N-{3-[3-methyl-4-(3-thioxo-morpholin-4-yl)-phenylcarbamoyl]-tetrahydrofuran-3-yl}-amide,
(137) 5-bromo-thiophene-2-carboxylic acid-N-{3-[3-methyl-4-(3-imino-morpholin-4-yl)-phenylcarbamoyl]-tetrahydrofuran-3-yl}-amide,
(138) 5-bromo-thiophene-2-carboxylic acid-N-{3-[3-chloro-4-(2-imino-piperidin-1-yl)-phenylcarbamoyl]-tetrahydrofuran-3-yl}-amide,
(139) 5-bromo-thiophene-2-carboxylic acid-N-{3-[3-methyl-4-(3-methylimino-morpholin-4-yl)-phenylcarbamoyl]-tetrahydrofuran-3-yl}-amide,
(140) 5-bromo-thiophene-2-carboxylic acid-N-{3-[3-chloro-4-(3-hydroxylimino-morpholin-4-yl)-phenylcarbamoyl]-tetrahydrofuran-3-yl}-amide,
(141) 5-bromo-thiophene-2-carboxylic acid-N-{3-[3-methyl-4-(2-cyanimino-piperidin-1-yl)-phenylcarbamoyl]-tetrahydrofuran-3-yl}-amide,
(142) 5-bromo-thiophene-2-carboxylic acid-N-{3-[3-chloro-4-(3-cyanimino-morpholin-4-yl)-phenylcarbamoyl]-tetrahydrofuran-3-yl}-amide,
(143) 5-bromo-thiophene-2-carboxylic acid-N-{3-[3-methyl-4-(5-oxo-[1,4]-oxazepan-4-yl)-phenylcarbamoyl]-tetrahydrofuran-3-yl}-amide, (144) 5-bromo-thiophene-2-carboxylic acid-N-{3-[3-fluoro-4-(5-oxo-[1,4]-oxazepan-4-yl)-phenylcarbamoyl]-tetrahydrofuran-3-yl}-amide,
(145) 5-bromo-thiophene-2-carboxylic acid-N-{3-[3-chloro-4-(5-oxo-[1,4]-oxazepan-4-yl)-phenylcarbamoyl]-tetrahydrofuran-3-yl}-amide,
(146) 5-bromo-thiophene-2-carboxylic acid-N-{3-[3-bromo-4-(5-oxo-[1,4]-oxazepan-4-yl)-phenylcarbamoyl]-tetrahydrofuran-3-yl}-amide,
(147) 5-bromo-thiophene-2-carboxylic acid-N-{3-[3-methyl-4-(4-methyl-2-oxo-[1,4]-diazepan-1-yl)-phenylcarbamoyl]-tetrahydrofuran-3-yl}-amide,
(148) 5-bromo-thiophene-2-carboxylic acid-N-{3-[3-chloro-4-(1-methyl-5-oxo-[1,4]-diazepan-4-yl)-phenylcarbamoyl]-tetrahydrofuran-3-yl}-amide,
(149) 5-bromo-thiophene-2-carboxylic acid-N-{3-[3-methyl-4-(5-thioxo-[1,4]-oxazepan-4-yl)-phenylcarbamoyl]-tetrahydrofuran-3-yl}-amide,
(150) 5-bromo-thiophene-2-carboxylic acid-N-{3-[3-methyl-4-(5-imino-[1,4]-oxazepan-4-yl)-phenylcarbamoyl]-tetrahydrofuran-3-yl}-amide,
(151) 5-bromo-thiophene-2-carboxylic acid-N-{3-[3-chloro-4-(5-methylimino-[1,4]-oxazepan-4-yl)-phenylcarbamoyl]-tetrahydrofuran-3-yl}-amide,
(152) 5-bromo-thiophene-2-carboxylic acid-N-{3-[3-methyl-4-(5-methoxyimino-[1,4]-oxazepan-4-yl)-phenylcarbamoyl]-tetrahydrofuran-3-yl}-amide,
(153) 5-bromo-thiophene-2-carboxylic acid-N-{3-[3-chloro-4-(5-cyanimino-[1,4]-oxazepan-4-yl)-phenylcarbamoyl]-tetrahydrofuran-3-yl}-amide,
(154) 5-bromo-thiophene-2-carboxylic acid-N-{3-[3-methyl-4-(3-oxo-morpholin-4-yl)-phenylcarbamoyl]-tetrahydro-thiophen-3-yl}-amide,
(155) 5-bromo-thiophene-2-carboxylic acid-N-{3-[3-chloro-4-(5-oxo-[1,4]-oxazepan-4-yl)-phenylcarbamoyl]-tetrahydro-thiophen-3-yl}-amide,
(156) 5-bromo-thiophene-2-carboxylic acid-N-{3-[3-methyl-4-(3-oxo-morpholin-4-yl)-phenylcarbamoyl]-1,1-dioxo-tetrahydro-thiophen-3-yl}-amide,
(157) 5-bromo-thiophene-2-carboxylic acid-N-{3-[3-chloro-4-(5-oxo-[1,4]-oxazepan-4-yl)-phenylcarbamoyl]-1,1-dioxo-tetrahydro-thiophen-3-yl}-amide,
(158) 5-bromo-thiophene-2-carboxylic acid-N-{3-[3-fluoro-4-(3-oxo-morpholin-4-yl)-phenylcarbamoyl]-1-methyl-pyrrolidin-3-yl}-amide,
(159) 5-bromo-thiophene-2-carboxylic acid-N-{3-[3-bromo-4-(3-oxo-morpholin-4-yl)-phenylcarbamoyl]-1-methyl-pyrrolidin-3-yl}-amide,
(160) 5-bromo-thiophene-2-carboxylic acid-N-{3-[3-methyl-4-(3-cyanimino-morpholin-4-yl)-phenylcarbamoyl]-1-methyl-pyrrolidin-3-y!}-amide,
(161) 5-bromo-thiophene-2-carboxylic acid-N-{3-[3-methyl-4-(5-oxo-[1,4]-oxazepan-4-yl)-phenylcarbamoyl]-1-methyl-pyrrolidin-3-yl}-amide,
(162) 5-bromo-thiophene-2-carboxylic acid-N-{3-[3-chloro-4-(5-oxo-[1,4]-oxazepan-4-yl)-phenylcarbamoyl]-1-methyl-pyrrolidin-3-yl}-amide,
(163) 5-bromo-thiophene-2-carboxylic acid-N-{3-[3-methyl-4-(5-methoxyimino-[1,4]-oxazepan-4-yl)-phenylcarbamoyl]-1-methyl-pyrrolidin-3-yl}-amide,
(164) 5-bromo-thiophene-2-carboxylic acid-N-{3-[3-chloro-4-(5-cyanimino-[1,4]-oxazepan-4-yl)-phenylcarbamoyl]-1-methyl-pyrrolidin-3-yl}-amide,
(165) 5-chloro-thiophene-2-carboxylic acid-N-{1-[3-methyl-4-(3-oxo-morpholin-4-yl)-phenylcarbamoyl]-1-(pyrazin-2-yl)-methyl}-amide,
(166) 5-chloro-thiophene-2-carboxylic acid-N-{(1R)-1-[3-methyl-4-(3-oxo-morpholin-4-yl)-phenylcarbamoyl]-1-phenyl-methyl}-amide,
(167) 5-chloro-thiophene-2-carboxylic acid-N-{(1S)-1-[3-methyl-4-(3-oxo-morpholin-4-yl)-phenylcarbamoyl]-1-phenyl-methyl}-amide,
(168) 5-bromo-thiophene-2-carboxylic acid-N-{1-methyl-1-[3-methyl-4-((4R)-4-methyl-2-oxo-oxazolidin-3-yl)-phenylcarbamoyl]-ethyl}-amide,
(169) 5-chloro-thiophene-2-carboxylic acid-N-{1-methyl-1-(3-methyl-4-[(4R)-4-methyl-2-oxo-oxazolidin-3-yl]-phenylcarbamoyl)-ethyl}-amide,
(170) 5-chloro-thiophene-2-carboxylic acid-N-{1-[3-methyl-4-(tetrahydro-pyrimidin-2-on-1-yl)-phenylcarbamoyl]-ethyl}-amide,
(171) 5-chloro-thiophene-2-carboxylic acid-N-{1-(1-methyl-pyrazol-3-yl)-1-[3-methyl-4-(3-oxo-morpholin-4-yl)-phenylcarbamoyl]-methyl}-amide,
(172) 5-chloro-thiophene-2-carboxylic acid-N-{(1R)-1-[3-methyl-4-(3-oxo-morpholin-4-yl)-phenylcarbamoyl]-2-[pyridin-4-yl]-ethyl}-amide,
(173) 5-bromo-thiophene-2-carboxylic acid-N-{2-(methoxy-carbonyl)-1-[3-methyl-4-(3-oxo-morpholin-4-yl)-phenylcarbamoyl]-ethyl}-amide,
(174) 5-bromo-thiophene-2-carboxylic acid-N-{(1R)-1-[3-methyl-4-(3-oxo-morpholin-4-yl)-phenylcarbamoyl]-2-[pyridin-4-yl]-ethyl}-amide,
(175) 5-chloro-thiophene-2-carboxylic acid-N-{1-[3-methyl-4-(3-cyanimino-morpholin-4-yl)-phenylcarbamoyl]-cyclopentyl}-amide,
(176) 5-chloro-thiophene-2-carboxylic acid-N-{1-[3-methyl-4-(5-cyanimino-[1,4]-oxazepan-4-yl)-phenylcarbamoyl]-cyclopentyl}-amide,
(177) 5-bromo-thiophene-2-carboxylic acid-N-{3-[3-methyl-4-(3-cyanimino-morpholin-4-yl)-phenylcarbamoyl]-tetrahydrofuran-3-yl}-amide,
(178) 5-chloro-thiophene-2-carboxylic acid-N-{3-[3-methyl-4-(3-cyanimino-morpholin-4-yl)-phenylcarbamoyl]-tetrahydrofuran-3-yl}-amide,
(179) 5-chloro-thiophene-2-carboxylic acid-N-{3-[3-bromo-4-(3-cyanimino-morpholin-4-yl)-phenylcarbamoyl]-tetrahydrofuran-3-yl}-amide,
(180) 5-bromo-thiophene-2-carboxylic acid-N-{3-[3-methyl-4-(5-cyanimino-[1,4]-oxazepan-4-yl)-phenylcarbamoyl]-tetrahydrofuran-3-yl}-amide,
(181) 5-chloro-thiophene-2-carboxylic acid-N-{3-[3-methyl-4-(5-cyanimino-[1,4]-oxazepan-4-yl)-phenylcarbamoyl]-tetrahydrofuran-3-yl}-amide,
(182) 5-chloro-thiophene-2-carboxylic acid-N-{3-[3-bromo-4-(5-cyanimino-[1,4]-oxazepan-4-yl)-phenylcarbamoyl]-tetrahydrofuran-3-yl}-amide,
(183) 5-bromo-thiophene-2-carboxylic acid-N-{2-[3-methyl-4-(3-cyanimino-morpholin-4-yl)-phenylcarbamoyl]-bicyclo[2.2.1]hept-2-yl}-amide,
(184) 5-bromo-thiophene-2-carboxylic acid-N-{2-[3-methyl-4-(3-cyanimino-morpholin-4-yl)-phenylcarbamoyl]-7-oxa-bicyclo[2.2.1]hept-2-yl}-amide,
(185) 5-bromo-thiophene-2-carboxylic acid-N-{2-[3-methyl-4-(3-oxo-morpholin-4-yl)-phenylcarbamoyl]-7-oxa-bicyclo[2.2.1]hept-5-en-2-yl}-amide,
(186) 5-chloro-thiophene-2-carboxylic acid-N-{2-[3-methyl-4-(3-cyanimino-morpholin-4-yl)-phenylcarbamoyl]-7-oxa-bicyclo[2.2.1]hept-2-yl}-amide,
(187) 5-bromo-thiophene-2-carboxylic acid-N-{2-[3-methyl-4-(5-cyanimino-[1,4]oxazepan-4-yl)-phenylcarbamoyl]-7-oxa-bicyclo[2.2.1]hept-2-yl}-amide, (188) 5-chloro-thiophene-2-carboxylic acid-N-{2-[3-methyl-4-(5-cyanimino-[1,4]oxazepan-4-yl)-phenylcarbamoyl]-7-oxa-bicyclo[2.2.1]hept-2-yl}-amide,
(189) 5-chloro-thiophene-2-carboxylic acid-N-{2-[3-chloro-4-(5-cyanimino-[1,4]oxazepan-4-yl)-phenylcarbamoyl]-7-oxa-bicyclo[2.2.1]hept-2-yl}-amide,
(190) 5-bromo-thiophene-2-carboxylic acid-N-{5-[3-methyl-4-(3-oxo-morpholin-4-yl)-phenylcarbamoyl]-spiro[2.4]hept-5-yl}-amide,
(191) 5-chloro-thiophene-2-carboxylic acid-N-{5-[3-chloro-4-(5-cyanimino-[1,4]oxazepan-4-yl)-phenylcarbamoyl]-spiro[2.4]hept-5-yl}-amide,
(192) 5-chloro-thiophene-2-carboxylic acid-N-{3-[3-methyl-4-(5-cyanimino-[1,4]oxazepan-4-yl)-phenylcarbamoyl]-bicyclo[3.1.0]hex-3-yl}-amide,
(193) 5-chloro-thiophene-2-carboxylic acid-N-{1-[3-methyl-4-(3-oxo-morpholin-4-yl)-phenylcarbamoyl]-cyclopent-3-en-1-yl}-amide,
(194) 5-bromo-thiophene-2-carboxylic acid-N-{1-[3-methyl-4-(2-oxo-tetrahydropyrimidin-1-yl)-phenylcarbamoyl]-cyclopentyl}-amide,
(195) 5-bromo-thiophene-2-carboxylic acid-N-{1-[3-methyl-4-(2-oxo-[1,3]oxazepan-3-yl)-phenylcarbamoyl]-cyclopentyl}-amide,
(196) 5-bromo-thiophene-2-carboxylic acid-N-{1-[3-methyl-4-(2-oxo-[1,3]oxazinan-3-yl)-phenylcarbamoyl]-cyclopentyl}-amide,
(197) 5-bromo-thiophene-2-carboxylic acid-N-{1-methyl-[3-methyl-4-(5-cyanimino-[1,4]oxazepan-4-yl)-phenylcarbamoyl]-ethyl}-amide,
(198) 5-bromo-thiophene-2-carboxylic acid-N-{1-methyl-[3-chloro-4-(5-cyanimino-[1,4]oxazepan-4-yl)-phenylcarbamoyl]-ethyl}-amide,
(199) 5-bromo-thiophene-2-carboxylic acid-N-{3-[3-methyl-4-(3-cyanimino-morpholin-4-yl)-phenylcarbamoyl]-tetrahydrofuran-3-yl}-amide,
(200) 5-chloro-thiophene-2-carboxylic acid-N-{3-[3-chloro-4-(3-cyanimino-morpholin-4-yl)-phenylcarbamoyl]-tetrahydrofuran-3-yl}-amide,
(201) 5-bromo-thiophene-2-carboxylic acid-N-{3-[3-methyl-4-(5-cyanimino-[1,4]-oxazepan-4-yl)-phenylcarbamoyl]-tetrahydrofuran-3-yl}-amide,
(202) 5-chloro-thiophene-2-carboxylic acid-N-{3-[3-chloro-4-(5-cyanimino-[1,4]-oxazepan-4-yl)-phenylcarbamoyl]-tetrahydrofuran-3-yl}-amide,
(203) 5-bromo-thiophene-2-carboxylic acid-N-{(1S)-2-methoxy-1-methyl-1-[3-methyl-4-(3-oxo-morpholin-4-yl)-phenylcarbamoyl]-ethyl}-amide,
(204) 5-bromo-thiophene-2-carboxylic acid-N-{1-[3-chloro-4-(3-oxo-morpholin-4-yl)-phenylcarbamoyl]-cyclohexyl}-amide,
(205) 5-chloro-thiophene-2-carboxylic acid-N-{2-[3-methyl-4-(3-oxo-morpholin-4-yl)-phenylcarbamoyl]-bicyclo[2.2.1]hept-2-yl}-amide, the tautomers, the enantiomers, the diastereomers, the mixtures thereof and the salts thereof are particularly preferred.

According to the invention the compounds of general formula I are obtained by methods known per se, for example by the following methods:

(a) In order to prepare a compound of general formula

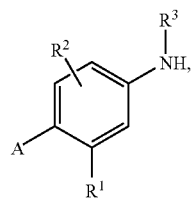

(II)

wherein A and $R^1$ to $R^3$ are as defined above:

1) Preparing a compound of general formula (II), wherein $R^3$ denotes a hydrogen atom and A, $R^1$ and $R^2$ are as defined above:

i) Reduction of the Nitro Group of a Compound of General Formula (III)

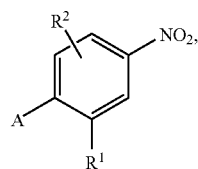

(III)

wherein A, $R^1$ and $R^2$ are as defined above:

The reduction of the nitro group is for example conveniently carried out in a solvent or mixture of solvents such as water, aqueous ammonium chloride solution, hydrochloric acid, sulphuric acid, phosphoric acid, formic acid, acetic acid, acetic anhydride with base metals such as iron, zinc, tin or sulphur compounds such as ammonium sulphide, sodium sulphide or sodium dithionite or by catalytic hydrogenation with hydrogen, for example under a pressure between 0.5 and 100 bar, but preferably between 1 and 50 bar, or with hydrazine as reducing agent, conveniently in the presence of a catalyst such as for example Raney nickel, palladium charcoal, platinum oxide, platinum on mineral fibres or rhodium, or with complex hydrides such as lithium aluminium hydride, sodium borohydride, sodium cyanborohydride, diisobutylaluminium hydride, conveniently in a solvent or mixture of solvents such as water, methanol, ethanol, isopropanol, pentan, hexane, cyclohexane, heptane, benzene, toluene, xylene, ethyl acetate, methylpropionate, glycol, glycoldimethylether, diethyleneglycoldimethylether, dioxane, tetrahydrofuran, N-methylpyrrolidinone, or N-ethyl-diisopropylamine, N—$C_{1-5}$-alkylmorpholine, N—$C_{1-5}$-alkylpiperidine, N—$C_{1-5}$-alkylpyrrolidine, triethylamine, pyridine, for example at temperatures between −30 and 250° C., but preferably between 0 and 150° C.

The compounds of general formula (III) may be obtained as follows a) Selective oxidation of compounds of general formula (IV):

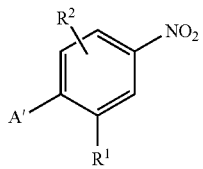
(IV)

wherein A' denotes a substituted cycloalkyleneimino group optionally containing other heteroatoms, and $R^1$ and $R^2$ are as defined above:

The oxidation of a methylene group adjacent to the nitrogen is carried out for example with oxidising agents such as potassium permanganate, potassium chromate, potassium dichromate, chromium(VI)oxide, mercury(II)chloride, selenium(IV)oxide, lead(IV)oxide, lead(II,IV)oxide, potassium peroxomonosulphate, hydrogen peroxide, sodium hypochlorite, optionally in the presence of a suitable catalyst such as nickel(II)chloride, cobalt(II)chloride, ruthenium(III)chloride, osmium(VIII)oxide, vanadium(IV)oxide and/or in the presence of a crown ether such as 18-crown-6, in a solvent or mixture of solvents such as water, formic acid, acetic acid, ethyl acetate, benzene, pyridine, dichloromethane, chloroform, tetrachloromethane, optionally under 2-phase conditions in the presence of a suitable phase transfer catalyst such as for example tetrabutylammonium chloride, tetrabutylammonium bromide, benzyl-triethyl-ammonium chloride or methyl-trioctyl-ammonium chloride, optionally in the presence of an acid such as acetic acid, hydrochloric acid, hydrobromic acid, sulphuric acid, phosphoric acid, sodium hydrogen sulphate, sodium dihydrogen phosphate and/or a base such as sodium hydroxide, potassium hydroxide, ammonia, pyridine, potassium phosphate, dipotassium hydrogen phosphate or sodium acetate, at temperatures between −30 and 250° C., but preferably between 0 and 150° C. For example this reaction may be carried out as described in J. H. Markgraf, C. A. Stickney, *J. heterocycl. Chem.* 2000, 37(1), 109.

The compounds of general formula (IV) may be obtained as follows:

a)i) Nucleophilic substitution with a compound of general formula

A'-H (V), wherein A' denotes a cycloalkyleneimino group optionally containing further heteroatoms, at the aromatic group of general formula

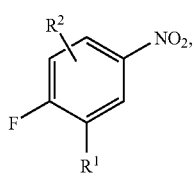
(VI)

wherein $R^1$ and $R^2$ are as defined above.

The nucleophilic substitution is conveniently carried out in a solvent or mixture of solvents such as ethanol, isopropanol, benzene, chlorobenzene, toluene, xylene, glycol, glycoldimethylether, diethyleneglycoldimethylether, dimethylformamide, N-methylpyrrolidinone, tetralin, dimethylsulphoxide, sulpholane, methylene chloride, chloroform, tetrachloromethane or N-ethyl-diisopropylamine, N—$C_{1-5}$-alkylmorpholine, N—$C_{1-5}$-alkylpiperidine, N—$C_{1-5}$-alkylpyrrolidine, triethylamine, pyridine, for example at temperatures between −30 and 250° C., but preferably between 0 and 150° C., optionally conveniently in the presence of bases such as potassium carbonate, sodium carbonate, potassium-tert.-butoxide, sodium ethoxide, potassium hexamethyldisilazane, sodium hydride or lithium diisopropylamide.

a)ii) transition metal-catalysed coupling reaction of a compound of general formula

A'-H (V)

wherein A' denotes a cycloalkyleneimino group optionally containing other heteroatoms, at the aromatic group of general formula

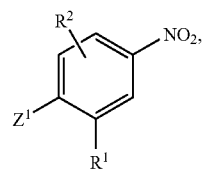
(VII)

wherein $R^1$ and $R^2$ are as defined above and $Z^1$ denotes a chlorine, bromine or iodine atom or a triflate group.

The reaction is expediently carried out in a solvent or mixture of solvents such as benzene, toluene, xylene, tetrahydrofuran, dioxane, diethyl ether, tert.-butyl-methyl-ether, ethyleneglycoldimethylether, diethyleneglycoldimethylether, sulpholane, dimethylformamide, N-methylpyrrolidinone, tetralin, dimethylsulphoxide, methylene chloride, chloroform or tetrachloromethane, for example at temperatures between −30 and 250° C., but preferably between 0 and 150° C., conveniently in the presence of transition metal catalysts such as nickel on activated charcoal, palladium charcoal, tetrakis-(triphenylphosphine)palladium(0), tris-(dibenzylideneacetone)-dipalladium(0), palladium(II)acetate, palladium(II)chloride, bis-(triphenylphosphine)-palladium(II)-chloride, bis-(tricyclohexylphosphine)-palladium(II)-chloride, bis-(triethylphosphine)palladium(II)-chloride, bis-(tri-o-tolylphosphine)-palladium(II)-chloride, optionally in the presence of ligands such as triphenylphosphine, tri-o-tolylphosphine, tri-tert.-butylphosphine, 1,3-bis-(diphenylphosphino)-propane, 2,2'-bis-(diphenyl-phosphino)-1,1'-dinaphthyl, 1,1'-bis-(diphenylphosphino)-ferrocene, Xantphos, and conveniently in the presence of a base such as sodium methoxide, sodium ethoxide, sodium-tert.-butoxide, potassium-tert.-butoxide, sodium-tert.-butyldimethyl-silanoate, potassium hexamethyldisilazane, lithium diisopropylamide, potassium carbonate, rubidium carbonate, caesium carbonate, potassium phosphate, sodium hydride, optionally in the presence of a complexing agent such as 18-crown-6-ether as well as conveniently using an inert gas atmosphere (for example nitrogen or argon) and optionally under pressure.

b) Acylation/sulphonylation and alkylation of a compound of general formula

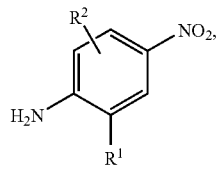
(VIII)

wherein $R^1$ and $R^2$ are as defined above, with a compound of general formula

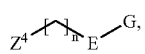
(IX)

wherein E denotes a carbonyl, oxycarbonyl, sulphonyl or a sulphamoyl group as mentioned in above optionally substituted at the nitrogen atom, G denotes a chlorine, bromine or iodine atom or an anhydride, $C_{1-5}$-alkoxy or benzotriazoloxy group or E and G together denote an isocyanato or cyano group and $Z^4$ denotes a nucleofugic leaving group, for example a chlorine, bromine or iodine atom, a tosylate, triflate or mesylate group, and n is a number between 2 and 5, while individual methylene groups may additionally be substituted or replaced by heteroatoms as described above, and subsequent intramolecular cyclisation by alkylation of the anilide nitrogen while cleaving the nucleofugic leaving group $Z^4$.

The acylation/sulphonylierung is conveniently carried out in a solvent or mixture of solvents such as benzene, chlorobenzene, toluene, xylene, glycoldimethylether, diethyleneglycoldimethylether, dimethylformamide, N-methylpyrrolidinone, tetralin, dimethylsulphoxide, sulpholane, methylene chloride, chloroform, tetrachloromethane, N-ethyl-diisopropylamine, N—$C_{1-5}$-alkylmorpholine, N—$C_{1-5}$-alkylpiperidine, N—$C_{1-5}$-alkylpyrrolidine, triethylamine, pyridine, for example at temperatures between −30 and 250° C., but preferably between 0 and 150° C., conveniently in the presence of bases such as pyridine, triethylamine, p-dimethylaminopyridine, potassium carbonate, sodium carbonate, potassium-tert.-butoxide, sodium methoxide, sodium ethoxide or basic ion exchangers.

The subsequent intramolecular alkylation is conveniently carried out in a solvent or mixture of solvents such as benzene, chlorobenzene, toluene, xylene, glycoldimethylether, diethyleneglycoldimethylether, dimethylformamide, dimethylsulphoxide, sulpholane, methylene chloride, tetrachloromethane, N-ethyl-diisopropylamine, N—$C_{1-5}$-alkylmorpholine, N—$C_{1-5}$-alkylpiperidine, N—$C_{1-5}$-alkylpyrrolidine, triethylamine, pyridine, for example at temperatures between −30 and 250° C., but preferably between 0 and 150° C., conveniently in the presence of bases such as pyridine, triethylamine, potassium carbonate, sodium carbonate, potassium-tert.-butoxide, sodium methoxide, sodium ethoxide, sodium hydride, potassium hexamethyldisilazane or lithium diisopropylamide.

c) Nucleophilic substitution with a compound of general formula

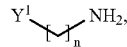
(X)

wherein $Y^1$ denotes a hydroxyl, amino or thiol function optionally blocked by a corresponding protective group and n is a number between 0 and 4, at the aromatic group of general formula

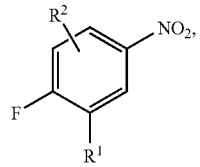
(VI)

wherein $R^1$ and $R^2$ are as defined above, and subsequent cyclisation by reaction with a compound of general formula

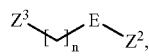
(XI)

wherein $Z^2$ and $Z^3$ are nucleofugic leaving groups such as chlorine, bromine or iodine atoms or triflate, mesylate or tosylate groups, E denotes the carbonyl or sulphonyl group and n is a number between 0 and 4, while individual methylene groups as described above may be substituted or replaced by optionally substituted heteroatoms or other groups.

The initial nucleophilic aromatic substitution is carried out for example as described under (a) 1) i) a)i). It is optionally followed by the unblocking of the nucleophilic group $Y^1$ by methods known from the literature or as described generally hereinafter.

The reaction of the compound thus obtained with the compound of general formula (X) is conveniently carried out in a solvent or mixture of solvents such as benzene, chlorobenzene, toluene, xylene, glycoldimethylether, diethyleneglycoldimethylether, dimethylformamide, N-methylpyrrolidinone, tetralin, dimethylsulphoxide, sulpholane, methylene chloride, chloroform, tetrachloromethane, N-ethyl-diisopropylamine, N—$C_{1-5}$-alkylmorpholine, N—$C_{1-5}$-alkylpiperidine, N—$C_{1-5}$-alkylpyrrolidine, triethylamine, pyridine, for example at temperatures between −30 and 250° C., but preferably between 0 and 150° C., conveniently in the presence of bases such as pyridine, triethylamine, p-dimethylaminopyridine, potassium carbonate, sodium carbonate, potassium-tert.-butoxide, sodium methoxide, sodium ethoxide or basic ion exchangers.

d) alkylation and subsequent acylation/sulphonylation of a compound of general formula

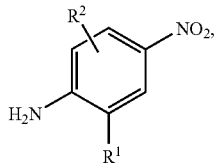

(VIII)

wherein R$^1$ and R$^2$ are as defined above, with a compound of general formula

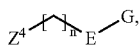

(IX)

wherein E denotes a carbonyl, oxycarbonyl, sulphonyl or a sulphamoyl group optionally substituted at the nitrogen atom as mentioned above, G denotes a chlorine, bromine or iodine atom or an anhydride, C$_{1-5}$-alkoxy or benzotriazoloxy group or E and G together denote an isocyano group and Z$^4$ denotes a nucleofugic leaving group, for example a chlorine, bromine or iodine atom, a tosylate, triflate or mesylate group, and n is a number between 2 and 5, while individual methylene groups as described above may additionally be substituted or replaced by heteroatoms, and subsequent intramolecular cyclisation by alkylation of the anilide nitrogen while cleaving the nucleofugic leaving group Z$^4$.

The alkylation is conveniently carried out in a solvent or mixture of solvents such as benzene, chlorobenzene, toluene, xylene, glycoldimethylether, diethyleneglycoldimethylether, dimethylformamide, dimethylsulphoxide, sulpholane, methylene chloride, tetrachloromethan, N-ethyl-diisopropylamine, N—C$_{1-5}$-alkylmorpholine, N—C$_{1-5}$-alkylpiperidine, N—C$_{1-5}$-alkylpyrrolidine, triethylamine, pyridine, for example at temperatures between −30 and 250° C., but preferably between 0 and 150° C., conveniently in the presence of bases such as pyridine, triethylamine, potassium carbonate, sodium carbonate, potassium-tert.-butoxide, sodium methoxide, sodium ethoxide, sodium hydride, potassium hexamethyldisilazane or lithium diisopropylamide.

The subsequent intramolecular acylation/sulphonylation is conveniently carried out in a solvent or mixture of solvents such as benzene, chlorobenzene, toluene, xylene, glycoldimethylether, diethyleneglycoldimethylether, dimethylformamide, N-methylpyrrolidinone, tetralin, dimethylsulphoxide, sulpholane, methylene chloride, chloroform, tetrachloromethane, N-ethyl-diisopropylamine, N—C$_{1-5}$-alkylmorpholine, N—C$_{1-5}$-alkylpiperidine, N—C$_{1-5}$-alkylpyrrolidine, triethylamine, pyridine, for example at temperatures between −30 and 250° C., but preferably between 0 and 150° C., conveniently in the presence of bases such as pyridine, triethylamine, p-dimethylaminopyridine, potassium carbonate, sodium carbonate, potassium-tert.-butoxide, sodium methoxide, sodium ethoxide or basic ion exchanger.

e) Sequential alkylation of a compound of general formula

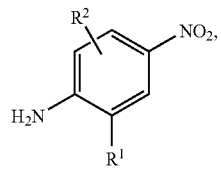

(VIII)

wherein R$^1$ and R$^2$ are defined as above, with a compound of general formula

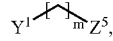

(XII)

wherein Z$^5$ denotes a nucleofugic leaving group such as for example a bromine or chlorine atom or a tosylate, triflate or mesylate group, Y$^1$ denotes a nucleophilic group such as a hydroxy group or an amino group optionally substituted as described above, optionally blocked by a suitable protective group, and m denotes a number between 2 and 5, while individual methylene groups as described above may additionally be substituted or replaced by heteroatoms, with subsequent acylation/sulphonylation with a compound of general formula

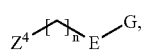

(IX)

wherein E denotes a carbonyl, oxycarbonyl, sulphonyl or a sulphamoyl group optionally substituted at the nitrogen atom as mentioned above, G denotes a chlorine, bromine or iodine atom or an anhydride, C$_{1-5}$-alkoxy or benzotriazoloxy group or E and G together denote an isocyanato or cyano group and Z$^4$ denotes a nucleofugic group, for example a bromine or chlorine atom or a tosylate, triflate or mesylate group, and n is a number between 2 and 5, while individual methylene groups as described above may additionally be substituted or replaced by heteroatoms, and subsequent intramolecular cyclisation by alkylation of the nucleophilic group Y$^1$ which has optionally been unblocked beforehand, cleaving the nucleofugic leaving group Z$^4$.

Both the necessary alkylations and the acylation/sulphonylation may be carried out analogously to the conditions described under (a) 1) i) b) or (a) 1) i) d).

f) Carbamoylation/urea formation with a compound of general formula

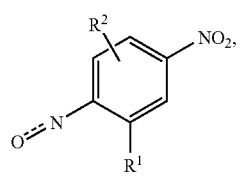

(XIII)

wherein R¹ and R² are defined as above, and which may be obtained by methods known from the literature from compounds of general formula (VIII), for example by reaction with phosgene in toluene, with a compound of general formula

(XIV)

wherein $Z^6$ is a nucleofugic leaving group, for example a chlorine, bromine or iodine atom, a tosylate, triflate or mesylate group, and E is a hydroxyl, amino or $C_{1-3}$-alkylamino function and n is a number between 2 and 4, while individual methylene groups may additionally be substituted as described above, and subsequent intramolecular cyclisation by alkylation of the anilide nitrogen, cleaving the nucleofugic leaving group $Z^6$.

The carbamoylation is conveniently carried out in a solvent or mixture of solvents such as benzene, chlorobenzene, toluene, xylene, glycoldimethylether, diethyleneglycoldimethylether, dimethylformamide, N-methylpyrrolidinone, tetralin, dimethylsulphoxide, sulpholane, methylene chloride, chloroform, tetrachloromethane, N-ethyl-diisopropylamine, N—$C_{1-5}$-alkylmorpholine, N—$C_{1-5}$-alkylpiperidine, N—$C_{1-5}$-alkylpyrrolidine, triethylamine, pyridine, for example at temperatures between −30 and 250° C., but preferably between 0 and 150° C.

The subsequent intramolecular alkylation is carried out for example analogously to the method described in (a) 1) i) b).

ii) Transition Metal-catalysed Coupling Reaction of a Compound of General Formula

A-H    (XV), wherein A is defined as mentioned above, at the aromatic group of general formula

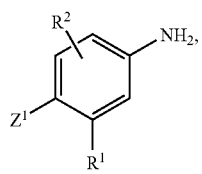
(XVI)

wherein R¹ and R² are defined as above and $Z^1$ denotes a chlorine, bromine or iodine atom or a triflate group.

The reaction is expediently carried out in a solvent or mixture of solvents such as benzene, toluene, xylene, tetrahydrofuran, dioxane, diethyl ether, tert.-butyl-methyl-ether, ethyleneglycoldimethylether, diethyleneglycoldimethylether, sulpholane, dimethylformamide, N-methylpyrrolidinone, tetralin, dimethylsulphoxide, methylene chloride, chloroform or tetrachloromethan, for example at temperatures between −30 and 250° C., but preferably between 0 and 200° C., conveniently in the presence of transition metal catalysts such as tetrakis-(triphenylphosphine)-palladium(0), tris-(dibenzylideneacetone)-dipalladium(0), palladium(II)acetate, palladium(II)chloride, bis-(triphenylphosphine)-palladium(II)-chloride, bis-(tricyclohexylphosphine)-palladium(II)-chloride, bis-(triethylphosphine)-palladium(II)-chloride, bis-(tri-o-tolylphosphine)-palladium(II)-chloride, optionally in the presence of ligands such as triphenylphosphine, tri-o-tolylphosphine, tri-tert.-butylphosphine, 1,3-bis-(diphenylphosphino)-propane, 2,2'-bis-(diphenylphosphino)-1,1'-dinaphthyl, 1,1'-bis-(diphenylphosphino)-ferrocene, Xantphos, or for example in the presence of a transition metal-catalyst such as copper(I)-iodide, copper(I)-bromide or copper(I)-acetate and conveniently in the presence of a base such as tetramethylguanidine, tetramethylethylenediamine or N,N'-dimethylethylenediamine and conveniently in the presence of a base such as sodium methoxide, sodium ethoxide, sodium-tert.-butoxide, potassium-tert.-butoxide, sodium-tert.-butyldimethyl-silanoate, potassium hexamethyldisilazane, lithiumdiisopropylamide, potassium carbonate, rubidium carbonate, caesium carbonate, potassium phosphate, sodium hydride, optionally in the presence of a complexing agent such as 18-crown-6-ether as well as conveniently using an inert gas atmosphere (for example nitrogen or argon) and optionally under pressure.

iii) Cyclisation Metathesis of a Compound of General Formula

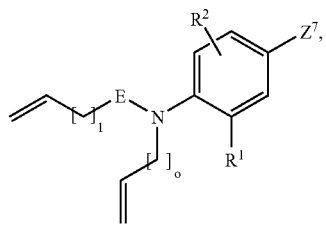
(XVII)

wherein R¹ and R² are defined as above, $Z^7$ denotes an optionally substituted amino group or the nitro group, E denotes an aminocarbonyl, aminosulphonyl group or a carbonyl or sulphonyl group optionally substituted according to the description above, while l and o independently of one another represent identical or different numbers between 1 and 3, which may be obtained by a sequence of alkylation and acylation/sulphonylation/carbamoylation/sulphamoylation with corresponding reagents according to the methods described above under (a) 1) i) c), for example, or other methods known from the literature, optionally followed by reduction, if $Z^7$ denotes a nitro group, according to the method described under (a) 1) i) and/or hydrogenation of the double bond formed, analogously to the methods described under (a) 1) i).

The cyclisation by a reaction of metathesis is conveniently carried out in a solvent or mixture of solvents such as benzene, chlorobenzene, toluene, xylene, methanol, ethanol, propanol, diethyl ether, tert.-butyl-methyl-ether, tetrahydrofuran, dioxane, glycoldimethylether, diethyleneglycoldimethylether, dimethylformamide, N-methylpyrrolidinone, tetralin, dimethylsulphoxide, sulpholane, methylene chloride, chloroform, tetrachloromethane, pyridine, in the presence of a catalyst such as benzylidene-bis-(tricyclohexylphosphine)-dichloro-ruthenium (1st generation Grubbs catalyst) or benzylidene-[1,3-bis(2,4,6-trimethylphenyl)-2-imidazolidinylidene]-dichloro-(tricyclohexylphosphine)-ruthenium (2nd generation Grubbs catalyst) for example at temperatures between −30 and 250° C., but preferably between 0 and 150° C., conveniently under an inert gas atmosphere, for example argon.

2) Preparing a compound of general formula (II), wherein R³ denotes a $C_{1-3}$-alkyl group and A and R¹ to R³ are defined as above:

Reductive amination of a compound of general formula (II), wherein $R^3$ denotes a hydrogen atom and A and $R^1$ to $R^3$ are defined as above:

The reaction with the corresponding $R^3$-aldehyde (formaldehyde or paraformaldehyde where $R^3$ is methyl, acetaldehyde or paraldehyde where $R^3$ is ethyl, propionaldehyde where $R^3$ is propyl) is conveniently carried out in a solvent or mixture of solvents such as methanol, ethanol, propanol, iso-propanol, butanol, tetrahydrofuran, dioxane, diethyl ether, tert.-butyl-methyl-ether, ethyleneglycoldimethylether, diethyleneglycoldimethylether, sulpholane, dimethylformamide, N-methylpyrrolidinone, tetralin, dimethylsulphoxide, methylene chloride, chloroform or tetrachloromethane, for example at temperatures between −30 and 250° C., but preferably between −10 and 150° C., optionally in the presence of a base such as sodium methoxide, sodium ethoxide, sodium-tert.-butoxide, potassium-tert.-butoxide, sodium-tert.-butyldimethyl-silanoate, potassium hexamethyldisilazane, lithiumdiisopropylamide, potassium carbonate, rubidium carbonate, caesium carbonate, potassium phosphate, sodium hydride, optionally in the presence of a complexing agent such as 18-crown-6-ether, followed by reduction of the imide formed by hydrogenation with hydrogen, for example under a pressure of between 0.5 and 100 bar, but preferably between 1 and 50 bar, conveniently in the presence of a catalyst such as for example Raney nickel, palladium charcoal, platinum oxide, platinum on mieral fibres or rhodium, or with complex hydrides such as lithium aluminium hydride, sodium borohydride, sodium cyanoborohydride, diisobutylaluminium hydride, for example at temperatures between −30 and 250° C., but preferably between 0 and 150° C.

3) Preparing a compound of general formula (II), wherein $R^1$ to $R^3$ are defined as above and according to the definition of A contain thiocarbonyl or optionally correspondingly substituted imino groups in the ring:
  i) thionylation of the corresponding carbonyl-analogous compound of general formula (XV), optionally with subsequent alkylation of the sulphur and reaction with a correspondingly substituted amine (for example methylamine, hydroxylamine, acetoxyamine, methoxyamine, cyanamide or corresponding analogous compounds), and subsequent coupling of the compound obtained with a compound of general formula (XVI) according to the description of (a) 1) ii)

The thionisation is conveniently carried out for example in a solvent or mixture of solvents such as pentane, hexane, cyclohexane, heptane, benzene, toluene, xylene, glycoldimethylether, diethyleneglycoldimethylether, dioxane, tetrahydrofuran, dichloromethane, chloroform, tetrachloromethane, 1,2-dichloroethane, N-methylpyrrolidinone, or N-ethyl-diisopropylamine, N—$C_{1-5}$-alkylmorpholine, N—$C_{1-5}$-alkylpiperidine, N—$C_{1-5}$-alkylpyrrolidine, triethylamine, pyridine, with reagents such as for example phosphorus pentasulphide, 2,2-bis-(4-methoxy-phenyl)-1,3,2,4-dithiadiphosphetan-2,4-disulphide (Lawesson's reagent) or mixtures of reagents such as for example phosphorus oxychloride followed by 1,1,1,3,3,3-hexamethyldisilazane, trifluorosulphonic acid anhydrid followed by hydrogen sulphide, or a mixture of hydrogen sulphide, chlorotrimethylsilan and lithium diisopropylamide, optionally in the presence of a base such as potassium carbonate, sodium carbonate, sodium hydrogen carbonate, pyridine, triethylamine for example at temperatures between −30 and 250° C., but preferably between −10 and 150° C. Any subsequent alkylation of the corresponding thiocarbonyl compounds is conveniently carried out for example in a solvent or mixture of solvents such as pentane, hexane, cyclohexane, heptane, benzene, toluene, xylene, glycoldimethylether, diethyleneglycoldimethylether, dioxane, tetrahydrofuran, dichloromethane, chloroform, tetrachloromethane, 1,2-dichloroethane, chlorobenzene, pyridine, water, methanol, ethanol, n-propanol, iso-propanol, n-butanol, acetone, butanone, acetonitrile or nitromethane, optionally under 2-phase conditions with the addition of a phase transfer catalyst such as tetrabutyl-ammonium-chloride, tetrabutyl-ammonium-bromide, methyl-trioctyl-ammonium-chloride or Aliquat 336 with reagents such as for example methyl iodide, ethylbromide, dimethylsulphate, diethylsulphate or trimethyloxonium-tetrafluoroborate, conveniently optionally in the presence of a base such as potassium carbonate, sodium carbonate, sodium hydrogen carbonate, pyridine, triethylamine, N-ethyl-diisopropylamine, N—$C_{1-5}$-alkylmorpholine, N—$C_{1-5}$-alkylpiperidine, N—$C_{1-5}$-alkylpyrrolidine, for example at temperatures between −30 and 250° C., but preferably between −10 and 150° C. The reaction with an amino compound following alkylation, in order to prepare the corresponding imine, is conveniently carried out for example in a solvent or mixture of solvents such as pentane, hexane, cyclohexane, heptane, benzene, toluene, xylene, glycoldimethylether, diethyleneglycoldimethylether, dioxane, tetrahydrofuran, dichloromethane, chloroform, tetrachloromethane, 1,2-dichloroethane, chlorobenzene, pyridine, water, methanol, ethanol, n-propanol, iso-propanol, n-butanol, acetone, butanone, acetonitrile or nitromethane, with corresponding reagents depending on the substitution of the imine such as for example ammonia, sodium amide, hydroxylamine, methoxyamine, ethoxyamine, propoxyamine, acetoxyamine or cyanamide, optionally in the presence of a base such as sodium hydride, potassium hydride, potassium carbonate, sodium carbonate, sodium hydrogen carbonate, pyridine, triethylamine and optionally under pressure, for example at temperatures between −30 and 250° C., but preferably between −20 and 120° C.

ii) thionylation of the corresponding carbonyl-analogous compound of general formula (III), which may be obtained by the methods described in (a) 1) i) a), b), c), d) and e), optionally with subsequent alkylation of the sulphur and reaction with a correspondingly substituted amine (for example methylamine, hydroxylamine, acetoxyamine, methoxyamine, cyanamide or corresponding analogous compounds), and subsequent reduction of the nitro group according to the method described under (a) 1) i), optionally with subsequent reductive amination according to the methods described under (a) 2).

The thionylation and the optional subsequent reaction of alkylation and imine formation may be carried out analogously to the methods described under (a) 3) i).

iii) Thionylation of the corresponding carbonyl-analogous compound of general formula (II), which may be obtained according to the methods described under (a) 1) i), ii), iii) and (a) 2), optionally followed by alkylation of the sulphur and reaction with a correspondingly substituted amine (for example methylamine, hydroxylamine, acetoxyamine, methoxyamine, cyanamide or corresponding analogous compounds), while during any subsequent alkylation the aniline amino group present is conveniently blocked by suitable protective groups which are cleaved after the reaction to obtain the imine.

The thionylation and the reaction of alkylation and imine formation that optionally follows may be carried out analogously to the methods described under (a) 3) i).

4) Preparing a compound of general formula (II), wherein $R^1$ to $R^3$ are defined as above and which contain in the ring imino groups which are optionally correspondingly substituted according to the definition of A:

i) alkylation of the carbonyl-analogous compounds of general formula (XV) and subsequent reaction with a correspondingly substituted amine (for example methylamine, hydroxylamine, acetoxyamine, methoxyamine, cyanamide or corresponding analogous compounds), and subsequent coupling of the compound obtained with a compound of general formula (XVI) according to the description of (a) 1) ii)

Both the alkylation and the following reaction with an amino compound to prepare the corresponding imine may be carried out as described under (a) 3) i).

ii) alkylation of the carbonyl-analogous compounds of general formula (III), which may be obtained according to the methods described under (a) 1) i) a), b), c), d) and e), and subsequent reaction with a correspondingly substituted amine (for example methylamine, hydroxylamine, acetoxyamine, methoxyamine, cyanamide or corresponding analogous compounds), and subsequent reduction of the nitro group according to the methods described under (a) 1) i), optionally followed by reductive amination by methods described under (a) 2).

Both the alkylation and the following reaction with an amino compound to prepare the corresponding imine may be carried out as described under (a) 3) i).

(b) In Order to Prepare a Compound of General Formula

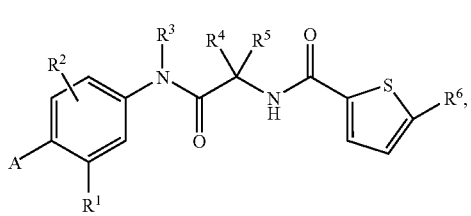

(I)

wherein A and $R^1$ to $R^6$ are defined as above:

1) acylation of a compound of general formula

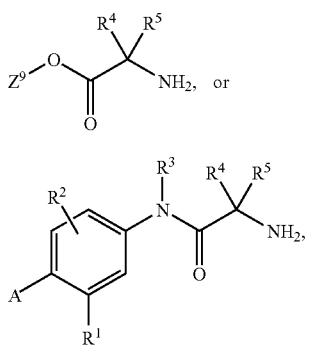

(XVIII)

(XIX)

where $Z^9$ denotes a protective group for the carboxyl function, which can subsequently be cleaved by methods known from the literature, and A and $R^1$ to $R^5$ are defined as above, while (XIX) may be obtained by the method described under (b) 2), with a carboxylic acid or a reactive carboxylic acid derivative of general formula

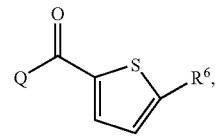

(XX)

wherein $R^6$ is defined as above and Q denotes a hydroxy or $C_{1-4}$-alkoxy group, a halogen atom or an acyloxy group.

The acylation is conveniently carried out with a corresponding halide or anhydride in a solvent such as methylene chloride, chloroform, carbon tetrachloride, ether, tetrahydrofuran, dioxane, benzene, toluene, acetonitrile, dimethylformamide, sodium hydroxide solution or sulpholane, optionally in the presence of an inorganic or organic base at temperatures between −20 and 200° C., but preferably at temperatures between −10 and 160° C.

The acylation may however also be carried out with the free acid, optionally in the presence of an acid-activating agent or a dehydrating agent, for example in the presence of isobutyl chloroformate, thionyl chloride, trimethylchlorosilane, hydrogen chloride, sulphuric acid, methanesulphonic acid, p-toluenesulphonic acid, phosphorus trichloride, phosphorus pentoxide, N,N'-dicyclohexylcarbodiimide, N,N'-dicyclohexylcarbodiimide/N-hydroxysuccinimide or 1-hydroxybenzotriazole, N,N'-carbonyldiimidazole, O-(benzotriazol-1-yl)-N,N,N',N'-tetramethyluronium tetrafluoroborate/N-methylmorpholine, O-(benzotriazol-1-yl)-N,N,N',N'-tetramethyluronium tetrafluoroborate/N-ethyldiisopropylamine, O-pentafluorophenyl-N,N,N,N'-tetramethyluronium-hexafluorophosphate/triethylamine, N,N'-thionyldiimidazole or triphenylphosphine/carbon tetrachloride, at temperatures between −20 and 200° C., but preferably at temperatures between −10 and 160° C.

Subsequently, for the following reactions, the protective group $Z^9$ may be cleaved by methods known from the literature.

Compounds of general formula (XVIII) may be obtained by methods known from the literature, wherein $R^4$ and $R^5$ do not denote hydrogen, for example according to the methods described in C. Cativiela, M. D. Diaz-de-Villegas, *Tetrahedron Asymm.*, 1998, 9, 3517-3599 or C. Cativiela, M. D. Diaz-de-Villegas, *Tetrahedron Asymm.*, 2000, 11, 645-732 or analogous methods.

2) Acylation of a compound of general formula

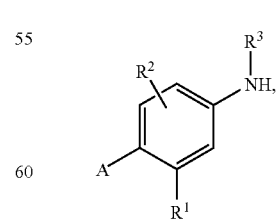

(II)

wherein A and $R^1$ to $R^3$ are defined as above, with a carboxylic acid or a reactive carboxylic acid derivative of general formula

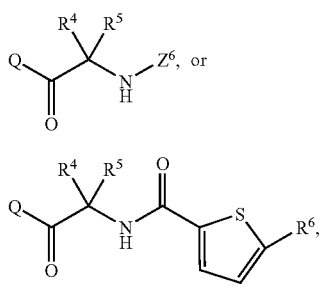

(XXI)

(XXII)

wherein $R^4$ to $R^6$ are defined as above, Q denotes a hydroxy or $C_{1-4}$-alkoxy group, a halogen atom or an acyloxy group and $Z^6$ denotes a protective group, which may subsequently be cleaved by methods known from the literature, while (XXII) may be obtained by the method described under (b) 1).

The acylation may be carried out analogously to the method described under (b) 1).

However, the acylation may also conveniently be carried out in a solvent or mixture of solvents such as dichloromethane, trichloromethane, benzene, chlorobenzene, toluene, xylene, hexamethyldisiloxane, acetonitrile, N-ethyl-diisopropylamine, N—$C_{1-5}$-alkylmorpholine, N—$C_{1-5}$-alkylpiperidine, N—$C_{1-5}$-alkylpyrrolidine, triethylamine, pyridine, in the presence of 4-trifluoromethyl-benzoic anhydride, silver triflate and titanium(IV)chloride, conveniently in the presence of a dehydrating agent such as molecular sieve, sodium sulphate, magnesium sulphate, or in the presence of 4-trifluoromethyl-benzoic anhydride and ytterbium(III)triflate, while water may also be added to the solvent mixture, for example at temperatures between −30 and 250° C., but preferably between 0 and 150° C. (I. Shiina, M. Miyashita, M. Nagai, T. Mukaiyama; *Heterocycles* 1995, 40 (1), 141-148.).

Compounds of general formula (XXI) may be obtained by methods known from the literature, wherein $R^4$ and $R^5$ do not denote hydrogen, for example according to the methods described in C. Cativiela, M. D. Diaz-de-Villegas, *Tetrahedron Asymm.*, 1998, 9, 3517-3599 or C. Cativiela, M. D. Diaz-de-Villegas, *Tetrahedron Asymm.*, 2000, 11, 645-732 or analogous methods.

3) Acylation of a compound of general formula (II), wherein A and $R^1$ to $R^3$ are defined as above, with a reactive carboxylic acid derivative of general formula

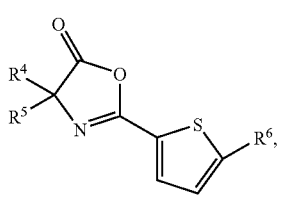

(XXIII)

wherein $R^4$ to $R^6$ are defined as above.

The acylation is conveniently carried out in a solvent or mixture of solvents such as dichloromethane, trichloromethane, carbon tetrachloride, benzene, chlorobenzene, toluene, xylene, hexamethyldisiloxane, ether, tetrahydrofuran, dioxane, acetonitrile, N-ethyl-diisopropylamine, N—$C_{1-5}$-alkylmorpholine, N—$C_{1-5}$-alkylpiperidine, N—$C_{1-5}$-alkylpyrrolidine, triethylamine, pyridine, optionally in the presence of a Lewis acid such as aluminium chloride, zinc iodide, zinc chloride, boron trifluoride, titanium (IV)chloride or trimethylaluminium at temperatures between −20 and 200° C., but preferably at temperatures between −10 and 160° C., for example using a microwave oven.

Compounds of general formula (XXIII) may be prepared from compounds of general formula (XXII) conveniently in a solvent or mixture of solvents such as dichloromethane, trichloromethane, carbon tetrachloride, benzene, chlorobenzene, toluene, xylene, hexamethyldisiloxane, ether, tetrahydrofuran, dioxane, acetonitrile, pyridine, optionally in the presence of N,N'-dicyclohexyl carbodiimide, N,N'-dicyclohexylcarbodiimide/N-hydroxysuccinimide or 1-hydroxybenzotriazole, N,N'-carbonyldiimidazole, O-(benzotriazol-1-yl)-N,N,N',N'-tetramethyluronium tetrafluoroborate/N-methylmorpholine, O-(benzotriazol-1-yl)-N,N,N',N'-tetramethyluronium tetrafluoroborate/N-ethyldiisopropylamine, or in a solvent or mixture of solvents such as dichloromethane, trichloromethane, carbon tetrachloride, benzene, chlorobenzene, toluene, xylene, hexamethyldisiloxane, ether, tetrahydrofuran, dioxane, acetonitrile, formic acid, acetic acid, acetic anhydride or propionic acid, at temperatures between −20 and 200° C., but preferably at temperatures between −10 and 160° C.

Other methods of amide coupling are described for example in P. D. Bailey, I. D. Collier, K. M. Morgan in "Comprehensive Functional Group Interconversions", Vol. 5, page 257 ff., Pergamon 1995.

In the reactions described above any reactive groups present such as hydroxy, carboxy, amino, alkylamino or imino groups may be protected during the reaction by conventional protective groups which are cleaved again after the reaction.

For example a suitable protective group for a hydroxy group is the methoxy, benzyloxy, trimethylsilyl, acetyl, benzoyl, tert.-butyl, trityl, benzyl or tetrahydro-pyranyl group, a suitable protective group for a carboxyl group is the trimethylsilyl, methyl, ethyl, tert.-butyl, benzyl or tetrahydropyranyl group and a suitable protective group for an amino, alkylamino or imino group is the acetyl, trifluoroacetyl, benzoyl, ethoxycarbonyl, tert.-butoxycarbonyl, benzyloxycarbonyl, benzyl, methoxybenzyl or 2,4-dimethoxybenzyl group and additionally a suitable protective group for the amino group is the phthalyl group.

Other protective groups and their cleaving are described in T. W. Greene, P. G. M. Wuts, "Protective Groups in Organic Synthesis", Wiley, 1991 and 1999.

Any protective group used is optionally subsequently cleaved for example by hydrolysis in an aqueous solvent, e.g. in water, isopropanol/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide or potassium hydroxide or by means of ether splitting, e.g. in the presence of iodotrimethylsilane, at temperatures between 0 and 100° C., preferably at temperatures between 10 and 50° C.

A benzyl, methoxybenzyl or benzyloxycarbonyl group, however, is cleaved by hydrogenolysis, for example, e.g. with hydrogen in the presence of a catalyst such as palladium/charcoal in a solvent such as methanol, ethanol, ethyl acetate, dimethylformamide, dimethylformamide/acetone or glacial acetic acid, optionally with the addition of an acid such as hydrochloric acid at temperatures between 0 and 50° C., but preferably at ambient temperature, and under a hydrogen pressure of 1 to 7 bar, but preferably 1 to 5 bar.

A methoxybenzyl group may also be cleaved in the presence of an oxidising agent such as cerium(IV)ammonium nitrate in a solvent such as methylene chloride, acetonitrile or acetonitrile/water at temperatures between 0 and 50° C., but preferably at ambient temperature.

A methoxy group is conveniently cleaved in the presence of boron tribromide in a solvent such as methylene chloride at temperatures between −35 and −25° C.

A 2,4-dimethoxybenzyl group, however, is preferably cleaved in trifluoroacetic acid in the presence of anisol.

A tert.-butyl or tert.-butyloxycarbonyl group is preferably cleaved by treatment with an acid such as trifluoroacetic acid or hydrochloric acid, optionally using a solvent such as methylene chloride, dioxane or ether.

A phthalyl group is preferably cleaved in the presence of hydrazine or a primary amine such as methylamine, ethylamine or n-butylamine in a solvent such as methanol, ethanol, isopropanol, toluene/water or dioxane at temperatures between 20 and 50° C.

An allyloxycarbonyl group is cleaved by treatment with a catalytic amount of tetrakis-(triphenylphosphine)-palladium (0), preferably in a solvent such as tetrahydrofuran and preferably in the presence of an excess of a base such as morpholine or 1,3-dimedone at temperatures between 0 and 100° C., preferably at ambient temperature and under inert gas, or by treatment with a catalytic amount of tris-(triphenylphosphine)-rhodium(I)chloride in a solvent such as aqueous ethanol and optionally in the presence of a base such as 1,4-diazabicyclo[2.2.2]octane at temperatures between 20 and 70° C.

Moreover, the compounds of general formula I obtained may be resolved into their enantiomers and/or diastereomers.

Thus, for example, the compounds of general formula I obtained which occur as racemates may be separated by methods known per se (cf. Allinger N. L. and Eliel E. L. in "Topics in Stereochemistry", Vol. 6, Wiley Interscience, 1971) into their optical enantiomers and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be, for example, (+) or (−)-menthol and an optically active acyl group in amides, for example, may be a (+)- or (−)-menthyloxycarbonyl.

Furthermore, the compounds of formula I may be converted into the salts thereof, particularly for pharmaceutical use into the physiologically acceptable salts with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

Moreover, if the new compounds of formula I contain a carboxy group, they may subsequently, if desired, be converted into the salts thereof with inorganic or organic bases, particularly for pharmaceutical use into the physiologically acceptable salts thereof. Suitable bases for this purpose include for example sodium hydroxide, potassium hydroxide, cyclohexylamine, ethanolamine, diethanolamine and triethanolamine.

As already mentioned, the compounds of general formula I and the tautomers, enantiomers, diastereomers and physiologically acceptable salts thereof have valuable pharmacological properties, particularly an antithrombotic activity which is preferably based on an effect on thrombin or factor Xa, for example on a thrombin-inhibiting or factor Xa-inhibiting activity, on a prolonging effect on the aPTT time and/or on an inhibitory effect on related serine proteases such as e.g. urokinase, factor VIIa, factor IXa, factor XaI and factor XIIa.

The compounds listed in the Experimental Section were investigated for their effect on the inhibition of factor Xa as follows:

Method:

Enzyme-kinetic measurement with chromogenic substrate. The quantity of p-nitroaniline (pNA) released from the colourless chromogenic substrate by human factor Xa is determined photometrically at 405 nm. It is proportional to the activity of the enzyme used. The inhibition of the enzyme activity by the test substance (in relation to the solvent control) is determined at various concentrations of test substance and from this the $IC_{50}$ is calculated, as the concentration which inhibits the factor Xa used by 50%.

Material:

Tris(hydroxymethyl)-aminomethane buffer (100 mMol) and sodium chloride (150 mMol), pH 8.0 plus 1 mg/ml Human Albumin Fraction V, protease-free Factor Xa (Calbiochem), spec. activity: 217 IU/mg, final concentration: 7 IU/ml for each reaction mixture Substrate S 2765 (Chromogenix), final concentration: 0.3 mM/l (1 KM) for each reaction mixture Test substance: final concentration 100, 30, 10, 3, 1, 0.3, 0.1, 0.03, 0.01, 0.003, 0.001 µMol/l Procedure:

10 µl of a 23.5-times concentrated starting solution of the test substance or solvent (control), 175 µl of TRIS/HSA buffer and 25 µl of a 65.8 U/L Factor Xa working solution are incubated for 10 minutes at 37° C. After the addition of 25 µl of S 2765 working solution (2.82 mMol/l) the sample is measured in a photometer (SpectraMax 250) at 405 nm for 600 seconds at 37° C.

Evaluation:

1. Determining the maximum increase (deltaOD/minutes) over 21 measuring points.
2. Determining the % inhibition based on the solvent control.
3. Plotting a dosage/activity curve (% inhibition vs substance concentration).
4. Determining the $IC_{50}$ by interpolating the X-value (substance concentration) of the dosage/activity curve at Y=50% inhibition.

All the compounds tested had an $IC_{50}$ value of less than 100 µmol/L.

The compounds prepared according to the invention are generally well tolerated.

In view of their pharmacological properties the new compounds and the physiologically acceptable salts thereof are suitable for the prevention and treatment of venous and arterial thrombotic diseases, such as for example the prevention and treatment of deep leg vein thrombosis, for preventing reocclusions after bypass operations or angioplasty (PT(C) A), and occlusion in peripheral arterial diseases, and for preventing and treating pulmonary embolism, disseminated intravascular coagulation and severe sepsis, for preventing and treating DVT in patients with exacerbated COPD, for treating ulcerative colitis, for preventing and treating coronary thrombosis, for preventing stroke and the occlusion of shunts.

In addition, the compounds according to the invention are suitable for antithrombotic support in thrombolytic treatment, such as for example with alteplase, reteplase, tenecteplase, staphylokinase or streptokinase, for preventing long-term restenosis after PT(C)A, for the prevention and treatment of ischaemic incidents in patients with all forms of coronary heart disease, for preventing metastasis and the growth of tumours and inflammatory processes, e.g. in the treatment of pulmonary fibrosis, for preventing and treating rheumatoid arthritis, for preventing and treating fibrin-dependent tissue adhesions and/or the formation of scar tissue and for promoting wound healing processes.

In view of their pharmacological properties the new compounds and the physiologically acceptable salts thereof are also suitable for the treatment of Alzheimer's and Parkinson's disease. One explanation for this arises for example from the following findings, from which it can be concluded that thrombin inhibitors or factor Xa inhibitors, by inhibiting thrombin formation or thrombin activity, may be valuable drugs for treating Alzheimer's and Parkinson's disease. Clinical and experimental studies indicate that neurotoxic mechanisms, for example the inflammation which is associated with the activation of proteases of the clotting cascade, are involved in the dying of neurones following brain injury. Various studies point to the involvement of thrombin in neurodegenerative processes, for example following a stroke, repeated bypass operations or traumatic brain injury. An increased thrombin activity has been demonstrated some days after peripheral nerve damage, for example. It has also been shown that thrombin causes a neurite retraction, as well as glia proliferation, and apoptosis in primary cultures of neurones and neuroblastoma cells (for a summary see: *Neurobiol. Aging* 2004, 25(6), 783-793). Moreover, various in vitro studies on the brains of patients with Alzheimer's disease indicated that thrombin plays a role in the pathogenesis of this disease (*Neurosci. Lett.* 1992, 146, 152-54). A concentration of immune-reactive thrombin has been detected in neurite plaques in the brains of Alzheimer's patients. It has been demonstrated in vitro that thrombin also plays a part in the regulation and stimulation of the production of the "Amyloid Precursor Protein" (APP) as well as in the cleaving of the APP into fragments which can be detected in the brains of Alzheimer's patients. Moreover, it has been demonstrated that the thrombin-induced microglial activation leads in vivo to the degeneration of nigral dopaminergic neurones. These findings lead one to conclude that microglial activation, triggered by endogenous substance(s) such as thrombin, for example, are involved in the neuropathological process of the cell death of dopaminergic neurones of the kind which occurs in patients with Parkinson's disease (*J. Neurosci.* 2003, 23, 5877-86).

The dosage required to achieve such an effect is appropriately 0.01 to 3 mg/kg, preferably 0.03 to 1.0 mg/kg by intravenous route, and 0.03 to 30 mg/kg, preferably 0.1 to 10 mg/kg by oral route, in each case administered 1 to 4 times a day.

For this purpose, the compounds of formula I prepared according to the invention may be formulated, optionally together with other active substances, with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, to produce conventional galenic preparations such as plain or coated tablets, capsules, powders, suspensions or suppositories.

The new compounds and the physiologically acceptable salts thereof may be used therapeutically in conjunction with acetylsalicylic acid, with inhibitors of platelet aggregation such as fibrinogen receptor antagonists (e.g. abciximab, eptifibatide, tirofiban, roxifiban), with physiological activators and inhibitors of the clotting system and the recombinant analogues thereof (e.g. Protein C, TFPI, antithrombin), with inhibitors of ADP-induced aggregation (e.g. clopidogrel, ticlopidine), with $P_2T$ receptor antagonists (e.g. cangrelor) or with combined thromboxane receptor antagonists/synthetase inhibitors (e.g. terbogrel).

The Examples that follow are intended to illustrate the invention, without restricting its scope:

Experimental Section

As a rule, melting points, IR, UV, $^1$H-NMR and/or mass spectra have been obtained for the compounds prepared. Unless otherwise stated, $R_f$ values were determined using ready-made silica gel 60 $F_{254}$ TLC plates (E. Merck, Darmstadt, Item no. 1.05714) without chamber saturation. The $R_f$ values given under the heading Alox were determined using ready-made aluminium oxide 60 $F_2$54 TLC plates (E. Merck, Darmstadt, Item no. 1.05713) without chamber saturation. The $R_f$ values given under the heading Reversed-phase-8 were determined using ready-made RP-8 $F_{254}s$ TLC plates (E. Merck, Darmstadt, Item no. 1.15684) without chamber saturation. The ratios given for the eluants refer to units by volume of the solvents in question. For chromatographic purification silica gel made by Messrs Millipore (MATREX™, 35-70 my) was used. Unless more detailed information is provided as to the configuration, it is not clear whether the products are pure stereoisomers or mixtures of enantiomers and diastereomers.

The following abbreviations are used in the descriptions of the experiments:

Boc tert.-butoxycarbonyl
DIPEA N-ethyl-diisopropylamine
DMSO dimethylsulphoxide
DMF N,N-dimethylformamide
sat. saturated
h hour(s)
HATU O-(7-azabenzotriazol-1-yl)-N,N,N',N'-tetramethyluronium-hexafluorophosphate
i. vac. in vacuo
conc. concentrated
min minute(s)
NMM N-methyl-morpholine
NMP N-methyl-pyrrolidin-2-one
o ortho
PfTU O-pentafluorophenyl-N,N,N',N'-tetramethyluronium-hexafluorophosphate
PPA propanephosphonic acid cycloanhydride
quant. quantitative
$R_f$ retention factor $R_t$ retention time
rac. racemic
TBTU O-(benzotriazol-1-yl)-N,N,N',N'-tetramethyluronium tetrafuoroborate
TEA triethylamine
TFA trifluoroacetic acid
THF tetrahydrofuran
tert. tertiary
Σ yield over all the steps carried out analogously as described The HPLC/MS data, where specified, were obtained under the following conditions:

HP 1100 with quarternary pump, Gilson G215 Autosampler, HP diode array detector.

The following was used as the mobile phase:
A: water with 0.1% trifluoroacetic acid
B: acetonitrile with 0.1% trifluoroacetic acid

| time in min | % A | % B | flow rate in ml/min |
| --- | --- | --- | --- |
| 0.0 | 95 | 5 | 0.4 |
| 0.15 | 95 | 5 | 0.4 |
| 4.65 | 2 | 98 | 0.4 |
| 6.0 | 2 | 98 | 0.4 |
| 6.5 | 95 | 5 | 0.4 |

The stationary phase used was a Waters column X-Terra™ MS $C_{18}$ 2.5 μm, 2.1 mm×50 mm (column temperature: constant at 25° C.)

The diode array detection took place in a wavelength range from 210-550 nm Range of mass-spectrometric detection: m/z 120 to m/z 1000

EXAMPLE 1

5-chloro-thiophene-2-carboxylic acid-N-{1-[3-chloro-4-(3-oxo-morpholin-4-yl)-phenylcarbamoyl]-ethyl}-amide

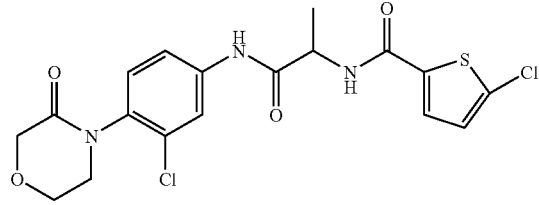

(a) 3-chloro-4-(morpholin-4-yl)-1-nitro-benzene 1.76 g (10.0 mmol) 3-chloro-4-fluoro-1-nitro-benzene are combined with 2.614 ml (30 mmol) morpholine in 5 ml DMF and heated to 105° C. with stirring for 15 min. The reaction mixture is poured into ice water, the resulting precipitate is suction filtered, washed with water and dried at 50° C. in the drying cupboard.

Yield: 2.40 g (99%)

$R_f$ value: 0.20 (silica gel; petroleum ether/ethyl acetate=4:1)

(b) 3-chloro-4-(3-oxo-morpholin-4-yl)-1-nitro-benzene 1.22 g (5.00 mmol) 3-chloro-4-(morpholin-4-yl)-1-nitro-benzene are combined together with 3.42 g (15.0 mmol) benzyl-triethyl-ammonium chloride in 50 ml dichloromethane with 2.37 g (15 mmol) finely powdered potassium permanganate and the reaction mixture is refluxed for 3 hours, then stirred for 16 hours at ambient temperature and again refluxed for 3 hours. The mixture is then stirred into a 20% aqueous solution of sodium-meta-bisulphite, the organic phase is separated off and the aqueous phase is extracted with chloroform. The combined organic phases are dried over magnesium sulphate, evaporated down and the residue is purified by chromatography on silica gel (eluant-gradient: dichloromethane/(ethanol/conc. ammonia solution) 100:0->95:5).

Yield: 280 mg (22%)

$R_f$ value: 0.08 (silica gel; dichloromethane)

$C_{10}H_9ClN_2O_4$ (256.64)

(c) 3-chloro-4-(3-oxo-morpholin-4-yl)-aniline 0.28 g (1.09 mmol) 3-chloro-4-(3-oxo-morpholin-4-yl)-1-nitro-benzene are combined with 100 mg Raney nickel in 20 ml of ethyl acetate and hydrogenated in a Parr apparatus at ambient temperature for 5 h at 5 atm hydrogen pressure. Then the Raney nickel is filtered off and the filtrate is evaporated down i. vac.

The residue is reacted without any further purification.

Yield: 230 mg (93%)

$R_f$ value: 0.5 (silica gel; dichloromethane/methanol=9:1+1% ammonia)

$C_{10}H_{11}ClN_2O_2$ (226.66)

Mass spectrum: $(M+H)^+$=227/229 (chlorine isotope)

(d) methyl 2-[(5-chloro-thiophene-2-carbonyl)-amino]-propionate 3.10 g (19.1 mmol) 5-chloro-thiophene-2-carboxylic acid are combined with 4.44 ml (40 mmol) NMM and 6.42 g (20 mmol) TBTU in 50 ml THF and then stirred for 2 hours under a nitrogen atmosphere at ambient temperature. Then 2.79 g (20 mmol) methyl 2-aminopropionate-hydrochloride and 50 ml THF are added and the mixture is stirred for a further 16 hours at ambient temperature. Then the reaction mixture is poured into water, extracted with ethyl acetate, the combined organic phases are washed with sat. sodium hydrogen carbonate solution, water, 0.5-molar hydrochloric acid, water and sat. sodium chloride solution, dried over magnesium sulphate and evaporated down completely i. vac.

Yield: 3.80 g (81%)

$R_f$ value: 0.63 (silica gel; petroleum ether/ethyl acetate=1:1)

$C_9H_{10}ClNO_3S$ (247.70)

Mass spectrum: $(M+H)^+$=248/250 (chlorine isotope)

(e) 2-[(5-chloro-thiophene-2-carbonyl)-amino]-propionic acid 3.80 g (15.3 mmol) methyl 2-[(5-chloro-thiophene-2-carbonyl)-amino]-propionate are suspended in 15.5 ml (15.5 mmol) 1-molar aqueous sodium hydroxide solution, combined with 15 ml of ethanol and then stirred for 4 hours at ambient temperature. After evaporation i. vac. the residue is combined with ice water, extracted with diethyl ether, the aqueous phase is poured into an ice/acetic acid mixture and the resulting precipitate is suction filtered. After washing with water the precipitate is dried at 60° C.

Yield: 2.90 g (81%)

$R_f$ value: 0.28 (silica gel; petroleum ether/ethyl acetate=1:2)

$C_8H_8ClNO_3S$ (233.67)

(f) 5-chloro-thiophene-2-carboxylic acid-N-{1-[3-chloro-4-(3-oxo-morpholin-4-yl)-phenylcarbamoyl]-ethyl}-amide Prepared analogously to Example 1d from 2-[(5-chloro-thiophene-2-carbonyl)-amino]-propionic acid and 3-chloro-4-(3-oxo-morpholin-4-yl)-aniline with TBTU and NMM in DMF and subsequent purification by chromatography on silica gel.

Yield: 100 mg (23%)

$R_f$ value: 0.75 (silica gel; ethyl acetate/ethanol=9:1+1% glacial acetic acid)

$C_{18}H_{17}Cl_2N_3O_4S$ (442.32)

Mass spectrum: $(M+H)^+$=442/444/446 (chlorine isotope)

EXAMPLE 2

5-bromo-thiophene-2-carboxylic acid-N-{(1R)-2-methoxy-1-[3-methyl-4-(3-oxo-morpholin-4-yl)-phenylcarbamoyl]-ethyl}-amide

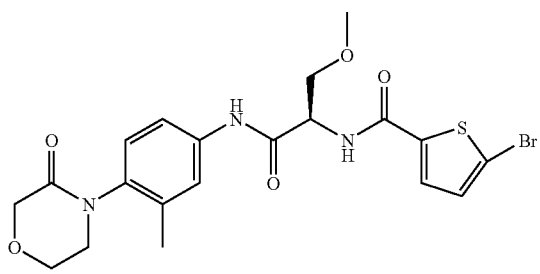

(a) (2R)-2-Boc-amino-3-methoxy-propionic acid 20 g (approx. 0.5 mol) 50% sodium hydride is added batchwise, with cooling in a bath of isopropanol/dry ice, to a mixture of 740 ml THF and 60 ml of methanol and then stirred for 15 min at ambient temperature. 20.52 g (100 mmol) N-Boc-D-serine in 100 ml THF are combined with half the sodium methoxide solution thus obtained and stirred for one hour at ambient temperature under a nitrogen atmosphere. Then 10 ml (22.80 g, 0.16 mol) iodomethane are added and the mixture is again stirred for one hour at ambient temperature. Then the remaining half of the sodium methoxide solution is added, the mixture is stirred for another hour at ambient temperature, and then 20 ml (45.60 g, 0.32 mol) of iodomethane are added. The mixture is then stirred for 18 hours at ambient temperature under a nitrogen atmosphere. The reaction mixture is evaporated down i. vac., the residue is dissolved in water and extracted with diethyl ether. The aqueous phase is adjusted to pH 4 with citric acid solution and extracted with ethyl acetate. The combined organic phases are washed with sat. sodium chloride solution, dried over sodium sulphate and evaporated down i. vac. The residue is taken up in dichloromethane and water, extracted with dichloromethane, the combined organic phases are washed with sat. sodium chloride solution and dried over sodium sulphate. Then the mixture is evaporated down completely i. vac.

Yield: 6.15 g (28%)

$R_f$ value: 0.45 (RP-8; methanol/5% sodium chloride solution=7:3)

$C_9H_{17}NO_5$ (219.24)

Mass spectrum: $(M+H)^+$=220

(b) (2R)-2-Boc-amino-3-methoxy-N-[3-methyl-4-(3-oxo-morpholin-4-yl)-phenyl]-propionic acid-amide Prepared analogously to Example 1d from (2R)-2-Boc-amino-3-methoxy-propionic acid and 3-methyl-4-(3-oxo-morpholin-4-yl)-aniline with TBTU and NMM in DMF.

Yield: 83%

$R_f$ value: 0.53 (silica gel; ethyl acetate/ethanol=9:1)

$C_{20}H_{29}N_3O_6$ (407.46)

(c) (2R)-2-amino-3-methoxy-N-[3-methyl-4-(3-oxo-morpholin-4-yl)-phenyl]-propionic acid-amide 1.70 g (4.17 mmol) (2R)-2-Boc-amino-3-methoxy-N-[(3-methyl-4-(3-oxo-morpholin-4-yl)-phenyl]-propionic acid-amide are combined with 10 ml (60 mmol) 6-molar hydrochloric acid in 10 ml dioxane and then stirred for 1.5 hours at ambient temperature. A further 5 ml (30 mmol) 6-molar hydrochloric acid are then added and the mixture is stirred for a further 1.5 hours. The reaction mixture is combined with ice, made alkaline with conc. ammonia solution and extracted with ethyl acetate. The combined organic phases are dried over magnesium sulphate and evaporated down completely. Then the aqueous phase is exhaustively extracted with dichloromethane, the combined organic phases are washed with a little water, dried over magnesium sulphate and evaporated down completely.

Yield: 1.05 g (82%)

$R_f$ value: 0.08 (silica gel; ethyl acetate/ethanol=9:1+1% conc. ammonia solution)

$C_{15}H_{21}N_3O_4$ (307.35)

Mass spectrum: $(M+H)^+$=308

(d) 5-bromo-thiophene-2-carboxylic acid-N-{(1R)-2-methoxy-1-[3-methyl-4-(3-oxo-morpholin-4-yl)-phenylcarbamoyl]-ethyl}-amide Prepared analogously to Example 1d from 5-bromo-thiophene-2-carboxylic acid and (2R)-2-amino-3-methoxy-N-[3-methyl-4-(3-oxo-morpholin-4-yl)-phenyl]-propionic acid-amide with TBTU and NMM in DMF.

Yield: 57%

$R_f$ value: 0.60 (silica gel; ethyl acetate/ethanol=9:1+1% conc. ammonia solution)

$C_{20}H_{22}BrN_3O_5S$ (496.38)

Mass spectrum: $(M+H)^+$=496/498 (bromine isotope)

The following compounds were prepared analogously:

| No. | Structural formula / Name | Yield | Mass peak(s) | $R_f$ value or $R_t$ |
|---|---|---|---|---|
| 3 | 5-chloro-thiophene-2-carboxylic acid-N-{(1R)-2-methoxy-1-[3-methyl-4-(3-oxo-morpholin-4-yl)-phenylcarbamoyl]-ethyl}-amide | Σ: 11.6% | (M + H)⁺ = 452/454 (chlorine isotope) | 0.60 (silica gel, ethyl acetate/ethanol = 9:1 + 1% ammonia) |
| 5 | 5-chloro-thiophene-2-carboxylic acid-N-{(1R)-1-[2-fluoro-5-methyl-4-(3-oxo-morpholin-4-yl)-phenylcarbamoyl]-2-methoxy-ethyl}-amide | Σ: 4.1% | (M + H)⁺ = 470/472 (chlorine isotope) | 0.69 (silica gel, ethyl acetate/ethanol = 9:1 + 1% ammonia) |
| 6 | 5-bromo-thiophene-2-carboxylic acid-N-{(1R)-1-[2-fluoro-5-methyl-4-(3-oxo-morpholin-4-yl)-phenylcarbamoyl]-2-methoxy-ethyl}-amide | Σ: 3.8% | (M + H)⁺ = 514/516 (bromine isotope) | 0.69 (silica gel, ethyl acetate/ethanol = 9:1 + 1% ammonia) |

EXAMPLE 4

5-chloro-thiophene-2-carboxylic acid-N-{1-[2-fluoro-5-methyl-4-(3-oxo-morpholin-4-yl)-phenylcarbamoyl]-ethyl}-amide

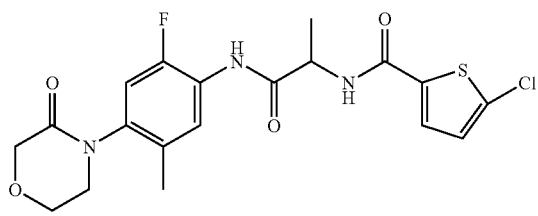

(a) 2-fluoro-5-methyl-4-(morpholin-4-yl)-aniline 1.63 g (8.00 mmol) 4-bromo-2-fluoro-5-methyl-aniline are heated to 160° C. together with 0.88 g (8.65 mmol) morpholin-3-one, 76.1 mg (0.40 mmol) copper(I)iodide, 85.2 μl (0.80 mmol) N,N'-dimethyl-ethylenediamine and 2.49 g (18.0 mmol) potassium carbonate in 15 ml of toluene with stirring in a Roth bomb with a glass insert for 7 hours. Then a further 0.20 g (1.98 mmol) morpholin-3-one, 80 mg (0.42 mmol) copper(I)iodide and 90 μl (0.85 mmol) N,N'-dimethyl-ethylenediamine are added and the mixture is heated for 16 hours to 160° C. The reaction mixture is diluted with ethyl acetate and filtered through a glass filter. The filtrate is washed with water and sat. sodium chloride solution, dried over magnesium sulphate and evaporated down i. vac. The residue is purified by chromatography on silica gel (eluant gradient: petroleum ether/ethyl acetate=1:1->1:2).

Yield: 2.40 g (99%)

$R_f$ value: 0.40 (silica gel; ethyl acetate)

(b) 5-chloro-thiophene-2-carboxylic acid-N-{1-[2-fluoro-5-methyl-4-(3-oxo-morpholin-4-yl)-phenylcarbamoyl]-ethyl}-amide Prepared analogously to Example 1d from 2-[(5-chloro-thiophene-2-carbonyl)-amino]-propionic acid and 2-fluoro-5-methyl-4-(3-oxo-morpholin-4-yl)-aniline with TBTU and NMM in DMF and subsequent purification by chromatography on silica gel.

Yield: 12%

R$_f$ value: 0.32 (silica gel; dichloromethane/ethanol=19:1)
C$_{19}$H$_{19}$ClFN$_3$O$_4$S (439.89)
Mass spectrum: (M+H)$^+$=440/442 (chlorine isotope)
The following compounds may be prepared analogously:
(1) 5-chloro-thiophene-2-carboxylic acid-N-{1-methyl-1-[2-fluoro-5-methyl-4-(3-oxo-morpholin-4-yl)-phenylcarbamoyl]-ethyl}-amide,
(2) 5-bromo-thiophene-2-carboxylic acid-N-{1-methyl-1-[2-fluoro-5-methyl-4-(3-oxo-morpholin-4-yl)-phenylcarbamoyl]-ethyl}-amide,
(3) 5-chloro-thiophene-2-carboxylic acid-N-(1-methyl-1-[N'-methyl-N'-{2-fluoro-5-methyl-4-(3-oxo-morpholin-4-yl)-phenyl}-carbamoyl]-ethyl)-amide,
(4) 5-bromo-thiophene-2-carboxylic acid-N-(1-methyl-1-[N'-methyl-N'-{2-fluoro-5-methyl-4-(3-oxo-morpholin-4-yl)-phenyl}-carbamoyl]-ethyl)-amide

EXAMPLE 7

5-chloro-thiophene-2-carboxylic acid-N-{1-[3-methyl-4-(3-thioxo-morpholin-4-yl)-phenylcarbamoyl]-ethyl}-amide

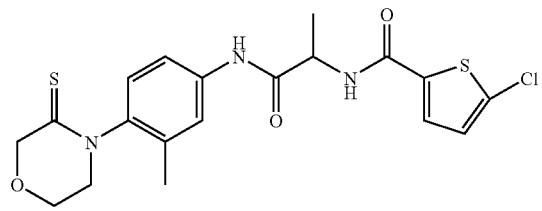

(a) 3-methyl-4-(3-thioxo-morpholin-4-yl)-aniline 0.93 g (4.50 mmol) 3-methyl-4-(3-oxo-morpholin-4-yl)-aniline are refluxed together with 0.91 g (2.25 mmol) 2,4-bis-(4-methoxy-phenyl)-1,3-dithia-2,4-diphosphetan-2,4-disulphide (Lawesson's reagent) in 25 ml of toluene with stirring for one hour. Then the reaction mixture is evaporated down i. vac., the residue is taken up in dichloromethane and extracted with 1-molar hydrochloric acid. The organic phase is evaporated down i. vac. and the residue is purified by chromatography on silica gel (eluant gradient: dichloromethane/ethanol=1:0->50:1) and the aqueous phase is washed with dichloromethane. Then the aqueous phase is made alkaline with 10-molar sodium hydroxide solution and extracted with dichloromethane. The combined organic phases are dried over sodium sulphate and evaporated down completely i. vac., the residue is combined with the product obtained by chromatography.

Yield: 0.71 g (71%)
R$_f$ value: 0.59 (silica gel; dichloromethane/ethanol=9:1)
C$_{11}$H$_{14}$N$_2$OS (222.31)
Mass spectrum: (M+H)$^+$=223

(b) 5-chloro-thiophene-2-carboxylic acid-N-{1-[3-methyl-4-(3-thioxo-morpholin-4-yl)-phenylcarbamoyl]-ethyl}-amide Prepared analogously to Example 1d from 2-[(5-chloro-thiophene-2-carbonyl)-amino]-propionic acid and 3-methyl-4-(3-thioxo-morpholin-4-yl)-aniline with TBTU and DIPEA in THF and subsequent purification by chromatography on silica gel.

Yield: 57%
R$_f$ value: 0.62 (silica gel; dichloromethane/ethanol=9:1)
C$_{19}$H$_{20}$ClN$_3$O$_3$S$_2$ (437.97)
Mass spectrum: (M+H)$^+$=438/440 (chlorine isotope)
The following compounds may be prepared analogously:
(1) 5-bromo-thiophene-2-carboxylic acid-N-{1-methyl-1-[3-methyl-4-(2-thioxo-piperidin-1-yl)-phenylcarbamoyl]-ethyl}-amide,
(2) 5-bromo-thiophene-2-carboxylic acid-N-{1-methyl-1-[3-methyl-4-(3-thioxo-morpholin-4-yl)-phenylcarbamoyl]-ethyl}-amide,
(3) 5-bromo-thiophene-2-carboxylic acid-N-{1-methyl-1-[3-methyl-4-(4-methyl-2-thioxo-piperazin-1-yl)-phenylcarbamoyl]-ethyl}-amide,
(4) 5-bromo-thiophene-2-carboxylic acid-N-{1-methyl-1-[3-methyl-4-(2-thioxo-piperazin-1-yl)-phenylcarbamoyl]-ethyl}-amide,
(5) 5-bromo-thiophene-2-carboxylic acid-N-{1-methyl-1-[3-methyl-4-(5-methyl-2-thioxo-pyrrolidin-1-yl)-phenylcarbamoyl]-ethyl}-amide,
(6) 5-bromo-thiophene-2-carboxylic acid-N-{1-methyl-1-[3-methyl-4-(2-thioxo-azepan-1-yl)-phenylcarbamoyl]-ethyl}-amide,
(7) 5-bromo-thiophene-2-carboxylic acid-N-{1-methyl-1-[3-methyl-4-(2-thioxo-[1,4]oxazepan-4-yl)-phenylcarbamoyl]-ethyl}-amide,
(8) 5-bromo-thiophene-2-carboxylic acid-N-{1-methyl-1-[3-methyl-4-(4-methyl-2-thioxo-[1,4]diazepan-1-yl)-phenylcarbamoyl]-ethyl}-amide,
(9) 5-bromo-thiophene-2-carboxylic acid-N-{1-[3-methyl-4-(3-thioxo-morpholin-4-yl)-phenylcarbamoyl]-cyclobutyl}-amide,
(10) 5-bromo-thiophene-2-carboxylic acid-N-{1-[3-methyl-4-(5-thioxo-[1,4]-oxazepan-4-yl)-phenylcarbamoyl]-cyclobutyl}-amide,
(11) 5-bromo-thiophene-2-carboxylic acid-N-{1-[3-methyl-4-(3-thioxo-morpholin-4-yl)-phenylcarbamoyl]-cyclopentyl}-amide,
(12) 5-bromo-thiophene-2-carboxylic acid-N-{1-[3-methyl-4-(5-thioxo-[1,4]-oxazepan-4-yl)-phenylcarbamoyl]-cyclopentyl}-amide,
(13) 5-bromo-thiophene-2-carboxylic acid-N-{3-[3-methyl-4-(3-thioxo-morpholin-4-yl)-phenylcarbamoyl]-tetrahydrofuran-3-yl}-amide,
(14) 5-bromo-thiophene-2-carboxylic acid-N-{3-[3-methyl4-(5-thioxo-[1,4]-oxazepan-4-yl)-phenylcarbamoyl]-tetrahydrofuran-3-yl}-amide

EXAMPLE 8

5-chloro-thiophene-2-carboxylic acid-N-{1-methyl-1-[3-methyl-4-(3-oxo-morpholin-4-yl)-phenylcarbamoyl]-ethyl}-amide

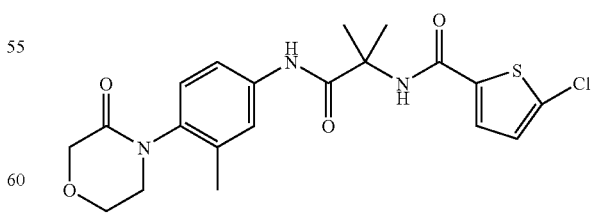

(a) 2-N-Boc-amino-isobuttersäure-N'-[3-methyl-4-(3-oxo-morpholin-4-yl)-phenyl]-amide Prepared analogously to Example 1d from 2-N-Boc-amino-isobutyric acid and 3-methyl-4-(3-oxo-morpholin-4- yl)-aniline with TBTU and NMM in DMF with subsequent purification by chromatography on silica gel.

Yield: 38%
$R_f$ value: 0.60 (silica gel; ethyl acetate/ethanol=9:1)
$C_{20}H_{29}N_3O_5$ (391.46)
Mass spectrum: (M+H)$^+$=392

(b) 2-amino-isobutyric acid-N-[3-methyl-4-(3-oxo-morpholin-4-yl)-phenyl]-amide

Prepared analogously to Example 2c from 2-N-Boc-amino-isobutyric acid-N'-[3-methyl-4-(3-oxo-morpholin-4-yl)-phenyl]-amide with 6-molar hydrochloric acid in dioxane.

Yield: 67%
$R_f$ value: 0.32 (silica gel; dichloromethane/methanol=9:1+ 1% conc. ammonia solution)

$C_{15}H_{21}N_3O_3$ (291.35)
Mass spectrum: (M+H)$^+$=292

(c) 5-chloro-thiophene-2-carboxylic acid-N-{1-methyl-1-[3-methyl-4-(3-oxo-morpholin-4-yl)-phenylcarbamoyl-ethyl}-amide Prepared analogously to Example 1d from 5-chloro-thiophene-2-carboxylic acid and 2-amino-isobutyric acid-N-[3-methyl-4-(3-oxo-morpholin-4-yl)-phenyl]-amide with TBTU and NMM in DMF.

Yield: 63%
$R_f$ value: 0.55 (silica gel; ethyl acetate/ethanol=9:1)
$C_{20}H_{22}ClN_3O_4S$ (435.93)
Mass spectrum: (M+H)$^+$=436/438 (chlorine isotope)

The following compounds were prepared analogously:

| No. | Structural formula / Name | Yield | Mass peak(s) | $R_f$ value or $R_t$ |
|---|---|---|---|---|
| 9 | 5-bromo-thiophene-2-carboxylic acid-N-{1-methyl-1-[3-methyl-4-(3-oxo-morpholin-4-yl)-phenylcarbamoyl]-ethyl}-amide | Σ: 19% | (M + H)$^+$ = 480/482 (bromine isotope) | 0.50 (silica gel, ethyl acetate/ethanol = 9:1) |
| 10 | 5-chloro-thiophene-2-carboxylic acid-N-{(1R)-2-benzyloxy-1-[3-methyl-4-(3-oxo-morpholin-4-yl)-phenylcarbamoyl]-ethyl}-amide | Σ: 95% | (M + H)$^+$ = 528/530 (chlorine isotope) | 0.67 (silica gel, ethyl acetate/ethanol = 9:1) |
| 16 | 5-chloro-thiophene-2-carboxylic acid-N-{(1S)-2-methoxy-1-[3-methyl-4-(3-oxo-morpholin-4-yl)-phenylcarbamoyl]-ethyl}-amide | Σ: 9.0% | (M + H)$^+$ = 452/454 (chlorine isotope) | 0.58 (silica gel, dichloromethane/methanol = 9:1) |

| No. | Structural formula / Name | Yield | Mass peak(s) | $R_f$ value or $R_t$ |
|---|---|---|---|---|
| 17 | 5-bromo-thiophene-2-carboxylic acid-N-{1-[3-methyl-4-(3-oxo-morpholin-4-yl)-phenylcarbamoyl]-cyclopropyl}-amide | Σ: 55% | (M + H)⁺ = 478/480 (bromine isotope) | 0.58 (silica gel, ethyl acetate/ethanol = 9:1 + 1% conc. NH₃) |
| 19 | 5-bromo-thiophene-2-carboxylic acid-N-{1-[3-methyl-4-(3-oxo-morpholin-4-yl)-phenylcarbamoyl]-cyclopentyl}-amide | Σ: 50% | (M − H)⁻ = 506/508 (bromine isotope) | 0.60 (silica gel, ethyl acetate/ethanol = 9:1 + 1% conc. NH₃) |
| 20 | 5-chloro-thiophene-2-carboxylic acid-N-{1-[3-methyl-4-(3-oxo-morpholin-4-yl)-phenylcarbamoyl]-cyclopentyl}-amide | Σ: 41% | (M − H)⁻ = 461/463 (chlorine isotope) | 0.60 (silica gel, ethyl acetate/ethanol = 9:1 + 1% conc. NH₃) |
| 21 | 5-bromo-thiophene-2-carboxylic acid-N-{3-[3-methyl-4-(3-oxo-morpholin-4-yl)-phenylcarbamoyl]-tetrahydrofuran-3-yl)-amide | Σ: 47% | (M − H)⁻ = 508/510 (bromine isotope) | 0.45 (silica gel, ethyl acetate/ethanol = 9:1 + 1% conc. NH₃) |
| 22 | 5-chloro-thiophene-2-carboxylic acid-N-{3-[3-methyl-4-(3-oxo-morpholin-4-yl)-phenylcarbamoyl]-tetrahydrofuran-3-yl}-amide | Σ: 40% | (M − H)⁻ = 463/465 (chlorine isotope) | 0.45 (silica gel, ethyl acetate/ethanol = 9:1 + 1% conc. NH₃) |

| No. | Structural formula / Name | Yield | Mass peak(s) | $R_f$ value or $R_t$ |
|---|---|---|---|---|
| 23 | 5-bromo-thiophene-2-carboxylic acid-N-{(1S)-2-methoxy-1-[3-methyl-4-(3-oxo-morpholin-4-yl)-phenylcarbamoyl]-ethyl}-amide | Σ: 6.6% | (M + H)$^+$ = 496/498 (bromine isotope) | 0.53(silica gel, dichloromethane/methanol = 9:1) |
| 32 | 5-bromo-thiophene-2-carboxylic acid-N-{1-[3-methyl-4-(3-oxo-morpholin-4-yl)-phenylcarbamoyl]-cyclobutan-1-yl}-amide | Σ: 41% | (M + H)$^+$ = 492/494 (bromine isotope) | 0.55(silica gel, dichloromethane/ethanol = 9:1) |
| 35 | 5-chloro-thiophene-2-carboxylic acid-N-{4-[3-methyl-4-(3-oxo-morpholin-4-yl)-phenylcarbamoyl]-tetrahydropyran-4-yl}-amide | Σ: 26% | (M + H)$^+$ = 478/480 (chlorine isotope) | 0.45(silica gel, ethyl acetate/ethanol = 9:1 + 1% conc. NH$_3$) |
| 36 | 5-bromo-thiophene-2-carboxylic acid-N-{4-[3-methyl-4-(3-oxo-morpholin-4-yl)-phenylcarbamoyl]-tetrahydropyran-4-yl}-amide | Σ: 22% | (M + H)$^+$ = 522/524 (bromine isotope) | 0.50(silica gel, ethyl acetate/ethanol = 9:1 + 1% conc. NH$_3$) |
| 41 | 5-chloro-thiophene-2-carboxylic acid-N-{(1R)-1-[3-methyl-4-(3-oxo-morpholin-4-yl)-phenylcarbamoyl]-2-[pyridin-4-yl]-ethyl}-amide | Σ: 24% | (M + H)$^+$ = 499/501 (chlorine isotope) | |

| Structural formula No. | Name | Yield | Mass peak(s) | R$_f$ value or R$_t$ |
|---|---|---|---|---|
| 43 | 5-bromo-thiophene-2-carboxylic acid-N-{(1R)-1-[3-methyl-4-(3-oxo-morpholin-4-yl)-phenylcarbamoyl]-2-[pyridin-4-yl]-ethyl}-amide | Σ: 26% | (M − H)⁻ = 543/545 (bromine isotope) | |

The following compounds may be prepared analogously:
(1) 5-chloro-thiophene-2-carboxylic acid-N-{1-[3-methyl-4-(3-oxo-morpholin-4-yl)-phenylcarbamoyl]-cyclobutyl}-amide,
(2) 5-bromo-thiophene-2-carboxylic acid-N-{5-dimethylamino-1-[3-methyl-4-(3-oxo-morpholin-4-yl)-phenylcarbamoyl]-pentyl}-amide,
(3) 5-bromo-thiophene-2-carboxylic acid-N-{5-acetylamino-1-[3-methyl-4-(3-oxo-morpholin-4-yl)-phenylcarbamoyl]-pentyl}-amide,
(4) 5-bromo-thiophene-2-carboxylic acid-N-{5-methylsulphonylamino-1-[3-methyl-4-(3-oxo-morpholin-4-yl)-phenylcarbamoyl]-pentyl}-amide,
(5) 5-bromo-thiophene-2-carboxylic acid-N-{3-methylsulphanyl-1-[3-methyl-4-(3-oxo-morpholin-4-yl)-phenylcarbamoyl]-propyl}-amide,
(6) 5-bromo-thiophene-2-carboxylic acid-N-{3-methylsulphonyl-1-[3-methyl-4-(3-oxo-morpholin-4-yl)-phenylcarbamoyl]-propyl}-amide,
(7) 5-bromo-thiophene-2-carboxylic acid-N-{3-(tetrazol-5-yl)-1-[3-methyl-4-(3-oxo-morpholin-4-yl)-phenylcarbamoyl]-propyl}-amide,
(8) 5-bromo-thiophene-2-carboxylic acid-N-{3-methyl-1-[3-methyl-4-(3-oxo-morpholin-4-yl)-phenylcarbamoyl]-butyl}-amide,
(9) 5-bromo-thiophene-2-carboxylic acid-N-{4-methoxy-4-oxo-1-[3-methyl-4-(3-oxo-morpholin-4-yl)-phenylcarbamoyl]-butyl}-amide,
(10) 5-bromo-thiophene-2-carboxylic acid-N-{4-dimethylamino-4-oxo-1-[3-methyl-4-(3-oxo-morpholin-4-yl)-phenylcarbamoyl]-butyl}-amide,
(11) 5-bromo-thiophene-2-carboxylic acid-N-{2-methoxy-1-[3-methyl-4-(3-oxo-morpholin-4-yl)-phenylcarbamoyl]-propyl}-amide,
(12) 5-bromo-thiophene-2-carboxylic acid-N-{1-[3-fluoro-4-(3-oxo-morpholin-4-yl)-phenylcarbamoyl]-cyclobutyl}-amide,
(13) 5-bromo-thiophene-2-carboxylic acid-N-{1-[3-chloro-4-(3-oxo-morpholin-4-yl)-phenylcarbamoyl]-cyclobutyl}-amide,
(14) 5-bromo-thiophene-2-carboxylic acid-N-{1-[3-bromo-4-(3-oxo-morpholin-4-yl)-phenylcarbamoyl]-cyclobutyl}-amide,
(15) 5-bromo-thiophene-2-carboxylic acid-N-{1-[3-trifluoromethyl-4-(3-oxo-morpholin-4-yl)-phenylcarbamoyl]-cyclobutyl}-amide,
(16) 5-bromo-thiophene-2-carboxylic acid-N-{1-[3-methoxy-4-(3-oxo-morpholin-4-yl)-phenylcarbamoyl]-cyclobutyl}-amide,
(17) 5-bromo-thiophene-2-carboxylic acid-N-{1-[3-methyl-4-(5-oxo-[1,4]-oxazepan-4-yl)-phenylcarbamoyl]-cyclobutyl}-amide,
(18) 5-bromo-thiophene-2-carboxylic acid-N-{1-[3-fluoro-4-(5-oxo-[1,4]-oxazepan-4-yl)-phenylcarbamoyl]-cyclobutyl}-amide,
(19) 5-bromo-thiophene-2-carboxylic acid-N-{1-[3-chloro-4-(5-oxo-[1,4]-oxazepan-4-yl)-phenylcarbamoyl]-cyclobutyl}-amide,
(20) 5-bromo-thiophene-2-carboxylic acid-N-{1-[3-bromo-4-(5-oxo-[1,4]-oxazepan-4-yl)-phenylcarbamoyl]-cyclobutyl}-amide,
(21) 5-bromo-thiophene-2-carboxylic acid-N-{1-[3-trifluoromethyl-4-(5-oxo-[1,4]-oxazepan-4-yl)-phenylcarbamoyl]-cyclobutyl}-amide,
(22) 5-bromo-thiophene-2-carboxylic acid-N-{1-[3-methoxy-4-(5-oxo-[1,4]-oxazepan-4-yl)-phenylcarbamoyl]-cyclobutyl}-amide,
(23) 5-bromo-thiophene-2-carboxylic acid-N-{3-[3-methyl-4-(3-oxo-morpholin-4-yl)-phenylcarbamoyl]-oxetan-3-yl}-amide,
(24) 5-bromo-thiophene-2-carboxylic acid-N-{3-[3-chloro-4-(3-oxo-morpholin-4-yl)-phenylcarbamoyl]-oxetan-3-yl}-amide,
(25) 5-bromo-thiophene-2-carboxylic acid-N-{3-[3-bromo-4-(3-oxo-morpholin-4-yl)-phenylcarbamoyl]-oxetan-3-yl}-amide,
(26) 5-bromo-thiophene-2-carboxylic acid-N-{3-[3-methyl-4-(5-oxo-[1,4]-oxazepan-4-yl)-phenylcarbamoyl]-oxetan-3-yl}-amide,
(27) 5-bromo-thiophene-2-carboxylic acid-N-{3-[3-chloro-4-(5-oxo-[1,4]-oxazepan-4-yl)-phenylcarbamoyl]-oxetan-3-yl}-amide,
(28) 5-bromo-thiophene-2-carboxylic acid-N-{3-[3-methyl-4-(3-oxo-morpholin-4-yl)-phenylcarbamoyl]-thietan-3-yl}-amide,
(29) 5-bromo-thiophene-2-carboxylic acid-N-{3-[3-chloro-4-(3-oxo-morpholin-4-yl)-phenylcarbamoyl]-thietan-3-yl}-amide,
(30) 5-bromo-thiophene-2-carboxylic acid-N-{3-[3-chloro-4-(5-oxo-[1,4]-oxazepan-4-yl)-phenylcarbamoyl]-thietan-3-yl}-amide,

(31) 5-bromo-thiophene-2-carboxylic acid-N-{3-[3-methyl-4-(3-oxo-morpholin-4-yl)-phenylcarbamoyl]-1,1-dioxo-thietan-3-yl}-amide,
(32) 5-bromo-thiophene-2-carboxylic acid-N-{3-[3-chloro-4-(5-oxo-[1,4]-oxazepan-4-yl)-phenylcarbamoyl]-1,1-dioxo-thietan-3-yl}-amide

EXAMPLE 11

Thiophene-2-carboxylic acid-N-{(1R)-2-benzyloxy-1-[3-methyl-4-(3-oxo-morpholin-4-yl)-phenylcarbamoyl]-ethyl}-amide

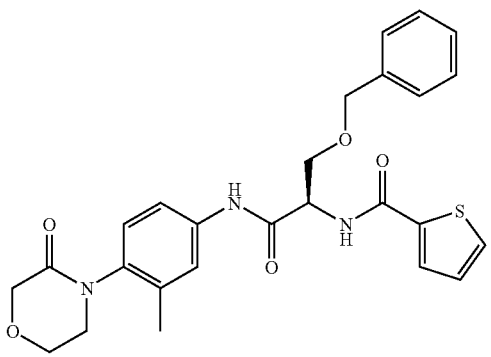

0.53 g (1.00 mmol) 5-chloro-thiophene-2-carboxylic acid-N-{(1R)-2-benzyloxy-1-[3-methyl-4-(3-oxo-morpholin-4-yl)-phenylcarbamoyl]-ethyl}-amide are combined with 100 mg 10% palladium-charcoal in a mixture of 10 ml of ethyl acetate and 20 ml of methanol and hydrogenated for 4 hours in a Parr apparatus at ambient temperature at 5 atm hydrogen pressure, and after the addition of another 200 mg 10% palladium-charcoal in each case hydrogenated again under the same conditions for 7.33 and 2.25 hours. Then the palladium-charcoal is filtered off and the filtrate is evaporated down i. vac. The residue is taken up in dichloromethane and purified by chromatography on silica gel (eluant-gradient: dichloromethane/(methanol/conc. ammonia solution=19:1)=1:0->50:1).

Yield: 190 mg (38%)
$R_f$ value: 0.55 (silica gel; ethyl acetate)
$C_{26}H_{27}N_3O_5S$ (493.58)
Mass spectrum: $(M+H)^+=494$

EXAMPLE 12

5-chloro-thiophene-2-carboxylic acid-N-{(1R)-2-hydroxy-1-[3-methyl-4-(3-oxo-morpholin-4-yl)-phenylcarbamoyl]-ethyl}-amide

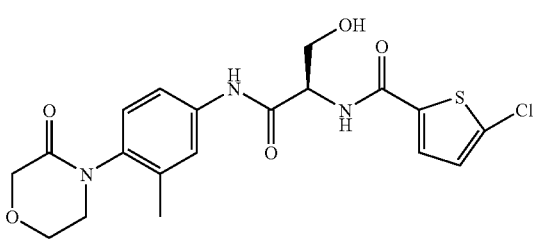

0.26 g (0.50 mmol) 5-chloro-thiophene-2-carboxylic acid-N-{(1R)-2-benzyloxy-1-[3-methyl-4-(3-oxo-morpholin-4-yl)-phenylcarbamoyl]-ethyl}-amide are combined with 741 mg pentamethylbenzene in 2.5 ml trifluoroacetic acid under a nitrogen atmosphere and heated to 50° C. for 3 hours with stirring. Then the mixture is poured into ice water, the resulting precipitate is suction filtered, washed with water and dried at 50° C. The solid is taken up in dichloromethane, evaporated down and then taken up again in 5 ml dichloromethane and 10 ml of methanol and 2 drops of conc. ammonia solution are added, the mixture is evaporated down i. vac., triturated in dichloromethane, suction filtered, washed with dichloromethane and diethyl ether and dried at 50° C. over potassium hydroxide and silica gel.

Yield: 80 mg (37%)
$R_f$ value: 0.51 (silica gel; ethyl acetate/ethanol=9:1+1% conc. ammonia solution)
$C_{19}H_{20}ClN_3O_5S$ (437.90)
Mass spectrum: $(M+H)^+=438/440$ (chlorine isotope)

EXAMPLE 13

5-bromo-thiophene-2-carboxylic acid-N-((1R)-2-methoxy-1-[methyl-{3-methyl-4-(3-oxo-morpholin-4-yl)-phenyl}-carbamoyl]-ethyl)-amide

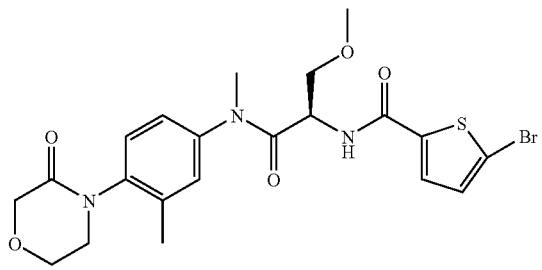

(a) 3,N-dimethyl-4-(3-oxo-morpholin-4-yl)-aniline 1.72 g (75 mmol) sodium are added batchwise to 30 ml of methanol while cooling with ice and stirring. After the reaction has ended 3.09 g (15 mmol) 3-methyl-4-(3-oxo-morpholin-4-yl)-aniline and 0.63 g (21 mmol) paraformaldehyde are added successively and the mixture is stirred for 15 hours at ambient temperature. Then 0.38 g (10.0 mmol) sodium borohydride are added and the mixture is heated to 50° C. with stirring for 3 hours. Then the reaction mixture is evaporated down i. vac., the residue is taken up in 1-molar sodium hydroxide solution and extracted with ethyl acetate. The combined organic phases are washed with sat. sodium chloride solution, dried over magnesium sulphate and evaporated down completely i. vac. The residue is purified by chromatography on silica gel (eluant: dichloromethane/ethanol=40:1).

Yield: 2.27 g (69%)
$R_f$ value: 0.60 (silica gel; dichloromethane/methanol=9:1)
$C_{12}H_{16}N_2O_2$ (220.27)
Mass spectrum: $(M+H)^+=221$ (b) (2R)-2-Boc-amino-3-methoxy-N-methyl-N-[3-methyl-4-(3-oxo-morpholin-4-yl)-phenyl]-propionic acid-amide Prepared analogously to Example 1d from (2R)-2-Boc-amino-3-methoxy-propionic acid and 3,N-dimethyl-4-(3-oxo-morpholin-4-yl)-aniline with TBTU and TEA in DMF.

Yield: 49%

$C_{21}H_{31}N_3O_6$ (421.49)
Mass spectrum: (M+H)$^+$=422

(c) (2R)-2-amino-3-methoxy-N-methyl-N-[3-methyl-4-(3-oxo-morpholin-4-yl)-phenyl]-propionic acid-amide Prepared analogously to Example 2c from (2R)-2-Boc-amino-3-methoxy-N-methyl-N-[(3-chloro-4-(3-oxo-morpholin-4-yl)-phenyl]-propionic acid-amide with hydrochloric acid in dioxane and subsequent purification by chromatography on silica gel.
Yield: 86%
$C_{16}H_{23}N_3O_4$ (321.37)
Mass spectrum: (M+H)$^+$=322

(d) 5-bromo-thiophene-2-carboxylic acid-N-((1R)-2-methoxy-1-[methyl-{3-methyl-4-(3-oxo-morpholin-4-yl)-phenyl}-carbamoyl]-ethyl)-amide Prepared analogously to Example 1d from 5-bromo-thiophene-2-carboxylic acid and (2R)-2-amino-3-methoxy-N-methyl-N-[3-methyl-4-(3-oxo-morpholin-4-yl)-phenyl]-propionic acid-amide with TBTU and TEA in DMF.
Yield: 9%
R$_f$ value: 0.45 (silica gel; methylene chloride/methanol=9:1)
$C_{21}H_{24}BrN_3O_5S$ (510.40)
Mass spectrum: (M+H)$^+$=510/512 (bromine isotope)

EXAMPLE 14

5-chloro-thiophene-2-carboxylic acid-N-{1-[3-methyl-4-(3-oxo-morpholin-4-yl)-phenylcarbamoyl]-1-pyridin-3-yl-methyl}-amide

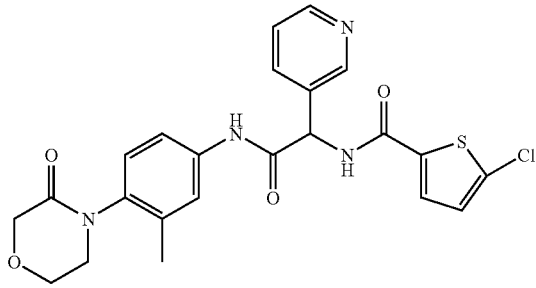

(a) 2-N-Boc-amino-2-pyridin-3-yl-N'-[3-methyl-4-(3-oxo-morpholin-4-yl)-phenyl]-acetamide Prepared analogously to Example 1d from 2-N-Boc-amino-2-pyridin-3-yl-acetic acid and 3-methyl-4-(3-oxo-morpholin-4-yl)-aniline with TBTU and DIPEA in THF with subsequent purification by chromatography on silica gel.
Yield: 72%
R$_f$ value: 0.49 (silica gel; dichloromethane/ethanol=9:1)
$C_{23}H_{28}N_4O_5$ (440.49)
Mass spectrum: (M+H)$^+$=441

(b) 2-amino-2-pyridin-3-yl-N-[3-methyl-4-(3-oxo-morpholin-4-yl)-phenyl]-acetamide 0.78 g (1.77 mmol) 2-N-Boc-amino-2-pyridin-3-yl-N'-[3-methyl-4-(3-oxo-morpholin-4-yl)-phenyl]-acetamide are combined with 5 ml trifluoroacetic acid in 50 ml dichloromethane and stirred for 5 hours at ambient temperature. After evaporation i. vac. the residue is taken up in dichloromethane, washed with sat. sodium hydrogen carbonate solution, dried over sodium sulphate and evaporated down i. vac.

Yield: 0.35 g (58%)
R$_f$ value: 0.10 (silica gel; dichloromethane/ethanol=9:1)
$C_{18}H_{20}N_4O_3$ (340.38)
Mass spectrum: (M+H)$^+$=341

(c) 5-chloro-thiophene-2-carboxylic acid-N-{1-[3-methyl-4-(3-oxo-morpholin-4-yl)-phenylcarbamoyl]-1-Pyridin-3-yl-methyl}-amide Prepared analogously to Example 1d from 5-chloro-thiophene-2-carboxylic acid and 2-amino-isobutyric acid-N-[3-methyl-4-(3-oxo-morpholin-4-yl)-phenyl]-amide with TBTU and DIPEA in DMF.
Yield: 72%
R$_f$ value: 0.41 (silica gel; dichloromethane/ethanol=9:1)
$C_{23}H_{21}ClN_4O_4S$ (484.96)
Mass spectrum: (M+H)$^+$=485/487 (chlorine isotope)

The following compounds may be prepared analogously:
(1) 5-chloro-thiophene-2-carboxylic acid-N-(1-methyl-1-[N'-methyl-N'-{3-methyl-4-(3-oxo-morpholin-4-yl)-phenyl}-carbamoyl]-ethyl)-amide,
(2) 5-bromo-thiophene-2-carboxylic acid-N-(1-methyl-1-[N'-methyl-N'-{3-methyl-4-(3-oxo-morpholin-4-yl)-phenyl}-carbamoyl]-ethyl)-amide

EXAMPLE 15

5-bromo-thiophene-2-carboxylic acid-N-{1-methyl-1-[3-chloro-4-(3-oxo-morpholin-4-yl)-phenylcarbamoyl]-ethyl}-amide

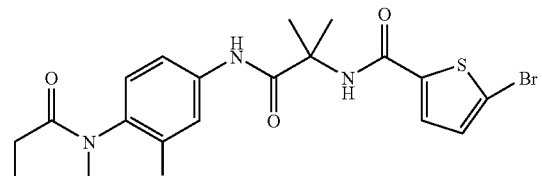

(a) 2-trifluoroacetylamino-isobutyric acid 5 g (48.5 mmol) 2-amino-isobutyric acid are added batchwise to a mixture of 8.0 ml (11.85 g, 56.4 mmol) trifluoroacetic anhydride in 15.3 ml (22.6 g, 0.20 mol) TFA while cooling in the ice bath and the mixture is then stirred for 15 hours at ambient temperature. The reaction mixture is evaporated down i. vac., the residue is dissolved in diethyl ether, combined with petroleum ether and evaporated down i. vac. until turbidity is setting in. Then it is left to crystallise out, filtered and the precipitate is dried at 80° C. in the drying cupboard.
Yield: 7.63 g (79%)
$C_6H_8F_3NO_3$ (199.13)
Mass spectrum: (M–H)$^-$=198

(b) 2-trifluoroacetylamino-isobutyric acid-chloride 0.54 g (2.71 mmol) 2-trifluoroacetylamino-isobutyric acid are combined with 1.8 ml (2.47 g, 20.8 mmol) thionyl chloride and refluxed for 2 hours with stirring. The mixture is then evaporated down i. vac. and any remaining thionyl chloride is eliminating by blowing dry nitrogen over it. The residue is taken up in diethyl ether and petroleum ether and evaporated down again by blowing dry nitrogen over it.

Yield: 0.14 g (24%)

$C_6H_7ClF_3NO_2$ (217.57)

(c) 2-trifluoroacetylamino-isobutyric acid-N-[3-chloro-4-(3-oxo-morpholin-4-yl)-phenyl]-amide 140 mg (0.64 mmol) 2-trifluoroacetylamino-isobutyric acid chloride are combined with 113 mg (0.50 mmol) 3-chloro-4-(3-oxo-morpholin-4-yl)-aniline and 139 μl (101 mg, 1.00 mmol) TEA in 2.0 ml THF and stirred for one hour at ambient temperature. Then 3 ml DMF are added, the mixture is heated to 50° C. with stirring for 1.5 hours and stirred for 7 days at ambient temperature. The reaction mixture is evaporated down completely i. vac., taken up in dichloromethane and purified by chromatography on silica gel (eluant:ethyl acetate).

Yield: 100 mg (47%)

$R_f$ value: 0.65 (silica gel; ethyl acetate/ethanol=9:1)

$C_{16}H_{17}ClF_3N_3O_4$ (407.77)

Mass spectrum: $(M+H)^+=408/410$ (chlorine isotope)

(d) 2-amino-isobutyric acid-N-[3-chloro-4-(3-oxo-morpholin-4-yl)-phenyl]-amide 100 mg (0.25 mmol) 2-trifluoroacetylamino-isobutyric acid-N-[3-chloro-4-(3-oxo-morpholin-4-yl)-phenyl]-amide in 3 ml of methanol are combined with 1.0 ml 1-molar lithium hydroxide solution. After one hour's stirring at ambient temperature 3 ml THF and 1.0 ml 1-molar lithium hydroxide solution are added and the mixture is stirred for 20 hours at ambient temperature. Then the reaction mixture is heated to 50° C. for 6 hours and then evaporated down i. vac. The residue is taken up in dichloromethane, washed with water, dried over magnesium sulphate, evaporated down i. vac., the residue is taken up in diethyl ether and again evaporated down completely i. vac.

Yield: 80 mg (quant.)

$R_f$ value: 0.15 (silica gel; ethyl acetate/ethanol=9:1)

$C_{14}H_{18}ClN_3O_3$ (311.76)

(e) 5-bromo-thiophene-2-carboxylic acid-N-{1-methyl-1-[3-chloro-4-(3-oxo-morpholin-4-yl)-phenylcarbamoyl]-ethyl}-amide Prepared analogously to Example 1d from 5-bromo-thiophene-2-carboxylic acid and 2-amino-isobutyric acid-N-[3-chloro-4-(3-oxo-morpholin-4-yl)-phenyl]-amide with TBTU and NMM in DMF.

Yield: 82%

$R_f$ value: 0.65 (silica gel; ethyl acetate/ethanol=9:1)

$C_{19}H_{19}BrClN_3O_4S$ (500.80)

Mass spectrum: $(M+H)^+=500/502/504$ (bromo- and chlorine isotope)

The following compound may be prepared analogously:

(1) 5-chloro-thiophene-2-carboxylic acid-N-{1-[3-methyl-4-(3-oxo-morpholin-4-yl)-phenylcarbamoyl]-cyclopropyl}-amide

EXAMPLE 18

5-bromo-thiophene-2-carboxylic acid-N-{1-[3-chloro-4-(5-oxo-[1,4]oxazepan-4-yl)-phenylcarbamoyl]-1-methyl-ethyl}-amide

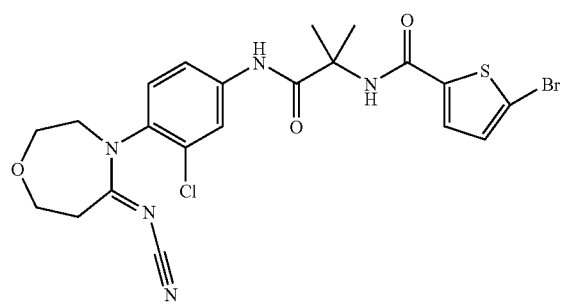

(a) 5-methoxy-2,3,6,7-tetrahydro-[1,4]oxazepine-monomethylsulphate 3.50 g (30.4 mmol) 4-oxacaprolactam are heated to 55° C. in 3.90 ml (41.1 mmol) dimethylsulphate with stirring for 19 h. Then the mixture is evaporated down i. vac., and the residue is taken up twice in toluene and dichloromethane and completely concentrated by evaporation. The residue is further reacted directly.

Yield: 8.10 g (quant.)

$C_6H_{11}NO_2*CH_3SO_4H$ (241.26/129.16)

(b) 5-cyanimino-[1,4]oxazepan 8.00 g (33.2 mmol) 5-methoxy-2,3,6,7-tetrahydro-[1,4] oxazepin-monomethylsulphate are combined with 4.40 ml (31.6 mmol) TEA in 65 ml of methanol and 3.20 g (76.1 mmol) cyanamide are added. The mixture is stirred for 3.5 h at ambient temperature and then evaporated down i. vac., the residue is taken up in diethyl ether and completely concentrated by evaporation i. vac. The residue is triturated in ethanol, filtered off and dried at 60° C.

Yield: 2.45 g (53%)

$R_f$ value: 0.60 (silica gel; dichloromethane/ethanol=9:1+1% conc. ammonia solution)

$C_6H_9N_3O$ (139.16)

Mass spectrum: $(M+H)^+=140$ (c) 3-chloro-4-(5-cyanimino-[1,4]oxazepan-4-yl)-1-nitro-benzene 1.50 g (10.8 mmol) 5-cyanimino-[1,4]oxazepan are heated to 75° C. for 80 min together with 1.95 g (11.1 mmol) 3-chloro-4-fluoro-1-nitro-benzene and 4.50 g (32.56 mmol) potassium carbonate in 35 ml DMF. After filtering, the filtrate is evaporated down i. vac. and the residue is purified by filtration through silica gel (eluant: ethyl acetate/ethanol=9:1). The residue is taken up in 10 ml of ethyl acetate and cooled overnight in the refrigerator. The precipitate was separated off and dried at 60° C. The mother liquor is completely concentrated by evaporation and the residue is purified by chromatography-on silica gel (eluant-gradient:dichloromethane/ (methanol/conc. ammonia solution 19:1)=100:0->93:7). The corresponding fractions are evaporated down, combined with ethyl acetate and inoculated by adding the precipitate obtained previously. The precipitate was filtered off, dried at 60° C. and combined with the precipitate obtained previously.

Yield: 1.45 g (46%)

$R_f$ value: 0.50 (silica gel; ethyl acetate+1% conc. ammonia solution)

$C_{12}H_{11}ClN_4O_3$ (294.69)

Mass spectrum: (M+H)$^+$=294/296 (chlorine isotope)

(d) 3-methyl-4-(5-cyanimino-[1,4]oxazepan-4-yl)-aniline

Prepared analogously to Example 1c from 3-chloro-4-(5-cyanimino-[1,4]oxazepan-4-yl)-1-nitro-benzene with Raney nickel under a hydrogen atmosphere in ethyl acetate with ethanol.

Yield: 88%

$R_f$ value: 0.59 (silica gel; dichloromethane/ethanol=9:1)

$C_{12}H_{13}ClN_4O$ (264.71)

(e) 5-bromo-thiophene-2-carboxylic acid-N-{1-[3-chloro-4-(5-cyanimino-[1,4]oxazepan-4-yl)-phenylcarbamoyl]-1-methyl-ethyl}-amide Prepared analogously to Example 33a from 1-[(5-bromo-thiophene-2-carbonyl)-amino]-cyclopentane-1-carboxylic acid and 3-chloro-4-(5-cyanimino-[1,4]oxazepan-4-yl)-aniline with HATU and NMM in NMP and subsequent purification by chromatography on silica gel.

Yield: 25%

$R_f$ value: 0.58 (silica gel; ethyl acetate+1% conc. ammonia solution)

$C_{21}H_{21}BrClN_5O_3S$ (538.85)

Mass spectrum: (M+H)$^+$=538/540/542 (bromo- and chlorine isotope)

The following compound was obtained analogously:

| No. | Structural formula | Name | Yield | Mass peak(s) | $R_f$ value or $R_t$ |
|---|---|---|---|---|---|
| 24 |  5-bromo-thiophene-2-carboxylic acid-N-{3-(3-methyl-4-[5-cyanimino-[1,4]oxazepan-4-yl]-phenylcarbamoyl)-tetrahydrofuran-3-yl}-amide | | 2.5% | (M + H)$^+$ = 546/548 (bromine isotope) | 0.40(silica gel, ethyl acetate/ethanol = 95:5) |

The following compounds may be prepared analogously:

(1) 5-bromo-thiophene-2-carboxylic acid-N-{1-[3-methyl-4-(3-imino-morpholin-4-yl)-phenylcarbamoyl]-cyclobutyl}-amide, (2) 5-bromo-thiophene-2-carboxylic acid-N-{1-[3-chloro-4-(3-imino-morpholin-4-yl)-phenylcarbamoyl]-cyclobutyl}-amide, (3) 5-bromo-thiophene-2-carboxylic acid-N-{1-[3-methyl-4-(3-methylimino-morpholin-4-yl)-phenylcarbamoyl]-cyclobutyl}-amide, (4) 5-bromo-thiophene-2-carboxylic acid-N-{1-[3-chloro-4-(3-hydroxyimino-morpholin-4-yl)-phenylcarbamoyl]-cyclobutyl}-amide, (5) 5-bromo-thiophene-2-carboxylic acid-N-{1-[3-methyl-4-(3-methoxyimino-morpholin-4-yl)-phenylcarbamoyl]-cyclobutyl}-amide, (6) 5-bromo-thiophene-2-carboxylic acid-N-{1-[3-methyl-4-(3-cyanimino-morpholin-4-yl)-phenylcarbamoyl]-cyclobutyl}-amide, (7) 5-bromo-thiophene-2-carboxylic acid-N-{1-[3-chloro-4-(3-cyanimino-morpholin-4-yl)-phenylcarbamoyl]-cyclobutyl}-amide, (8) 5-bromo-thiophene-2-carboxylic acid-N-{1-[3-methyl-4-(3-nitroimino-morpholin-4-yl)-phenylcarbamoyl]-cyclobutyl}-amide, (9) 5-bromo-thiophene-2-carboxylic acid-N-{1-[3-methyl-4-(5-imino-[1,4]-oxazepan-4-yl)-phenylcarbamoyl]-cyclobutyl}-amide,

(10) 5-bromo-thiophene-2-carboxylic acid-N-{1-[3-chloro-4-(5-methylimino-[1,4]-oxazepan-4-yl)-phenylcarbamoyl]-cyclobutyl}-amide,

(11) 5-bromo-thiophene-2-carboxylic acid-N-{1-[3-methyl-4-(5-hydroxylimino-[1,4]-oxazepan-4-yl)-phenylcarbamoyl]-cyclobutyl}-amide,

(12) 5-bromo-thiophene-2-carboxylic acid-N-{1-[3-methyl-4-(5-methoxyimino-[1,4]-oxazepan-4-yl)-phenylcarbamoyl]-cyclobutyl}-amide,

(13) 5-bromo-thiophene-2-carboxylic acid-N-{1-[3-chloro-4-(5-cyanimino-[1,4]-oxazepan-4-yl)-phenylcarbamoyl]-cyclobutyl}-amide,

(14) 5-bromo-thiophene-2-carboxylic acid-N-{1-[3-methyl-4-(2-imino-piperidin-1-yl)-phenylcarbamoyl]-cyclopentyl}-amide,

(15) 5-bromo-thiophene-2-carboxylic acid-N-{1-[3-chloro-4-(3-imino-morpholin-4-yl)-phenylcarbamoyl]-cyclopentyl}-amide,

(16) 5-bromo-thiophene-2-carboxylic acid-N-{1-[3-methyl-4-(3-methylimino-morpholin-4-yl)-phenylcarbamoyl]-cyclopentyl}-amide,

(17) 5-bromo-thiophene-2-carboxylic acid-N-{1-[3-chloro-4-(3-hydroxylimino-morpholin-4-yl)-phenylcarbamoyl]-cyclopentyl}-amide,

(18) 5-bromo-thiophene-2-carboxylic acid-N-{1-[3-methyl-4-(3-methoxyimino-morpholin-4-yl)-phenylcarbamoyl]-cyclopentyl}-amide,

(19) 5-bromo-thiophene-2-carboxylic acid-N-{1-[3-methyl-4-(3-cyanimino-morpholin-4-yl)-phenylcarbamoyl]-cyclopentyl}-amide,

(20) 5-bromo-thiophene-2-carboxylic acid-N-{1-[3-chloro-4-(2-cyanimino-piperidin-1-yl)-phenylcarbamoyl]-cyclopentyl}-amide,

(21) 5-bromo-thiophene-2-carboxylic acid-N-{1-[3-methyl-4-(3-nitroimino-morpholin-4-yl)-phenylcarbamoyl]-cyclopentyl}-amide,
(22) 5-bromo-thiophene-2-carboxylic acid-N-{1-[3-methyl-4-(5-imino-[1,4]-oxazepan-4-yl)-phenylcarbamoyl]-cyclopentyl}-amide,
(23) 5-bromo-thiophene-2-carboxylic acid-N-{1-[3-chloro-4-(5-methylimino-[1,4]-oxazepan-4-yl)-phenylcarbamoyl]-cyclopentyl}-amide,
(24) 5-bromo-thiophene-2-carboxylic acid-N-{1-[3-methyl-4-(5-hydroxylimino-[1,4]-oxazepan-4-yl)-phenylcarbamoyl]-cyclopentyl}-amide,
(25) 5-bromo-thiophene-2-carboxylic acid-N-{1-[3-methyl-4-(5-methoxyimino-[1,4]-oxazepan-4-yl)-phenylcarbamoyl]-cyclopentyl}-amide,
(26) 5-bromo-thiophene-2-carboxylic acid-N-{1-[3-chloro-4-(5-cyanimino-[1,4]-oxazepan-4-yl)-phenylcarbamoyl]-cyclopentyl}-amide,
(27) 5-bromo-thiophene-2-carboxylic acid-N-{3-[3-chloro-4-(3-hydroxylimino-morpholin-4-yl)-phenylcarbamoyl]-oxetan-3-yl}-amide,
(28) 5-bromo-thiophene-2-carboxylic acid-N-{3-[3-methyl-4-(3-methoxyimino-morpholin-4-yl)-phenylcarbamoyl]-oxetan-3-yl}-amide,
(29) 5-bromo-thiophene-2-carboxylic acid-N-{3-[3-methyl-4-(5-imino-[1,4]-oxazepan-4-yl)-phenylcarbamoyl]-oxetan-3-yl}-amide,
(30) 5-bromo-thiophene-2-carboxylic acid-N-{3-[3-chloro-4-(5-methylimino-[1,4]-oxazepan-4-yl)-phenylcarbamoyl]-oxetan-3-yl}-amide,
(31) 5-bromo-thiophene-2-carboxylic acid-N-{3-[3-methyl-4-(3-imino-morpholin-4-yl)-phenylcarbamoyl-thietan-3-yl}-amide,
(32) 5-bromo-thiophene-2-carboxylic acid-N-{3-[3-chloro-4-(5-methylimino-[1,4]-oxazepan-4-yl)-phenylcarbamoyl]-thietan-3-yl}-amide,
(33) 5-bromo-thiophene-2-carboxylic acid-N-{3-[3-methyl-4-(3-imino-morpholin-4-yl)-phenylcarbamoyl-tetrahydrofuran-3-yl}-amide,
(34) 5-bromo-thiophene-2-carboxylic acid-N-{3-[3-chloro-4-(2-imino-piperidin-1-yl)-phenylcarbamoyl]-tetrahydrofuran-3-yl}-amide,
(35) 5-bromo-thiophene-2-carboxylic acid-N-{3-[3-methyl-4-(3-methylimino-morpholin-4-yl)-phenylcarbamoyl]-tetrahydrofuran-3-yl}-amide,
(36) 5-bromo-thiophene-2-carboxylic acid-N-{3-[3-chloro-4-(3-hydroxylimino-morpholin-4-yl)-phenylcarbamoyl]-tetrahydrofuran-3-yl}-amide,
(37) 5-bromo-thiophene-2-carboxylic acid-N-{3-[3-methyl-4-(3-methoxyimino-morpholin-4-yl)-phenylcarbamoyl]-tetrahydrofuran-3-yl}-amide,
(38) 5-bromo-thiophene-2-carboxylic acid-N-{3-[3-methyl-4-(2-cyanimino-piperidin-1-yl)-phenylcarbamoyl]-tetrahydrofuran-3-yl}-amide,
(39) 5-bromo-thiophene-2-carboxylic acid-N-{3-[3-chloro-4-(3-cyanimino-morpholin-4-yl)-phenylcarbamoyl]-tetrahydrofuran-3-yl}-amide,
(40) 5-bromo-thiophene-2-carboxylic acid-N-{3-[3-methyl-4-(3-nitroimino-morpholin-4-yl)-phenylcarbamoyl]-tetrahydrofuran-3-yl}-amide,
(41) 5-bromo-thiophene-2-carboxylic acid-N-{3-[3-methyl-4-(5-imino-[1,4]-oxazepan-4-yl)-phenylcarbamoyl]-tetrahydrofuran-3-yl}-amide,
(42) 5-bromo-thiophene-2-carboxylic acid-N-{3-[3-chloro-4-(5-methylimino-[1,4]-oxazepan-4-yl)-phenylcarbamoyl]-tetrahydrofuran-3-yl}-amide,
(43) 5-bromo-thiophene-2-carboxylic acid-N-{3-[3-methyl-4-(5-hydroxylimino-[1,4]-oxazepan-4-yl)-phenylcarbamoyl]-tetrahydrofuran-3-yl}-amide,
(44) 5-bromo-thiophene-2-carboxylic acid-N-{3-[3-methyl-4-(5-methoxyimino-[1,4]-oxazepan-4-yl)-phenylcarbamoyl]-tetrahydrofuran-3-yl}-amide,
(45) 5-bromo-thiophene-2-carboxylic acid-N-{3-[3-methyl-4-(3-imino-morpholin-4-yl)-phenylcarbamoyl]-1-methyl-pyrrolidin-3-yl}-amide,
(46) 5-bromo-thiophene-2-carboxylic acid-N-{3-[3-methyl4-(3-methylimino-morpholin-4-yl)-phenylcarbamoyl]-1-methyl-pyrrolidin-3-yl}-amide,
(47) 5-bromo-thiophene-2-carboxylic acid-N-{3-[3-methyl-4-(3-cyanimino-morpholin-4-yl)-phenylcarbamoyl]-1-methyl-pyrrolidin-3-yl}-amide,
(48) 5-bromo-thiophene-2-carboxylic acid-N-{3-[3-chloro-4-(5-methylimino-[1,4]-oxazepan-4-yl)-phenylcarbamoyl]-1-methyl-pyrrolidin-3-yl}-amide,
(49) 5-bromo-thiophene-2-carboxylic acid-N-{3-[3-methyl-4-(5-methoxyimino-[1,4]-oxazepan-4-yl)-phenylcarbamoyl]-1-methyl-pyrrolidin-3-yl}-amide,
(50) 5-bromo-thiophene-2-carboxylic acid-N-{3-[3-chloro-4-(5-cyanimino-[1,4]-oxazepan-4-yl)-phenylcarbamoyl]-1-methyl-pyrrolidin-3-yl}-amide,
(51) 5-chloro-thiophene-2-carboxylic acid-N-{1-[3-methyl-4-(3-cyanimino-morpholin-4-yl)-phenylcarbamoyl]-cyclopentyl}-amide,
(52) 5-chloro-thiophene-2-carboxylic acid-N-{1-[3-methyl-4-(5-cyanimino-[1,4]-oxazepan-4-yl)-phenylcarbamoyl]-cyclopentyl}-amide,
(53) 5-bromo-thiophene-2-carboxylic acid-N-{2-[3-methyl-4-(3-cyanimino-morpholin-4-yl)-phenylcarbamoyl]-bicyclo[2.2.1]hept-2-yl}-amide,
(54) 5-bromo-thiophene-2-carboxylic acid-N-{2-[3-methyl-4-(3-cyanimino-morpholin-4-yl)-phenylcarbamoyl]-7-oxa-bicyclo[2.2.1]hept-2-yl}-amide,
(55) 5-chloro-thiophene-2-carboxylic acid-N-{2-[3-methyl-4-(3-cyanimino-morpholin-4-yl)-phenylcarbamoyl]-7-oxa-bicyclo[2.2.1]hept-2-yl}-amide,
(56) 5-bromo-thiophene-2-carboxylic acid-N-{2-[3-methyl-4-(5-cyanimino-[1,4]oxazepan-4-yl)-phenylcarbamoyl]-7-oxa-bicyclo[2.2.1]hept-2-yl}-amide,
(57) 5-chloro-thiophene-2-carboxylic acid-N-{2-[3-methyl-4-(5 cyanimino-[1,4]oxazepan-4-yl)-phenylcarbamoyl]-7-oxa-bicyclo[2.2.1]hept-2-yl}-amide,
(58) 5-chloro-thiophene-2-carboxylic acid-N-{2-[3-chloro-4-(5-cyanimino-[1,4]oxazepan-4-yl)-phenylcarbamoyl]-7-oxa-bicyclo[2.2.1]hept-2-yl}-amide,
(59) 5-chloro-thiophene-2-carboxylic acid-N-{5-[3-chloro-4-(5-cyanimino-[1,4]-oxazepan-4-yl)-phenylcarbamoyl]-spiro[2.4]hept-5-yl}-amide,
(60) 5-chloro-thiophene-2-carboxylic acid-N-{3-[3-methyl-4-(5-cyanimino-[1,4]-oxazepan-4-yl)-phenylcarbamoyl]-bicyclo[3.1.0]hex-3-yl}-amide,
(61) 5-bromo-thiophene-2-carboxylic acid-N-{1-methyl-[3-methyl-4-(5-cyanimino-[1,4]oxazepan-4-yl)-phenylcarbamoyl]-ethyl}-amide,

EXAMPLE 25

5-chloro-thiophene-2-carboxylic acid-N-{1-[3-methyl-4-(3-oxo-morpholin-4-yl)-phenylcarbamoyl]-1-(pyrazin-2-yl)-methyl}-amide

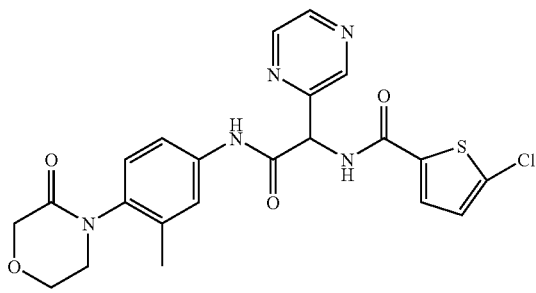

(a) 2-(benzhydryliden-amino)-2-(pyrazin-2-yl)-acetate ethyl 10.03 g (37.5 mmol) N-benzhydrylidene-glycine-ethyl ester are combined with 5.6 ml (7.17 g, 62.6 mmol) 2-chloropyrazine, 12.09 g (37.5 mmol) tetrabutylammonium bromide and 15.53 g (112.4 mmol) potassium carbonate in 70 ml DMF and the mixture is stirred for 3 days at 100° C. The reaction mixture is evaporated down i. vac., the residue is combined with dichloromethane and water and stirred for 12 hours at ambient temperature. Then it is extracted with dichloromethane, the combined organic phases are dried over sodium sulphate and evaporated down i. vac. The residue is purified by twofold chromatography on silica gel (petroleum ether/ethyl acetate=95:5-5>0:100 and 100:0->60:40).

Yield: 5.45 g (42%)
$R_f$ value: 0.18 (silica gel; petroleum ether/ethyl acetate=8:2)
$C_{21}H_{19}N_3O_2$ (345.40)
Mass spectrum: $(M+H)^+=346$ (b) ethyl 2-amino-2-(pyrazin-2-yl)-acetate 19.1 ml (19.1 mmol) 1-molar hydrochloric acid are added dropwise to 5.45 g (15.8 mmol) ethyl 2-(benzhydrylidene-amino)-2-(pyrazin-2-yl)-acetate in 90 ml diethyl ether and the mixture is stirred for 12 hours at ambient temperature. Then it is extracted with diethyl ether, the aqueous phase is evaporated down i. vac. and the residue is taken up twice in ethanol and evaporated down completely i. vac.

Yield: 3.01 g (88%)
$R_f$ value: 0.79 (RP8; methanol/5% NaCl solution=6:4)
$C_8H_{11}N_3O_2$*HCl (217.65/181.19)
Mass spectrum: $(M+H)^+=182$ (c) ethyl 2-Boc-amino-2-(pyrazin-2-yl)-acetate 1.21 g (5.56 mmol) ethyl 2-amino-2-(pyrazin-2-yl)-acetate-hydrochloride are combined with 0.77 ml (0.56 g, 5.54 mmol) TEA in 20 ml dichloromethane and stirred for 30 min at ambient temperature. Then 1.58 g (7.23 mmol) Boc-anhydride are added and the mixture is stirred for 12 hours at ambient temperature. The reaction mixture is filtered, washed with water, the organic phase is dried over sodium sulphate and evaporated down completely i. vac.

Yield: 1.75 g (quant., contaminated)
$R_f$ value: 0.65 (silica gel; dichloromethane/ethanol=9:1)
$C_{13}H_{19}N_3O_4$ (281.31)
Mass spectrum: $(M+H)^+=282$ (d) 2-Boc-amino-2-(pyrazin-2-yl)-acetic acid 1.75 g (6.22 mmol) ethyl 2-Boc-amino-2-(pyrazin-2-yl)-acetate are combined with 15 ml 1-molar lithium hydroxide solution in 50 ml of ethanol. After three hours' stirring at ambient temperature the reaction mixture is evaporated down, diluted with water and neutralised with semisaturated potassium hydrogen sulphate solution. The reaction mixture is evaporated down i. vac., taken up in ethanol and evaporated down completely. The residue is taken up in ethanol, filtered and the solution is evaporated down completely i. vac., taken up in diethyl ether and again evaporated down completely i. vac.

Yield: 1.40 g (89%)
$R_f$ value: 0.62 (RP-8; methanol/5% NaCl solution=6:4)
$C_{11}H_{15}N_3O_4$ (253.26)
Mass spectrum: $(M+H)^+=254$ (e) 2-Boc-amino-2-(pyrazin-2-yl)-acetic acid-N-[3-methyl-4-(3-oxo-morpholin-4-yl)-phenyl]-amide Prepared analogously to Example 1d from 2-Boc-amino-2-(pyrazin-2-yl)-acetic acid and 3-methyl-4-(3-oxo-morpholin-4-yl)-aniline with TBTU and DIPEA in THF.

Yield: 30%
$R_f$ value: 0.66 (silica gel; ethyl acetate/ethanol=8:2)
$C_{22}H_{27}N_5O_5$ (441.48)
Mass spectrum: $(M+H)^+=442$ (f) 2-amino-2-(pyrazin-2-yl)-acetic acid-N-[3-methyl-4-(3-oxo-morpholin-4-yl)-phenyl]-amide 190 mg (0.43 mmol) 2-Boc-amino-2-(pyrazin-2-yl)-acetic acid-N-[3-methyl-4-(3-oxo-morpholin-4-yl)-amide are combined with 1 ml TFA in 4 ml dichloromethane and stirred for 1.5 hours at ambient temperature. Then the reaction mixture is evaporated down i. vac., the residue is taken up in ether and again evaporated down completely i. vac.

Yield: 220 mg (80%)
$R_f$ value: 0.06 (silica gel; dichloromethane/ethanol=9:1)
$C_{17}H_{19}N_5O_3$*2 $CF_3COOH$ (569.41/341.37)
Mass spectrum: $(M+H)^+=342$ (g) 5-chloro-thiophene-2-carboxylic acid-N-{1-(pyrazin-2-yl)-1-[3-methyl-4-(3-oxo-morpholin-4-yl)-phenylcarbamoyl]-methyl}-amide Prepared analogously to Example 1d from 2-amino-2-(pyrazin-2-yl)-acetic acid-N-[3-methyl-4-(3-oxo-morpholin-4-yl)-amide and 5-chloro-thiophene-2-carboxylic acid with TBTU and DIPEA in THF.

Yield: 75%
$R_f$ value: 0.49 (silica gel; dichloromethane/ethanol=9:1)
$C_{22}H_{20}ClN_5O_4S$ (485.94)
Mass spectrum: $(M+H)^+=486/488$ (chlorine isotope)

EXAMPLE 26

5-chloro-thiophene-2-carboxylic acid-N-{(1R)-1-[3-methyl-4-(3-oxo-morpholin-4-yl)-phenylcarbamoyl]-1-phenyl-methyl}-amide

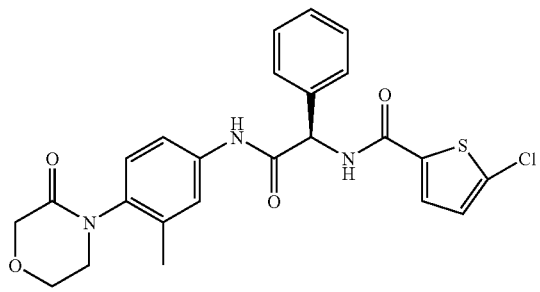

(a) ethyl (2R)-2-[(5-chloro-thiophene-2-carbonyl)-amino]-2-phenyl-acetate

Prepared analogously to Example 1d from 5-chloro-thiophene-2-carboxylic acid and (R)-phenyl-glycine-ethyl ester with TBTU and NMM in THF.
Yield: 96%
$R_f$ value: 0.61 (silica gel; dichloromethane/ethanol=98:2)
$C_{15}H_{14}ClNO_3S$ (323.80)
Mass spectrum: $(M+H)^+ = 324/326$ (chlorine isotope)

(b) (2R)-2-[(5-chloro-thiophene-2-carbonyl)-amino]-2-phenyl-acetic acid

Prepared analogously to Example 1e from ethyl (2R)-2-[(5-chloro-thiophene-2-carbonyl)-amino]-2-phenyl-acetate with 1-molar sodium hydroxide solution in ethanol.
Yield: 96%
$R_f$ value: 0.10 (silica gel; dichloromethane/ethanol=9:1)
$C_{13}H_{10}ClNO_3S$ (295.74)
Mass spectrum: $(M+H)^+ = 296/298$ (chlorine isotope)

(c) 5-chloro-thiophene-2-carboxylic acid-N-{(1R)-1-[3-methyl-4-(3-oxo-morpholin-4-yl)-phenylcarbamoyl]-1-phenyl-methyl}-amide 300 mg (1.01 mmol) (2R)-2-[(5-chloro-thiophene-2-carbonyl)-amino]-2-phenyl-acetic acid are placed together with 209 mg (1.01 mmol) 3-methyl-4-(3-oxo-morpholin-4-yl)-aniline and 335 µl (308 mg, 3.05 mmol) NMM in 60 ml dichloromethane at 0° C., 1.19 ml (2.00 mmol) 50% PPA in ethyl acetate are added and the mixture is stirred for 16 hours at ambient temperature. After evaporation i. vac. the residue is purified by chromatography on silica gel (eluant-gradient: dichloromethane/ethanol=100:0->→94:6).

Yield: 230 mg (47%)

$R_f$ value: 0.49 (silica gel; dichloromethane/ethanol=9:1)

$C_{24}H_{22}ClN_3O_4S$ (483.97)

Mass spectrum: $(M+H)^+ = 484/486$ (chlorine isotope)

The following compound was obtained analogously:

| No. | Structural formula<br>Name | Yield | Mass peak(s) | $R_f$ value or $R_t$ |
|---|---|---|---|---|
| 27 | 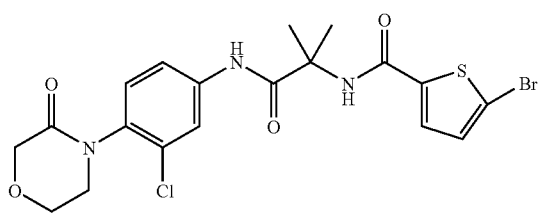<br>5-chloro-thiophene-2-carboxylic acid-N-{(1S)-1-[3-methyl-4-(3-oxo-morpholin-4-yl)-phenylcarbamoyl]-1-phenyl-methyl}-amide | Σ: 22% | $(M+H)^+ =$ 484/486 (chlorine isotope) | 0.33(silica gel, dichloromethane/ ethanol = 19:1) |

EXAMPLE 28

5-bromo-thiophene-2-carboxylic acid-N-{1-methyl-1-[3-chloro-4-(3-oxo-morpholin-4-yl)-phenylcarbamoyl]-ethyl}-amide (a) trifluoroacetic acid-N-{1-methyl-1-[3-chloro-4-(3-oxo-morpholin-4-yl)-phenylcarbamoyl]-ethyl}-amide 140 mg (0.64 mmol) 2-(trifluoroacetyl-amino)-isobutyric acid-chloride are placed in 2.0 ml THF and 113 mg (0.50 mmol) 3-chloro-4-(3-oxo-morpholin-4-yl)-aniline as well as 139 μl (101 mg, 1.00 mmol) TEA are added. After the addition of 3 ml DMF the mixture is stirred for 1.5 hours at 50° C. and 7 days at ambient temperature. After evaporation i. vac. the residue is purified by chromatography on silica gel (eluant: ethyl acetate).

Yield: 100 mg (47%)
$R_f$ value: 0.65 (silica gel; ethyl acetate/ethanol=9:1)
$C_{16}H_{17}ClF_3N_3O_4$ (407.77)
Mass spectrum: $(M+H)^+=408/410$ (chlorine isotope)

(b) 2-amino-isobutyric acid-N-[3-chloro-4-(3-oxo-morpholin-4-yl)-phenyl]-amide 100 mg (0.25 mmol) trifluoroacetic acid-N-{1-methyl-1-[3-chloro-4-(3-oxo-morpholin-4-yl)-phenylcarbamoyl] ethyl}-amide are combined with 1 ml 1-molar lithium hydroxide solution in 3 ml of methanol. After stirring for 2 hours at ambient temperature 3 ml THF and 1 ml 1-molar lithium hydroxide solution are added and the mixture is stirred for 20 hours at ambient temperature and for 6 hours at 50° C. Then it is evaporated down i. vac., the residue is taken up in dichloromethane, washed with water and dried over magnesium sulphate. After evaporation i. vac. the residue is taken up in ether and again evaporated down i. vac.

Yield: 80 mg (quant.)
$R_f$ value: 0.15 (silica gel; ethyl acetate/ethanol=9:1)
$C_{14}H_{18}ClN_3O_3$ (311.76)

(c) 5-bromo-thiophene-2-carboxylic acid-N-{1-methyl-1-[3-chloro-4-(3-oxo-morpholin-4-yl)-phenylcarbamoyl]-ethyl}-amide Prepared analogously to Example 1d from 5-bromo-thiophene-2-carboxylic acid and 2-amino-isobutyric acid-N-[3-chloro-4-(3-oxo-morpholin-4-yl)-phenyl]-amide with TBTU and NMM in DMF.

Yield: 82%
$R_f$ value: 0.65 (silica gel; ethyl acetate/ethanol=9:1)
$C_{19}H_{19}BrClN_3O_4S$ (500.80)
Mass spectrum: $(M+H)^+=500/502/504$ (bromo- and chlorine isotope)

The following compounds may be prepared analogously:
(1) 5-chloro-thiophene-2-carboxylic acid-N-{1-methyl-1-[3-methoxy-4-(3-oxo-morpholin-4-yl)-phenylcarbamoyl]-ethyl}-amide,
(2) 5-bromo-thiophene-2-carboxylic acid-N-{1-methyl-1-[3-methoxy-4-(3-oxo-morpholin-4-yl)-phenylcarbamoyl]-ethyl}-amide

EXAMPLE 29

5-bromo-thiophene-2-carboxylic acid-N-{(1R)-2-methoxy-1-methyl-1-[3-methyl-4-(3-oxo-morpholin-4-yl)-phenylcarbamoyl]-ethyl}-amide

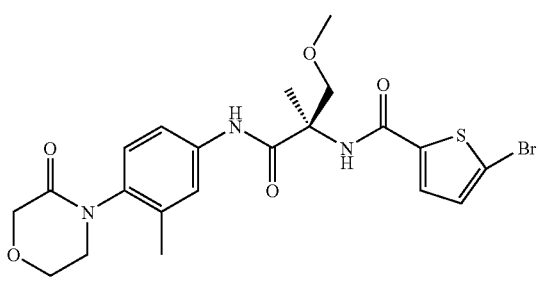

(a) N-Boc-α, O-dimethyl-D-serine-methylester 438 mg (2.00 mmol) N-Boc-α-methyl-D-serine in 40 ml acetonitrile are combined batchwise with a total of 1.25 ml (2.84 g, 20.0 mmol) iodomethane and 2.32 g (10.0 mmol) silver oxide and stirred for 3 days at ambient temperature. After filtration through fibreglass the mixture is is evaporated down i. vac., the residue is taken up in diethyl ether and evaporated down completely i. vac.

Yield: 0.45 g (91%)
$R_f$ value: 0.15 (silica gel; petroleum ether/ethyl acetate=19:1)
$C_{11}H_{21}NO_5$ (247.29)
Mass spectrum: $(M+H)^+=248$ (b) N-Boc-α, O-dimethyl-D-serine lithium salt 400 mg (1.62 mmol) N-Boc-α, O-dimethyl-D-serine-methylester are combined with 8 ml (8 mmol) 1-molar lithium hydroxide solution in 5 ml of methanol and stirred for 21 hours at ambient temperature. After evaporation of the reaction mixture i. vac. the residue is taken up 3 times in toluene and evaporated down completely i. vac. and then washed with THF. The residue obtained is further reacted directly without any further purification and analysis.

$C_{10}H_{18}LiNO_5$ (239.20)

(c) (2R)-2-Boc-amino-3-methoxy-2-methyl-propionic acid-N-[3-methyl-4-(3-oxo-morpholin-4-yl)-phenyl]-amide Prepared analogously to Example 1d from N-Boc-α, O-dimethyl-D-serine-lithium salt and 3-methyl-4-(3-oxo-morpholin-4-yl)-aniline with TBTU and NMM in DMF.

Yield: 16%
$R_f$ value: 0.63 (silica gel; ethyl acetate/ethanol=9:1)
$C_{21}H_{31}N_3O_6$ (421.49)
Mass spectrum: $(M+H)^+=422$ (d) (2R)-2-amino-3-methoxy-2-methyl-propionic acid-N-[3-methyl-4-(3-oxo-morpholin-4-yl)-phenyl]-amide 100 mg (0.24 mmol) (2R)-2-Boc-amino-3-methoxy-2-methyl-propionic acid-N-[3-methyl-4-(3-oxo-morpholin-4-yl)-phenyl]-amide are combined with 20 ml ethereal hydrochloric acid solution and 5 ml each of dichloromethane and methanol are added. After three hours' stirring at ambient temperature the reaction mixture is evaporated down, taken up in diethyl ether and again evaporated down completely i. vac.

Yield: 90 mg (quant.)
$R_f$ value: 0.35 (silica gel; ethyl acetate/ethanol=9:1+1% ammonia solution)
$C_{16}H_{23}N_3O_4 \cdot HCl$ (357.83/321.37)

(e) 5-bromo-thiophene-2-carboxylic acid-N-{(1R)-2-methoxy-1-methyl-1-[3-methyl-4-(3-oxo-morpholin-4-yl)-phenylcarbamoyl]-ethyl}-amide 5 Prepared analogously to Example 1d from 5-bromo-thiophene-2-carboxylic acid and (2R)-2-amino-3-methoxy-2-methyl-propionic acid-N-[3-methyl-4-(3-oxo-morpholin-4-yl)-phenyl]-amide with TBTU and NMM in DMF.

Yield: 31%
$R_f$ value: 0.64 (silica gel; ethyl acetate/ethanol=9:1+1% ammonia solution)
$C_{21}H_{24}BrN_3O_5S$ (510.40)
Mass spectrum: $(M+H)^+=510/512$ (bromine isotope)

The following compounds were obtained analogously:

| No. | Structural formula Name | Yield | Mass peak(s) | $R_f$ value or $R_t$ |
|---|---|---|---|---|
| 30 | ![structure] 5-chloro-thiophene-2-carboxylic acid-N-{(1S)-2-methoxy-1-methyl-1-[3-methyl-4-(3-oxo-morpholin-4-yl)-phenylcarbamoyl]-ethyl}-amide | Σ: 20% | $(M+H)^+$ = 466/468 (chlorine isotope) | 0.60(silica gel, ethyl acetate/ethanol = 9:1 + 1% $NH_3$ solution) |
| 31 | ![structure] 5-bromo-thiophene-2-carboxylic acid-N-{(1S)-2-methoxy-1-methyl-1-[3-methyl-4-(3-oxo-morpholin-4-yl)-phenylcarbamoyl]-ethyl}-amide | Σ: 23% | $(M+H)^+$ = 510/512 (bromine isotope) | 0.60(silica gel, ethyl acetate/ethanol = 9:1 + 1% $NH_3$ solution) |

The following compounds may be prepared analogously:
(1) 5-chloro-thiophene-2-carboxylic acid-N-{(1R)-2-methoxy-1-methyl-1-[3-methyl-4-(3-oxo-morpholin-4-yl)-phenylcarbamoyl]-ethyl}-amide,
(2) 5-bromo-thiophene-2-carboxylic acid-N-{(1R)-2-methoxy-1-methyl-1-[3-chloro-4-(3-oxo-morpholin-4-yl)-phenylcarbamoyl]-ethyl}-amide,
(3) 5-bromo-thiophene-2-carboxylic acid-N-{(1S)-2-methoxy-1-methyl-1-[3-chloro-4-(3-oxo-morpholin-4-yl)-phenylcarbamoyl]-ethyl}-amide

EXAMPLE 33

5-bromo-thiophene-2-carboxylic acid-N-{1-[3-chloro-4-(3-oxo-morpholin-4-yl)-phenylcarbamoyl]-cyclohex-1-yl}-amide

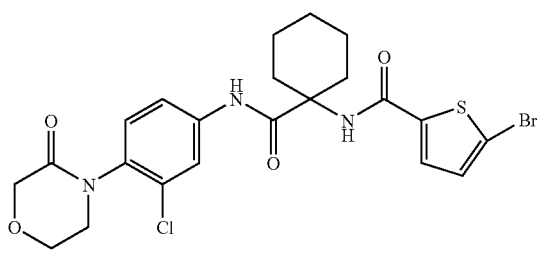

(a) 1-Boc-amino-cyclohexane-1-carboxylic acid-N-[3-chloro-4-(3-oxo-morpholin-4-yl)-phenyl]-amide 122 mg (0.50 mmol) 1-Boc-amino-cyclohexyl-1-carboxylic acid are combined with 110 µl (101 mg, 1.00 mmol) NMM and 202 mg (0.53 mmol) HATU in 2.0 ml DMF and after 10 min stirring at ambient temperature 113 mg (0.50 mmol) 3-chloro-4-(3-oxo-morpholin-4-yl)-aniline are added. After stirring for 3 days at ambient temperature, 6 hours at 95° C. and 16 hours at ambient temperature the reaction mixture is poured into water, made alkaline with sodium hydrogen carbonate solution and extracted with ethyl acetate. The combined organic phases are washed with 0.5-molar potassium hydrogen sulphate solution, water and sat. sodium chloride solution, dried over magnesium sulphate and evaporated down i. vac. The residue is purified by chromatography on silica gel (eluant-gradient: petroleum ether/ethyl acetate=2:3->1:3).

Yield: 90 mg (40%)
$R_f$ value: 0.60 (silica gel; ethyl acetate)
$C_{22}H_{30}ClN_3O_5$ (451.94)

(b) 1-amino-cyclohexane-1-carboxylic acid-N-[3-chloro-4-(3-oxo-morpholin-4-yl)-phenyl]-amide Prepared analogously to Example 2c from 1-Boc-amino-cyclohexane-1-carboxylic acid-N-[3-chloro-4-(3-oxo-morpholin-4-yl)-phenyl]-amide and 6-molar hydrochloric acid in dioxane.

Yield: quant.
$R_f$ value: 0.60 (silica gel; ethyl acetate/ethanol=9:1+1% ammonia solution)
$C_{17}H_{22}ClN_3O_3$*HCl (388.29/351.83)

(c) 5-bromo-thiophene-2-carboxylic acid-N-{1-[3-chloro-4-(3-oxo-morpholin-4-yl)-phenylcarbamoyl]-cyclohex-1-yl}-amide Prepared analogously to Example 1d from 5-bromo-thiophene-2-carboxylic acid and 1-amino-cyclohexane-1-carboxylic acid-N-[3-chloro-4-(3-oxo-morpholin-4-yl)-phenyl]-amide with TBTU and NMM in DMF.

Yield: 17%

$R_f$ value: 0.80 (silica gel; ethyl acetate/ethanol=9:1+1% ammonia solution)

$C_{22}H_{23}BrClN_3O_4S$ (540.86)

Mass spectrum: $(M+H)^+=540/542/544$ (bromo- and chlorine isotope)

The following compound was obtained analogously:

| No. | Structural formula Name | Yield | Mass peak(s) | $R_f$ value or $R_t$ |
|---|---|---|---|---|
| 47 | 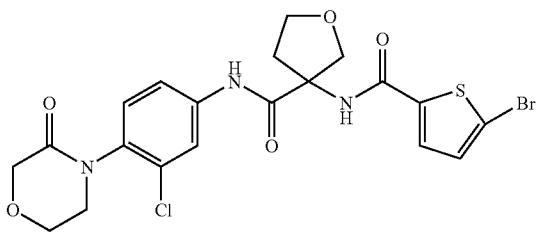<br>5-bromo-thiophene-2-carboxylic acid-N-{1-(3-chloro-4-[3-oxo-morpholin-4-yl]-phenylcarbamoyl)-cyclopent-1-yl}-amide | 5.0% | $(M + H)^+ =$ 526/528/560 (bromine and chlorine isotopes) | 0.70 (silica gel, ethyl acetate/methanol = 9:1 + 1% conc. $NH_3$ solution) |

The following compounds may be prepared analogously:

(1) 5-chloro-thiophene-2-carboxylic acid-N-{1-[3-methyl-4-(3-oxo-morpholin-4-yl)-phenylcarbamoyl]-cyclohexyl}-amide, (2) 5-bromo-thiophene-2-carboxylic acid-N-{1-[3-methyl-4-(3-oxo-morpholin-4-yl)-phenylcarbamoyl]-cyclohexyl}-amide, (3) 5-bromo-thiophene-2-carboxylic acid-N-{1-[3-methyl-4-(3-oxo-morpholin-4-yl)-phenylcarbamoyl]-cyclohexyl}-amide, (4) 5-bromo-thiophene-2-carboxylic acid-N-{1-[3-fluoro-4-(3-oxo-morpholin-4-yl)-phenylcarbamoyl]-cyclopentyl}-amide, (5) 5-bromo-thiophene-2-carboxylic acid-N-{1-[3-bromo-4-(3-oxo-morpholin-4-yl)-phenylcarbamoyl]-cyclopentyl}-amide, (6) 5-bromo-thiophene-2-carboxylic acid-N-{1-[3-trifluoromethyl-4-(3-oxo-morpholin-4-yl)-phenylcarbamoyl]-cyclopentyl}-amide, (7) 5-bromo-thiophene-2-carboxylic acid-N-{1-[3-methoxy-4-(3-oxo-morpholin-4-yl)-phenylcarbamoyl]-cyclopentyl}-amide, (8) 5-bromo-thiophene-2-carboxylic acid-N-{1-[3-nitro-4-(3-oxo-morpholin-4-yl)-phenylcarbamoyl]-cyclopentyl}-amide, (9) 5-bromo-thiophene-2-carboxylic acid-N-{1-[3-methyl4-(5-oxo-[1,4]-oxazepan-4-yl)-phenylcarbamoyl]-cyclopentyl}-amide,

(10) 5-bromo-thiophene-2-carboxylic acid-N-{1-[3-fluoro-4-(5-oxo-[1,4]-oxazepan-4-yl)-phenylcarbamoyl]-cyclopentyl}-amide,

(11) 5-bromo-thiophene-2-carboxylic acid-N-{1-[3-chloro-4-(5-oxo-[1,4]-oxazepan-4-yl)-phenylcarbamoyl]-cyclopentyl}-amide,

(12) 5-bromo-thiophene-2-carboxylic acid-N-{1-[3-bromo-4-(5-oxo-[1,4]-oxazepan-4-yl)-phenylcarbamoyl]-cyclopentyl}-amide,

(13) 5-bromo-thiophene-2-carboxylic acid-N-{1-[3-trifluoromethyl-4-(5-oxo-[1,4]-oxazepan-4-yl)-phenylcarbamoyl]-cyclopentyl}-amide,

(14) 5-bromo-thiophene-2-carboxylic acid-N-{1-[3-methoxy-4-(5-oxo-[1,4]-oxazepan-4-yl)-phenylcarbamoyl]-cyclopentyl}-amide

EXAMPLE 34

5-bromo-thiophene-2-carboxylic acid-N-{3-[3-chloro-4-(3-oxo-morpholin-4-yl)-phenylcarbamoyl]-tetrahydrofuran-3-yl}-amide

(a) 3-Boc-amino-tetrahydrofuran-3-carboxylic acid-N-[3-chloro-4-(3-oxo-morpholin-4-yl)-phenyl]-amide Prepared analogously to Example 26c from 3-Boc-amino-tetrahydrofuran-3-carboxylic acid and 3-chloro-4-(3-oxo-morpholin-4-yl)-aniline with PPA and TEA in THF.

Yield: 16%

$R_f$ value: 0.45 (silica gel; ethyl acetate)

$C_{20}H_{26}ClN_3O_6$ (439.89)

(b) 3-amino-tetrahydrofuran-3-carboxylic acid-N-[3-chloro-4-(3-oxo-morpholin-4-yl)-phenyl]-amide 70 mg (0.16 mmol) 3-Boc-amino-tetrahydrofuran-3-carboxylic acid-N-[3-chloro-4-(3-oxo-morpholin-4-yl)-phenyl]-amide are dissolved at 0° C. in ethanolic hydrochloric acid and stirred for 16 hours at ambient temperature. After evaporation i. vac. the residue is taken up in ether and evaporated down completely i. vac.

Yield: 55 mg (92%)

$R_f$ value: 0.30 (silica gel; ethyl acetate/ethanol=9:1+1% ammonia solution)

$C_{15}H_{18}ClN_3O_4$*HCl (376.24/339.78)

(c) 5-bromo-thiophene-2-carboxylic acid-N-{3-[3-chloro-4-(3-oxo-morpholin-4-yl)-phenylcarbamoyl]-tetrahydrofuran-3-yl}-amide Prepared analogously to Example 1d from 5-bromo-thiophene-2-carboxylic acid and 3-amino-tetrahydrofuran-3-carboxylic acid-N-[3-chloro-4-(3-oxo-morpholin-4-yl)-phenyl]-amide with TBTU and NMM in DMF.

Yield: 58%

$R_f$ value: 0.60 (silica gel; ethyl acetate/ethanol=9:1+1% ammonia solution)

$C_{20}H_{19}BrClN_3O_5S$ (528.81)

Mass spectrum: (M+H)$^+$=528/530/532 (bromo- and chlorine isotope)

The following compounds may be prepared analogously:
(1) 5-bromo-thiophene-2-carboxylic acid-N-{3-[3-fluoro-4-(3-oxo-morpholin-4-yl)-phenylcarbamoyl]-tetrahydrofuran-3-yl}-amide,
(2) 5-bromo-thiophene-2-carboxylic acid-N-{3-[3-chloro-4-(3-oxo-morpholin-4-yl)-phenylcarbamoyl]-tetrahydrofuran-3-yl}-amide,
(3) 5-bromo-thiophene-2-carboxylic acid-N-{3-[3-bromo-4-(3-oxo-morpholin-4-yl)-phenylcarbamoyl]-tetrahydrofuran-3-yl}-amide,
(4) 5-bromo-thiophene-2-carboxylic acid-N-{3-[3-trifluoromethyl-4-(3-oxo-morpholin-4-yl)-phenylcarbamoyl]-tetrahydrofuran-3-yl}-amide,
(5) 5-bromo-thiophene-2-carboxylic acid-N-{3-[3-methoxy-4-(3-oxo-morpholin-4-yl)-phenylcarbamoyl]-tetrahydrofuran-3-yl}-amide,
(6) 5-bromo-thiophene-2-carboxylic acid-N-{3-[3-nitro-4-(3-oxo-morpholin-4-yl)-phenylcarbamoyl]-tetrahydrofuran-3-yl}-amide,
(7) 5-bromo-thiophene-2-carboxylic acid-N-{3-[3-methyl-4-(3-oxo-morpholin-4-yl)-phenylcarbamoyl]-tetrahydro-thiophen-3-yl}-amide,
(8) 5-bromo-thiophene-2-carboxylic acid-N-{3-[3-chloro-4-(5-oxo-[1,4]-oxazepan-4-yl)-phenylcarbamoyl]-tetrahydro-thiophen-3-yl}-amide,
(9) 5-bromo-thiophene-2-carboxylic acid-N-{3-[3-methyl-4-(3-oxo-morpholin-4-yl)-phenylcarbamoyl]-1,1-dioxo-tetrahydro-thiophen-3-yl}-amide,
(10) 5-bromo-thiophene-2-carboxylic acid-N-{3-[3-chloro-4-(5-oxo-[1,4]-oxazepan-4-yl)-phenylcarbamoyl]-1,1-dioxo-tetrahydro-thiophen-3-yl}-amide

EXAMPLE 37

5-bromo-thiophene-2-carboxylic acid-N-{1-methyl-1-[3-methyl-4-((4R)-4-methyl-2-oxo-oxazolidin-3-yl)-phenylcarbamoyl]-ethyl}-amide

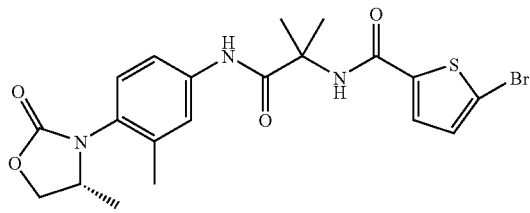

(a) tert.-butyl 2-[(5-bromo-thiophene-2-carbonyl)-amino]-isobutyrate 2.41 g (12.3 mmol) tert.-butyl 2-amino-isobutyrate hydrochloride are combined with 7.0 ml (11.4 g, 96 mmol) thionyl chloride in 15 ml dichloromethane and refluxed for 2 hours. After evaporation i. vac., taking up the residue in toluene and evaporation i. vac. once more, the residue is added in 10 ml dichloromethane to a mixture of 2.41 g (12.3 mmol) tert.-butyl 2-amino-isobutyrate in 20 ml dichloromethane with 5.14 ml (3.73 g, 36.9 mmol) TEA and stirred for 16 hours at ambient temperature. Then it is extracted with water, the aqueous phase is extracted with dichloromethane, the combined organic phases are dried over magnesium sulphate and evaporated down completely i. vac.

Yield: 3.83 g (89%)

$C_{13}H_{18}BrNO_3S$ (348.26)

Mass spectrum: (M+H)$^+$=348/350 (bromine isotope)

(b) 2-[(5-bromo-thiophene-2-carbonyl)-amino]-isobutyric acid

Prepared analogously to Example 25f from tert.-butyl 2-[(5-bromo-thiophene-2-carbonyl)-amino]-isobutyrate with TFA in dichloromethane.

Yield: 88%

$R_f$ value: 0.33 (silica gel; dichloromethane/methanol=9:1)

$C_9H_{10}BrNO_3S$ (292.15)

Mass spectrum: (M+H)$^+$=292/294 (bromine isotope)

(c) N-[(1R)-2-hydroxy-1-methyl-ethyl)-2-methyl-4-nitro-aniline

Prepared analogously to Example 1a from 4-fluoro-3-methyl-nitrobenzene and D-alaninol in DMF.

Yield: 50%

$R_f$ value: 0.58 (silica gel; dichloromethane/methanol=9:1)

$C_{10}H_{14}N_2O_3$ (210.23)

Mass spectrum: (M+H)$^+$=211

(d) 3-methyl-4-[(4R)-4-methyl-2-oxo-oxazolidin-3-yl]-nitrobenzene 1.49 g (7.09 mmol) N-[(1R)-2-hydroxy-1-methyl-ethyl)-2-methyl-4-nitro-aniline are combined with 2.47 ml (1.79 g, 17.7 mmol) TEA in 40 ml THF and while cooling in the ice bath and under a nitrogen atmosphere 5.6 ml (5.24 g, 10.6 mmol) 20% phosgene solution in toluene are added. After 16 hours' stirring at ambient temperature the reaction mixture is poured into water, extracted with ethyl acetate, the combined organic phases are washed with sat. sodium chloride solution and dried over magnesium sulphate. After evaporation i. vac. the residue is purified by chromatography on silica gel (eluant-gradient:dichloromethane/methanol=10:0->9:1).

Yield: 1.38 g (82%)

$R_f$ value: 0.25 (silica gel; dichloromethane)

$C_{11}H_{12}N_2O_4$ (236.22)

Mass spectrum: (M+H)$^+$=237

(e) 3-methyl-4-[(4R)-4-methyl-2-oxo-oxazolidin-3-yl]-aniline

Prepared analogously to Example 1c from 3-methyl-4-[(4R)-4-methyl-2-oxo-oxazolidin-3-yl)-nitrobenzene with hydrogen and Raney nickel in ethyl acetate.

Yield: 64%

$R_f$ value: 0.56 (silica gel; dichloromethane/methanol=9:1)

$C_{11}H_{14}N_2O_2$ (206.24)

Mass spectrum: (M+H)$^+$=207

(f) 5-bromo-thiophene-2-carboxylic acid-N-{1-methyl-1-(3-methyl-4-[(4R)-4-methyl-2-oxo-oxazolidin-3-yl]-phenylcarbamoyl)-ethyl}-amide Prepared analogously to Example 33a from 2-[(5-bromo-thiophene-2-carbonyl)-amino]-isobutyric acid and 3-methyl-4-[(4R)-4-methyl-2-oxo-oxazolidin-3-yl)-aniline with HATU and NMM in DMF.

Yield: 0.43 g (61%)

$R_f$ value: 0.77 (silica gel; ethyl acetate/ethanol=9:1)

$C_{20}H_{22}BrN_3O_4S$ (480.38)

Mass spectrum: (M+H)$^+$=480/482 (bromine isotope)

The following compound was obtained analogously:

| No. | Structural formula Name | Yield | Mass peak(s) | $R_f$ value or $R_t$ |
|---|---|---|---|---|
| 38 | 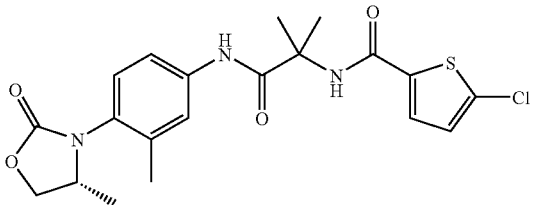<br>5-chloro-thiophene-2-carboxylic acid-N-{1-methyl-1-(3-methyl-4-[(4R)-4-methyl-2-oxo-oxazolidin-3-yl]-phenylcarbamoyl)-ethyl}-amide | 89% | (M + H)⁺ 436/438 (chlorine isotope) | 0.52(silica gel, dichloromethane/methanol = 9:1) |

The following compounds may be prepared analogously:
(1) 5-chloro-thiophene-2-carboxylic acid-N-{1-[3-chloro-4-(4-methyl-oxazolidin-3-yl)-phenylcarbamoyl]-ethyl}-amide,
(2) 5-bromo-thiophene-2-carboxylic acid-N-{1-methyl-1-[3-methyl-4-(4,4-dimethyl-oxazolidin-2-on-3-yl)-phenylcarbamoyl]-ethyl}-amide,
(3) 5-bromo-thiophene-2-carboxylic acid-N-{1-methyl-1-[3-methyl-4-(2-oxo-[1,3]oxazinan-3-yl)-phenylcarbamoyl]-ethyl}-amide,
(4) 5-bromo-thiophene-2-carboxylic acid-N-{1-methyl-1-[3-methyl-4-(4,4-dimethyl-2-oxo-imidazolidin-3-yl)-phenylcarbamoyl]-ethyl}-amide,
(5) 5-bromo-thiophene-2-carboxylic acid-N-{1-methyl-1-[3-methyl-4-(2-oxo-[1,3]oxazepan-3-yl)-phenylcarbamoyl]-ethyl}-amide,
(6) 5-bromo-thiophene-2-carboxylic acid-N-{1-methyl-1-[3-methyl-4-(2-oxo-[1,3]diazepan-1-yl)-phenylcarbamoyl]-ethyl}-amide,
(7) 5-bromo-thiophene-2-carboxylic acid-N-{1-methyl-1-[3-methyl-4-(1,1-dioxo-[1,2,5]thiadiazolidin-2-yl)-phenylcarbamoyl]-ethyl}-amide,
(8) 5-bromo-thiophene-2-carboxylic acid-N-{1-methyl-1-[3-methyl-4-(1,1-dioxo-[1,2,6]thiadiazinan-2-yl)-phenylcarbamoyl]-ethyl}-amide

EXAMPLE 39

5-chloro-thiophene-2-carboxylic acid-N-{1-[3-methyl-4-(tetrahydro-pyrimidin-2-on-1-yl)-phenylcarbamoyl]-ethyl}-amide

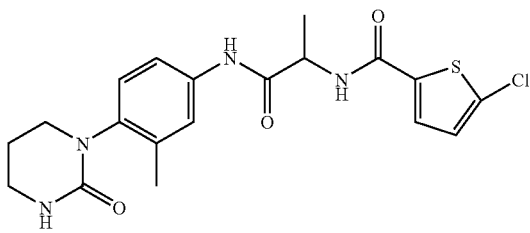

(a) N-(3-chloro-propyl)-N'-(2-methyl-4-nitro-phenyl)-urea 1.14 g (7.48 mmol) 2-methyl-4-nitro-aniline are combined with 0.86 ml (1.00 g, 8.38 mmol) 3-chloropropyl-isocyanate in 15 ml dioxane while cooling with ice and stirred for 3 days at ambient temperature. The precipitate formed was filtered off and dried at 45° C. in the drying cupboard.

Yield: 0.45 g (22%)

$R_f$ value: 0.52 (silica gel; dichloromethane/ethanol=9:1)
$C_{11}H_{14}ClN_3O_3$ (271.70)
Mass spectrum: (M+H)⁺=272/274 (chlorine isotope)

(b) 3-methyl-4-(tetrahydro-pyrimidin-2-on-1-yl)-nitrobenzene 450 mg (1.66 mmol) N-(3-chloro-propyl)-N'-(2-methyl-4-nitro-phenyl)-urea are combined with 195 mg (1.74 mmol) potassium-tert.-butoxide in 2 ml DMF at 40° C. and stirred for 20 hours at 40° C. Then ice is added and the mixture is extracted with dichloromethane. The combined organic phases are dried over sodium sulphate, evaporated down i. vac. and the residue is purified by chromatography on silica gel (eluant-gradient: dichloromethane/ethanol=100:0->96:4).

Yield: 290 mg (74%)

$R_f$ value: 0.41 (silica gel; dichloromethane/ethanol=9:1)
$C_{11}H_{13}N_3O_3$ (235.24)
Mass spectrum: (M+H)⁺=236

(c) 3-methyl-4-(tetrahydro-pyrimidin-2-on-1-yl)-aniline 0.28 g (1.09 mmol) 3-methyl-4-(tetrahydro-pyrimidin-2-on-1-yl)-nitrobenzene are combined with 85 mg 20% palladium-charcoal in 40 ml of methanol and hydrogenated in a Parr apparatus at ambient temperature for 20 hours at 3 atm hydrogen pressure. Then the palladium charcoal is filtered off and the filtrate is evaporated down i. vac. The residue is reacted without any further purification.

Yield: 240 mg (95%)

$R_f$ value: 0.22 (silica gel; dichloromethane/ethanol=9:1)
$C_{11}H_{15}N_3O$ (205.26)
Mass spectrum: (M+H)⁺=206

(d) 5-chloro-thiophene-2-carboxylic acid-N-{1-[3-methyl-4-(tetrahydro-pyrimidin-2-on-1-yl)-phenylcarbamoyl]-ethyl}-amide Prepared analogously to Example 1d from 2-[(5-chloro-thiophene-2-carbonyl)-amino]-propionic acid and 3-methyl-4-(tetrahydro-pyrimidin-2-on-1-yl)-aniline with TBTU and DIPEA in THF.

Yield: 69%

$R_f$ value: 0.69 (silica gel; dichloromethane/ethanol=4:1)
$C_{19}H_{21}ClN_4O_3S$ (420.91)
Mass spectrum: (M+H)⁺=421/423

EXAMPLE 40

5-chloro-thiophene-2-carboxylic acid-N-{1-(1-methyl-pyrazol-3-yl)-1-[3-methyl-4-(3-oxo-morpholin-4-yl)-phenylcarbamoyl]-methyl}-amide

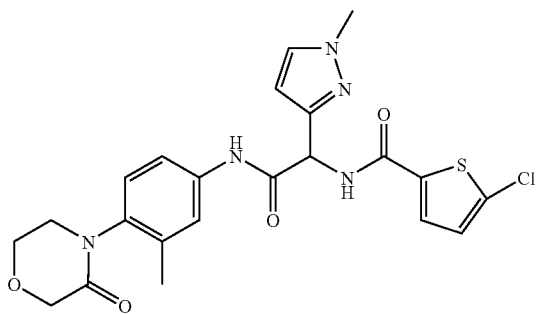

(a) methyl ethoxycarbonyl-methoxyimino-(1-methyl-pyrazol-3-yl)-acetate 5.00 g (20.7 mmol) ethoxycarbonyl-methoxyimino-(pyrazol-3-yl)-acetic acid are combined with 5.73 g (41.5 mmol) potassium carbonate in 20 ml DMF and stirred at ambient temperature until the development of gas has ended. Then 2.58 ml (5.88 g, 41.5 mmol) methyl iodide are added and the mixture is stirred for 2 hours at 50° C. After evaporation i. vac. the residue is combined with water and ethyl acetate, the organic phase is washed with water, dried over magnesium sulphate and evaporated down completely i. vac. The residue is purified by chromatography on silica gel (eluant-gradient: petroleum ether/ethyl acetate=80:20->65:35).

Yield: 2.61 g (26%, contaminated by regioisomer)
$R_f$ value: 0.25 (silica gel; petroleum ether/ethyl acetate=1:1)
$C_{11}H_{15}N_3O_5$ (269.25)
Mass spectrum: $(M+H)^+=270$ (b) (1-methyl-pyrazol-3-yl)-glycine-methylester 2.61 g (9.69 mmol) methyl ethoxycarbonyl-methoxy-imino-(1-methyl-pyrazol-3-yl)-acetate are combined with 0.55 g 5% palladium-charcoal in 60 ml of ethanol and hydrogenated in a Parr apparatus at 50° C. for 16 hours at 3.5 atm hydrogen pressure. Then the mixture is filtered off and the filtrate is evaporated down i. vac. The residue is reacted without any further purification.

Yield: 1.90 g (quant., contaminated)
$R_f$ value: 0.30 (silica gel; dichloromethane/ethanol=9:1)
$C_7H_{11}N_3O_2$ (169.18)
Mass spectrum: $(M+H)^+=170$ (c) methyl [(5-chloro-thiophene-2-carbonyl)-amino]-(1-methyl-pyrazol-3-yl)-acetate Prepared analogously to Example 1d from 5-chloro-thiophene-2-carboxylic acid and (1-methyl-pyrazol-3-yl)-glycine-methylester with TBTU and TEA in THF.

Yield: 63%
$R_f$ value: 0.80 (silica gel; dichloromethane/ethanol=19:1)
$C_{12}H_{12}ClN_3O_3S$ (313.76)
Mass spectrum: $(M+H)^+=314/316$ (chlorine isotope)

(d) [(5-chloro-thiophene-2-carbonyl)-amino]-(1-methyl-pyrazol-3-yl)-acetic acid 0.58 g (1.85 mmol) methyl [(5-chloro-thiophene-2-carbonyl)-amino]-(1-methyl-pyrazol-3-yl)-acetate are dissolved in 12 ml THF and 10 ml of water and 3.7 ml (3.7 mmol) 1-molar lithium hydroxide solution are added. After stirring for 2 hours at ambient temperature the reaction mixture is evaporated down to ⅓ of its volume, diluted with some water and adjusted to pH 2-3 with sat. potassium hydrogen sulphate solution. After extraction with ethyl acetate the combined organic phases are dried over sodium sulphate and evaporated down completely.

Yield: 450 mg (81%)
$R_f$ value: 0.10 (silica gel; dichloromethane/ethanol=4:1)
$C_{11}H_{10}ClN_3O_3S$ (299.73)
Mass spectrum: $(M+H)^+=300/302$ (chlorine isotope)

(e) 5-chloro-thiophene-2-carboxylic acid-N-{1-(1-methyl-pyrazol-3-yl)-1-[3-methyl-4-(3-oxo-morpholin-4-yl)-phenylcarbamoyl]-methyl}-amide Prepared analogously to Example 26c from [(5-chloro-thiophene-2-carbonyl)-amino]-(1-methyl-pyrazol-3-yl)-acetic acid and 3-methyl-4-(3-oxo-morpholin-4-yl)-aniline with 50% PPA in ethyl acetate and NMM in dichloromethane.

Yield: 82%
$R_f$ value: 0.55 (silica gel; dichloromethane/ethanol=9:1)
$C_{22}H_{22}ClN_5O_4S$ (487.96)
Mass spectrum: $(M+H)^+=488/490$ (chlorine isotope)

EXAMPLE 42

5-bromo-thiophene-2-carboxylic acid-N-{2-(methoxy-carbonyl)-1-[3-methyl-4-(3-oxo-morpholin-4-yl)-phenylcarbamoyl]-ethyl}-amide

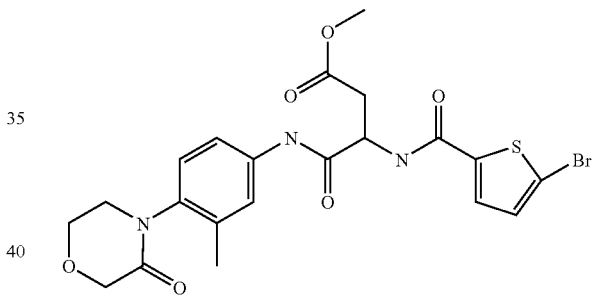

(a) 3-(benzyl-oxycarbonyl-amino)-1-[3-methyl-4-(3-oxo-morpholin-4-yl)-phenyl]-pyrrolidine-2,5-dione 410 mg (1.99 mmol) 3-methyl-4-(3-oxo-morpholin-4-yl)-aniline in 10 ml THF are added dropwise to a solution of 450 mg (1.81 mmol) 3-(benzyl-oxycarbonyl-amino)-bernstein-saureanhydrid in 20 ml THF with stirring at ambient temperature and stirred for a further 15 hours. Then the mixture is evaporated down completely i. vac., the residue is taken up in 20 ml acetic anhydride and 444 mg (5.42 mmol) sodium acetate are added. The mixture is stirred for 1.5 hours at 80° C., then ice water is added and the mixture is stirred vigorously for a further 16 hours at ambient temperature. The precipitate formed was filtered off and dried i. vac.

Yield: 350 mg (44%)
$R_t$ value: 2.61 min
$C_{23}H_{23}N_3O_6$ (437.46)
Mass spectrum: $(M+H)^+=438$ (b) 2-amino-3-(methoxy-carbonyl)-propionic acid-N-[3-methyl-4-(3-oxo-morpholin-4-yl)-phenyl]-amide 350 mg (0.80 mmol) 3-(benzyl-oxycarbonyl-amino)-1-[3-methyl-4-(3-oxo-morpholin-4-yl)-phenyl]-pyrrolidine-2,5-dione are combined with 150 mg palladium(II)hydroxide in a mixture of 200 ml of methanol and 50 ml THF and hydrogenated in a Parr apparatus at ambient temperature for 41 hours at 3 atm hydrogen pressure. Then the mixture is filtered off and the filtrate is evaporated down i. vac. The residue is reacted directly without any further purification.

(c) 5-bromo-thiophene-2-carboxylic acid-N-{2-methoxy-carbonyl-1-[3-methyl-4-(3-oxo-morpholin-4-yl)-phenylcarbamoyl]-ethyl}-amide Prepared analogously to Example 1d from 5-chloro-thiophene-2-carboxylic acid and 2-amino-3-(methoxy-carbonyl)-propionic acid-N-[3-methyl-4-(3-oxo-morpholin-4-yl)-phenyl]-amide with TBTU and NMM in DMF.

Yield: 26%

$C_{21}H_{22}BrN_3O_6S$ (524.39)

Mass spectrum: $(M+H)^+$=524/526 (bromine isotope)

EXAMPLE 44

5-bromo-thiophene-2-carboxylic acid-N-{1-methyl-3-[3-methyl-4-(3-oxo-morpholin-4-yl)-phenylcarbamoyl]-pyrrolidin-3-yl}-amide

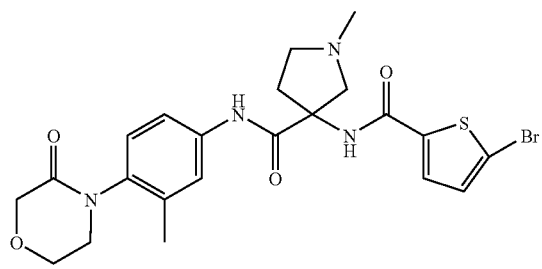

(a) 3-N-Boc-amino-1-methyl-pyrrolidine-3-carboxylic acid 461 mg (2.00 mmol) 3-N-Boc-amino-pyrrolidine-3-carboxylic acid are kept at 5 bar in 5 ml of methanol together with 0.17 ml (2.2 mmol) 37% formaldehyde solution and 100 mg 10% palladium-charcoal for 3.5 h at ambient temperature under a hydrogen atmosphere. After filtering and evaporation i. vac. the residue is taken up twice in toluene and evaporated down completely i. vac. The residue is further reacted without any further purification.

Yield: 0.47 g (96%)

$R_f$ value: 0.60 (RP-8; 5% sodium chloride solution/methanol=3:2)

$C_{11}H_{20}N_2O_4$ (244.29)

Mass spectrum: $(M+H)^+$=245

(b) 3-Boc-amino-1-methyl-N-[3-methyl-4-(3-oxo-morpholin-4-yl)-phenyl]-pyrrolidine-3-carboxylic acid-amide Prepared analogously to Example 1d from 3-N-Boc-amino-1-methyl-pyrrolidine-3-carboxylic acid and 3-methyl-4-(3-oxo-morpholin-4-yl)-aniline with TBTU and NMM in DMF.

Yield: 32%

$R_f$ value: 0.20 (silica gel; ethyl acetate/methanol=4:1+1% conc. ammonia solution)

$C_{22}H_{32}N_4O_5$ (432.51)

Mass spectrum: $(M+H)^+$=433

(c) 3-amino-1-methyl-N-[3-methyl-4-(3-oxo-morpholin-4-yl)-phenyl]-pyrrolidine-3-carboxylic acid-amide 270 mg (0.62 mmol) 3-Boc-amino-1-methyl-N-[(3-methyl-4-(3-oxo-morpholin-4-yl)-phenyl]-propionic acid-amide are stirred in 20 ml (60 mmol) 6-molar hydrochloric acid for 1.5 h at ambient temperature. The reaction mixture is evaporated down i. vac., combined with ice, made alkaline with 1-normal sodium hydroxide solution and extracted with dichloromethane. The combined organic phases are washed with a little water, dried over magnesium sulphate and evaporated down completely.

Yield: 0.170 g (82%)

$R_f$ value: 0.50 (silica gel; dichloromethane/methanol=4:1+1% conc. ammonia solution)

$C_{17}H_{24}N_4O_3$ (332.40)

Mass spectrum: $(M+H)^+$=333

(d) 5-bromo-thiophene-2-carboxylic acid-N-{1-methyl-3-[3-methyl-4-(3-oxo-morpholin-4-yl)-phenylcarbamoyl]-pyrrolidin-3-yl}-amide Prepared analogously to Example 1d from 5-bromo-thiophene-2-carboxylic acid and 3-amino-1-methyl-N-[3-methyl-4-(3-oxo-morpholin-4-yl)-phenyl]-pyrrolidine-carboxylic acid-amide with TBTU and NMM in DMF.

Yield: 37%

$R_f$ value: 0.40 (silica gel; dichloromethane/methanol=9:1+1% conc. ammonia solution)

$C_{22}H_{25}BrN_4O_4S$ (521.43)

Mass spectrum: $(M+H)^+$=521/523 (bromine isotope)

The following compounds may be prepared analogously:

(1) 5-chloro-thiophene-2-carboxylic acid-N-{1-methyl-3-[3-methyl-4-(3-oxo-morpholin-4-yl)-phenylcarbamoyl]-pyrrolidin-3-yl}-amide, (2) 5-bromo-thiophene-2-carboxylic acid-N-{1-methyl-3-[3-chloro-4-(3-oxo-morpholin-4-yl)-phenylcarbamoyl]-pyrrolidin-3-yl}-amide, (3) 5-chloro-thiophene-2-carboxylic acid-N-{1-methyl-4-[3-methyl-4-(3-oxo-morpholin-4-yl)-phenylcarbamoyl]-piperidin-4-yl}-amide, (4) 5-bromo-thiophene-2-carboxylic acid-N-{1-methyl-4-[3-methyl-4-(3-oxo-morpholin-4-yl)-phenylcarbamoyl]-piperidin-4-yl}-amide, (5) 5-bromo-thiophene-2-carboxylic acid-N-{1-methyl-4-[3-chloro-4-(3-oxo-morpholin-4-yl)-phenylcarbamoyl]-piperidin-4-yl}-amide, (6) 5-bromo-thiophene-2-carboxylic acid-N-{3-[3-methyl-4-(3-oxo-morpholin-4-yl)-phenylcarbamoyl]-1-methyl-azetidin-3-yl}-amide, (7) 5-bromo-thiophene-2-carboxylic acid-N-{3-[3-chloro-4-(3-oxo-morpholin-4-yl)-phenylcarbamoyl]-1-methyl-azetidin-3-yl}-amide, (8) 5-bromo-thiophene-2-carboxylic acid-N-{3-[3-chloro-4-(5-oxo-[1,4]-oxazepan-4-yl)-phenylcarbamoyl]-1-methyl-azetidin-3-yl}-amide, (9) 5-bromo-thiophene-2-carboxylic acid-N-{3-[3-fluoro-4-(3-oxo-morpholin-4-yl)-phenylcarbamoyl]-1-methyl-pyrrolidin-3-yl}-amide,

(10) 5-bromo-thiophene-2-carboxylic acid-N-{3-[3-bromo-4-(3-oxo-morpholin-4-yl)-phenylcarbamoyl]-1-methyl-pyrrolidin-3-yl}-amide,

(11) 5-bromo-thiophene-2-carboxylic acid-N-{3-[3-methyl-4-(5-oxo-[1,4]-oxazepan-4-yl)-phenylcarbamoyl]-1-methyl-pyrrolidin-3-yl}-amide,

(12) 5-bromo-thiophene-2-carboxylic acid-N-{3-[3-chloro-4-(5-oxo-[1,4]-oxazepan-4-yl)-phenylcarbamoyl]-1-methyl-pyrrolidin-3-yl}-amide

EXAMPLE 45

5-bromo-thiophene-2-carboxylic acid-N-{1-methyl-1-[3-methyl-4-(2-oxo-tetrahydropyrimidin-1-yl)-phenylcarbamoyl]-ethyl}-amide

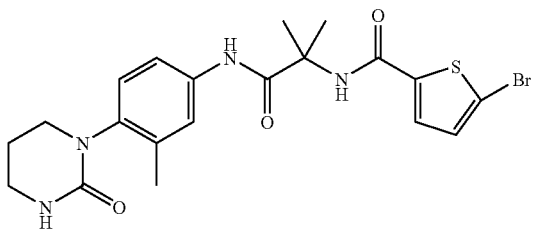

Prepared analogously to Example 33a from 3-methyl-4-(tetrahydro-pyrimidin-2-on-1-yl)-aniline and 2-[(5-bromo-thiophene-2-carbonyl)-amino]-isobutyric acid with HATU and NMM in DMF.

Yield: 48%
$R_f$ value: 0.29 (silica gel; dichloromethane/methanol=9:1)
$C_{20}H_{23}BrN_4O_3S$ (479.39)
Mass spectrum: $(M+H)^+=479/481$ (bromine isotope)

The following compounds may be prepared analogously:
(1) 5-bromo-thiophene-2-carboxylic acid-N-{1-methyl-1-[3-methyl-4-(7-oxo-[1,4]diazepan-1-yl)-phenylcarbamoyl]-ethyl}-amide,
(2) 5-bromo-thiophene-2-carboxylic acid-N-{1-methyl-1-[3-methyl-4-(1,1-dioxo-isothiazolidin-2-yl)-phenylcarbamoyl]-ethyl}-amide,
(3) 5-bromo-thiophene-2-carboxylic acid-N-{1-methyl-1-[3-methyl-4-(1,1-dioxo-[1,2]thiazinan-2-yl)-phenylcarbamoyl]-ethyl}-amide,
(4) 5-bromo-thiophene-2-carboxylic acid-N-{1-methyl-1-[3-methyl-4-(1,1-dioxo-[1,2,5]thiadiazinan-2-yl)-phenylcarbamoyl]-ethyl}-amide,
(5) 5-bromo-thiophene-2-carboxylic acid-N-{1-methyl-1-[3-methyl-4-(3,3-dioxo-[1,3,4]oxathiazinan-4-yl)-phenylcarbamoyl]-ethyl}-amide,
(6) 5-bromo-thiophene-2-carboxylic acid-N-{1-methyl-1-[3-methyl-4-(1,1-dioxo-[1,2]thiazepan-2-yl)-phenylcarbamoyl]-ethyl}-amide

EXAMPLE 46

5-bromo-thiophene-2-carboxylic acid-N-{1-methyl-1-[3-methyl-4-(5-oxo-[1,4]oxazepan-4-yl)-phenylcarbamoyl]-ethyl}-amide

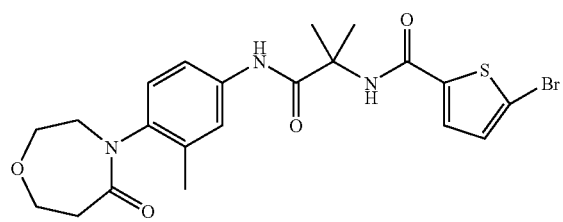

(a) 3-methyl-4-(5-oxo-[1,4]oxazepan-4-yl)-1-nitro-benzene
1.00 g (6.45 mmol) 2-fluoro-5-nitro-toluene are placed together with 816 mg (7.09 mmol) 4-oxa-caprolactam in 4 ml DMF under a nitrogen atmosphere at ambient temperature and 309 mg (7.09 mmol) 55% sodium hydride, dispersed in paraffin oil, are added with stirring. After 15 min the mixture is poured into ice water, acidified with 6-normal hydrochloric acid solution and extracted with ethyl acetate. The combined organic phases are washed with sat. sodium chloride solution and 2-normal sodium carbonate solution, the aqueous phases are extracted with ethyl acetate and the combined organic phases are dried over magnesium sulphate. After evaporation i. vac. the mixture is twice taken up in toluene and in each case evaporated down completely i. vac. The residue is purified by chromatography on silica gel (eluant-gradient: petroleum ether/ethyl acetate=9:1->0:1).

Yield: 620 mg (38%)
$R_f$ value: 0.65 (silica gel; ethyl acetate+1% conc. ammonia solution)
$C_{12}H_{14}N_2O_4$ (250.25)
Mass spectrum: $(M+H)^+=251$ (b) 3-methyl-4-(5-oxo-[1,4]oxazepan-4-yl)-aniline
Prepared analogously to Example 1c from 3-methyl-4-(5-oxo-[1,4]oxazepan-4-yl)-1-nitro-benzene with Raney nickel under a hydrogen atmosphere in methanol.

Yield: 95%
$C_{12}H_{16}N_2O_2$ (220.27)
Mass spectrum: $(M+H)^+=221$ (c) 5-bromo-thiophene-2-carboxylic acid-N-{1-methyl-1-(3-methyl-4-[5-oxo-[1,4]oxazepan-4-yl]-phenylcarbamoyl)-ethyl}-amide
Prepared analogously to Example 33a from 2-[(5-bromo-thiophene-2-carbonyl)-amino]-isobutyric acid and 3-methyl-4-[5-oxo-[1,4]oxazepan-4-yl)-aniline with HATU and NMM in DMF.

Yield: 77%
$R_f$ value: 0.42 (silica gel; dichloromethane/methanol=9:1)
$C_{21}H_{24}BrN_3O_4S$ (494.40)
Mass spectrum: $(M+H)^+=494/496$ (bromine isotope)

The following compounds may be prepared analogously:
(1) 5-bromo-thiophene-2-carboxylic acid-N-{1-methyl-1-[3-cyano-4-(3-oxo-morpholin-4-yl)-phenylcarbamoyl]-ethyl}-amide,
(2) 5-chloro-thiophene-2-carboxylic acid-N-{1-methyl-1-[3-methyl-4-(4-methyl-2-oxo-piperazin-1-yl)-phenylcarbamoyl]-ethyl}-amide,
(3) 5-bromo-thiophene-2-carboxylic acid-N-{1-methyl-1-[3-methyl-4-(4-methyl-2-oxo-piperazin-1-yl)-phenylcarbamoyl]-ethyl}-amide,
(4) 5-bromo-thiophene-2-carboxylic acid-N-{1-methyl-1-[3-chloro-4-(4-methyl-2-oxo-piperazin-1-yl)-phenylcarbamoyl]-ethyl}-amide,
(5) 5-bromo-thiophene-2-carboxylic acid-N-{1-methyl-1-[3-bromo-4-(4-methyl-2-oxo-piperazin-1-yl)-phenylcarbamoyl]-ethyl}-amide,
(6) 5-chloro-thiophene-2-carboxylic acid-N-{1-methyl-1-[3-chloro-4-(3-oxo-morpholin-4-yl)-phenylcarbamoyl]-ethyl}-amide,
(7) 5-chloro-thiophene-2-carboxylic acid-N-{1-methyl-1-[3-bromo-4-(3-oxo-morpholin-4-yl)-phenylcarbamoyl]-ethyl}-amide,
(8) 5-bromo-thiophene-2-carboxylic acid-N-{1-methyl-1-[3-bromo-4-(3-oxo-morpholin-4-yl)-phenylcarbamoyl]-ethyl}-amide,
(9) 5-chloro-thiophene-2-carboxylic acid-N-{2-methoxy-1-[methoxymethyl]-1-[3-methyl-4-(3-oxo-morpholin-4-yl)-phenylcarbamoyl]-ethyl}-amide,

(10) 5-bromo-thiophene-2-carboxylic acid-N-{2-methoxy-1-[methoxymethyl]-1-[3-methyl-4-(3-oxo-morpholin-4-yl)-phenylcarbamoyl]-ethyl}-amide,
(11) 5-bromo-thiophene-2-carboxylic acid-N-{2-methoxy-1-[methoxymethyl]-1-[3-chloro-4-(3-oxo-morpholin-4-yl)-phenylcarbamoyl]-ethyl}-amide,
(12) 5-chloro-thiophene-2-carboxylic acid-N-{1-acetyl-3-[3-methyl-4-(3-oxo-morpholin-4-yl)-phenylcarbamoyl]-pyrrolidin-3-yl}-amide,
(13) 5-chloro-thiophene-2-carboxylic acid-N-{1-methoxycarbonyl-3-[3-methyl-4-(3-oxo-morpholin-4-yl)-phenylcarbamoyl]-pyrrolidin-3-yl}-amide,
(14) 5-chloro-thiophene-2-carboxylic acid-N-{1-acetyl-4-[3-methyl-4-(3-oxo-morpholin-4-yl)-phenylcarbamoyl]-piperidin-4-yl}-amide,
(15) 5-bromo-thiophene-2-carboxylic acid-N-{1-acetyl-4-[3-methyl-4-(3-oxo-morpholin-4-yl)-phenylcarbamoyl]-piperidin-4-yl}-amide,
(16) 5-bromo-thiophene-2-carboxylic acid-N-{1-methyl-1-[3-methyl-4-(2-oxo-piperidin-1-yl)-phenylcarbamoyl]-ethyl}-amide,
(17) 5-bromo-thiophene-2-carboxylic acid-N-{1-methyl-1-[3-methyl-4-(2-oxo-3,6-dihydro-2H-pyridin-1-yl)-phenylcarbamoyl]-ethyl}-amide,
(18) 5-bromo-thiophene-2-carboxylic acid-N-{1-methyl-1-[3-methyl-4-(3-oxo-thiomorpholin-4-yl)-phenylcarbamoyl]-ethyl}-amide,
(19) 5-bromo-thiophene-2-carboxylic acid-N-{1-methyl-1-[3-methyl-4-(3-oxo-[1,4]oxazepan-4-yl)-phenylcarbamoyl]-ethyl}-amide,
(20) 5-bromo-thiophene-2-carboxylic acid-N-{1-methyl-1-[3-methyl-4-(2-oxo-[1,4]diazepan-1-yl)-phenylcarbamoyl]-ethyl}-amide,
(21) 5-bromo-thiophene-2-carboxylic acid-N-{1-methyl-1-[3-methyl-4-(7-oxo-[1,4]diazepan-1-yl)-phenylcarbamoyl]-ethyl}-amide,
(22) 5-bromo-thiophene-2-carboxylic acid-N-{1-methyl-1-[3-methyl-4-(4-methyl-7-oxo-[1,4]diazepan-1-yl)-phenylcarbamoyl]-ethyl}-amide,
(23) 5-bromo-thiophene-2-carboxylic acid-N-{1-methyl-1-[3-methyl-4-(4-methyl-2-oxo-[1,4]diazepan-1-yl)-phenylcarbamoyl]-ethyl}-amide

EXAMPLE 48

5-bromo-thiophene-2-carboxylic acid-N-{3-[3-methyl-4-(5-oxo-[1,4]oxazepan-4-yl)-phenylcarbamoyl]-tetrahydrofuran-3-yl}-amide

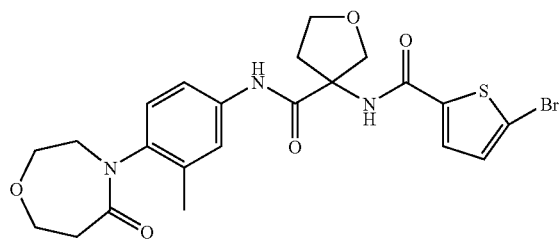

(a) 3-Boc-amino-tetrahydrofuran-3-carboxylic acid-N-[3-methyl-4-(5-oxo-[1,4]oxazepan-4-yl)-phenyl]-amide
Prepared analogously to Example 33a from 3-Boc-amino-tetrahydrofuran-1-carboxylic acid and 3-methyl-4-(5-oxo-[1,4]oxazepan-4-yl)-phenyl]-amide with HATU and NMM in DMF.

Yield: quant.
$C_{22}H_{31}N_3O_6$ (433.50)
Mass spectrum: $(M+H)^+=434$ (b) 3-amino-tetrahydrofuran-3-carboxylic acid-N-[3-methyl-4-(5-oxo-[1,4]oxazepan-4-yl)-phenyl]-amide
Prepared analogously to Example 14b from 3-Boc-amino-tetrahydrofuran-3-carboxylic acid-N-[3-methyl-4-(5-oxo-[1,4]oxazepan-4-yl)-phenyl]-amide with TFA in dichloromethane.

Yield: quant.
$C_{17}H_{23}N_3O_4$ (333.38)
Mass spectrum: $(M+H)^+=334$ (c) 5-bromo-thiophene-2-carboxylic acid-N-13-[3-methyl-4-(5-oxo-[1,4]oxazepan-4-yl)-phenylcarbamoyl]-tetrahydrofuran-3-yl}-amide
Prepared analogously to Example 1d from 5-bromo-thiophene-2-carboxylic acid and 1-amino-cyclohexane-1-carboxylic acid-N-[3-chloro-4-(3-oxo-morpholin-4-yl)-phenyl]-amide with TBTU and TEA in DMF.

Yield: 50%
$R_f$ value: 0.53 (silica gel; dichloromethane/methanol=9:1)
$C_{22}H_{24}BrN_3O_5S$ (522.41)
Mass spectrum: $(M+H)^+=522/524$ (bromine isotope)

The following compounds may be prepared analogously:

(1) 5-bromo-thiophene-2-carboxylic acid-N-{3-[3-fluoro-4-(5-oxo-[1,4]-oxazepan-4-yl)-phenylcarbamoyl]-tetrahydrofuran-3-yl}-amide,
(2) 5-bromo-thiophene-2-carboxylic acid-N-{3-[3-chloro-4-(5-oxo-[1,4]-oxazepan-4-yl)-phenylcarbamoyl]-tetrahydrofuran-3-yl}-amide,
(3) 5-bromo-thiophene-2-carboxylic acid-N-{3-[3-bromo-4-(5-oxo-[1,4]-oxazepan-4-yl)-phenylcarbamoyl]-tetrahydrofuran-3-yl}-amide,
(4) 5-bromo-thiophene-2-carboxylic acid-N-{3-[3-methyl-4-(4-methyl-2-oxo-[1,4]-diazepan-1-yl)-phenylcarbamoyl]-tetrahydrofuran-3-yl}-amide,
(5) 5-bromo-thiophene-2-carboxylic acid-N-{3-[3-chloro-4-(1-methyl-5-oxo-[1,4]-diazepan-4-yl)-phenylcarbamoyl]-tetrahydrofuran-3-yl}-amide,
(6) 5-bromo-thiophene-2-carboxylic acid-N-{3-[3-trifluoromethyl-4-(5-oxo-[1,4]-oxazepan-4-yl)-phenylcarbamoyl]-tetrahydrofuran-3-yl}-amide

EXAMPLE 49

5-chloro-thiophene-2-carboxylic acid-N-{1-[3-methyl-4-(3-oxo-morpholin-4-yl)-phenylcarbamoyl]-cyclopent-3-en-1-yl}-amide

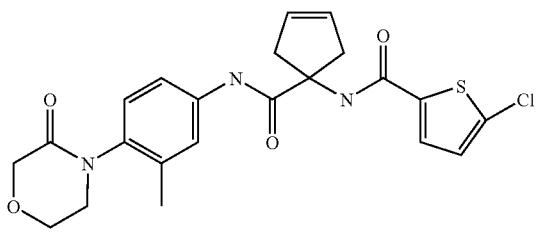

(a) 1-Boc-amino-cyclopent-3-ene-1-carboxylic acid-N-[3-methyl-4-(3-oxo-morpholin-4-yl)-phenyl]-amide Prepared analogously to Example 26c from 1-Boc-amino-cyclopent-3-ene-1-carboxylic acid and 3-methyl-4-(3-oxo-morpholin-4-yl)-aniline in THF with NMM and PPA in ethyl acetate.
Yield: 28%
$R_f$ value: 0.52 (silica gel; dichloromethane/ethanol=9:1)
$C_{22}H_{29}N_3O_5$ (415.48)
Mass spectrum: $(M+H)^+=416$ (b) 1-amino-cyclopent-3-ene-1-carboxylic acid-N-[3-methyl-4-(3-oxo-morpholin-4-yl)-phenyl]-amide
Prepared analogously to Example 14b from 1-Boc-amino-cyclopent-3-ene-1-carboxylic acid-N-[3-methyl-4-(3-oxo-morpholin-4-yl)-phenyl]-amide with TFA in dichloromethane.
Yield: 69%
$R_f$ value: 0.10 (silica gel; dichloromethane/ethanol=9:1)
$C_{17}H_{21}N_3O_3$ (315.37)
Mass spectrum: $(M+H)^+=316$ (c) 5-chloro-thiophene-2-carboxylic acid-N-{1-[3-methyl-4-(3-oxo-morpholin-4-yl)-phenylcarbamoyl]-cyclopent-3-en-1-yl}-amide
Prepared analogously to Example 1d from 5-chloro-thiophene-2-carboxylic acid and 1-amino-cyclopent-3-ene-1-carboxylic acid-N-[3-methyl-4-(3-oxo-morpholin-4-yl)-phenyl]-amide with TBTU and TEA in THF.
Yield: 97%
$R_f$ value: 0.50 (silica gel; dichloromethane/ethanol=9:1)
$C_{22}H_{22}ClN_3O_4S$ (459.95)
Mass spectrum: $(M+H)^+=458/460$ (chlorine isotope)

EXAMPLE 50

5-bromo-thiophene-2-carboxylic acid-N-{1-[3-methyl-4-(tetrahydropyrimidin-2-on-1-yl)-phenylcarbamoyl]-cyclopent-1-yl}-amide

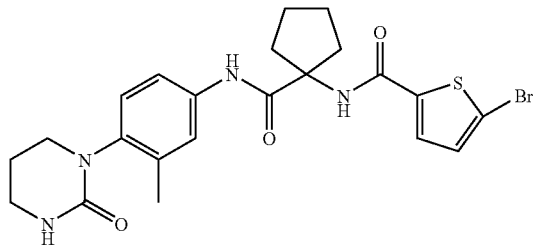

(a) methyl 1-[(5-bromo-thiophene-2-carbonyl)-amino]-cyclopentane-1-carboxylate
Prepared analogously to Example 37a from methyl 1-amino-cyclopentane-1-carboxylate hydrochloride and 5-bromo-thiophene-2-carboxylic acid with thionyl chloride in dichloromethane with TEA.
Yield: 88%
$C_{12}H_{14}BrNO_3S$ (332.22)
Mass spectrum: $(M+H)^+=332/334$ (bromine isotope)

(b) 1-[(5-bromo-thiophene-2-carbonyl)-amino]-cyclopentane-1-carboxylic acid
Prepared analogously to Example 1e from methyl 1-[(5-bromo-thiophene-2-carbonyl)-amino]-cyclopentane-1-carboxylate in methanol with 1-normal sodium hydroxide solution.
Yield: 94%
$C_{11}H_{12}BrNO_3S$ (318.19)
Mass spectrum: $(M+H)^+=318/320$ (bromine isotope)

(c) 5-bromo-thiophene-2-carboxylic acid-N-{1-[3-methyl-4-(tetrahydro-pyrimidin-2-on-1-yl)-phenylcarbamoyl]-cyclopent-1-yl}-amide
Prepared analogously to Example 33a from 1-[(5-bromo-thiophene-2-carbonyl)-amino]-cyclopentane-1-carboxylic acid and 3-methyl-4-(tetrahydro-pyrimidin-2-on-1-yl)-aniline with HATU and NMM in DMF.
Yield: 66%
$R_f$ value: 0.29 (silica gel; dichloromethane/methanol=9:1)
$C_{22}H_{25}BrN_4O_3S$ (505.43)
Mass spectrum: $(M+H)^+=505/507$ (bromine isotope)

EXAMPLE 51

5-bromo-thiophene-2-carboxylic acid-N-{1-[3-methyl-4-(2-oxo-[1,3]oxazepan-3-yl)-phenylcarbamoyl]-cyclopent-1-yl}-amide

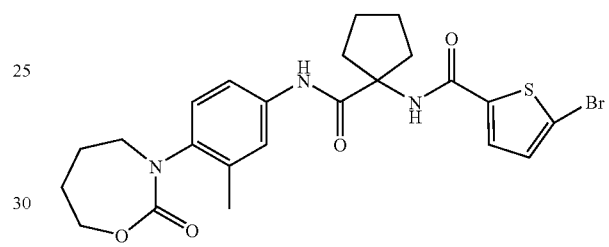

(a) 4-isocyanato-3-methyl-1-nitro-benzene
7.50 g (49.3 mmol) 2-methyl-4-nitro-aniline are combined with 7.20 ml (59.2 mmol) diphosgene in 200 ml of toluene and refluxed for 2 h with stirring. The reaction mixture is evaporated down i. vac., the residue is twice taken up in toluene and evaporated down completely i. vac. The residue is further reacted without any further purification.
Yield: 8.78 g (quant.)

(b) 4-chloro-butyl 2-methyl-4-nitro-phenyl-carbamate
17.8 g (0.10 mol) 4-isocyanato-3-methyl-1-nitro-benzene are placed in 750 ml of toluene and a solution of 11.7 ml (0.10 mol) 4-chloro-butan-1-ol in 50 ml of toluene is added dropwise. Then the reaction mixture is heated for 16 hours to 75° C., then evaporated down i. vac. and twice taken up with toluene and concentrated by evaporation completely i. vac. The residue is purified by recrystallisation from cyclohexane.
Yield: 16.2 g (57%)
$R_t$ value: 5.27 min
$C_{12}H_{15}ClN_2O_4$ (286.71)
Mass spectrum: $(M+H)^+=286/288$ (chlorine isotope)

(c) 3-methyl-4-(2-oxo-[1,3]oxazepan-3-yl)-1-nitro-benzene
Prepared analogously to Example 39b from 4-chloro-butyl 2-methyl-4-nitro-phenyl-carbamate with potassium-tert.-butoxide in DMF.
Yield: 12%
$R_t$ value: 4.26 min
$C_{12}H_{14}N_2O_4$ (235.24)
Mass spectrum: $(M+H)^+=236$ (d) 3-methyl-4-(2-oxo-[1,3]oxazepan-3-yl)-aniline
Prepared analogously to Example 40b from 3-methyl-4-(2-oxo-[1,3]oxazepan-3-yl)-1-nitro-benzene with palladium-charcoal under a hydrogen atmosphere in THF.

Yield: quant.
R_f value: 2.76 min
$C_{12}H_{16}N_2O_2$ (220.27)
Mass spectrum: (M+H)$^+$=221

(e) 5-bromo-thiophene-2-carboxylic acid-N-{1-[3-methyl-4-(2-oxo-[1,3]oxazepan-3-yl)-phenylcarbamoyl]-cyclopentan-1-yl}-amide Prepared analogously to Example 33a from 1-[(5-bromo-thiophene-2-carbonyl)-amino]-cyclopentane-1-carboxylic acid and 3-methyl-4-(2-oxo-[1,3]oxazepan-3-yl)-aniline with HATU and NMM in DMF and subsequent purification by chromatography on silica gel.

Yield: 52%
R_f value: 0.42 (silica gel; dichloromethane/methanol=9:1)
$C_{23}H_{26}BrN_3O_4S$ (520.44)
Mass spectrum: (M+H)$^+$=520/522 (bromine isotope)

EXAMPLE 52

5-bromo-thiophene-2-carboxylic acid-N-{1-[3-methyl-4-(2-oxo-[1,3]oxazinan-3-yl)-phenylcarbamoyl]-cyclopent-1-yl}-amide

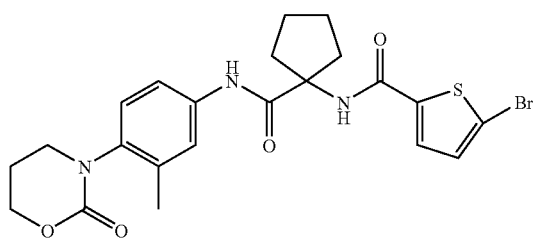

(a) 3-chloro-propyl 2-methyl-4-nitro-phenyl-carbamate

Prepared analogously to Example 51b from 4-isocyanato-3-methyl-1-nitro-benzene and 3-chloro-propan-1-ol in toluene.

Yield: 59%
$C_{11}H_{13}ClN_2O_4$ (272.69)
Mass spectrum: (M+H)$^+$=273/275 (chlorine isotope)

(b) 3-methyl-4-(2-oxo-[1.3]oxazinan-3-yl)-1-nitro-benzene 7.80 g (28.6 mmol) 3-chloro-propyl 2-methyl-4-nitro-phenyl-carbamate are combined with 4.74 g (34.3 mmol) potassium carbonate in 100 ml acetonitrile and heated to 90° C. for 2 h. Then some more acetonitrile is added, after filtering the filtrate is evaporated down i. vac., the residue is stirred in diethyl ether at ambient temperature, filtered off and dried.

Yield: 5.74 g (85%)
R_f value: 0.42 (silica gel; dichloromethane/methanol=50:1)
$C_{11}H_{12}N_2O_4$ (236.22)
Mass spectrum: (M+H)$^+$=237

(c) 3-methyl-4-(2-oxo-[1,3]oxazinan-3-yl)-aniline

Prepared analogously to Example 1c from 3-methyl-4-(2-oxo-[1,3]oxazinan-3-yl)-1-nitro-benzene with Raney nickel under a hydrogen atmosphere in THF.

Yield: 44%
R_f value: 0.52 (silica gel; dichloromethane/methanol=9:1)
$C_{11}H_{12}N_2O_2$ (206.24)
Mass spectrum: (M+H)$^+$=207

(d) 5-bromo-thiophene-2-carboxylic acid-N-{1-[3-methyl-4-(2-oxo-[1,3]oxazinan-3-yl)-phenylcarbamoyl]-cyclopentan-1-yl}-amide Prepared analogously to Example 33a from 1-[(5-bromo-thiophene-2-carbonyl)-amino]-cyclopentane-1-carboxylic acid and 3-methyl-4-(2-oxo-[1,3]oxazinan-3-yl)-aniline with HATU and NMM in DMF and subsequent purification by chromatography on silica gel.

Yield: 41%
R_f value: 0.43 (silica gel; dichloromethane/methanol=9:1)
$C_{22}H_{24}BrN_3O_4S$ (506.42)
Mass spectrum: (M+H)$^+$=506/508 (bromine isotope)

EXAMPLE 53

5-chloro-thiophene-2-carboxylic acid-N-{2-[3-methyl-4-(3-oxo-morpholin-4-yl)-phenylcarbamoyl]-bicyclo[2.2.1]hept-2-yl}-amide

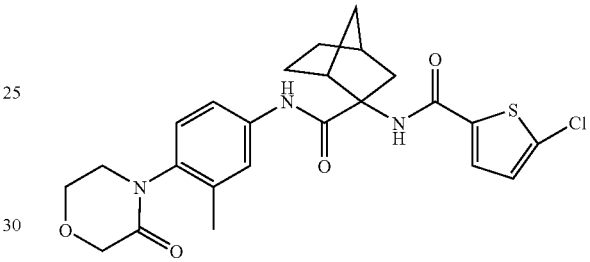

(a) 2-[(5-chloro-thiophene-2-carbonyl)-amino]-bicyclo[2.2.1]heptane-2-carboxylic acid 1.99 g (12.2 mmol) 5-chloro-thiophene-2-carboxylic acid are combined with 3.56 ml (49.0 mmol) thionyl chloride in 120 ml dichloromethane and refluxed for 1.75 h with stirring. The mixture is evaporated down i. vac. and the residue is taken up 3 times in dichloromethane and concentrated by evaporation. Then the residue is taken up in 75 ml acetonitrile and within 5 min added dropwise with stirring at 70° C. to a mixture obtained by the addition of 3.67 ml (13.6 mmol) N,O-bis-(trimethylsilyl)-trifluoroacetamide to 1.90 g 2-amino-bicyclo[2.2.1]heptane-2-carboxylic acid in 150 ml acetonitrile, subsequent stirring for 3.25 h at ambient temperature and the addition of 3.74 ml (26.9 mmol) TEA. The mixture is stirred for a further 2 h at 70° C. and then filtered. The filtrate is evaporated down i. vac., the residue is stirred for 30 min in 150 ml of water, adjusted to pH 10 with 2-normal sodium carbonate solution, stirred for 5 min and filtered. While being cooled in the ice bath the filtrate is adjusted to pH 2.5 with 1-molar hydrochloric acid, the precipitate obtained is filtered off and dried at 55° C.

Yield: 2.35 g (51%), slightly contaminated
R_f value: 0.70 (silica gel; ethyl acetate/ethanol=9:1+1% acetic acid)
$C_{13}H_{14}ClNO_3S$ (299.77)
Mass spectrum: (M+H)$^+$=300/302 (chlorine isotope)

(b) 5-chloro-thiophene-2-carboxylic acid-N-{2-[3-methyl-4-(3-oxo-morpholin-4-yl)-phenylcarbamoyl]-bicyclo[2.2.1]hept-2-yl}-amide Prepared analogously to Example 1d from 2-[(5-chloro-thiophene-2-carbonyl)-amino]-bicyclo[2.2.1]heptane-2-carboxylic acid and 3-methyl-4-(2-oxo-morpholin-4-yl)-aniline with TBTU and NMM in DMF.

Yield: 44%

R$_f$ value: 0.40 (silica gel; ethyl acetate/ethanol=19:1+1% conc. ammonia solution)

C$_{24}$H$_{26}$ClN$_3$O$_4$S (488.00)

Mass spectrum: (M+H)$^+$=488/490 (chlorine isotope)

The following compounds may be prepared analogously:
(1) 5-bromo-thiophene-2-carboxylic acid-N-{2-[3-methyl-4-(3-oxo-morpholin-4-yl)-phenylcarbamoyl]-7-oxa-bicyclo[2.2.1]hept-5-en-2-yl}-amide,
(2) 5-bromo-thiophene-2-carboxylic acid-N-{5-[3-methyl-4-(3-oxo-morpholin-4-yl)-phenylcarbamoyl]-spiro[2.4]hept-5-yl}-amide

EXAMPLE 54

5-bromo-thiophene-2-carboxylic acid-N-{3-[3-chloro-4-(5-cyanimino-[1,4]oxazepan-4-yl)-phenylcarbamoyl]-tetrahydrofuran-3-yl}-amide

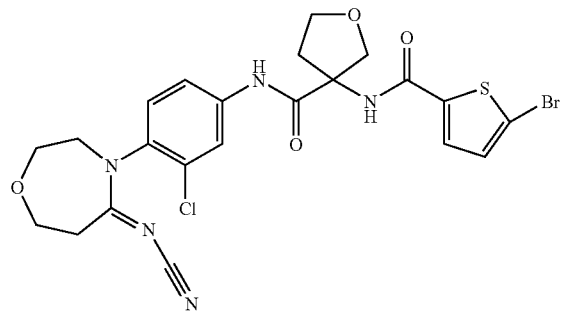

(a) 3-amino-tetrahydrofuran-3-carboxylic acid 3.50 g (15.1 mmol) 3-Boc-amino-tetrahydrofuran-3-carboxylic acid are stirred together with 150 ml 1-molar hydrochloric acid for 1 h at ambient temperature, then frozen and freeze-dried. The residue is further reacted without any further purification.

Yield: 2.58 g (quant.)

C$_5$H$_9$NO$_3$*HCl (167.59/131.13)

Mass spectrum: (M+H)$^+$=132

(b) 3-[(5-bromo-thiophene-2-carbonyl)-amino]-tetrahydrofuran-3-carboxylic acid

Prepared analogously to Example 53a from 3-amino-tetrahydrofuran-3-carboxylic acid and 5-bromo-thiophene-2-carboxylic acid with thionyl chloride and N,O-bis-(trimethylsilyl)-trifluoroacetamid in dichloromethane with triethylamine.

Yield: 69%

C$_{10}$H$_{10}$BrNO$_4$S (320.16)

Mass spectrum: (M+H)$^+$=320/322

(c) 2-(5-bromo-thiophen-2-yl)-3,7-dioxa-1-aza-spiro[4.41]non-1-en-4-one 1.50 g (4.69 mmol) 3-[(5-bromo-thiophene-2-carbonyl)-amino]-tetrahydrofuran-3-carboxylic acid are stirred for 2 h in 45 ml acetic anhydride at 85° C. The reaction mixture is evaporated down i. vac., the residue is taken up twice each in toluene and dichloromethane and completely concentrated by evaporation. The residue is further reacted directly without any further purification.

Yield: 1.45 g (quant.)

R$_f$ value: 0.85 (silica gel; petroleum ether/ethyl acetate=1:1)

C$_{10}$H$_8$BrNO$_3$S (302.15)

Mass spectrum: (M+H)$^+$=303/305 (bromine isotope)

(d) 5-bromo-thiophene-2-carboxylic acid-N-{3-[3-chloro-4-(5-cyanimin-[1,4]oxazepan-4-yl)-phenylcarbamoyl]-tetrahydrofuran-3-yl}-amide 320 mg (1.06 mmol) 2-(5-bromo-thiophene-2-yl)-3,7-dioxa-1-aza-spiro[4,4]non-1-en-4-one are stirred with 3-chloro-4-(5-oxo-[1,4]oxazepan-4-yl)-aniline in 2.5 ml of toluene with 3.1 ml NMP and 315 µl glacial acetic acid in a microwave oven at 125° C. for 55 min. Then 80 mg (0.26 mmol) 2-(5-bromo-thiophen-2-yl)-3,7-dioxa-1-aza-spiro[4,4]non-1-en-4-one are added and the mixture is stirred for another 20 min at 125° C. in the microwave oven. Then the reaction mixture is poured into in semisat. sodium hydrogen carbonate solution and extracted with ethyl acetate. The combined organic phases are washed with semisat. and sat. sodium chloride solution, dried over magnesium sulphate and evaporated down i. vac. The residue is purified by chromatography on a preparative HPLC apparatus (Gilson, StableBond C$_{18}$-Material, eluant-gradient: water/acetonitrile 95:5->5:95+0.01% formic acid).

Yield: 145 mg (24%)

R$_f$ value: 0.25 (silica gel; ethyl acetate+0.5% conc. ammonia solution)

C$_{22}$H$_{21}$BrClN$_5$O$_4$S (566.86)

Mass spectrum: (M+H)$^+$=566/568/570 (bromo- and chlorine isotope)

The following compounds may be prepared analogously:
(1) 5-chloro-thiophene-2-carboxylic acid-N-{3-[3-chloro-4-(5-cyanimino-[1,4]-oxazepan-4-yl)-phenylcarbamoyl]-tetrahydrofuran-3-yl}-amide,
(2) 5-bromo-thiophene-2-carboxylic acid-N-{3-[3-chloro-4-(3-cyanimino-morpholin-4-yl)-phenylcarbamoyl]-tetrahydrofuran-3-yl}-amide,
(3) 5-chloro-thiophene-2-carboxylic acid-N-{3-[3-chloro-4-(3-cyanimino-morpholin-4-yl)-phenylcarbamoyl]-tetrahydrofuran-3-yl}-amide,
(4) 5-bromo-thiophene-2-carboxylic acid-N-{3-[3-methyl-4-(3-cyanimino-morpholin-4-yl)-phenylcarbamoyl]-tetrahydrofuran-3-yl}-amide,
(5) 5-chloro-thiophene-2-carboxylic acid-N-{3-[3-methyl-4-(3-cyanimino-morpholin-4-yl)-phenylcarbamoyl]-tetrahydrofuran-3-yl}-amide,
(6) 5-chloro-thiophene-2-carboxylic acid-N-{3-[3-bromo-4-(3-cyanimino-morpholin-4-yl)-phenylcarbamoyl]-tetrahydrofuran-3-yl}-amide,
(7) 5-chloro-thiophene-2-carboxylic acid-N-{3-[3-methyl-4-(5-cyanimino-[1,4]-oxazepan-4-yl)-phenylcarbamoyl]-tetrahydrofuran-3-yl}-amide,
(8) 5-chloro-thiophene-2-carboxylic acid-N-{3-[3-bromo-4-(5-cyanimino-[1,4]-oxazepan-4-yl)-phenylcarbamoyl]-tetrahydrofuran-3-yl}-amide,
(9) 5-bromo-thiophene-2-carboxylic acid-N-{3-[3-methyl-4-(5-cyanimino-[1,4]-oxazepan-4-yl)-phenylcarbamoyl]-tetrahydrofuran-3-yl}-amide, The Examples that follow describe the preparation of pharmaceutical formulations which contain as active substance any desired compound of general formula (I):

EXAMPLE I

Dry ampoule containing 75 mg of active substance per 10 ml
Composition:

| | |
|---|---|
| Active substance | 75.0 mg |
| Mannitol | 50.0 mg |
| Water for injections | ad 10.0 ml |

Preparation:
Active substance and mannitol are dissolved in water. After packaging the solution is freeze-dried. To produce the solution ready for use for injections, the product is dissolved in water.

EXAMPLE II

Dry ampoule containing 35 mg of active substance per 2 ml
Composition:

| | |
|---|---|
| Active substance | 35.0 mg |
| Mannitol | 100.0 mg |
| Water for injections | ad 2.0 ml |

Preparation:
Active substance and mannitol are dissolved in water. After packaging, the solution is freeze-dried. To produce the solution ready for use for injections, the product is dissolved in water.

EXAMPLE III

Tablet containing 50 mg of active substance
Composition:

| | | |
|---|---|---|
| (1) | Active substance | 50.0 mg |
| (2) | Lactose | 98.0 mg |
| (3) | Maize starch | 50.0 mg |
| (4) | Polyvinylpyrrolidone | 15.0 mg |
| (5) | Magnesium stearate | 2.0 mg |
| | | 215.0 mg |

Preparation:
(1), (2) and (3) are mixed together and granulated with an aqueous solution of (4). (5) is added to the dried granulated material. From this mixture tablets are pressed, biplanar, faceted on both sides and with a dividing notch on one side. Diameter of the tablets: 9 mm.

EXAMPLE IV

Tablet containing 350 mg of active substance
Composition:

| | | |
|---|---|---|
| (1) | Active substance | 350.0 mg |
| (2) | Lactose | 136.0 mg |
| (3) | Maize starch | 80.0 mg |
| (4) | Polyvinylpyrrolidone | 30.0 mg |
| (5) | Magnesium stearate | 4.0 mg |
| | | 600.0 mg |

Preparation:
(1), (2) and (3) are mixed together and granulated with an aqueous solution of (4). (5) is added to the dried granulated material. From this mixture tablets are pressed, biplanar, faceted on both sides and with a dividing notch on one side. Diameter of the tablets: 12 mm.

EXAMPLE V

Capsules containing 50 mg of active substance
Composition:

| | | |
|---|---|---|
| (1) | Active substance | 50.0 mg |
| (2) | Dried maize starch | 58.0 mg |
| (3) | Powdered lactose | 50.0 mg |
| (4) | Magnesium stearate | 2.0 mg |
| | | 160.0 mg |

Preparation:
(1) is triturated with (3). This trituration is added to the mixture of (2) and (4) with vigorous mixing.
This powder mixture is packed into size 3 hard gelatine capsules in a capsule filling machine.

EXAMPLE VI

Capsules containing 350 mg of active substance
Composition:

| | | |
|---|---|---|
| (1) | Active substance | 350.0 mg |
| (2) | Dried maize starch | 46.0 mg |
| (3) | Powdered lactose | 30.0 mg |
| (4) | Magnesium stearate | 4.0 mg |
| | | 430.0 mg |

Preparation:
(1) is triturated with (3). This trituration is added to the mixture of (2) and (4) with vigorous mixing.
This powder mixture is packed into size 0 hard gelatine capsules in a capsule filling machine.

EXAMPLE VII

Suppositories containing 100 mg of active substance

| 1 suppository contains: | |
|---|---|
| Active substance | 100.0 mg |
| Polyethyleneglycol (M.W. 1500) | 600.0 mg |
| Polyethyleneglycol (M.W. 6000) | 460.0 mg |
| Polyethylenesorbitan monostearate | 840.0 mg |
| | 2,000.0 mg |

Preparation:

The polyethyleneglycol is melted together with polyethylenesorbitan monostearate. At 40° C. the ground active substance is homogeneously dispersed in the melt. It is cooled to 38° C. and poured into slightly chilled suppository moulds.

What is claimed is:

1. A compound of the formula

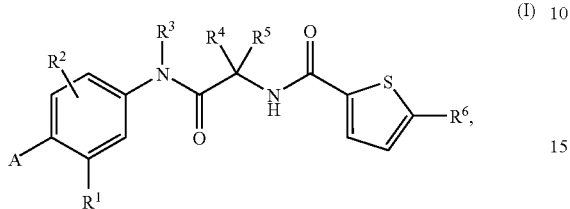

wherein

A denotes a group of general formula

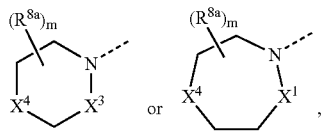

wherein m is the number 1 or 2, $R^{8a}$ in each case independently of one another denotes a hydrogen or halogen atom or a $C_{1-5}$-alkyl, hydroxy, hydroxy-$C_{1-5}$-alkyl, $C_{1-5}$-alkoxy, $C_{1-5}$-alkoxy-$C_{1-5}$-alkyl, amino, $C_{1-5}$-alkylamino, di-($C_{1-5}$-alkyl)-amino, amino-$C_{1-5}$-alkyl, $C_{1-5}$-alkylamino-$C_{1-5}$-alkyl, di-($C_{1-5}$-alkyl)-amino-$C_{1-5}$-alkyl, aminocarbonyl, $C_{1-5}$-alkylaminocarbonyl, di-($C_{1-5}$-alkyl)-aminocarbonyl or $C_{1-5}$-alkylcarbonylamino group, while in the previously mentioned substituted 5- to 7-membered groups A the heteroatoms F, Cl, Br, I, O or N optionally introduced with $R^{8a}$ as substituent are not separated by precisely one carbon atom from a heteroatom selected from among N, O, S, $R^{8b}$ each independently of one another denote a hydrogen atom or a $C_{1-5}$-alkyl group, $X^1$ denotes a carbonyl, thiocarbonyl, C=$NR^{8c}$, C=N—$OR^{8c}$, C=N—$NO_2$, C=N—CN or sulphonyl group, $R^{8c}$ each independently of one another denote a hydrogen atom, a $C_{1-5}$-alkyl, $C_{1-5}$-alkylcarbonyl, $C_{1-5}$-alkyloxycarbonyl or $C_{1-5}$-alkylsulphonyl group, $X^2$ denotes an oxygen atom or a —$NR^{8b}$ group, $X^3$ denotes a carbonyl, thiocarbonyl, C=$NR^{8c}$, C=N—$OR^{8c}$, C=N—$NO_2$, C=N—CN or sulphonyl group, $X^4$ denotes an oxygen or sulphur atom or a —$NR^{8c}$group, $R^1$ denotes a fluorine, chlorine, bromine or iodine atom, a $C_{1-3}$-alkyl or $C_{1-3}$-alkoxy group, while the hydrogen atoms of the $C_{1-3}$-alkyl or $C_{1-3}$-alkoxy group may optionally be wholly or partly replaced by fluorine atoms, a $C_{2-3}$-alkenyl, $C_{2-3}$-alkynyl, nitrile, nitro or amino group, $R^2$ denotes a hydrogen or halogen atom or a $C_{1-3}$-alkyl group, $R^3$ denotes a hydrogen atom or a $C_{1-3}$-alkyl group, $R^4$ and $R^5$ in each case independently of one another denote a hydrogen atom, a $C_{2-6}$-alkenyl or $C_{2-6}$-alkynyl group, a straight-chain or branched $C_{1-6}$-alkyl group, while the hydrogen atoms of the straight-chain or branched $C_{1-6}$-alkyl group may optionally be wholly or partly replaced by fluorine atoms, and may optionally be substituted by a $C_{3-5}$-cycloalkyl group, a nitrile, hydroxy, a $C_{1-5}$-alkyloxy group, while the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-5}$-alkyloxy, $C_{1-5}$-alkyloxycarbonyl-$C_{1-5}$-alkyloxy, mercapto, $C_{1-5}$-alkylsulphanyl, $C_{1-5}$-alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, aminosulphonyl, $C_{1-5}$-alkylaminosulphonyl, di-($C_{1-5}$-alkyl)-aminosulphonyl, $C_{3-6}$-cycloalkyleneiminosulphonyl, amino, $C_{1-5}$-alkylamino, di-($C_{1-5}$-alkyl)-amino, $C_{1-5}$-alkylcarbonylamino, $C_{1-5}$-alkylsulphonylamino, N—($C_{1-5}$-alkylsulphonyl)-$C_{1-5}$-alkylamino or $C_{3-6}$-cycloalkylcarbonylamino group, a carboxy, aminocarbonyl, $C_{1-5}$-alkylaminocarbonyl, $C_{3-6}$-cycloalkylaminocarbonyl, di-($C_{1-5}$-alkyl)-aminocarbonyl, $C_{1-5}$-alkoxycarbonyl, $C_{4-6}$-cycloalkyleneiminocarbonyl group, a phenyl, heteroaryl, phenyl-$C_{1-5}$-alkyl or heteroaryl-$C_{1-5}$-alkyl group, which may optionally be mono-to trisubstituted in the phenyl or heteroaryl moiety by identical or different substituents selected from the group consisting of halogen atoms, $C_{1-5}$-alkyl, di-($C_{1-5}$-alkyl)-amino, hydroxy, $C_{1-5}$-alkyloxy, mono-, di- or trifluoromethoxy, carboxy and $C_{1-5}$-alkyloxycarbonyl groups, a 3- to 7-membered cycloalkyl, cycloalkyleneimino, cycloalkyl-$C_{1-5}$-alkyl or cycloalkyleneimino-$C_{1-3}$-alkyl group, wherein in 4- to 7-membered cyclic groups in the cyclic moiety a methylene group may optionally be replaced by an —N($R^{8c}$) group, an oxygen or sulphur atom or a —S(O) or —S(O)$_2$ group, or wherein in 4- to 7-membered cyclic groups in the cyclic moiety two adjacent methylene groups may together optionally be replaced by a —C(O)N($R^{8b}$) or —S(O)$_2$N($R^{8b}$) group, or wherein in 6- to 7-membered cyclic groups in the cyclic moiety three adjacent methylene groups may optionally be replaced together by a substituted —OC(O)N($R^{8b}$) or —N($R^{8b}$)C(O)N($R^{8b}$) or —N($R^{8b}$)S(O)$_2$N($R^{8b}$) group, with the proviso that a 3- to 7-membered cycloalkyl, cycloalkyleneimino, cycloalkyl-$C_{1-5}$-alkyl or cycloalkyleneimino-$C_{1-3}$-alkyl group as hereinbefore defined wherein two heteroatoms selected from among oxygen and nitrogen are separated from one another by precisely one optionally substituted —$CH_2$ group, is excluded, while a 3- to 7-membered cycloalkyl, cycloalkyleneimino, cycloalkyl-$C_{1-5}$-alkyl or cycloalkyleneimino-$C_{1-3}$-alkyl group as hereinbefore defined may be substituted at one or two —$CH_2$ groups by one or two $C_{1-3}$-alkyl groups in each case, or $R^4$ and $R^5$ together with the carbon atom to which they are bound form a $C_{3-8}$-cycloalkyl or $C_{3-8}$-cycloalkenyl group, while a $C_{3-8}$-cycloalkyl or $C_{4-8}$-cycloalkenyl group may be substituted at an individual carbon atom by a $C_{2-5}$-alkylene group or simultaneously at two different carbon atoms by a $C_{1-4}$-alkylene group, forming a corresponding spirocyclic group or a bridged bicyclic group, while one of the methylene groups of a $C_{4-8}$-cycloalkyl or $C_{5-8}$-cycloalkenyl group or a corresponding spirocyclic group or a corresponding bridged bicyclic group as hereinbefore described may be replaced by an oxygen or sulphur atom or an —N($R^{8c}$), or a carbonyl, sulphinyl or sulphonyl group, and/or two directly adjacent methylene groups of a $C_{4-8}$-cycloalkyl group may be replaced together by a —C(O)N($R^{8b}$) or —S(O)$_2$N($R^{8b}$) group, and/or three directly adjacent methylene groups of a $C_{6-8}$-cycloalkyl group may be replaced together by a —OC(O)N($R^{8b}$), —N($R^{8b}$)C(O)N($R^{8b}$) or —N($R^{8b}$)S(O)$_2$N($R^{8b}$) group, while 1 to 3 carbon atoms of a $C_{3-8}$-cycloalkyl group or a corresponding spirocyclic group or a corresponding bridged bicyclic group as hereinbefore described may optionally be substituted independently of one another by in each case one or two fluorine atoms or one or two identical or different $C_{1-5}$-alkyl, nitrile, hydroxy, $C_{1-5}$-alkyloxy, $C_{1-5}$-alkylcarbonyloxy, carboxy-$C_{1-5}$-alkyl, $C_{1-5}$-alkyloxycarbonyl-$C_{1-5}$-alkyl, $C_{1-5}$-alkylsulphanyl, $C_{1-5}$-alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, aminosulphonyl, $C_{1-5}$-alkylaminosulphonyl, di-($C_{1-5}$-alkyl)-aminosulphonyl, $C_{3-6}$-cycloalkyleneiminosulphonyl, amino, $C_{1-5}$-alkylamino, di-($C_{1-5}$-alkyl)-amino, $C_{1-5}$-alkylcarbonylamino, $C_{1-5}$-alkyl-sulphonylamino, N—($C_{1-5}$-alkylsulphonyl)-$C_{1-5}$-alkylamino or $C_{3-6}$-cycloalkylcarbonylamino groups, while 1 to 2 carbon atoms of a $C_{3-8}$-cycloalkenyl group may optionally be substituted independently of one another by in each case a $C_{1-5}$-alkyl, nitrile, carboxy-$C_{1-5}$-alkyl, $C_{1-5}$-alkyloxycarbonyl-$C_{1-5}$-alkyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{3-6}$-cycloalkyleneiminocarbonyl, aminosulphonyl, $C_{1-5}$-alkylaminosulphonyl, di-($C_{1-5}$-alkyl)-aminosulphonyl, $C_{3-6}$-cycloalkyleneiminosulphonyl group, and 1 to 2 carbon atoms of a $C_{4-8}$-cycloalkenyl group which are not bound to another carbon atom by a double bond may optionally be substituted independently of one another by one or two fluorine atoms or a hydroxy, $C_{1-5}$-alkyloxy, $C_{1-5}$-alkylcarbonyloxy, $C_{1-5}$-alkylsulphanyl, $C_{1-5}$-alkylsulphonyl, amino, $C_{1-5}$-alkylamino, di-($C_{1-5}$-alkyl)-amino, $C_{1-5}$-alkylcarbonylamino, $C_{1-5}$-alkyl-sulphonylamino, N—($C_{1-5}$-alkylsulphonyl)-$C_{1-5}$-alkylamino or $C_{3-6}$-cycloalkylcarbonylamino group, with the proviso that a $C_{3-8}$-cycloalkyl or $C_{3-8}$-cycloalkenyl group of this kind, formed from $R^4$ and $R^5$ together, or a corresponding spirocyclic group or a corresponding bridged bicyclic group as hereinbefore described, wherein two heteroatoms in the cyclic group selected from among oxygen and nitrogen are separated from one another by precisely one optionally substituted —CH$_2$ group, and/or wherein one or both methylene groups of the cyclic group which are directly connected to the carbon atom to which the groups $R^4$ and $R^5$ are bound, are replaced by a heteroatom selected from among oxygen, nitrogen and sulphur, and/or wherein a substituent bound to the cyclic group, which is characterised in that a heteroatom selected from among an oxygen, nitrogen, sulphur and halogen atom is bound directly to the cyclic group, is separated from another heteroatom selected from among oxygen, nitrogen and sulphur, with the exception of the sulphone group, by precisely one, optionally substituted, methylene group, and/or wherein two oxygen atoms are joined together directly, and/or wherein a heteroatom selected from among oxygen, nitrogen and sulphur is linked directly to a carbon atom which is linked to another carbon atom by a double bond, and/or which contains a cyclic group with three ring members, one or more of which corresponds to an oxygen or sulphur atom or —N($R^{8c}$) group, is excluded, $R^6$ denotes a hydrogen, fluorine, chlorine, bromine or iodine atom, a nitrile group, a $C_{1-3}$-alkyl group, or a $C_{1-3}$-alkoxy group, while the hydrogen atoms of the $C_{1-3}$-alkyl or $C_{1-3}$-alkoxy group may optionally be wholly or partly replaced by fluorine atoms, $R^7$ independently of one another denote a $C_{1-3}$-alkyl, while the hydrogen atoms may optionally be wholly or partly replaced by fluorine atoms, hydroxy, $C_{1-3}$-alkyloxy, while the hydrogen atoms may optionally be wholly or partly replaced by fluorine atoms, amino, $C_{1-3}$-alkylamino, di-($C_{1-3}$-alkyl)-amino, $C_{3-6}$-cycloalkyleneimino, carboxy, nitrile, $C_{1-3}$-alkoxycarbonyl, aminocarbonyl, $C_{1-3}$-alkylaminocarbonyl or a di-($C_{1-3}$-alkyl)-aminocarbonyl group, while, unless otherwise stated, by the term "heteroaryl group" mentioned hereinbefore in the definitions is meant a monocyclic 5- or 6-membered heteroaryl group, while the 6-membered heteroaryl group contains one, two or three nitrogen atoms and the 5-membered heteroaryl group contains an imino group optionally substituted by a $C_{1-3}$-alkyl, phenyl or phenyl-$C_{1-3}$-alkyl group, or an oxygen or sulphur atom or an imino group optionally substituted by a $C_{1-3}$-alkyl, phenyl, amino-$C_{2-3}$-alkyl, $C_{1-3}$-alkylamino-$C_{2-3}$-alkyl, di-($C_{1-3}$-alkyl)-amino-$C_{2-3}$-alkyl, a $C_{3-6}$-cycloalkyleneimino-$C_{1-3}$-alkyl or phenyl-$C_{1-3}$-alkyl group or an oxygen or sulphur atom and additionally a nitrogen atom or an imino group optionally substituted by a $C_{1-3}$-alkyl or phenyl-$C_{1-3}$-alkyl group and two or three nitrogen atoms, and the above-mentioned monocyclic heteroaryl groups in the carbon skeleton may be substituted by one or two groups $R^7$, and moreover a phenyl ring optionally substituted by a fluorine, chlorine or bromine atom or a group $R^7$ may be fused to the above-mentioned monocyclic heteroaryl groups via two adjacent carbon atoms and the bond is effected via a nitrogen atom or a carbon atom of the heterocyclic moiety or a fused-on phenyl ring, while, unless otherwise stated, by the term "halogen atom" mentioned hereinbefore in the definitions is meant an atom selected from among fluorine, chlorine, bromine and iodine, while, unless otherwise stated, the alkyl, alkenyl, alkynyl and alkoxy groups contained in the foregoing definitions which have more than two carbon atoms may be straight-chain or branched and the alkyl groups in the previously mentioned dialkylated groups, for example the dialkylamino groups, may be identical or different, and the hydrogen atoms of the methyl or ethyl groups contained in the foregoing definitions, unless otherwise stated, may be wholly or partly replaced by fluorine atoms, or a tautomer or salt thereof.

2. A compound of the formula I according to claim 1, wherein:

A denotes a group of general formula

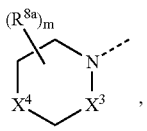

wherein m is the number 1 or 2, $R^{8a}$ each independently of one another denote a hydrogen or fluorine atom or a $C_{1-3}$-alkyl, hydroxy, hydroxy-$C_{1-3}$-alkyl, $C_{1-3}$-alkoxy, $C_{1-3}$-alkoxy-$C_{1-3}$-alkyl, amino, $C_{1-3}$-alkylamino, di-($C_{1-3}$-alkyl)-amino, amino-$C_{1-3}$-alkyl, $C_{1-3}$-alkylamino-$C_{1-3}$-alkyl or di-($C_{1-3}$-alkyl)-amino-$C_{1-3}$-alkyl group, while in the previously mentioned substituted 5- to 7-membered groups A the heteroatoms F, O or N optionally introduced with $R^{8a}$ as substituent are not separated by precisely one carbon atom from a heteroatom selected from among N, O, S, $R^{8b}$ denotes a hydrogen atom or a $C_{1-3}$-alkyl group, $X^1$ denotes a carbonyl, thiocarbonyl, C=$NR^{8c}$, C=N—$OR^{8c}$, C=N—$NO_2$, C=N—CN or sulphonyl group, $R^{8c}$ each independently of one another denote a hydrogen atom, a $C_{1-3}$-alkyl, $C_{1-3}$-alkylcarbonyl, or a $C_{1-4}$-alkyloxycarbonyl group, $X^2$ denotes an oxygen atom or a —$NR^{8b}$ group, $X^3$ denotes a carbonyl, thiocarbonyl, C=$NR^{8c}$, C=N—$OR^{8c}$, C=N—$NO_2$, C=N—CN or sulphonyl group, $X^4$ denotes an oxygen atom or a —$NR^{8c}$ group, $R^1$ denotes a fluorine, chlorine, bromine or iodine atom, a methyl or a methoxy group, while the hydrogen atoms of the methyl or methoxy group may optionally be wholly or partly replaced by fluorine atoms, $R^2$ denotes a hydrogen or fluorine atom, $R^3$ denotes a hydrogen atom, $R^4$ denotes a straight-chain or branched $C_{1-4}$-alkyl group, while the hydrogen atoms may optionally be wholly or partly replaced by fluorine atoms, and may optionally be substituted by a hydroxy, a $C_{1-3}$-alkyloxy group, while the hydrogen atoms of the $C_{1-3}$-alkyloxy group may be wholly or partly replaced by fluorine atoms, a benzyloxy, $C_{1-3}$-alkylcarbonyloxy, $C_{1-3}$-alkyloxycarbonyl, aminocarbonyl, $C_{1-3}$-alkylaminocarbonyl, di-($C_{1-3}$-alkyl)-aminocarbonyl, $C_{3-6}$-cycloalkyleneiminocarbonyl, aminosulphonyl, $C_{1-3}$-alkylaminosulphonyl, di-($C_{1-3}$-alkyl)-aminosulphonyl, $C_{3-6}$-cycloalkyleneiminosulphonyl,
amino, $C_{1-3}$-alkylamino, di-($C_{1-3}$-alkyl)-amino, $C_{1-3}$-alkylcarbonylamino, or $C_{1-3}$-alkylsulphonylamino group, a phenyl, heteroaryl-$C_{1-2}$-alkyl or C-linked heteroaryl group while the heteroaryl group is selected from among pyrrolyl, oxazolyl, imidazolyl, furanyl, thiophenyl, thiazolyl, 1,2,3-triazolyl, 1,2,4-triazolyl, tetrazolyl, pyridynyl, pyrimidynyl and pyrazynyl, and may optionally be mono- to disubstituted in the phenyl or heteroaryl moiety by identical or different substituents selected from among halogen atoms, $C_{1-3}$-alkyl, hydroxy, $C_{1-3}$-alkyloxy, mono-, di- and trifluoromethoxy groups, $R^5$ denotes a hydrogen atom, a straight-chain or branched $C_{1-4}$-alkyl group, while the hydrogen atoms may optionally be wholly or partly replaced by fluorine atoms, and may optionally be substituted by a $C_{1-3}$-alkyloxy group, while the hydrogen atoms of the $C_{1-3}$-alkyloxy group may optionally be wholly or partly replaced by fluorine atoms, or $R^4$ and $R^5$ together with the carbon atom to which they are bound form a $C_{3-7}$-cycloalkyl or $C_{4-7}$-cycloalkenyl group, while a $C_{3-7}$-cycloalkyl or $C_{4-7}$-cycloalkenyl group may be substituted at an individual carbon atom by a $C_{2-5}$-alkylene group or may be substituted simultaneously at two different carbon atoms by a $C_{1-4}$-alkylene group forming a corresponding spirocyclic group or a bridged bicyclic group, while one of the methylene groups of a $C_{4-7}$-cycloalkyl or $C_{4-7}$-cycloalkenyl group or a corresponding spirocyclic group as described above or a corresponding bridged bicyclic group may be replaced by an oxygen or sulphur atom or a sulphonyl or —N($R^{8c}$) group, and/or two directly adjacent methylene groups of a $C_{4-7}$-cycloalkyl group may together be replaced by a —C(O)N($R^{8b}$) or —C(O)O group, while 1 to 2 carbon atoms of a $C_{3-7}$-cycloalkyl group or a corresponding spirocyclic group as described above or a corresponding bridged bicyclic group may optionally be substituted independently of one another by a $C_{1-3}$-alkyl, hydroxy, $C_{1-3}$-alkyloxy, di-($C_{1-3}$-alkyl)-amino group, with the proviso that a $C_{3-7}$-cycloalkyl or $C_{4-7}$-cycloalkenyl group of this kind formed from $R^4$ and $R^5$ together or a corresponding spirocyclic group as described above or a corresponding bridged bicyclic group, wherein [a] methylene groups of the cyclic group which are directly connected to the carbon atom to which the groups $R^4$ and $R^5$ are bound, are replaced by a heteroatom selected from among oxygen, nitrogen and sulphur, and/or wherein a substituent bound to the cyclic group, which is characterised in that a heteroatom selected from among oxygen and nitrogen is bound directly to the cyclic group, is separated from another heteroatom selected from among oxygen, nitrogen and sulphur, with the exception of the sulphone group, by precisely one, optionally substituted, methylene group, and/or wherein a heteroatom selected from among oxygen, nitrogen and sulphur is linked directly to a carbon atom, which is linked to another carbon atom by a double bond, and/or which contains a cyclic group with three ring members, of which one or more corresponds to an oxygen or sulphur atom or an —N(R$^{8c}$) group, is excluded, R$^6$ denotes a chlorine or bromine atom, while, unless otherwise stated, by the term "halogen atom" mentioned hereinbefore in the definitions is meant an atom selected from among fluorine, chlorine, bromine and iodine, while, unless otherwise stated, the alkyl and alkoxy groups contained in the foregoing definitions which have more than two carbon atoms may be straight-chain or branched and the alkyl groups in the previously mentioned dialkylated groups, for example the dialkylamino groups, may be identical or different, and the hydrogen atoms of the methyl or ethyl groups contained in the foregoing definitions, unless otherwise stated, may be wholly or partly replaced by fluorine atoms, or a tautomer or salt thereof.

3. A compound of the formula I according to claim 1, wherein:

A denotes a group of the formula

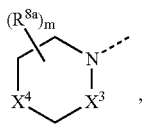

wherein m is the number 1 or 2,

R$^{8a}$ each independently of one another denote a hydrogen or fluorine atom or a C$_{1-3}$-alkyl, hydroxy, hydroxy-C$_{1-3}$-alkyl, C$_{1-3}$-alkoxy, C$_{1-3}$-alkoxy-C$_{1-3}$-alkyl, amino, C$_{1-3}$-alkylamino, di-(C$_{1-3}$-alkyl)-amino, amino-C$_{1-3}$-alkyl, C$_{1-3}$-alkylamino-C$_{1-3}$-alkyl, di-(C$_{1-3}$-alkyl)-amino-C$_{1-3}$-alkyl group, while in the previously mentioned substituted 5- to 7-membered groups A the heteroatoms F, O or N optionally introduced with R$^{8a}$ as substituent are not separated by precisely one carbon atom from a heteroatom selected from among N, O, S, R$^{8b}$ denotes a hydrogen atom or a C$_{1-3}$-alkyl group, X$^1$ denotes a carbonyl, thiocarbonyl, C=NR$^{8c}$, C=N—OR$^{8c}$, C=N—CN or sulphonyl group, R$^{8c}$ denotes a hydrogen atom, a C$_{1-3}$-alkyl, C$_{1-3}$-alkylcarbonyl, or a C$_{1-4}$-alkyloxycarbonyl group, X$^2$ denotes an oxygen atom or a —NR$^{8b}$ group, X$^3$ denotes a carbonyl, thiocarbonyl, C=NR$^{8c}$, C=N—OR$^{8c}$, C=N—CN or sulphonyl group, X$^4$ denotes an oxygen atom or a —NR$^{8c}$ group, R$^1$ denotes a chlorine or bromine atom, a methyl, trifluoromethyl or a methoxy group, R$^2$ denotes a hydrogen or fluorine atom, R$^3$ denotes a hydrogen atom, R$^4$ denotes a methyl group which may optionally be substituted by a hydroxy, methoxy, benzyloxy, methoxycarbonyl or pyridyn-4-yl group, or a 1-methyl-pyrazyn-3-yl, phenyl, pyridyn-3-yl or pyrazin-2-yl group, R$^5$ denotes a hydrogen atom or a methyl group, or R$^4$ and R$^5$ together with the carbon atom to which they are bound form a C$_{3-6}$-cycloalkyl or C$_{5-6}$-cycloalkenyl group, while a C$_{5-6}$-cycloalkyl or C$_{5-6}$-cycloalkenyl group may be substituted simultaneously at two different carbon atoms by a C$_{1-2}$-alkylene group forming a bridged bicyclic group, while one of the methylene groups of a C$_{4-6}$-cycloalkyl or C$_{5-6}$-cycloalkenyl group or of a corresponding bridged bicyclic group as described above, may be replaced by an oxygen atom or an —N(R$^{8c}$) group, with the proviso that a C$_{3-6}$-cycloalkyl or C$_{5-6}$-cycloalkenyl group of this kind, formed from R$^4$ and R$^5$ together or a corresponding bridged bicyclic group as described above, wherein methylene groups of the cyclic group which are directly connected to the carbon atom to which the groups R$^4$ and R$^5$ are bound, are replaced by a heteroatom selected from among oxygen and nitrogen, and/or wherein a heteroatom selected from among oxygen and nitrogen is linked directly to a carbon atom, which is linked to another carbon atom by a double bond, and/or which contains a cyclic group with three ring members, of which one or more corresponds to an oxygen atom or —N(R$^{8c}$) group, is excluded, R$^6$ denotes a chlorine or bromine atom while, unless otherwise stated, by the term "halogen atom" mentioned hereinbefore in the definitions is meant an atom selected from among fluorine, chlorine, bromine and iodine, while, unless otherwise stated, the alkyl and alkoxy groups contained in the foregoing definitions, which have more than two carbon atoms may be straight-chain or branched and the alkyl groups in the previously mentioned dialkylated groups, for example the dialkylamino groups, may be identical or different, and the hydrogen atoms of the methyl or ethyl groups contained in the foregoing definitions, unless otherwise stated, may be wholly or partly replaced by fluorine atoms, or a tautomer or salt thereof.

4. A compound of the formula I according to claim 1, wherein R$^4$ and R$^5$ do not denote hydrogen.

5. A compound of the formula I according to claim 1, wherein R$^4$ and R$^5$ together with the carbon atom to which they are bound form a cyclic group.

6. A compound of the formula I according to claim 1, wherein R$^4$ and R$^5$ together with the carbon atom to which they are bound form a cyclic group, while in the cyclic group or the corresponding bridged bicyclic group or the spirocyclic group according to the above-mentioned method a methylene group is replaced by an oxygen atom or a N(R$^{8c}$) group.

7. A compound of the formula I according to claim 1, wherein R$^4$ and R$^5$ together with the carbon atom to which they are bound, denote a cyclic group of the formula

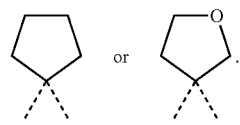

8. A compound of the formula I according to claim 1, wherein $R^4$ and $R^5$ together with the carbon atom to which they are bound denotes a bridged bicyclic group of the formula

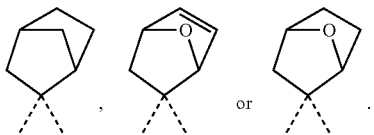

9. A compound of the formula I according to claim 1, wherein the group A denotes the group of the formula

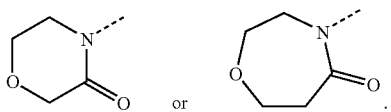

10. A compound of the formula I according to claim 1, wherein the group A denotes the group of the formula

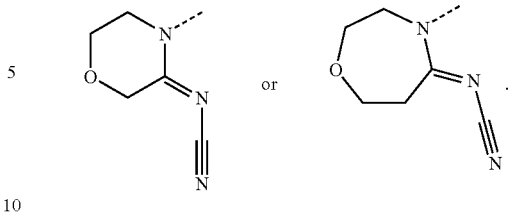

11. A compound of the formula I according to claim 1, wherein $R^6$ denotes a bromine atom.

12. A physiologically acceptable salt of a compound according to claims 1 to 11.

13. A pharmaceutical composition containing a compound according to at least one of claims 1 to 11 or a physiologically acceptable salt thereof together with one or more inert carriers and/or diluents.

14. A method for preventing or treating thrombus formation which comprises administering to a patient having a thrombus or prone to thrombus formation an antithrombotic amount of a compound of the formula I according to claims 1-12 or a physiologically acceptable salt thereof.

* * * * *